United States Patent
Holloway et al.

(10) Patent No.: US 8,278,322 B2
(45) Date of Patent: Oct. 2, 2012

(54) HCV NS3 PROTEASE INHIBITORS

(75) Inventors: M. Katharine Holloway, Lansdale, PA (US); Nigel J. Liverton, Harleysville, PA (US); John A. McCauley, Maple Glen, PA (US); Michael T. Rudd, Collegeville, PA (US); Joseph P. Vacca, Telford, PA (US); Steven W. Ludmerer, North Wales, PA (US); David B. Olsen, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1147 days.

(21) Appl. No.: 11/989,886

(22) PCT Filed: Jul. 28, 2006

(86) PCT No.: PCT/US2006/029635
§ 371 (c)(1),
(2), (4) Date: Jan. 31, 2008

(87) PCT Pub. No.: WO2007/016441
PCT Pub. Date: Feb. 8, 2007

(65) Prior Publication Data
US 2011/0028494 A1 Feb. 3, 2011

Related U.S. Application Data

(60) Provisional application No. 60/704,256, filed on Aug. 1, 2005, provisional application No. 60/724,509, filed on Oct. 7, 2005.

(51) Int. Cl.
*A61K 31/44* (2006.01)
*A61K 31/519* (2006.01)
*A61K 31/33* (2006.01)
*A61K 38/12* (2006.01)
*C07D 225/00* (2006.01)
*C07D 267/22* (2006.01)
*C07D 245/00* (2006.01)

(52) U.S. Cl. ............... 514/306; 514/258.1; 514/183; 530/317; 540/450; 540/451; 540/454; 540/455; 540/460

(58) Field of Classification Search ............ 514/306, 514/258.1, 183, 9; 530/317; 540/450, 451, 540/454, 455, 460
See application file for complete search history.

(56) References Cited

U.S. PATENT DOCUMENTS

| | | | |
|---|---|---|---|
| 3,480,613 A | 11/1969 | Walton | |
| 6,323,180 B1 | 11/2001 | Llinas-Brunet et al. | |
| 6,329,417 B1 * | 12/2001 | Llinas-Brunet et al. | 514/422 |
| 6,608,027 B1 | 8/2003 | Tsantrizos et al. | |
| 6,777,395 B2 | 8/2004 | Bhat et al. | |
| 6,955,174 B2 | 10/2005 | Joye et al. | |
| 7,470,664 B2 | 12/2008 | Holloway et al. | |
| 2002/0019363 A1 | 2/2002 | Ismaili et al. | |
| 2002/0107138 A1 | 8/2002 | Hoveyda et al. | |
| 2002/0107181 A1 * | 8/2002 | Chen et al. | 514/9 |
| 2003/0181363 A1 * | 9/2003 | Llinas-Brunet et al. | 514/9 |
| 2003/0236216 A1 | 12/2003 | Devos et al. | |
| 2004/0006007 A1 | 1/2004 | Gosselin et al. | |
| 2004/0063658 A1 | 4/2004 | Roberts et al. | |
| 2004/0067901 A1 | 4/2004 | Bhat et al. | |
| 2004/0106559 A1 * | 6/2004 | Wang et al. | 514/18 |
| 2004/0229776 A1 | 11/2004 | Chen et al. | |
| 2004/0229818 A1 | 11/2004 | Llinas-Brunet et al. | |
| 2004/0254159 A1 | 12/2004 | Hasvold et al. | |
| 2004/0266668 A1 | 12/2004 | Nakajima et al. | |
| 2005/0020503 A1 | 1/2005 | Llinas-Brunet et al. | |
| 2005/0038240 A1 | 2/2005 | Connolly et al. | |
| 2006/0257980 A1 | 11/2006 | Li | |
| 2007/0027071 A1 | 2/2007 | Holloway et al. | |

FOREIGN PATENT DOCUMENTS

EP 1719773 A1 11/2006
(Continued)

OTHER PUBLICATIONS

West, Solid state chemistry and its application, Wilsy, New York, 1988. pp, 358, 365.*
Vippagunta et al. "Crystalline solid," Advanced, drug, Delivery, 2001, vol. 48, pp. 3-26.*
Ulrich "Crystallization," Chapter 4, Kirk-Othmer Encyclopedia of Chemical techology, John, Wiley and Sons, 2002.*
(Continued)

*Primary Examiner* — Shengjun Wang
(74) *Attorney, Agent, or Firm* — Julie M. Lake; Sheldon O. Heber

(57) ABSTRACT

The present invention relates to macrocyclic compounds of formula (I) that are useful as inhibitors of the hepatitis C virus (HCV) NS3 protease, their synthesis, and their use for treating or preventing HCV infections.

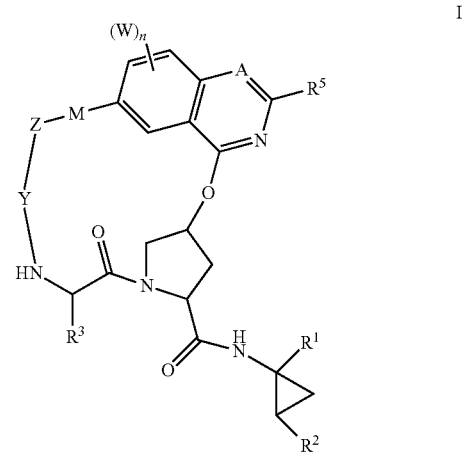

40 Claims, No Drawings

FOREIGN PATENT DOCUMENTS

| | | |
|---|---|---|
| GB | 2 337 262 A | 11/1999 |
| GB | 2337262 A | 11/1999 |
| GB | 2430621 A | 4/2007 |
| WO | 97/41211 A1 | 11/1997 |
| WO | WO 97/41211 A1 | 11/1997 |
| WO | 98/22496 A2 | 5/1998 |
| WO | WO 98/22496 A2 | 5/1998 |
| WO | 98/46630 A1 | 10/1998 |
| WO | WO 98/46630 A1 | 10/1998 |
| WO | 99/07733 A2 | 2/1999 |
| WO | 99/07734 A2 | 2/1999 |
| WO | WO 99/07733 A2 | 2/1999 |
| WO | WO 99/07734 A2 | 2/1999 |
| WO | 99/38888 A1 | 8/1999 |
| WO | WO 99/38888 A1 | 8/1999 |
| WO | 99/43691 A1 | 9/1999 |
| WO | WO 99/43691 A1 | 9/1999 |
| WO | 99/50230 A1 | 10/1999 |
| WO | WO 99/50230 A1 | 10/1999 |
| WO | 99/64442 A1 | 12/1999 |
| WO | WO 99/64442 A1 | 12/1999 |
| WO | 00/09543 A2 | 2/2000 |
| WO | 00/09546 A2 | 2/2000 |
| WO | WO 00/09543 A2 | 2/2000 |
| WO | 00/25780 A1 | 5/2000 |
| WO | WO 00/25780 A1 | 5/2000 |
| WO | 00/59929 A1 | 10/2000 |
| WO | WO 00/59929 A1 | 10/2000 |
| WO | 01/00622 A1 | 1/2001 |
| WO | WO 01/00622 A1 | 1/2001 |
| WO | 01/47883 A1 | 7/2001 |
| WO | WO 01/47883 A1 | 7/2001 |
| WO | 01/60379 A1 | 8/2001 |
| WO | WO 01/60379 A1 | 8/2001 |
| WO | 01/68663 A1 | 9/2001 |
| WO | WO 01/68663 A1 | 9/2001 |
| WO | 01/77091 A2 | 10/2001 |
| WO | 01/77113 A2 | 10/2001 |
| WO | 01/79246 A2 | 10/2001 |
| WO | WO 01/77091 A2 | 10/2001 |
| WO | WO 01/79246 A2 | 10/2001 |
| WO | 01/90121 A2 | 11/2001 |
| WO | WO 01/90121 A2 | 11/2001 |
| WO | 01/92282 A2 | 12/2001 |
| WO | WO 01/92282 A2 | 12/2001 |
| WO | 02/04425 A1 | 1/2002 |
| WO | 02/06246 A1 | 1/2002 |
| WO | WO 02/04425 A1 | 1/2002 |
| WO | WO 02/06246 A1 | 1/2002 |
| WO | 02/18404 A2 | 3/2002 |
| WO | 02/20497 A1 | 3/2002 |
| WO | WO 02/18404 A2 | 3/2002 |
| WO | WO 02/20497 A1 | 3/2002 |
| WO | 02/32920 A2 | 4/2002 |
| WO | WO 02/32920 A2 | 4/2002 |
| WO | 02/48116 A2 | 6/2002 |
| WO | 02/48165 A2 | 6/2002 |
| WO | 02/48172 A2 | 6/2002 |
| WO | WO 02/48116 A2 | 6/2002 |
| WO | WO 02/48165 A2 | 6/2002 |
| WO | WO 02/48172 A2 | 6/2002 |
| WO | 02/051425 A1 | 7/2002 |
| WO | 02/057287 A2 | 7/2002 |
| WO | 02/057425 A2 | 7/2002 |
| WO | WO 02/51425 A1 | 7/2002 |
| WO | WO 02/057287 A2 | 7/2002 |
| WO | WO 02/057425 A2 | 7/2002 |
| WO | 02/100415 A2 | 12/2002 |
| WO | WO 02/100415 A2 | 12/2002 |
| WO | 03/015755 A1 | 2/2003 |
| WO | WO 03/015755 A1 | 2/2003 |
| WO | 03/026589 A2 | 4/2003 |
| WO | 03/026675 A1 | 4/2003 |
| WO | WO 03/026589 A2 | 4/2003 |
| WO | WO 03/026675 A1 | 4/2003 |
| WO | 03/062192 A1 | 7/2003 |
| WO | 03/062211 A1 | 7/2003 |
| WO | WO 03/062192 A1 | 7/2003 |
| WO | 03/064455 A2 | 8/2003 |
| WO | 03/068244 A1 | 8/2003 |
| WO | WO 03/064455 A2 | 8/2003 |
| WO | WO 03/068244 A1 | 8/2003 |
| WO | 03/093290 A2 | 11/2003 |
| WO | WO 03/093290 A2 | 11/2003 |
| WO | 03/099274 A1 | 12/2003 |
| WO | 2004/000858 A2 | 12/2003 |
| WO | WO 03/099274 A1 | 12/2003 |
| WO | WO 04/000858 A2 | 12/2003 |
| WO | 2004/002422 A2 | 1/2004 |
| WO | 2004/002999 A2 | 1/2004 |
| WO | 2004/003000 A2 | 1/2004 |
| WO | 2004/003138 A2 | 1/2004 |
| WO | 2004/007512 A2 | 1/2004 |
| WO | WO 2004/002422 A2 | 1/2004 |
| WO | WO 2004/002999 A2 | 1/2004 |
| WO | WO 2004/003000 A2 | 1/2004 |
| WO | WO 2004/003138 A2 | 1/2004 |
| WO | WO 2004/007512 A2 | 1/2004 |
| WO | 2004/011478 A2 | 2/2004 |
| WO | 2004/013300 A2 | 2/2004 |
| WO | WO 2004/011478 A2 | 2/2004 |
| WO | WO 2004/013300 A2 | 2/2004 |
| WO | 2004/028481 A2 | 4/2004 |
| WO | WO 2004/028481 A2 | 4/2004 |
| WO | 2004/041201 A2 | 5/2004 |
| WO | 2004/087714 A1 | 10/2004 |
| WO | WO 2004/087714 A1 | 10/2004 |
| WO | 2004/093915 A1 | 11/2004 |
| WO | 2004/103996 A1 | 12/2004 |
| WO | 2004/110442 A1 | 12/2004 |
| WO | 2005/003147 A2 | 1/2005 |
| WO | WO 2005/003147 A2 | 1/2005 |
| WO | 2005/016927 A1 | 2/2005 |
| WO | WO 2005/016927 A1 | 2/2005 |
| WO | 2005/023819 A1 | 3/2005 |
| WO | 2005/034941 A1 | 4/2005 |
| WO | 2005/046712 A1 | 5/2005 |
| WO | WO 2005/046712 A1 | 5/2005 |
| WO | 2005/070955 A1 | 8/2005 |
| WO | 2005/080399 A1 | 9/2005 |
| WO | 2006/008556 A1 | 1/2006 |
| WO | 2006/020082 A1 | 2/2006 |
| WO | 2006/021341 A1 | 3/2006 |
| WO | 2006/027628 A2 | 3/2006 |
| WO | 2006/029912 A1 | 3/2006 |
| WO | 2006/046030 A1 | 5/2006 |
| WO | 2006/046039 A2 | 5/2006 |
| WO | 2006/119061 A2 | 11/2006 |
| WO | 2006/119975 A1 | 11/2006 |
| WO | 2007/015787 A1 | 2/2007 |
| WO | 2007/015855 A1 | 2/2007 |
| WO | 2007/016441 A1 | 2/2007 |
| WO | 2007/028789 A1 | 3/2007 |
| WO | 2007/029029 A2 | 3/2007 |
| WO | 2007/131966 A1 | 11/2007 |
| WO | 2007/145894 A2 | 12/2007 |
| WO | 2007/148135 A1 | 12/2007 |
| WO | 2008/051475 A2 | 5/2008 |
| WO | 2008/051477 A2 | 5/2008 |
| WO | 2008/051514 A2 | 5/2008 |
| WO | 2008/057028 A1 | 5/2008 |
| WO | 2008/057208 A2 | 5/2008 |
| WO | 2008/057209 A1 | 5/2008 |
| WO | 2008/112108 A1 | 9/2008 |
| WO | 2009/005687 A1 | 1/2009 |
| WO | 2009/010804 A1 | 1/2009 |
| WO | 2009/064955 A1 | 5/2009 |
| WO | 2009/064975 A1 | 5/2009 |

OTHER PUBLICATIONS

Brian W. Dymock et al., Novel Approaches to the Treatment of Hepatitis C Virus Infection, 11 *Antiviral Chemistry & Chemotherapy* 79-96 (2000).

Hugo R. Rosen & David R. Gretch, Hepatitis C virus: current understanding and prospects for future therapies, 5 *Molec. Med. Today* 393-99 (1999).

Darius Moradpour & Hubert E. Blum, Current and evolving therapies for hepatitis C, 11 *Euro. J. Gastroenterol. Hepatol.* 1189-1202 (1999).

Ralf Bartenschlager, Candidate Targets for Hepatitis C Virus-Specific Antiviral Therapy, 40(5-6) *Intervirology* 378-93 (1997).

Georg M. Lauer & Bruce D. Walker, Hepatitis C Virus Infection, 345(1) *N. Engl. J. Med.* 41-52 (2001); correction: 345(19) *N. Engl. J. Med.* 1425-26 (2001).

Brain W. Dymock, Emerging therapies for hepatitis C virus infection, 6 *Emerging Drugs* 13-42 (2001).

Charlene Crabb, Infectious Diseases. Hard-Won Advances Spark Excitement about Hepatitis C, *Science* 506-507 (2001).

Rogers E. Harry-O'Kuru et al., A Short, Flexible Route toward 2'-C-Branched Ribonucleosides, 62 *J. Org. Chem.* 1754-59 (1997).

Michael S. Wolfe & Rogers E. Harry-O'Kuru, A Concise Synthesis of 2'-C-Methylribonucleosides, 36(42) *Tetrahedron Letters* 7611-14 (1995).

Scott J. Miller et al., Application of Ring-Closing Metathesis to the Synthesis of Rigidified Amino Acids and Peptides, 118 *J. Am. Chem. Soc.* 9606-14 (1996).

Jason S. Kingsbury et al., A Recyclable Ru-Based Metathesis Catalyst, 121 *J. Am. Chem. Soc.* 791-99 (1999).

Matthias Scholl et al., Synthesis and Activity of a New Generation of Ruthenium-Based Olefin Metathesis Catalysts Coordinated with 1,3-Dimesityl-4,5-dihydroimidazol-2-ylidene Ligands, 1(6) *Organic Letters* 953-56 (1999).

Alois Furstner et al., Total Synthesis and Structural Refinement of the Cyclic Tripyrrole Pigment Nonylprodigiosin, 64 *J. Org. Chem.* 8275-80 (1999).

Tina M. Trnka & Robert H. Grubbs, The Development of L2X2R-CHR Olefin Metathesis Catalysts: An Organometallic Success Story, 34 *Acc. Chem. Res.* 18-29 (2001).

A. Srikrishna et al., Enantiospecific Construction of the BC-ring System of Taxanes, 45 *Tetrahedron Letters* 2939-42 (2004).

Yung-Son Hon et al., Dibromomethane as one-carbon source in organic synthesis: a versatile methodology to prepare the cyclic and acyclic alpha-methylene or alpha-keto acid derivatives from the corresponding terminal alkenes, 60 *Tetrahedron* 4837-60 (2004).

Eusebio Juaristi & Hugo A. Jimenez-Vazquez, Single Electron Transfer Mechanism in the Reaction of 1,3-Dithianyllithium and Alkyl Iodides, 56 *J. Org. Chem.* 1623-30 (1991).

Paola Conti et al., Chemoenzymatic Synthesis of the Enantiomers of Desoxymuscarine, 9 *Tetrahedron: Asymmetry* 657-65 (1998).

Robert M. Coates & Mark W. Johnson, Stereoselective Synthesis of Moenocinol and Assignment of Its Carbon-13 Nuclear Magnetic Resonance Spectrum, 45 *J. Org. Chem.* 2685-97 (1980).

D. Becker & N. Haddad, Steric Effects in Intramolecular [2+2] Photocycloaddition of C=C Double Bonds to Cyclohexenones, 49(4) *Tetrahedron* 947-64 (1993).

Richard A. Bunce et al., Tandem SN2-Michael Reactions for the Preparation of Simple Five- and Six-Membered-Ring Nitrogen and Sulfur Heterocycles, 57 *J. Org. Chem.* 1727-33 (1992).

Masao Tokuda et al., Aminyl Radical Cyclization by Means of Anodic Oxidation. Stereoselective Synthesis of cis-1-Methyl-2,5-Disubstituted Pyrrolidines, 26(49) *Tetrahedron Letters* 6085-88 (1985).

Robert Haner et al., 174. Generation and Reactions of Lithiated tert-Butyl and 2,6-Di(tert-butyl)-4-methylphenyl Cyclopropanecarboxylates, 69 *Helvetica Chimica Acta* 1655-65 (1986).

Herbert O. House et al., Cyclization of Unsaturated Hydroxylamine Derivatives, 41(5) *J. Org. Chem.* 855-63 (1976).

Theophil Eicher et al., Bryophyte Constituents; 7: New Synthesis of (+)-Rosmarinic Acid and Related Compounds, *Synthesis* 755-62 (Jun. 1996).

Michael C. Venuti et al., Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline, 31 *J. Med. Chem.* 2136-45 (1988).

Marc-Andre Poupart et al., Solid-Phase Synthesis of Peptidomimetic Inhibitors for the Hepatitis C Virus NS3 Protease, 66(14) *J. Org. Chem.* 4743-51 (2001).

Brian W Dymock et al., "Novel Approaches to the Treatment of Hepatitis C Virus Infection," 11 Antiviral Chemistry & Chemotherapy 79-96 (2000).

Hugo R. Rosen & David R. Gretch, "Hepatitis C virus: current understanding and prospects for future therapies," 5 Molec. Med. Today 393-99 (1999).

Darius Moradpour & Hubert E Blum, "Current and evolving therapies for hepatitis C," 11 Euro. J. Gastroenterol. Hepatol. 1189-1202 (1999).

Ralf Bartenschlager, "Candidate Targets for Hepatitis C Virus-Specific Antiviral Therapy," 40(5-6) Intervirology 378-93 (1997).

Georg M. Lauer & Bruce D. Walker, "Hepatitis C Virus Infection," 345(1) N. Engl. J. Med. 41-52 (2001); correction: 345 (19) N. Engl. J. Med. 1425-26 (2001).

Brain W. Dymock, "Emerging therapies for hepatitis C virus infection," 6 Emerging Drugs 13-42 (2001).

Charlene Crabb, Infectious Diseases. "Hard-Won Advances Spark Excitement about Hepatitis C," Science 506-507 (2001).

Rogers E. Harry-O'Kuru et al., "A Short, Flexible Route toward 2'-C-Branched Ribonucleosides," 62 J. Org. Chem. 1754-59 (1997).

Michael S. Wolfe & Rogers E. Harry-O'Kuru, "A Concise Synthesis of 2'-C-Methylribonucleosides," 36(42) Tetrahedron Letters 7611-14 (1995).

Scott J. Miller et al., "Application of Ring-Closing Metathesis to the Synthesis of Rigidified Amino Acids and Peptides," 118 J. Am. Chem. Soc. 9606-14 (1996).

Jason S. Kingsbury et al., "A Recyclable Ru-Based Metathesis Catalyst," 121 J. Am. Chem. Soc. 791-99 (1999).

Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).

Alois Furstner et al., "Total Synthesis and Structural Refinement of the Cyclic Tripyrrole Pigment Nonylprodigiosin," 64 J. Org. Chem. 8275-80 (1999).

Tina M. Trnka & Robert H. Grubbs, "The Development of L2X2R-CHR Olefin Metathesis Catalysts: An Organometallic Success Story," 34 Acc. Chem. Res. 18-29 (2001).

A. Srikrishna et al., "Enantiospecific Construction of the BC-ring System of Taxanes," 45 Tetrahedron Letters 2939-42 (2004).

Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).

Eusebio Juaristi & Hugo A. Jimenez-Vazquez, "Single Electron Transfer Mechanism in the Reaction of 1,3-Dithianyllithium and Alkyl Iodides," 56 J. Org. Chem. 1623-30 (1991).

Paola Conti et al., "Chemoenzymatic Synthesis of the Enantiomers of Desoxymuscarine," 9 Tetrahedron: Asymmetry 657-65 (1998).

Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).

D. Becker & N. Haddad, "Steric Effects in Intramolecular [2+2] Photocycloaddition of C=C Double Bonds to Cyclohexenones," 49(4) Tetrahedron 947-64 (1993).

Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).

Masao Tokuda et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).

Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).

Herbert O. House et al., "Cyclization of Unsaturated Hydroxylamine Derivatives," 41(5) J. Org. Chem. 855-63 (1976).

Theophil Eicher et al., "Bryophyte Constituents; 7: New Synthesis of (+)-Rosmarinic Acid and Related Compounds," Synthesis 755-62 (Jun. 1996).

Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).

Marc-Andre Poupart et al., "Solid-Phase Synthesis of Peptidomimetic Inhibitors for the Hepatitis C Virus NS3 Protease," 66(14) J. Org. Chem. 4743-51 (2001).

Nigel J. Liverton et al., Molecular Modeling Based Approach to Potent P2-P4 Macrocyclic Inhibitors of Hepatitis C NS3/NS4A Protease, 130 J. Am. Chem. Soc. 4607-09 (2008).

Anthony C. Allison & Elsie M. Eugui, "Immunosuppressive and other anti-rheumatic activities of mycophenolate mofetil," 44 Agents and Actions Supplements 165-88 (1993).

Joel Kirschbaum, "Amantadine," 12 Profiles of Drug Substances, Excipients and Related Methodology 1-36 (1983).

T. K. Chakaborty et al., "Alpha-Phenylglycinol as chiral auxilliary in diastereoselective Strecker synthesis of alpha-amino acids," 51(33) Tetrahedron 9179-90 (1995).

W. Clark Still et al., "Rapid Chromatographic Technique for Preparative Separations with Moderate Resolution," 43(14) J. Org. Chem. 2923-25 (1978).

Michael D. Cooke et al., :The occurrence of a hydride shift in the aromatization of 1,4-epoxy-1,2-dihydronaphthalenes, 11 J. Chem. Soc. Perkin Trans. I: Phys. Org. Chem. 1377 (1984).

Paul Aeberli et al., "Neuropharmacological investigation of N-benzylsulfamides," 10(4) J. Med. Chem. 636-42 (1967).

Nathalie Goudreau & Montse Llinas-Brunet, "The Therapeutic Potential of NS3 Protease Inhibitors in HCV Infection," 14(9) Expert Opinion 1129-44 (2005).

Volker Lohmann et al., "Selective Stimulation of Hepatitis C Virus and Pestivirus NS5B RNA Polymerase Activity by GTP," 274(16) J. Bio. Chem. 10807-15 (1999).

V. Lohmann et al., "Replication of Subgenomic Hepatitis C Virus RNAs in a Hepatoma Cell Line," 285 Science 110-13 (1999).

Kevin X. Chen et al. "Novel Potent Hepatitis C Virus NS3 Serine Protease Inhibitors Derived from Proline-Based Macrocycles," 49 J. Med. Chem. 995-1005 (2006).

Yuri Goldberg et al., "Highly regioselective bromination of 2,3-dimethylanisole with N-bromosuccinimide," 57 J. Org. Chem. 6374-76 (1992).

Manfred Schlosser et al., "8-Methoxyisoquinoline derivatives through ortho-selective metallation of 2-(3-methoxyphenyl)ethylamines," 32(17) Tetrahedron Letters 1965-66 (1991).

Angela Casini et al., "Carbonic Anhydrase inhibitors inhibition of cytosolic isozymes I and II with sulfamide derivatives," 13(5) Bioorg. Med. Chem. Lett. 837-40 (2003).

Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).

Duane E. Rudisill & J. K. Stille, "Palladium-catalyzed synthesis of 2-substituted indoles," 54(25) J. Org. Chem. 5856-66 (2002).

Makoto Satoh et al., "Palladium-Catalyzed Cross-Coupling Reaction of (1-Ethoxy-1-alken-2-yl)boranes With ortho-Functionalized Iodoarenes. A Novel and Convenient Synthesis of Benzo-Fused Heteroaromatic Compounds," Synthesis Communications 373-377 (Apr. 1987).

Yuusaku Yokoyama et al., "Palladium-Catalyzed Reaction of 3-Bromoindole Derivative with Allyl Esters in the Presence of Hexa-n-butyldistannane," 31(8) Heterocycles 1505-11 (1990).

Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).

John A. McCauley et al., "Bismacrocyclic Inhibitors of Hepatitis C NS3/4a Protease," 47 Angew. Chem. Int. Ed. 9104-07 (2008).

Ashok Arasappan et al., "P2-P4 Macrocyclic inhibitors of hepatitis C virus NS3-4A serine protease," 16 Bioorganic & Medicinal Chemistry Letters 3960-65 (2006).

Youwei Yan et al., Complex of NS3 protease and NS4A peptide of BK strain hepatitis C virus: A 2.2 Angstrom resolution structure in a hexagonal crystal form, 7 Protein Science 837 (1998).

Youla S. Tsantrizos, The Design of a Potent Inhibitor of the Hepatitis C Virus NS3 Protease: BILN 2061—From the NMR Tube to the Clinic, 76 Biopolymers (Peptide Science) 309-323 (2004).

* cited by examiner

HCV NS3 PROTEASE INHIBITORS

CROSS-REFERENCE TO RELATED APPLICATIONS

This application is a U.S. National Phase Application of International Patent Application No. PCT/US2006/029635, filed Jul. 28, 2006. This application also claims the benefit of priority to U.S. Provisional Patent Application No. 60/704,256, filed Aug. 1, 2005, and to U.S. Provisional Patent Application No. 60/724,509, filed Oct. 7, 2005.

The present invention relates to macrocyclic compounds that are useful as inhibitors of the hepatitis C virus (HCV) NS3 protease, their synthesis, and their use for treating or preventing HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 3.9 million infected people in the United States alone, according to the U.S. Center for Disease Control, roughly five times the number of people infected with the human immunodeficiency virus (HIV). According to the World Health Organization, there are more than 170 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring.

Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The current state of the art in the treatment of HCV infection has been discussed in the following references: B. Dymock, et al., "Novel approaches to the treatment of hepatitis C virus infection," *Antiviral Chemistry & Chemotherapy*, 11: 79-96 (2000); H. Rosen, et al., "Hepatitis C virus: current understanding and prospects for future therapies," *Molecular Medicine Today*, 5: 393-399 (1999); D. Moradpour, et al., "Current and evolving therapies for hepatitis C," *European J. Gastroenterol. Hepatol.*, 11: 1189-1202 (1999); R. Bartenschlager, "Candidate Targets for Hepatitis C Virus-Specific Antiviral Therapy," *Intervirology*, 40: 378-393 (1997); G. M. Lauer and B. D. Walker, "Hepatitis C Virus Infection," *N. Engl. J. Med.*, 345: 41-52 (2001); B. W. Dymock, "Emerging therapies for hepatitis C virus infection," *Emerging Drugs*, 6: 13-42 (2001); and C. Crabb, "Hard-Won Advances Spark Excitement about Hepatitis C," *Science*: 506-507 (2001).

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein, and is considered a prime drug target since it is responsible for an intramolecular cleavage at the NS3/4A site and for downstream intermolecular processing at the NS4A/4B, NS4B/5A and NS5A/5B junctions. Previous research has identified classes of peptides, such as hexapeptides as well as tripeptides discussed in U.S. patent applications US2005/0020503, US2004/0229818, and US2004/00229776, showing degrees of activity in inhibiting the NS3 protease. The aim of the present invention is to provide further compounds which exhibit activity against the HCV NS3 protease.

SUMMARY OF THE INVENTION

The present invention relates to novel macrocyclic compounds of formula (I) and/or pharmaceutically acceptable salts and/or hydrates thereof. These compounds are useful in the inhibition of HCV (hepatitis C virus) NS3 (non-structural 3) protease, the prevention or treatment of one or more of the symptoms of HCV infection, either as compounds or their pharmaceutically acceptable salts and/or hydrates (when appropriate), or as pharmaceutical composition ingredients, whether or not in combination with other HCV antivirals, anti-infectives, immunomodulators, antibiotics or vaccines. More particularly, the present invention relates to a compound of formula (I) and/or a pharmaceutically acceptable salt and/or hydrate thereof:

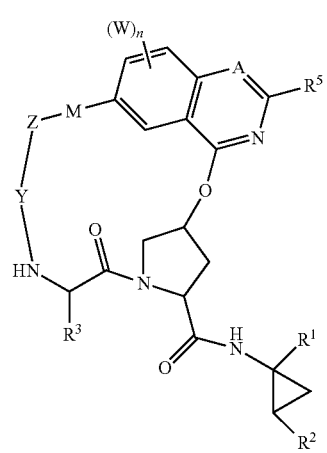

I wherein:

n is 1 or 2;

$R^1$ is $CO_2R^{10}$, $CONR^{10}SO_2R^6$, $CONR^{10}SO_2NR^8R^9$, or tetrazolyl;

$R^2$ is $C_1$-$C_6$ alkyl, $C_2$-$C_6$ alkenyl or $C_3$-$C_8$ cycloalkyl, wherein said alkyl, alkenyl or cycloalkyl is optionally substituted with 1 to 3 halo;

$R^3$ is $C_1$-$C_8$ alkyl, $C_3$-$C_8$ cycloalkyl, $C_3$-$C_8$ cycloalkyl($C_1$-$C_8$) alkyl, aryl($C_1$-$C_8$)alkyl, or Het, wherein aryl is phenyl or naphthyl and said alkyl, cycloalkyl, or aryl is optionally substituted with 1 to 3 substituents selected from the group consisting of halo, $OR^{10}$, $SR^{10}$, $N(R^{10})_2$, $N(C_1$-$C_6$ alkyl)O($C_1$-$C_6$ alkyl), $C_1$-$C_6$ alkyl, $C_1$-$C_6$ haloalkyl, halo($C_1$-$C_6$ alkoxy), $NO_2$, $CN$, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;

Het is a 5-6 membered saturated cyclic ring having 1, 2 or 3 heteroatoms selected from N, O and S, wherein said ring is optionally substituted with 1 to 3 substituents selected from the group consisting of halo, $OR^{10}$, $SR^{10}$, $N(R^{10})_2$, $N(C_1$-$C_6$ alkyl)O($C_1$-$C_6$ alkyl), $C_1$-$C_6$ alkyl, $C_1$-$C_6$ haloalkyl, halo($C_1$-$C_6$ alkoxy), $NO_2$, $CN$, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;

$R^4$ is H, $C_1$-$C_8$ alkyl, $C_3$-$C_8$ cycloalkyl($C_1$-$C_8$)alkyl, or aryl ($C_1$-$C_8$)alkyl; wherein aryl is phenyl or naphthyl and said alkyl, cycloalkyl, or aryl is optionally substituted with 1 to 3 substituents selected from the group consisting of halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;

$R^5$ is H, halo, OH, $C_1$-$C_6$ alkoxy, $C_1$-$C_6$ alkyl, CN, $CF_3$, $SR^{10}$, $SO_2(C_1$-$C_6$ alkyl), $C_3$-$C_8$ cycloalkyl, $C_3$-$C_8$ cycloalkoxy, $C_1$-$C_6$ haloalkyl, $N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, $OR^{10}$, $SR^{10}$, $N(R^7)_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, $NO_2$, CN, $CF_3$, $SO_2(C_1$-$C_6$alkyl), $NR^{10}SO_2R^6$, $SO_2N(R^6)_2$, $S(O)(C_1$-$C_6$ alkyl), $NHCOOR^6$, $NHCOR^6$, $NHCONHR^6$, $CO_2R^{10}$, $C(O)R^{10}$, and $CON(R^{10})_2$; wherein the 2 adjacent substituents of said cycloalkyl, cycloalkoxy, aryl, heteroaryl or heterocyclyl are optionally taken together to form a 3-6 membered cyclic ring containing 0-3 heteroatoms selected from N, O and S;

$R^6$ is $C_1$-$C_8$ alkyl, $C_3$-$C_8$ cycloalkyl, $C_3$-$C_8$ cycloalkyl($C_1$-$C_5$) alkyl, aryl, aryl($C_1$-$C_4$)alkyl, heteroaryl, heteroaryl($C_1$-$C_4$ heterocyclyl, or heterocyclyl($C_1$-$C_8$ alkyl), wherein said alkyl, cycloalkyl, aryl, heteroaryl, or heterocyclyl is optionally substituted with 1 to 2 W' substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

Y is C(=O), $SO_2$, or C(=N—CN);

Z is $C(R^{10})_2$, O, or $N(R^4)$;

M is $C_1$-$C_{12}$ alkylene or $C_2$-$C_{12}$ alkenylene or $C_2$-$C_{12}$ alkynylene, wherein said alkylene or alkenylene is optionally substituted with 1, 2 or 3 substituents selected from the group consisting of $C_1$-$C_8$ alkyl, $C_3$-$C_8$ cycloalkyl($C_1$-$C_8$ alkyl), and aryl($C_1$-$C_8$ alkyl); wherein 2 substituents on adjacent carbon atoms of M are optionally taken together to form a 3-6 membered cyclic ring containing 0-3 heteroatoms selected from N, O and S, or 2 substituents on the same carbon atom of M are optionally taken together to form a 3-6 membered cyclic ring containing 0-3 heteroatoms selected from N, O and S;

A is $C(R^{11})$ or N;

when $R^5$ is other than H, $R^{11}$ is H, $C_1$-$C_6$ alkyl, halo, $OR^{10}$, $SR^{10}$, or $N(R^{10})_2$;

when $R^5$ is H, $R^{11}$ is H, $C_1$-$C_6$ alkyl, halo, OH, $C_1$-$C_6$ alkoxy, CN, $CF_3$, $SR^{10}$, $SO_2(C_1$-$C_6$ alkyl), $C_3$-$C_8$ cycloalkyl, $C_3$-$C_8$ cycloalkoxy, $C_1$-$C_6$ haloalkyl, $N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, $OR^{10}$, $SR^{10}$, $N(R^7)_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, $NO_2$, CN, $CF_3$, $SO_2(C_1$-$C_6$ alkyl), $NR^{10}SO_2R^6$, $SO_2N(R^6)_2$, $S(O)(C_1$-$C_6$ alkyl), $NHCOOR^6$, $NHCOR^6$, $NHCONHR^6$, $CO_2R^{10}$, $C(O)R^{10}$, and $CON(R^{10})_2$; wherein the 2 adjacent substituents of said cycloalkyl, cycloalkoxy, aryl, heteroaryl or heterocyclyl are optionally taken together to form a 3-6 membered cyclic ring containing 0-3 heteroatoms selected from N, O and S;

or $R^5$ and $R^{11}$ are optionally taken together to form a 5- to 6-membered saturated, unsaturated non-aromatic, or aromatic cyclic ring having 0-2 heteroatoms selected from N, O and S;

each $R^7$ is independently H, $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W' substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently H, halo, $OR^7$, $C_1$-$C_6$ alkyl, CN, $CF_3$, $NO_2$, $SR^7$, $CO_2R^7$, $CON(R^7)_2$, $C(O)R^7$, $N(R^{10})C(O)R^7$, $SO_2(C_1$-$C_6$ alkyl), $S(O)(C_1$-$C_6$ alkyl), $C_3$-$C_8$ cycloalkyl, $C_3$-$C_8$ cycloalkoxy, $C_1$-$C_6$ haloalkyl, $N(R^7)_2$, $N(C_1$-$C_6$ alkyl)$O(C_1$-$C_6$ alkyl), halo($C_1$-$C_6$ alkoxy), $NR^{10}SO_2R^7$, $SO_2N(R^7)_2$, $NHCOOR^7$, $NHCONHR^7$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein 2 adjacent W moieties are optionally taken together with the atoms to which they are attached to form a 5- to 6-membered saturated, unsaturated non-aromatic, or aromatic cyclic ring having 0-2 heteroatoms selected from N, O and S;

each W' is independently halo, $OR^{10}$, $C_1$-$C_6$ alkyl, CN, $CF_3$, $NO_2$, $SR^{10}$, $CO_2R^{10}$, $CON(R^{10})_2$, $C(O)R^{10}$, $N(R^{10})C(O)R^{10}$, $SO_2(C_1$-$C_6$ alkyl), $S(O)(C_1$-$C_6$ alkyl), $C_3$-$C_8$ cycloalkyl, $C_3$-$C_8$ cycloalkoxy, $C_1$-$C_6$ haloalkyl, $N(R^{10})_2$, $N(C_1$-$C_6$ alkyl)$O(C_1$-$C_6$ alkyl), halo($C_1$-$C_6$ alkoxy), $NR^{10}SO_2R^{10}$, $SO_2N(R^{10})_2$, $NHCOOR^{10}$, $NHCONHR^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein 2 adjacent W' moieties are optionally taken together with the atoms to which they are attached to form a 5- to 6-membered saturated, unsaturated non-aromatic, or aromatic cyclic ring having 0-2 heteroatoms selected from N, O and S;

$R^8$ is $C_1$-$C_8$ alkyl, $C_3$-$C_8$ cycloalkyl, $C_3$-$C_8$ cycloalkyl($C_1$-$C_8$ alkyl), aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein said alkyl, cycloalkyl, aryl, heteroaryl or heterocyclyl is optionally substituted with 1 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR^{10}$, $SR^{10}$, $N(R^{10})_2$, $N(C_1$-$C_6$ alkyl)O ($C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3-6 membered cyclic ring containing 0-3 heteroatoms selected from N, O and S;

$R^9$ is $C_1$-$C_8$ alkyl, $C_3$-$C_8$ cycloalkyl, $C_3$-$C_8$ cycloalkyl($C_1$-$C_8$ alkyl), $C_1$-$C_8$ alkoxy, $C_3$-$C_8$ cycloalkoxy, aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein said alkyl, cycloalkyl, alkoxy, cycloalkoxy, aryl, heteroaryl or heterocyclyl is optionally substituted with 1 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR^{10}$, $SR^{10}$, $N(R^{10})_2$, $N(C_1$-$C_6$ alkyl)O($C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3-6 membered cyclic ring containing 0-3 heteroatoms selected from N, O and S;

or $R^8$ and $R^9$ are optionally taken together, with the nitrogen atom to which they are attached, to form a 4-8 membered monocyclic ring containing 0-2 additional heteroatoms selected from N, O and S; and each $R^{10}$ is independently H or $C_1$-$C_6$ alkyl.

The present invention also includes pharmaceutical compositions containing a compound of the present invention and methods of preparing such pharmaceutical compositions. The present invention further includes methods of treating or preventing one or more symptoms of HCV infection.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts and/or hydrates thereof. These compounds and their pharmaceutically acceptable salts and/or hydrates are HCV protease inhibitors (e.g., HCV NS3 protease inhibitors). The present invention also includes compounds of formulae II, II-A, II-B, III, III-A and III-B wherein variables n, $R^1$, $R^2$, $R^3$, Y, Z, M, W, A, $R^5$ and $R^{11}$ are as defined for formula I.

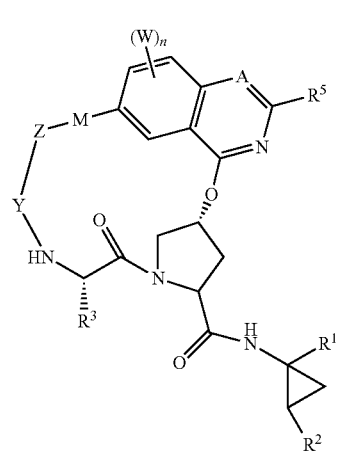

II

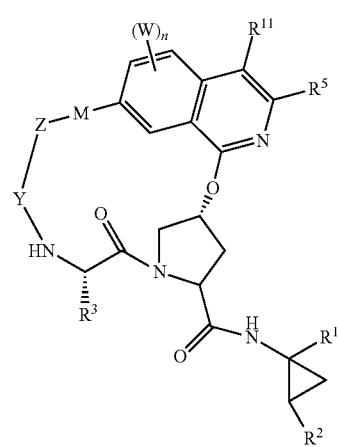

II-A

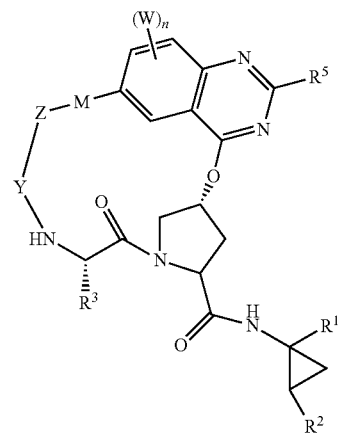

II-B

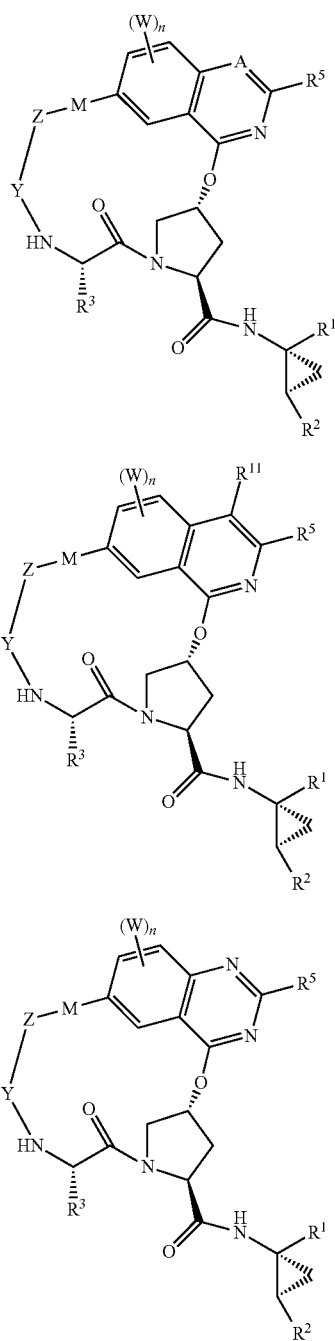

A first embodiment of the present invention is a compound of formula I, II, IIA, II-B, III, III-A, or III-B, or a pharmaceutically acceptable salt or hydrate thereof, wherein $R^1$ is $CO_2R^{10}$ or $CONR^{10}SO_2R^6$, and all other variables are as originally defined (i.e., as defined in the Summary of the Invention). In a first aspect of the first embodiment, $R^1$ is $CONR^{10}SO_2R^6$; and all other variables are as defined in the first embodiment. In a feature of the first aspect of the first embodiment, $R^1$ is $CONHSO_2R^6$ wherein $R^6$ is $C_3$-$C_8$ cycloalkyl, $C_1$-$C_8$ alkyl, aryl, aryl($C_1$-$C_4$)alkyl, wherein said alkyl, cycloalkyl, or aryl is optionally substituted with 1 to 2 W' substituents; and all other variables are as defined in the first embodiment. In a second feature of the first aspect of the first embodiment, $R^1$ is $CONHSO_2R^6$ wherein $R^6$ is cyclopropyl; and all other variables are as defined in the first embodiment. In a third feature of the first aspect of the first embodiment, $R^1$ is $CONHSO_2R^6$ wherein $R^6$ is phenyl; and all other variables are as defined in the first embodiment. In a fourth feature of the first aspect of the first embodiment, $R_1$ is $CONHSO_2R^6$ wherein $R^6$ is benzyl; and all other variables are as defined in the first embodiment. In a fifth feature of the first aspect of the first embodiment, $R^1$ is $CONHSO_2R^6$ wherein $R^6$ is methyl, ethyl, n-propyl, i-propyl, n-butyl, i-butyl or t-butyl; and all other variables are as defined in the first embodiment. In a second aspect of the first embodiment, $R^1$ is $CO_2R^{10}$; and all other variables are as defined in the first embodiment. In a feature of the second aspect of the first embodiment, $R^{10}$ is $CO_2H$; and all other variables are as defined in the first embodiment.

A second embodiment of the present invention is a compound of formula I, II, II-A, II-B, III, III-A, or III-B, or a pharmaceutically acceptable salt or hydrate thereof, wherein $R^1$ is $CONHSO_2NR^8R^9$; and all other variables are as originally defined. In a first aspect of the second embodiment, $R^8$ is $C_1$-$C_8$ alkyl, $C_3$-$C_8$ cycloalkyl, $C_3$-$C_8$ cycloalkyl($C_1$-$C_8$ alkyl), aryl, aryl($C_1$-$C_4$ alkyl), heteroaryl, or heteroaryl($C_1$-$C_4$ alkyl); and $R^9$ is $C_1$-$C_8$ alkyl, $C_3$-$C_8$ cycloalkyl, $C_3$-$C_8$ cycloalkyl($C_1$-$C_8$ alkyl), $C_1$-$C_8$ alkoxy, aryl, aryl($C_1$-$C_4$ alkyl), heteroaryl, or heteroaryl($C_1$-$C_4$ alkyl), wherein said alkyl, cycloalkyl, alkoxy, aryl, or heteroaryl in both $R^8$ and $R^9$ is optionally substituted with 1 to 4 substituents selected from the group consisting of aryl, heteroaryl, $C_1$-$C_6$ alkyl, halo($C_1$-$C_6$ alkoxy), halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$, wherein each aryl is independently phenyl or naphthyl and each heteroaryl is independently a 5- or 6-membered aromatic ring having 1, 2 or 3 heteroatoms selected from N, O and S, attached through a ring carbon or nitrogen, and wherein the 2 adjacent substituents of said cycloalkyl, aryl, or heteroaryl are optionally taken together to form a 3-6 membered cyclic ring containing 0-3 heteroatoms selected from N, O and S; or $R^8$ and $R^9$ are optionally taken together, with the nitrogen atom to which they are attached, to form a 4-8 membered monocyclic ring containing 0-2 additional heteroatoms selected from N, O and S; and all other variables are as defined in the second embodiment.

In a second aspect of the second embodiment, $R^8$ is $C_1$-$C_8$ alkyl, $C_3$-$C_8$ cycloalkyl($C_1$-$C_8$ alkyl), aryl, aryl($C_1$-$C_4$ alkyl), heteroaryl, or heteroaryl($C_1$-$C_4$ alkyl); and $R^9$ is $C_1$-$C_8$ alkyl, $C_3$-$C_8$ cycloalkyl($C_1$-$C_8$ alkyl), $C_1$-$C_8$ alkoxy, aryl, aryl($C_1$-$C_4$ alkyl), heteroaryl, or heteroaryl($C_1$-$C_4$ alkyl), wherein said alkyl, cycloalkyl, alkoxy, aryl, or heteroaryl in both $R^8$ and $R^9$ is optionally substituted with 1 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$, wherein each aryl is independently phenyl or naphthyl and each heteroaryl is independently a 5- or 6-membered aromatic ring having 1, 2 or 3 heteroatoms selected from N, O and S, attached through a ring carbon or nitrogen, and wherein the 2 adjacent substituents of said cycloalkyl, aryl, or heteroaryl are optionally taken together to form a 3-6 membered cyclic ring containing 0-3 heteroatoms selected from N, O and S; or $R^8$ and $R^9$ are optionally taken together, with the nitrogen atom to which they are attached, to form a 4-6 membered monocyclic ring containing 0-2 additional heteroatoms selected from N, O and S; and all other variables are as defined in the second embodiment.

In a first feature of the second aspect of the second embodiment, $R^8$ is $C_1$-$C_3$ alkyl, wherein said alkyl is optionally substituted with 1 to 3 substituents selected from the group consisting of halo, $OR^{10}$, $SR^{10}$, $N(R^{10})_2$, $N(C_1$-$C_6$ alkyl)O($C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; and $R^9$ is $C_1$-$C_3$ alkyl, $C_1$-$C_3$ alkoxy, phenyl, or —$(CH_2)_{1-2}$-phenyl, wherein said alkyl or alkoxy is optionally substituted with 1 to 3 substituents selected from the group consisting of halo, OR10, $SR^{10}$, $N(R^{10})_2$, $N(C1$-$C6$ alkyl)O($C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; or $R^8$ and $R^9$ are optionally taken together, with the nitrogen atom to which they are attached, to form a 4- to 6-membered monocyclic saturated ring containing 0-1 additional heteroatoms selected from N and O; and all other variables are as defined in the second embodiment. In a second feature of the second aspect of the second embodiment, $R^8$ is methyl; and all other variables are as defined in the second embodiment. In a third feature of the second aspect of the second embodiment, $R^9$ is methyl, methoxy, ethyl, i-propyl, phenyl, or benzyl; and all other variables are as defined in the second embodiment. In a fourth feature of the second aspect of the second embodiment, $R^8$ and $R^9$ are taken together to form a heterocyclic ring selected from the following:

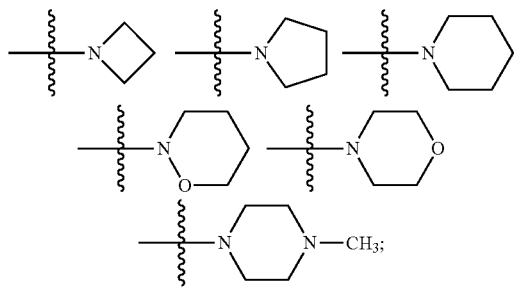

and all other variables are as defined in the second embodiment. In a fifth feature of the second aspect of the second embodiment, $R^8$ is methyl and $R^9$ is methoxy; and all other variables are as defined in the second embodiment.

A third embodiment of the present invention is a compound of formula I, II, II-A, II-B, III, III-A, or III-B, or a pharmaceutically acceptable salt or hydrate thereof, wherein $R^2$ is $C_1$-$C_6$ alkyl or $C_2$-$C_6$ alkenyl; and all other variables are as originally defined or as defined in any one of the preceding embodiments. In a first aspect of the third embodiment, $R^2$ is $C_1$-$C_4$ alkyl or $C_2$-$C_4$ alkenyl; and all other variables are as originally defined or as defined in any one of the preceding embodiments. In a second aspect of the third embodiment, $R^2$ is $C_2$-$C_4$ alkenyl; and all other variables are as originally defined or as defined in any one of the preceding embodiments. In a feature of the second aspect of the third embodiment, $R^2$ is vinyl; and all other variables are as defined in the second embodiment or as defined in any one of the preceding embodiments. In a third aspect of the third embodiment, $R^2$ is $C_1$-$C_4$ alkyl; and all other variables are as originally defined or as defined in any one of the preceding embodiments. In a feature of the third aspect of the third embodiment, $R^2$ is ethyl; and all other variables are as defined in the third embodiment or as defined in any one of the preceding embodiments.

A fourth embodiment of the present invention is a compound of formula I, II, II-A, III, III-A, or III-B, or a pharmaceutically acceptable salt or hydrate thereof, wherein $R^3$ is $C_3$-$C_8$ cycloalkyl, Het, or $C_1$-$C_8$ alkyl optionally substituted with 1 to 3 halo substituents; and all other variables are as originally defined or as defined in any one of the preceding embodiments. In a first aspect of the fourth embodiment, $R^3$ is $C_5$-$C_7$ cycloalkyl, piperidinyl, pyrrolidinyl, tetrahydrofuranyl, tetrahydropyranyl, or $C_1$-$C_8$ alkyl optionally substituted with 1 to 3 halo substituents; and all other variables are as defined in the fourth embodiment or as defined in any one of the preceding embodiments. In a second aspect of the fourth embodiment, $R^3$ is $C_5$-$C_6$ cycloalkyl or $C_1$-$C_8$ alkyl optionally substituted with 1 to 3 halo substituents; and all other variables are as defined in the fourth embodiment or as defined in any one of the preceding embodiments. In a third aspect of the fourth embodiment, $R^3$ is propyl or butyl; and all other variables are as defined in the fourth embodiment or as defined in any one of the preceding embodiments. In a feature of the third aspect of the fourth embodiment, $R^3$ is i-propyl, n-butyl, i-butyl or t-butyl; and all other variables are as defined in the fourth embodiment or as defined in any one of the preceding embodiments. In a fourth aspect of the fourth embodiment, $R^3$ is cyclopentyl or cyclohexyl; and all other variables are as defined in the fourth embodiment or as defined in any one of the preceding embodiments. In a fifth aspect of the fourth embodiment, $R^3$ is $CH_2CF_3$ or $CH_2CHF_2$; and all other variables are as defined in the fourth embodiment or as defined in any one of the preceding embodiments.

A fifth embodiment of the present invention is a compound of formula I, II, II-A, II-B, III, III-A, or III-B, or a pharmaceutically acceptable salt or hydrate thereof, wherein $R^5$ is H or halo; and all other variables are as originally defined or as defined in any one of the preceding embodiments. In one aspect of the fifth embodiment, $R^5$ is H, F, or Cl; and all other variables are defined in the fifth embodiment or as defined in any one of the preceding embodiments. In another aspect of the fifth embodiment, $R^5$ is H; and all other variables are defined in the fifth embodiment or as defined in any one of the preceding embodiments.

A sixth embodiment of the present invention is a compound of formula I, II, II-A, II-B, III, III-A, or III-B, or a pharmaceutically acceptable salt or hydrate thereof, wherein $R^5$ is aryl or heteroaryl; wherein aryl is phenyl or naphthyl and heteroaryl is a 5- or 6-membered aromatic ring having 1, 2 or 3 heteroatoms selected from N, O and S, attached through a ring carbon or nitrogen; and wherein said aryl or heteroaryl is optionally substituted with 1 to 4 substituents selected from the group consisting of halo, $OR^{10}$, $SR^{10}$, $N(R^7)_2$, $N(C_1$-$C_6$ alkyl)O($C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, $NO_2$, CN, $CF_3$, $SO_2(C_1$-$C_6$ alkyl), $NR^{10}SO_2R^6$, $SO_2N(R^6)_2$, $S(O)(C_1$-$C_6$ alkyl), $NHCOOR^6$, $NHCOR^6$, $NHCONHR^6$, $CO_2R^{10}$, $C(O)R^{10}$, and $CON(R^{10})_2$; and all other variables are as originally defined or as defined in any one of the preceding embodiments.

In a first aspect of the sixth embodiment, $R^5$ is aryl wherein aryl is optionally substituted with 1 to 4 substituents selected from the group consisting of halo, $OR^{10}$, $SR^{10}$, $N(R^7)_2$, $N(C_1$-$C_6$ alkyl)O($C_1$-$C_6$ alkyl), $C_1$-$C_6$ alkyl, $C_1$-$C_6$ haloalkyl, halo ($C_1$-$C_6$ alkoxy), $C_3$-$C_6$ cycloalkyl, $C_3$-$C_6$ cycloalkoxy, $NO_2$, CN, $CF_3$, $SO_2(C_1$-$C_6$ alkyl), $NR^{10}SO_2R^6$, $SO_2N(R^6)_2$, $S(O)(C_1$-$C_6$ alkyl), $NHCOOR^6$, $NHCOR^6$, $NHCONHR^6$, $CO_2R^{10}$, $C(O)R^{10}$, and $CON(R^{10})_2$; and all other variables are as defined in the sixth embodiment or as defined in any one of the preceding embodiments. In a second aspect of the sixth embodiment, $R^5$ is

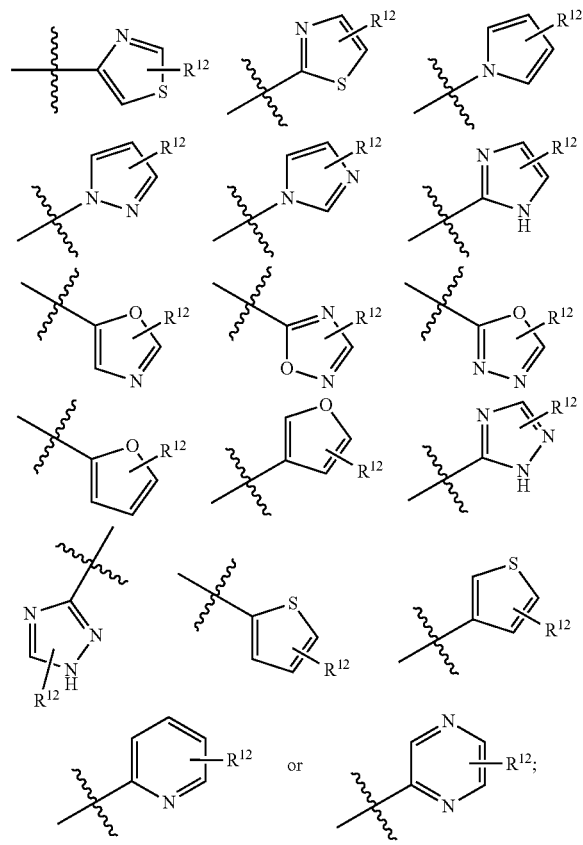

wherein $R^{12}$ is H, $C_1$-$C_6$ alkyl, $C_1$-$C_6$ alkoxy, $N(R^7)_2$, $NHCOR^{13}$, $NHCONHR^{13}$ or $NHCOOR^{13}$ and each $R^{13}$ is independently $C_1$-$C_6$ alkyl or $C_3$-$C_6$ cycloalkyl; and all other variables are as defined in the sixth embodiment or as defined in any one of the preceding embodiments. In a third aspect of the sixth embodiment, $R^5$ is

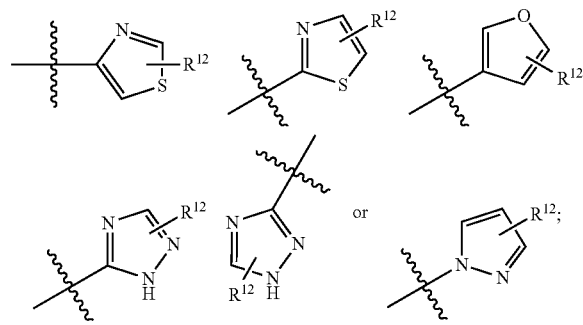

wherein $R^{12}$ is H, $C_1$-$C_6$ alkyl, $C_1$-$C_6$ alkoxy, $N(R^7)_2$, $NHCOR^{13}$, $NHCONHR^{13}$ or $NHCOOR^{13}$ and each $R^{13}$ is independently $C_1$-$C_6$ alkyl or $C_3$-$C_6$ cycloalkyl; and all other variables are as defined in the sixth embodiment or as defined in any one of the preceding embodiments.

In a fourth aspect of the sixth embodiment, $R^5$ is unsubstituted phenyl; and all other variables are as defined in the sixth embodiment or as defined in any one of the preceding embodiments.

A seventh embodiment of the present invention is a compound of formula I, II, II-A, II-B, III, III-A, or III-B, or a pharmaceutically acceptable salt or hydrate thereof, wherein $R^5$ is $C_1$-$C_6$ alkyl, $C_3$-$C_8$ cycloalkyl, $C_1$-$C_6$ haloalkyl, or heterocyclyl wherein heterocyclyl is a 5- to 7-membered saturated or unsaturated non-aromatic ring having 1, 2, 3 or 4 heteroatoms selected from N, O and S, attached through a ring carbon or nitrogen; and wherein said heterocyclyl, cycloalkyl, or alkyl is optionally substituted with 1 to 4 substituents selected from the group consisting of halo, $OR^{10}$, $SR^{10}$, $N(R^7)_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, $NO_2$, CN, $CF_3$, $SO_2(C_1$-$C_6$ alkyl), $NR^{10}SO_2R^6$, $SO_2N(R^6)_2$, $S(O)(C_1$-$C_6$ alkyl), $NHCOOR^6$, $NHCOR^6$, $NHCONHR^6$, $CO_2R^{10}$, $C(O)R^{10}$, and $CON(R^{10})_2$; wherein the 2 adjacent substituents of said cycloalkyl or heterocyclyl are optionally taken together to form a 3-6 membered cyclic ring containing 0-3 heteroatoms selected from N, O and S; and all other variables are as originally defined or as defined in any one of the preceding embodiments. In a first aspect of the seventh embodiment, $R^5$ is $C_1$-$C_6$ alkyl; and all other variables are as defined in the seventh embodiment or as defined in any one of the preceding embodiments. In a feature of the first aspect of the seventh embodiment, $R^5$ is methyl; and all other variables are as defined in the seventh embodiment or as defined in any one of the preceding embodiments. In a second aspect of the seventh embodiment, $R^5$ is heterocyclyl wherein heterocyclyl is a 5- to 7-membered saturated or unsaturated non-aromatic ring having 1, 2, 3 or 4 heteroatoms selected from N, O and S, attached through a ring carbon or nitrogen; and wherein said heterocyclyl, cycloalkyl, or alkyl is optionally substituted with 1 to 4 substituents selected from the group consisting of halo, $OR^{10}$, $SR^{10}$, $N(R^7)_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, $NO_2$, CN, $CF_3$, $SO_2(C_1$-$C_6$ alkyl), $NR^{10}SO_2R^6$, $SO_2N(R^6)_2$, $S(O)(C_1$-$C_6$ alkyl), $NHCOOR^6$, $NHCOR^6$, $NHCONHR^6$, $CO_2R^{10}$, $C(O)R^{10}$, and $CON(R^{10})_2$; wherein the 2 adjacent substituents of said heterocyclyl are optionally taken together to form a 3-6 membered cyclic ring containing 0-3 heteroatoms selected from N, O and S; and all other variables are as defined in the seventh embodiment or as defined in any one of the preceding embodiments. In a feature of the second aspect of the seventh embodiment, $R^5$ is N-morpholinyl; and all other variables are as defined in the seventh embodiment or as defined in any one of the preceding embodiments. In a third aspect of the seventh embodiment, $R^5$ is $C_1$-$C_6$ haloalkyl; and all other variables are as defined in the seventh embodiment or as defined in any one of the preceding embodiments. In a feature of the third aspect of the seventh embodiment, $R^5$ is $CF_3$; and all other variables are as defined in the seventh embodiment or as defined in any one of the preceding embodiments.

An eighth embodiment of the present invention is a compound of formula I, II, II-A, II-B, III, III-A, or III-B, or a pharmaceutically acceptable salt or hydrate thereof, wherein $R^5$ is $N(R^7)_2$; and all other variables are as originally defined or as defined in any one of the preceding embodiments. In one aspect of the eighth embodiment, $R^5$ is $N(R^7)_2$ wherein $R^7$ is H or $C_1$-$C_6$ alkyl; and all other variables are as defined in the eighth embodiment or as defined in any one of the preceding embodiments.

A ninth embodiment of the present invention is a compound of formula I, II, II-A, III, or III-A, or a pharmaceutically acceptable salt or hydrate thereof, wherein $R^{11}$ is H, $C_1$-$C_6$ alkyl, $C_1$-$C_6$ alkoxy, hydroxy or halo; and all other variables are as originally defined or as defined in any one of the preceding embodiments. In a first aspect of the ninth embodiment, $R^{11}$ is $C_1$-$C_6$ alkoxy; and all other variables are as defined in the ninth embodiment or as defined in any one of the preceding embodiments. In a feature of the first aspect of the ninth embodiment, $R^{11}$ is methoxy; and all other variables are as defined in the ninth embodiment or as defined in any one of the preceding embodiments. In a second aspect of the ninth embodiment, $R^{11}$ is $C_1$-$C_6$ alkyl; and all other variables are as defined in the ninth embodiment or as defined in any one of the preceding embodiments. In a feature of the second aspect of the ninth embodiment, $R^{11}$ is methyl; and all other variables are as defined in the ninth embodiment or as defined in any one of the preceding embodiments. In a third aspect of the ninth embodiment, $R^{11}$ is halo or hydroxy; and all other variables are as defined in the ninth embodiment or as defined in any one of the preceding embodiments. In a feature of the third aspect of the ninth embodiment, $R^{11}$ is OH, Cl, or Br; and all other variables are as defined in the ninth embodiment or as defined in any one of the preceding embodiments. In a fourth aspect of the ninth embodiment, $R^{11}$ is H; and all other variables are as defined in the ninth embodiment or as defined in any one of the preceding embodiments.

A tenth embodiment of the present invention is a compound of formula I, II, II-A, III, or III-A, or a pharmaceutically acceptable salt or hydrate thereof, wherein $R^5$ and $R^{11}$ are taken together to form a 5- to 6-membered saturated, unsaturated non-aromatic, or aromatic cyclic ring having 1-2 oxygen atoms; and all other variables are as originally defined or as defined in any one of the preceding embodiments.

An eleventh embodiment of the present invention is a compound of formula IV-A or IV-B, or a pharmaceutically acceptable salt or hydrate thereof, wherein $R^5$ is H, halo, aryl, heteroaryl, or $N(R^7)_2$; $R^1$ is $CO_2R^{10}$ or $CONHSO_2R^6$ wherein $R^6$ is $C_3$-$C_6$ cycloalkyl, $C_1$-$C_6$ alkyl, phenyl or benzyl; and all other variables are as originally defined or as defined in any one of the preceding embodiments.

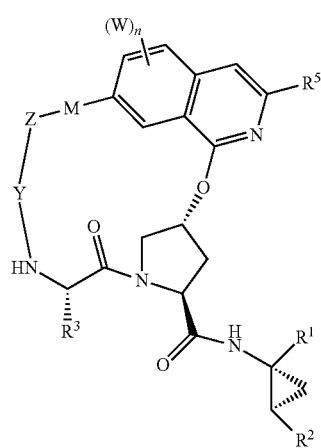

IV-A

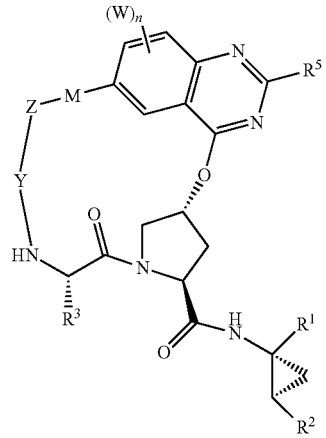

IV-B

A twelfth embodiment of the present invention is a compound of formula I, II, II-A, II-B, III, III-A, or III-B, or a pharmaceutically acceptable salt or hydrate thereof, wherein Y is C=O or $SO_2$; and all other variables are as originally defined or as defined in any one of the preceding embodiments. In one aspect of the twelfth embodiment, Y is C=O; and all other variables are as defined in the twelfth embodiment or as defined in any one of the preceding embodiments.

A thirteenth embodiment of the present invention is a compound of formula I, II, II-A, II-B, III, III-A, or III-B, or a pharmaceutically acceptable salt or hydrate thereof, wherein Z is O, NH, $N(C_1$-$C_8$ alkyl) or $C(R^{10})_2$; and all other variables are as originally defined or as defined in any one of the preceding embodiments. In one aspect of the thirteenth embodiment, Z is O, NH, $N(CH_3)$, or $CH_2$; and all other variables are as defined in the thirteenth embodiment or as defined in any one of the preceding embodiments.

A fourteenth embodiment of the present invention is a compound of formula I, II, II-A, II-B, III, III-A, or III-B, or a pharmaceutically acceptable salt or hydrate thereof, wherein M is $C_1$-$C_8$ alkylene or $C_2$-$C_8$ alkenylene, wherein said alkylene or alkenylene is optionally substituted with 1 or 2 substituents selected from $C_1$-$C_8$ alkyl, $C_3$-$C_8$ cycloalkyl($C_1$-$C_8$ alkyl), or aryl($C_1$-$C_8$ alkyl); and all other variables are as originally defined or as defined in any one of the preceding embodiments. In a first aspect of the fourteenth embodiment, M is unsubstituted $C_1$-$C_8$ alkylene or unsubstituted $C_2$-$C_8$ alkenylene; and all other variables are as defined in the fourteenth embodiment or as defined in any one of the preceding embodiments. In a second aspect of the fourteenth embodiment, M is unsubstituted $C_4$ alkylene or unsubstituted $C_4$ alkenylene; and all other variables are as defined in the fourteenth embodiment or as defined in any one of the preceding embodiments. In a third aspect of the fourteenth embodiment, M is unsubstituted $C_5$ alkylene or unsubstituted $C_5$ alkenylene; and all other variables are as defined in the fourteenth embodiment or as defined in any one of the preceding embodiments. In a fourth aspect of the fourteenth embodiment, M is unsubstituted $C_6$ alkylene or unsubstituted $C_6$ alkenylene; and all other variables are as defined in the fourteenth embodiment or as defined in any one of the preceding embodiments. In a fifth aspect of the fourteenth embodiment, M is unsubstituted $C_7$ alkylene or unsubstituted $C_7$ alkenylene; and all other variables are as defined in the fourteenth embodiment or as defined in any one of the preceding embodiments. In a feature of the first aspect of the fourteenth embodiment, M is:

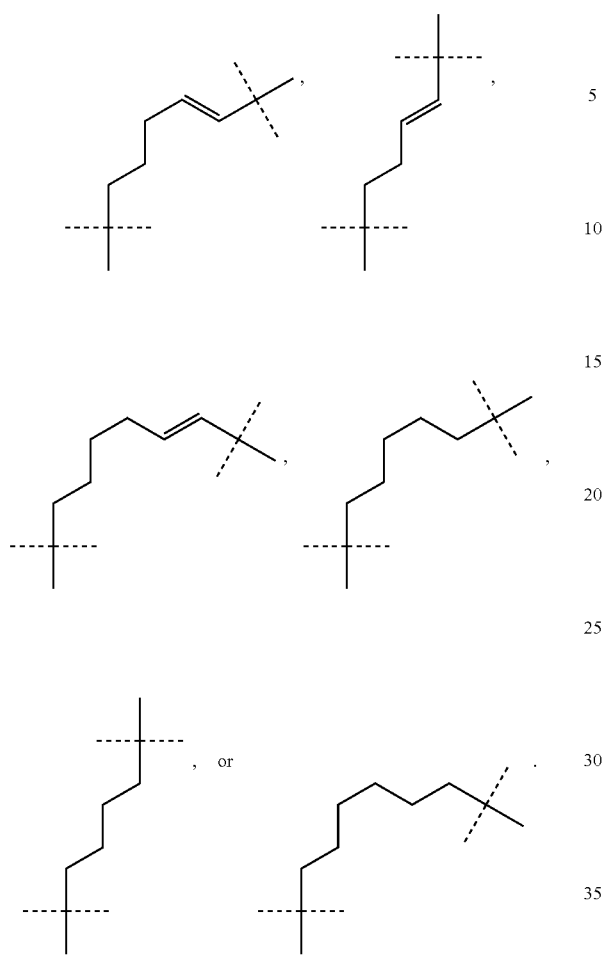

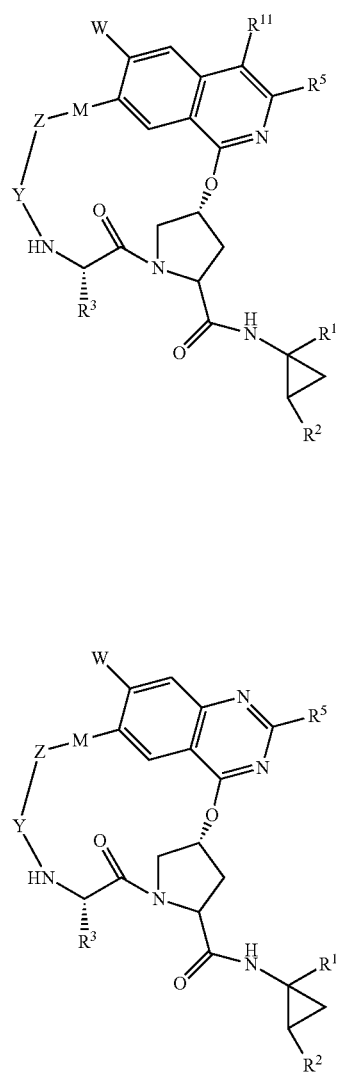

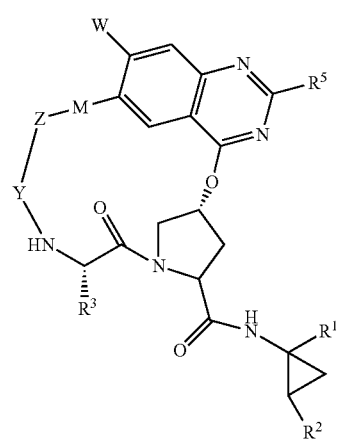

A fifteenth embodiment of the present invention is a compound of formula I, II, II-A, II-B, III, III-A, or III-B, or a pharmaceutically acceptable salt or hydrate thereof, wherein n is 1; and all other variables are as originally defined or as defined in any one of the preceding embodiments. In one aspect of the fifteenth embodiment, W is ortho to the variable M as depicted in formulae Ia, IIa, II-Aa, II-Ba, IIIa, III-Aa, III-Ba, IV-Aa and IV-Ba.

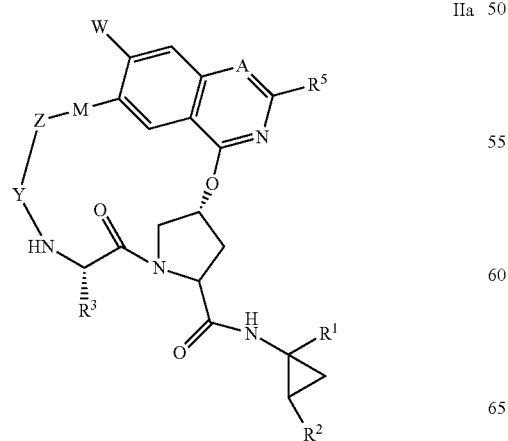

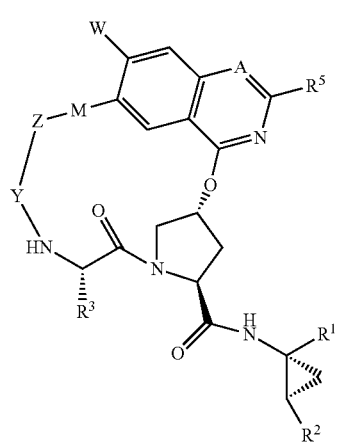

17
-continued

III-Aa

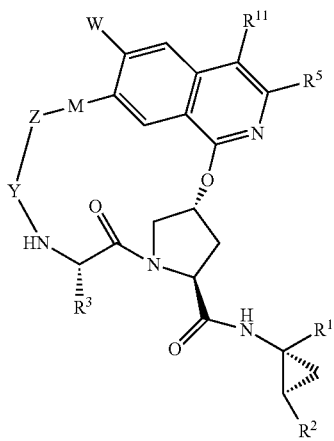

III-Ba

IV-Aa

18
-continued

IV-Ba

A sixteenth embodiment of the present invention is a compound of formula I, II, II-A, II-B, III, III-A, or III-B, or a pharmaceutically acceptable salt or hydrate thereof, wherein n is 2; and all other variables are as originally defined or as defined in any one of the preceding embodiments. In one aspect of the sixteenth embodiment, the 2 adjacent W moieties are taken together to form a 5- to 6-membered saturated, unsaturated non-aromatic, or aromatic cyclic ring having 0-2 heteroatoms selected from N, O and S. In another aspect of the sixteenth embodiment, the 2 adjacent W moieties are taken together to form a 5-membered saturated cyclic ring having 0-2 heteroatoms selected from N, O and S.

A seventeenth embodiment of the present invention is a compound of formula I, II, II-A, II-B, III, III-A, or III-B, or a pharmaceutically acceptable salt or hydrate thereof, wherein W is H, $C_1$-$C_6$ alkyl, $C_1$-$C_6$ alkoxy, OH, halo, halo($C_1$-$C_6$ alkoxy), C(O)N($R^7$)$_2$, C(O)$R^7$, N($R^7$)$_2$, or heterocyclyl; and all other variables are as originally defined or as defined in any one of the preceding embodiments. In a first aspect of the seventeenth embodiment, W is H; and all other variables are as defined in the seventeenth embodiment or as defined in any one of the preceding embodiments. In a second aspect of the seventeenth embodiment, W is $C_1$-$C_6$ alkoxy; and all other variables are as defined in the seventeenth embodiment or as defined in any one of the preceding embodiments. In a feature of the second aspect of the seventeenth embodiment, W is methoxy; and all other variables are as defined in the seventeenth embodiment or as defined in any one of the preceding embodiments. In a third aspect of the seventeenth embodiment, W is $C_1$-$C_6$ alkyl, halo, OH, or N($R^7$)$_2$ wherein $R^7$ is H or $C_1$-$C_6$ alkyl; and all other variables are as defined in the seventeenth embodiment or as defined in any one of the preceding embodiments. In a feature of the third aspect of the seventeenth embodiment, W is methyl; and all other variables are as defined in the seventeenth embodiment or as defined in any one of the preceding embodiments. In a fourth aspect of the seventeenth embodiment, W is halo($C_1$-$C_6$ alkoxy); and all other variables are as defined in the seventeenth embodiment or as defined in any one of the preceding embodiments. In a feature of the fifth aspect of the seventeenth embodiment, W is $OCF_3$, $OCHF_2$, $OC(CH_3)_3$, or $OCH(CH_3)_2$; and all other variables are as defined in the seventeenth embodiment or as defined in any one of the preceding embodiments. In a sixth aspect of the seventeenth embodiment, W is C(O)N($R^7$)$_2$, C(O)$R^7$, or heterocyclyl; and all other variables are as defined in the seventeenth embodiment or as defined in any one of the preceding embodiments. In a feature of the sixth aspect of the seventeenth embodiment, W is C(O)N(R$^7$)$_2$ wherein R$^7$ is H or C$_1$-C$_6$ alkyl; C(O)R$^7$ wherein R$^7$ is a 5-membered heteroaryl having 1 heteroatom O or S; or heterocyclyl wherein heterocyclyl is a 6-membered saturated ring having 1 or 2 heteroatoms selected from N, O and S; and all other variables are as defined in the seventeenth embodiment or as defined in any one of the preceding embodiments.

An eighteenth embodiment of the present invention is a compound, or a pharmaceutically acceptable salt or hydrate thereof, selected from the group consisting of the compounds III-1 to III-38.

III-1

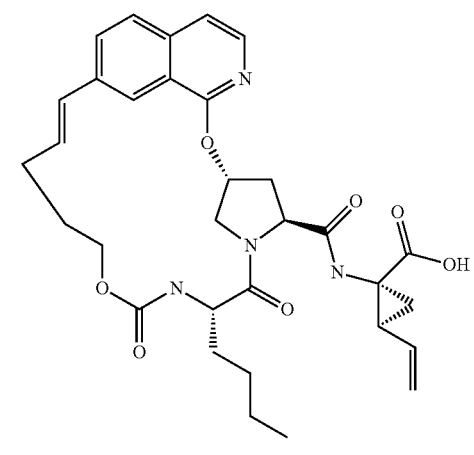

III-2

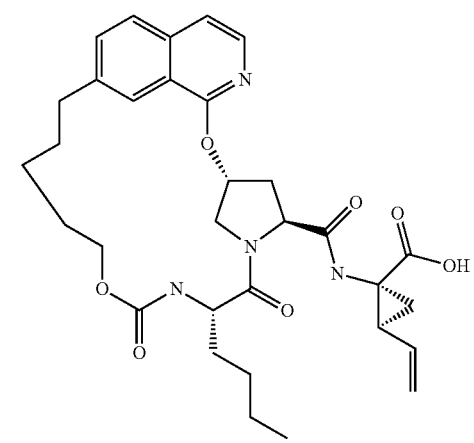

III-3

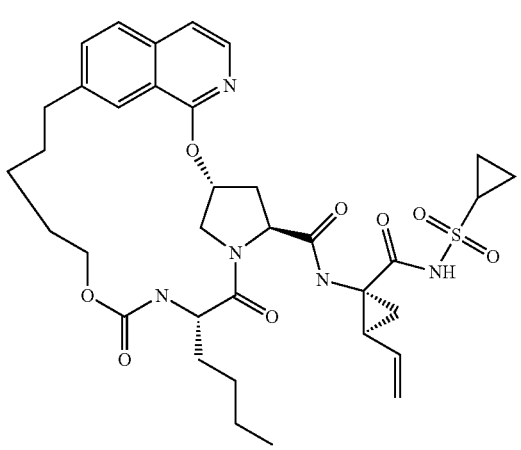

III-4

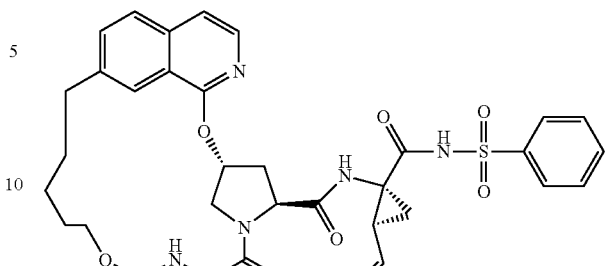

III-5

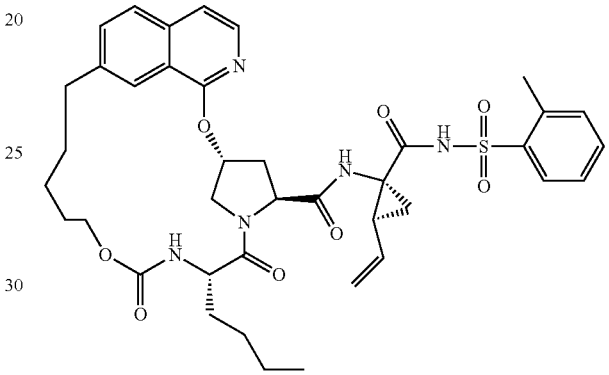

III-6

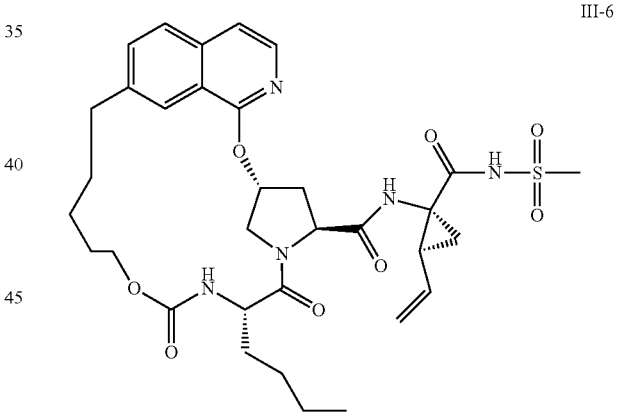

III-7

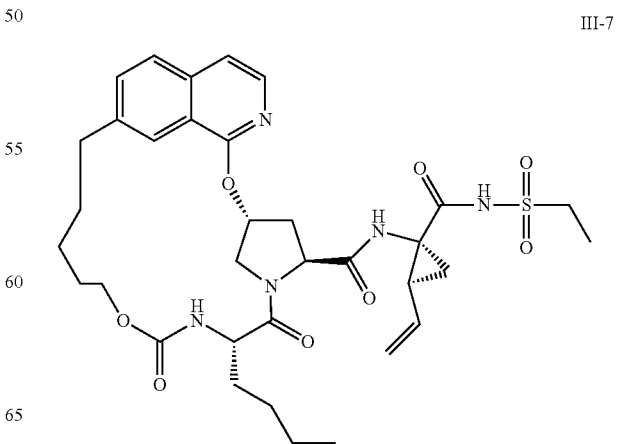

-continued
III-8
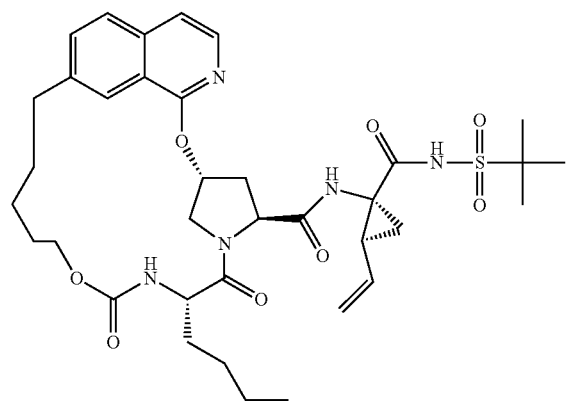
III-9
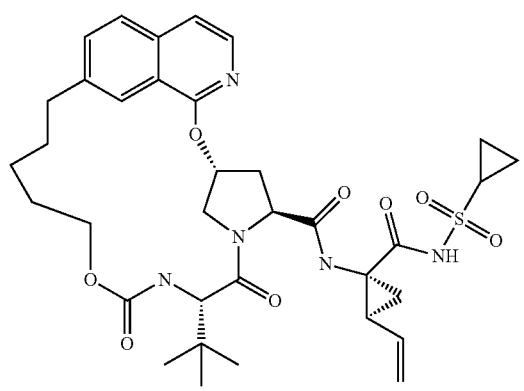
III-10
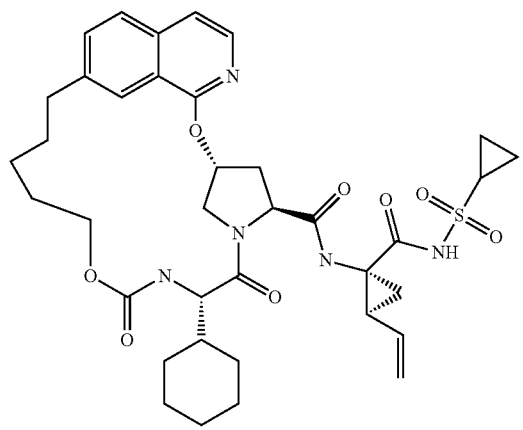
-continued
III-11
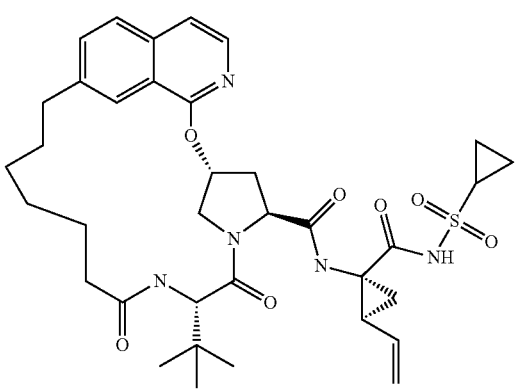
III-12
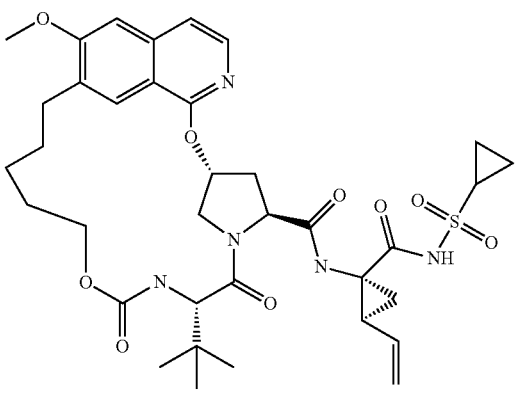
III-13
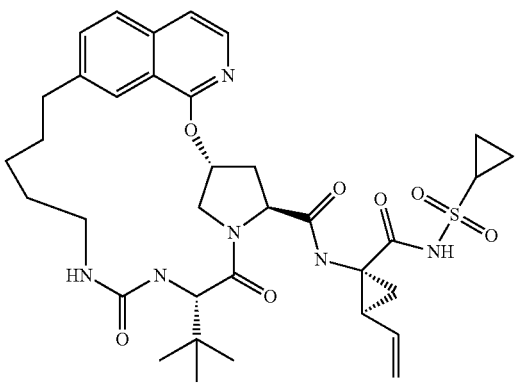
III-14
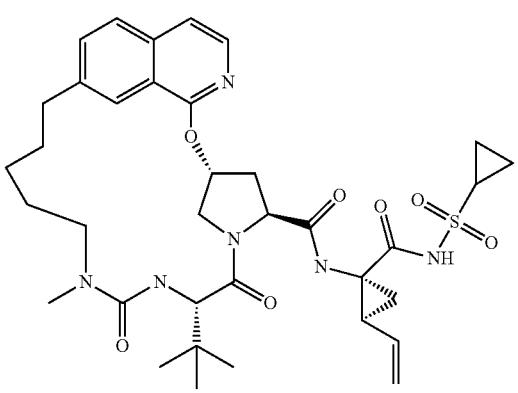

III-15
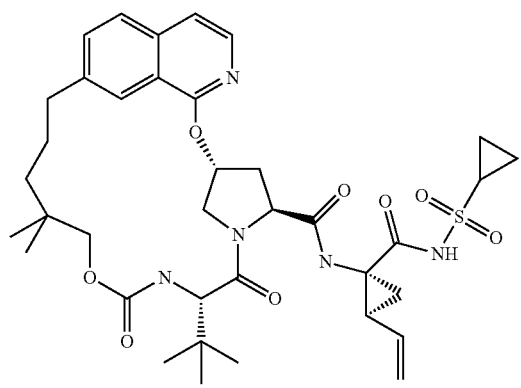
III-16
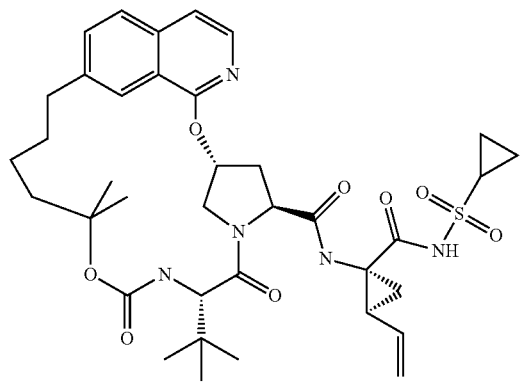
III-17
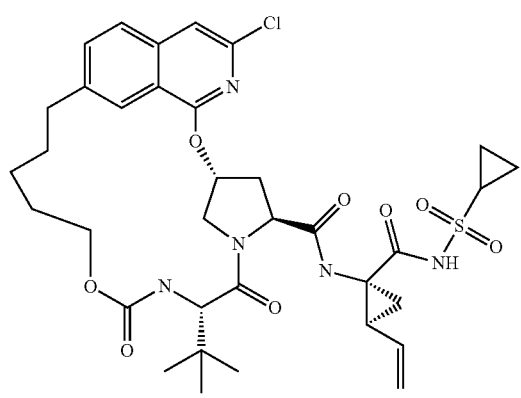
III-18
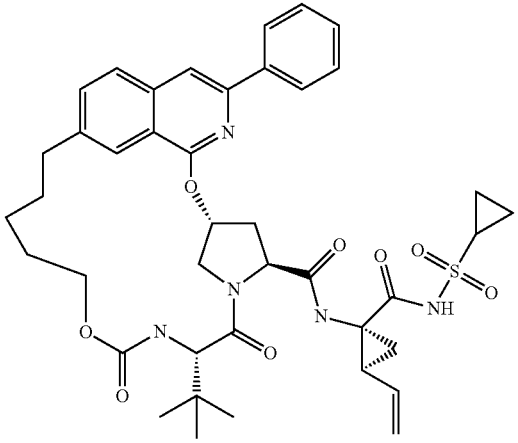
III-19
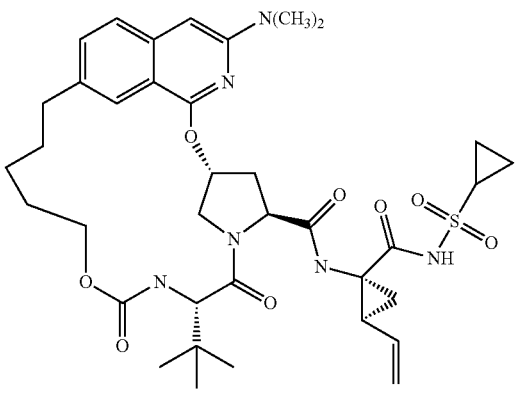
III-20
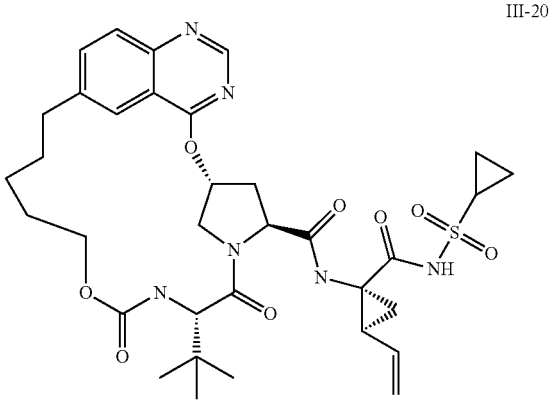

III-21
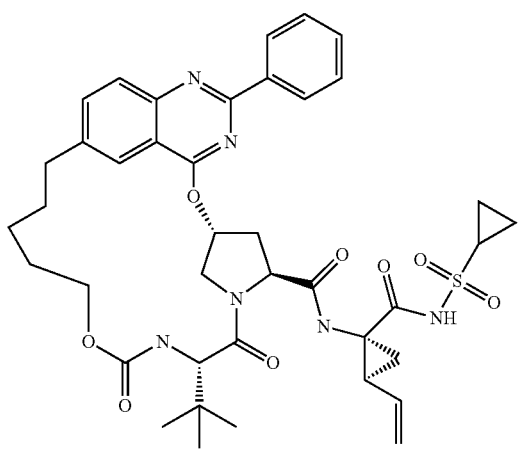
III-22
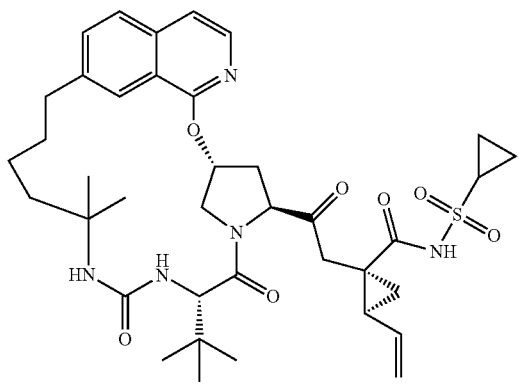
III-23
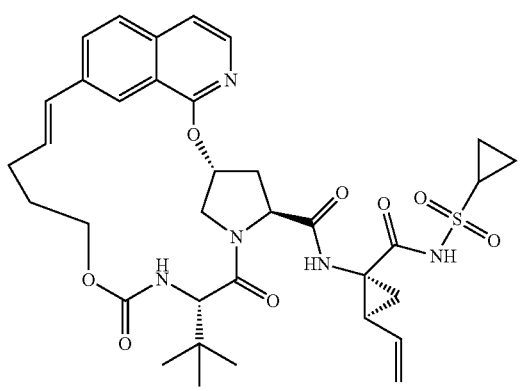
III-24
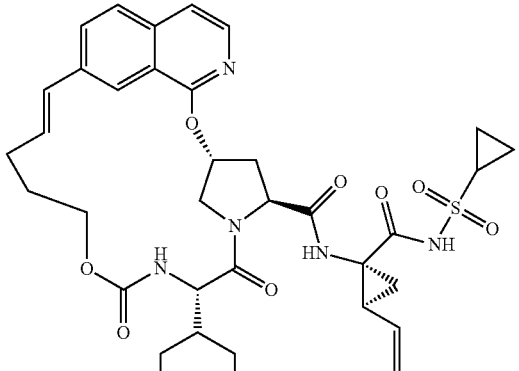
III-25
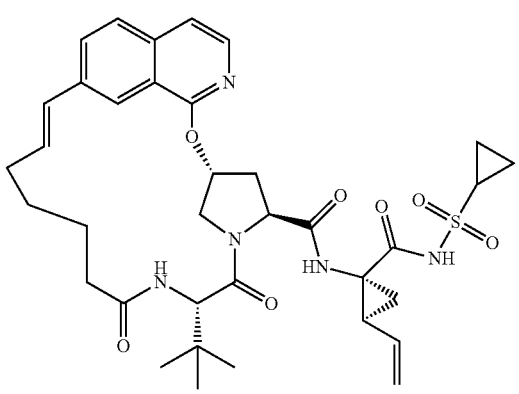
III-26
III-27
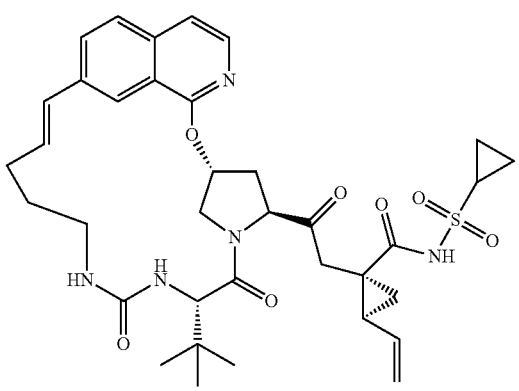

III-28
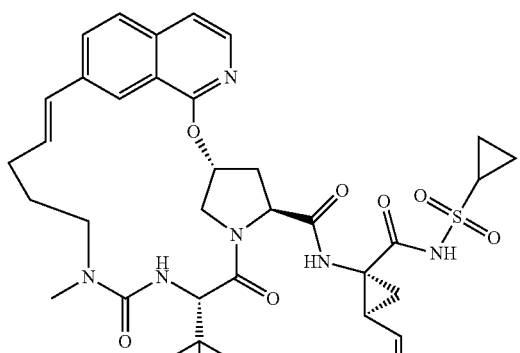
III-29
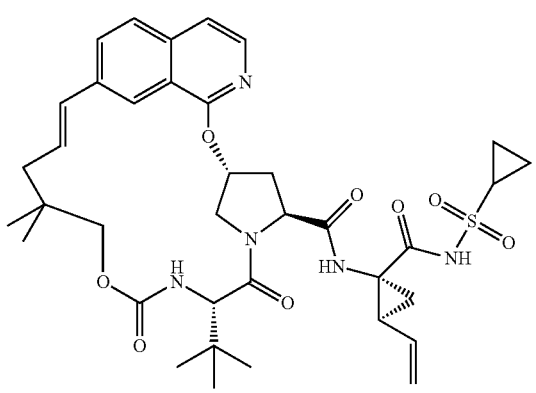
III-30
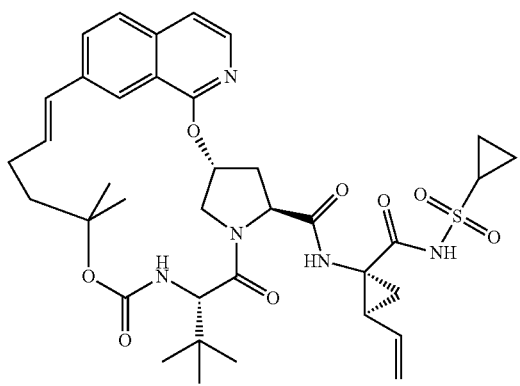
III-31
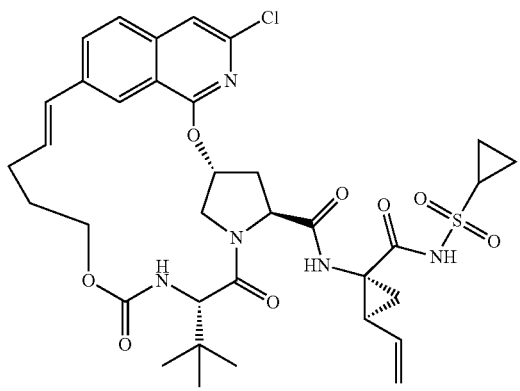
III-32
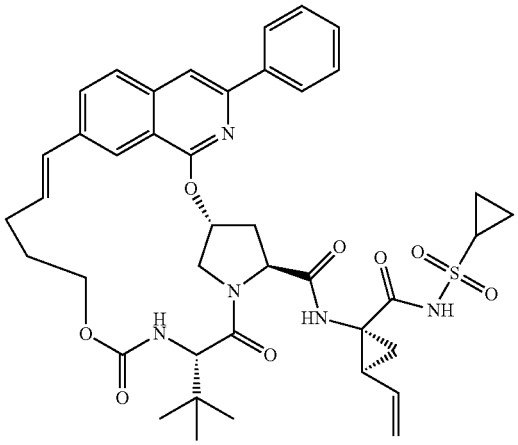
III-33
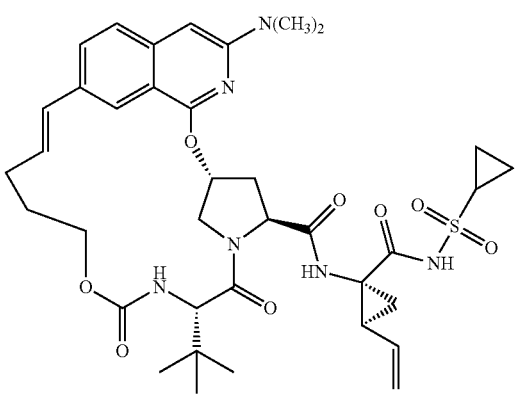
III-34
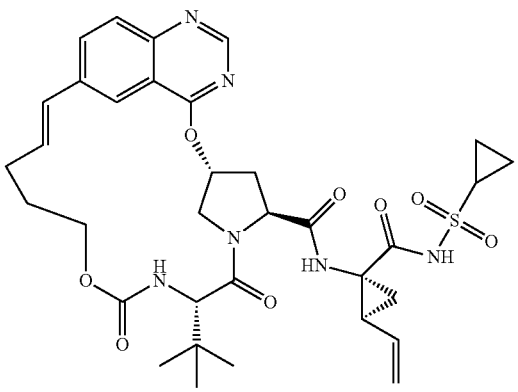

III-35

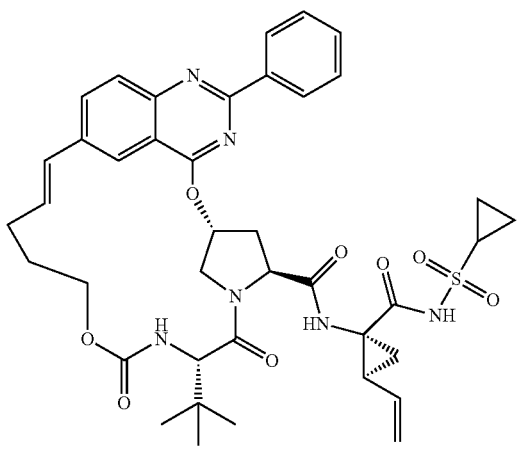

III-36

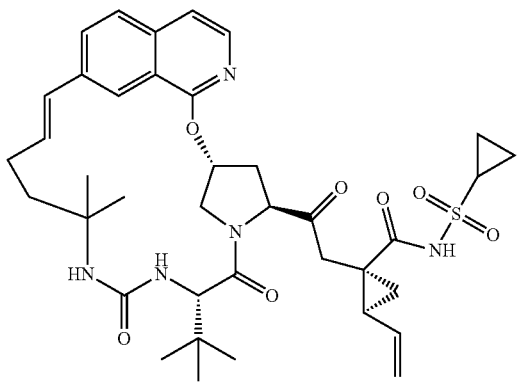

III-37

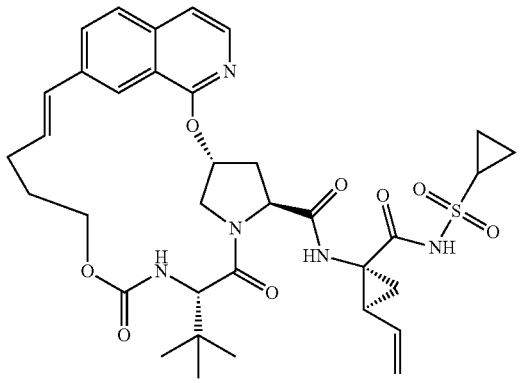

III-38

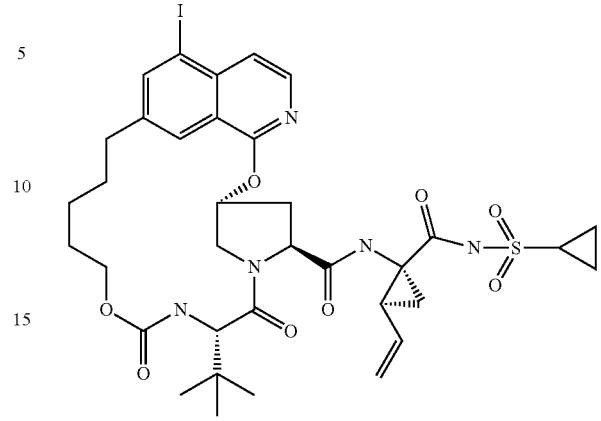

A nineteenth embodiment of the present invention is a compound of formula III, or a pharmaceutically acceptable salt or hydrate thereof, wherein $R^1$ is $CONHSO_2R^6$, $R^6$ is $C_3$-$C_8$ cycloalkyl, $C_1$-$C_8$ alkyl, aryl, or aryl($C_1$-$C_4$)alkyl, $R^2$ is $C_1$-$C_4$ alkyl or $C_2$-$C_4$ alkenyl, $R^3$ is $C_5$-$C_6$ cycloalkyl or $C_1$-$C_8$ alkyl optionally substituted with 1 to 3 halo substituents, $R^5$ is H, halo, aryl, heteroaryl or $N(R^7)_2$, and all other variables are as originally defined or as defined in any one of the preceding embodiments. In a first aspect of the nineteenth embodiment, $R^5$ is H, and all other variables are as defined in the nineteenth embodiment or as defined in any one of the preceding embodiments. In a feature of the first aspect of the nineteenth embodiment, $R^3$ is $C_5$-$C_6$ cycloalkyl or $C_3$-$C_5$-alkyl, and all other variables are as defined in the nineteenth embodiment or as defined in any one of the preceding embodiments. In another feature of the first aspect of the nineteenth embodiment, $R^6$ is $C_3$-$C_5$ cycloalkyl, and all other variables are as defined in the nineteenth embodiment or as defined in any one of the preceding embodiments. In a second aspect of the nineteenth embodiment, $R^2$ is $C_2$-$C_4$ alkenyl, $R^5$ is H, $R^6$ is $C_3$-$C_8$ cycloalkyl, W is $R^7$ or H, Y is C(=O), Z is O, and n is 1, and all other variables are as defined in the nineteenth embodiment or as defined in any one of the preceding embodiments. In a third aspect of the nineteenth embodiment, M is selected from the group consisting of:

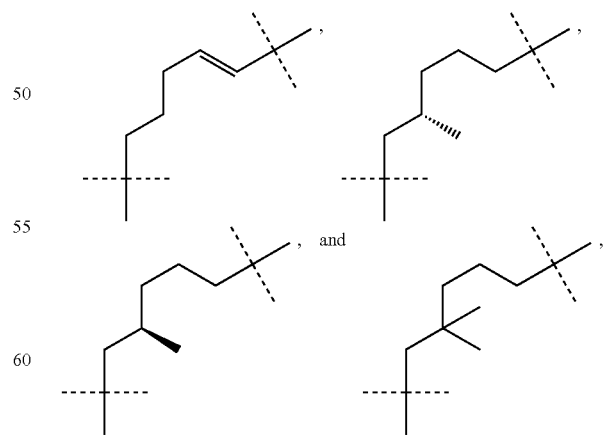

and all other variables are as defined in the nineteenth embodiment or as defined in any one of the preceding embodiments.

A twentieth embodiment of the present invention is a compound, or a pharmaceutically acceptable salt or hydrate thereof, selected from the group consisting of the compounds III-39 to III-187.
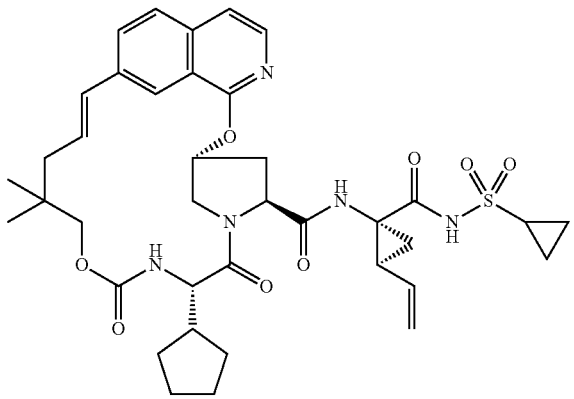
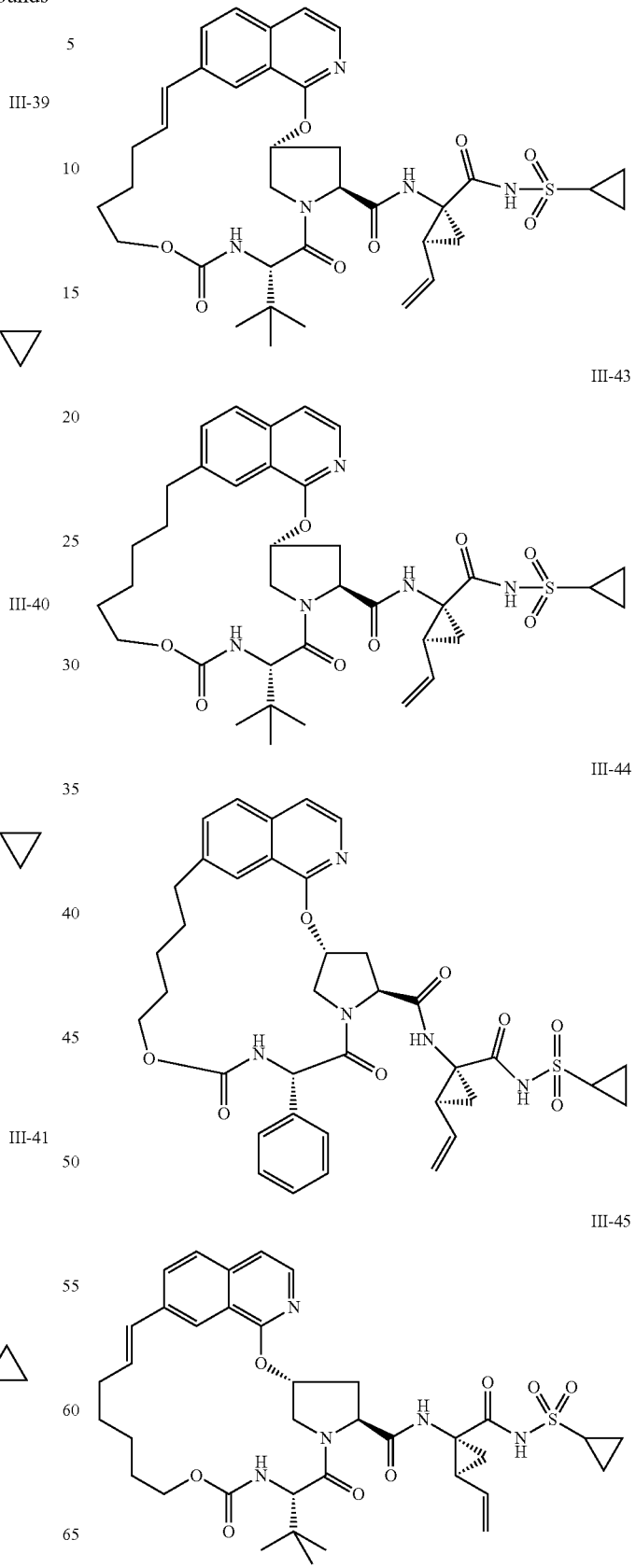

-continued
III-46
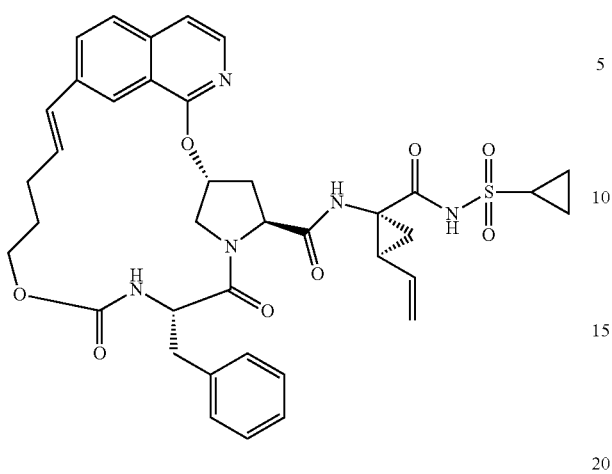
III-47
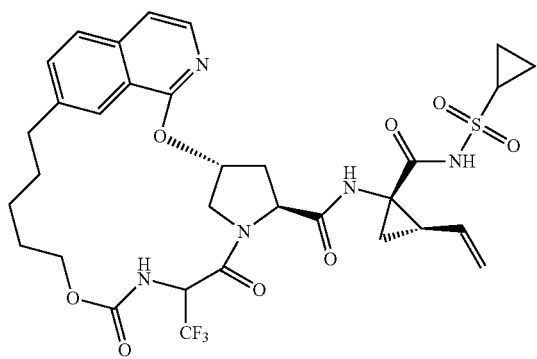
III-48
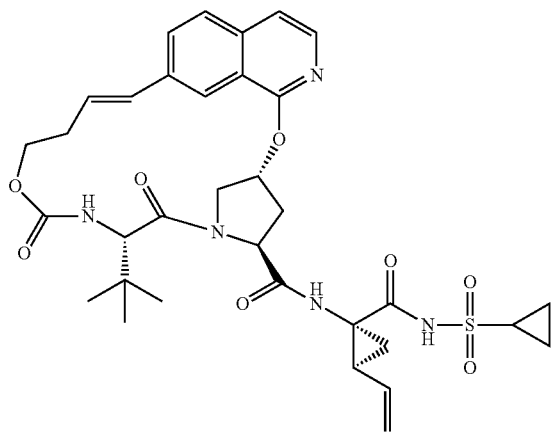
-continued
III-49
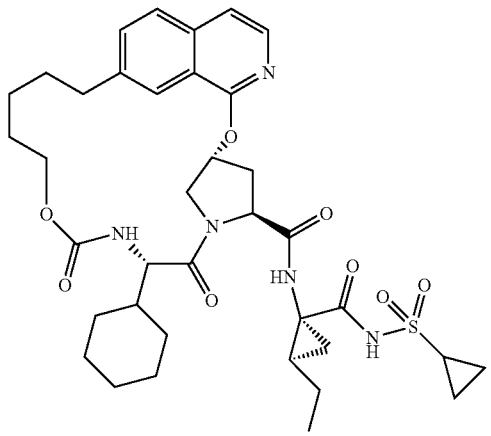
III-50
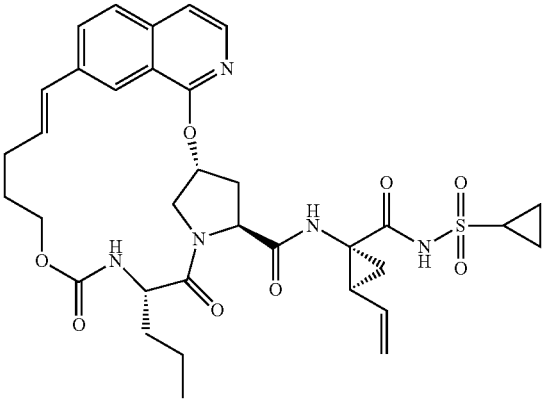
III-51
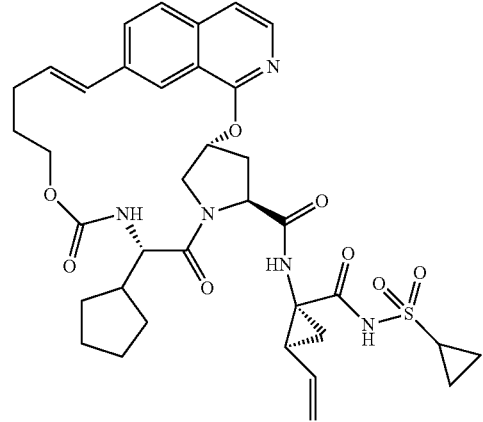

III-52
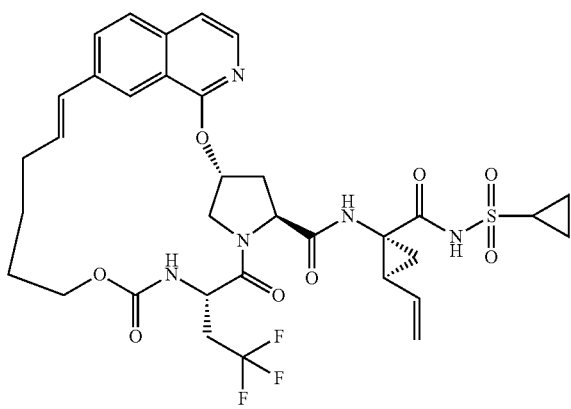
III-53
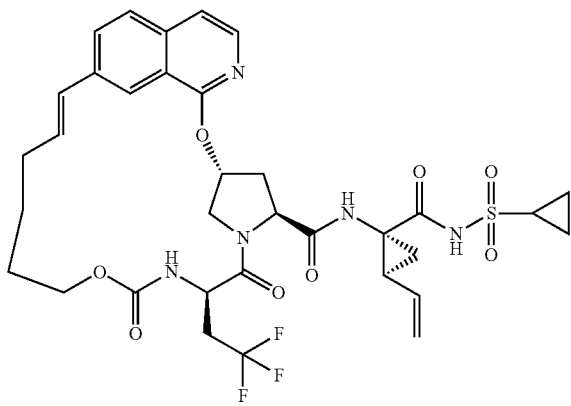
III-54
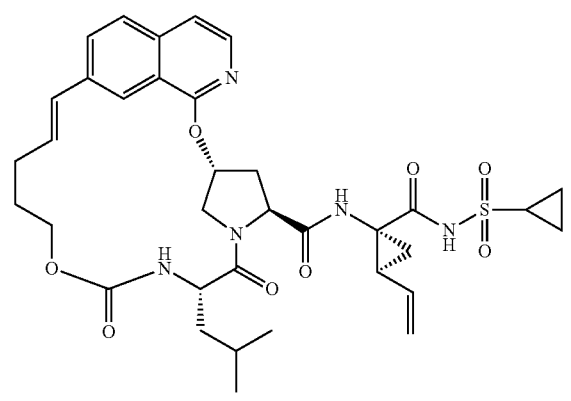
III-55
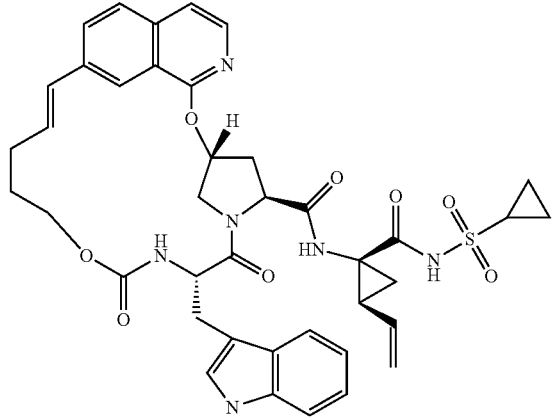
III-56
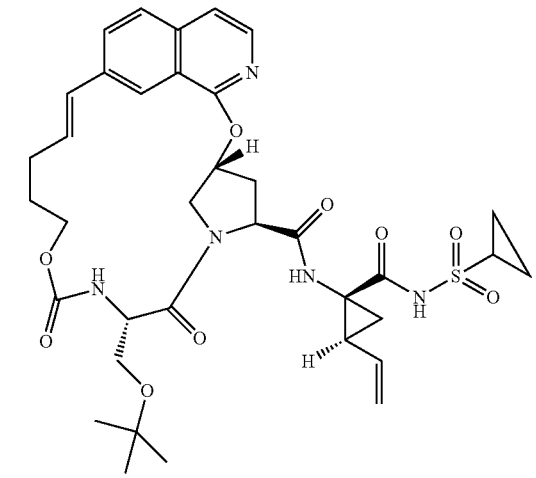
III-57
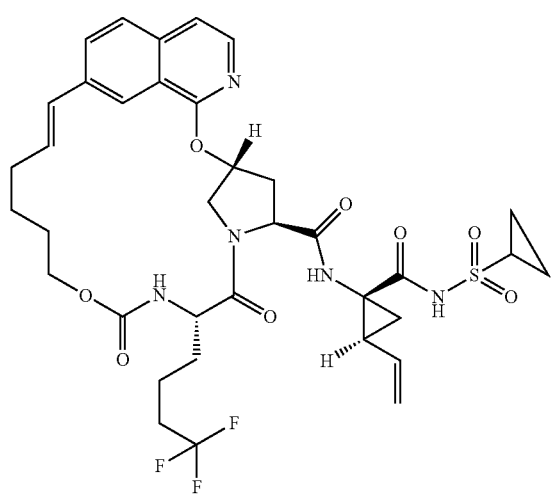

III-58
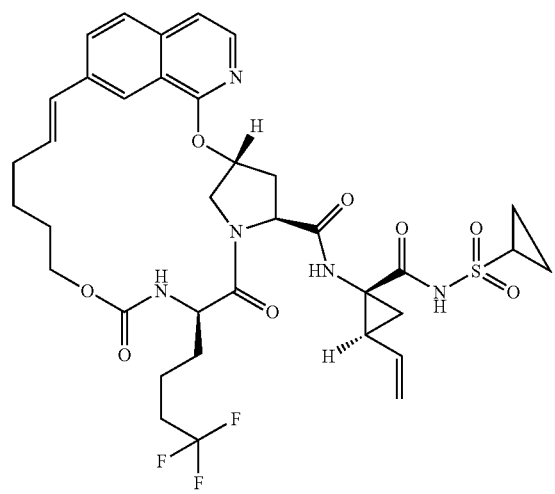
III-61
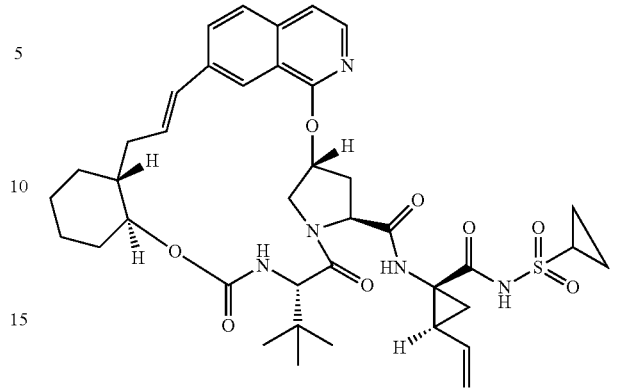
III-62
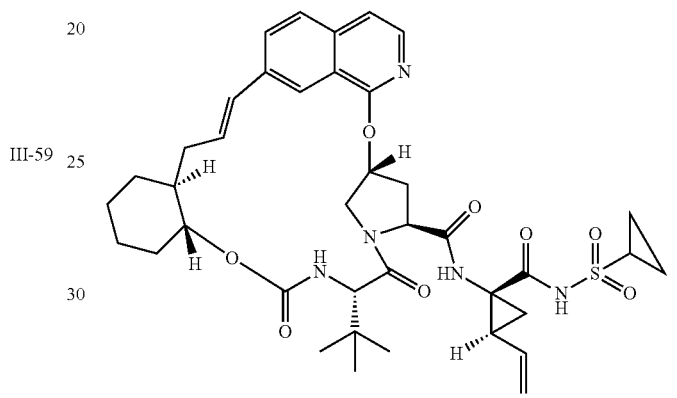
III-59
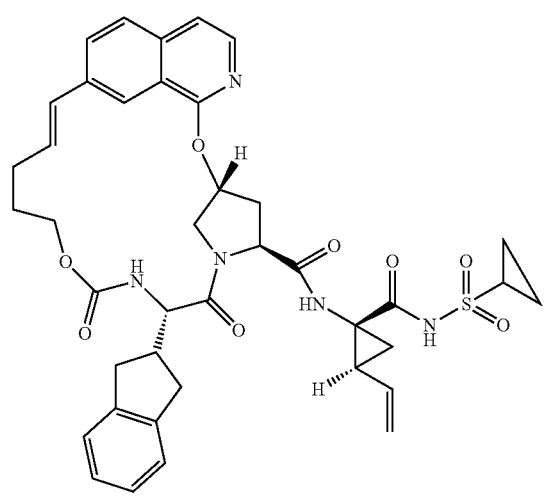
III-63
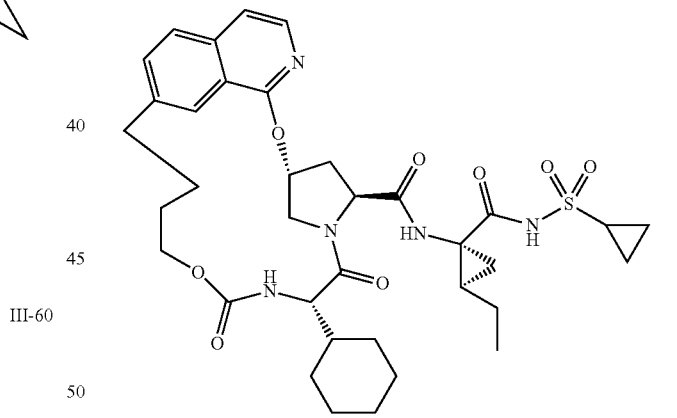
III-60
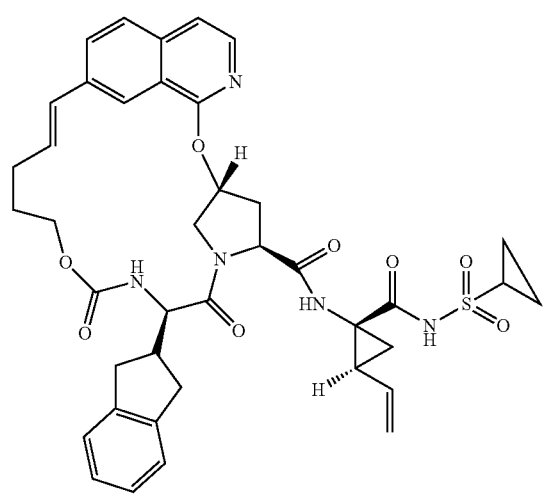
III-64
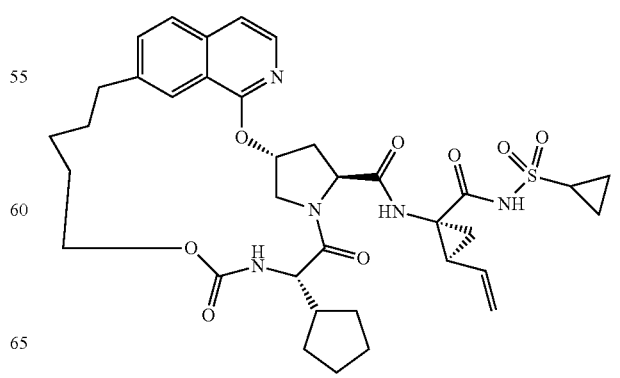

III-65
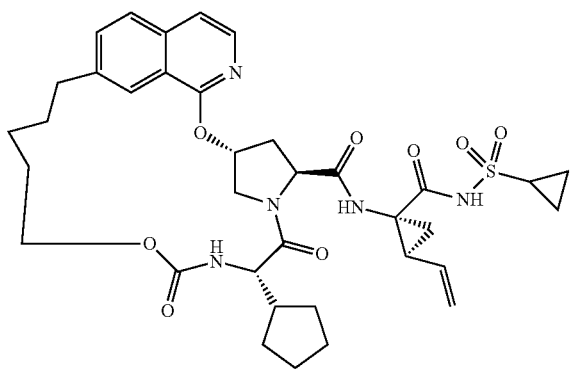
III-66
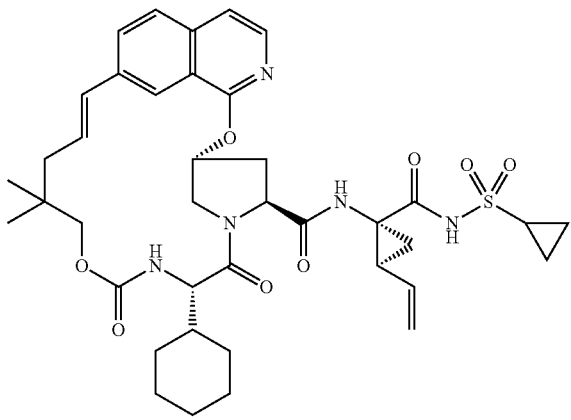
III-67
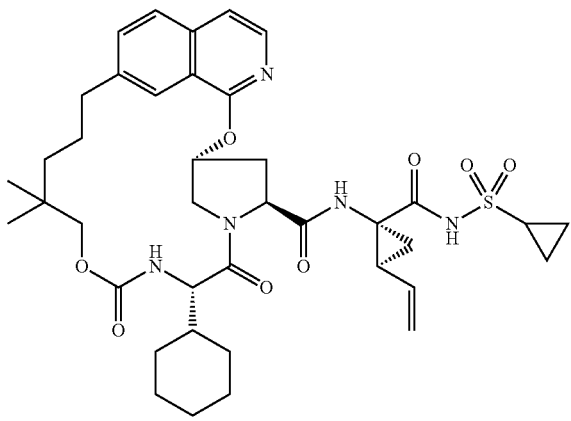
III-68
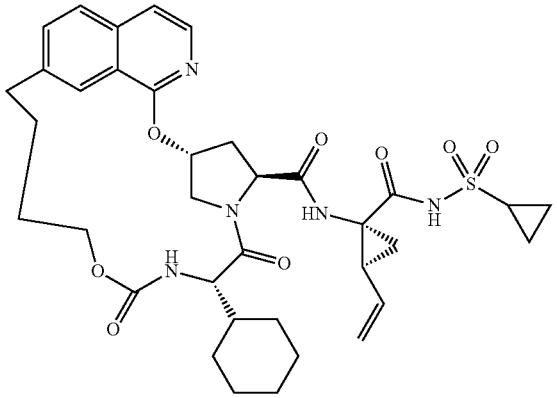
III-69
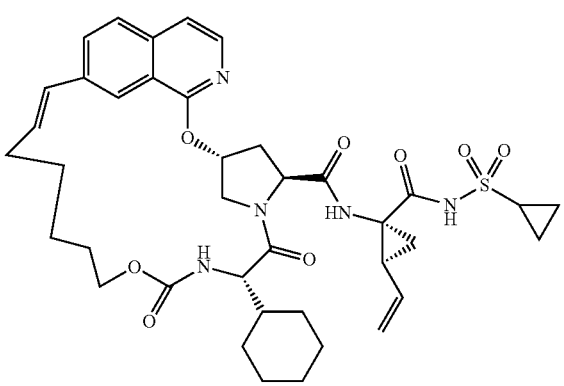
III-70
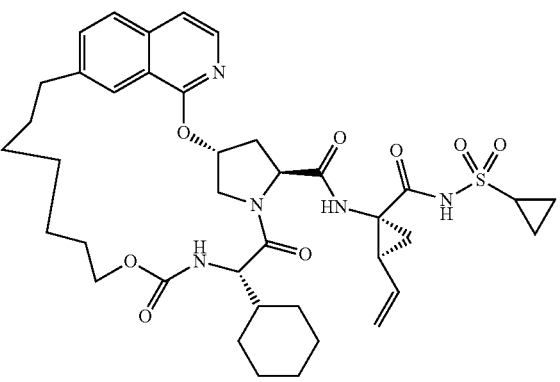
III-71
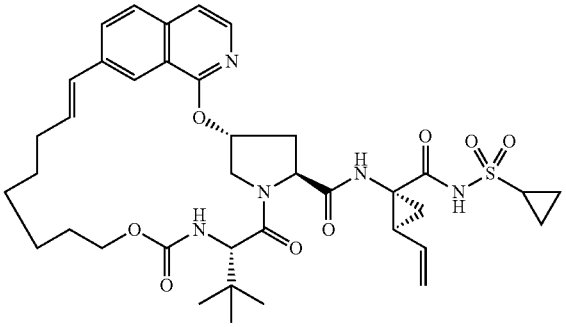

III-72
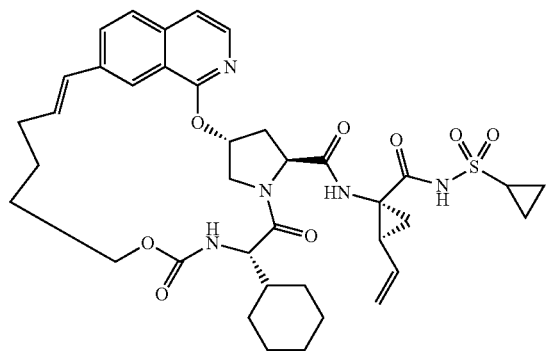
III-73
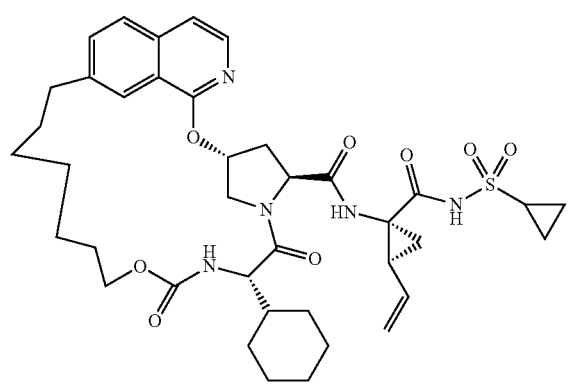
III-74
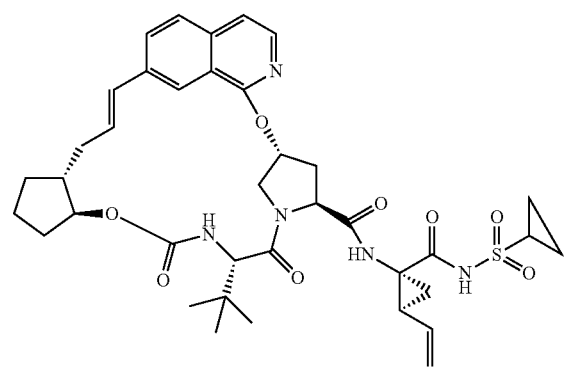
III-75
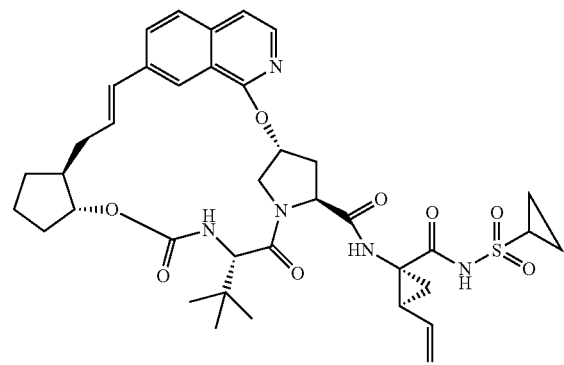
III-76
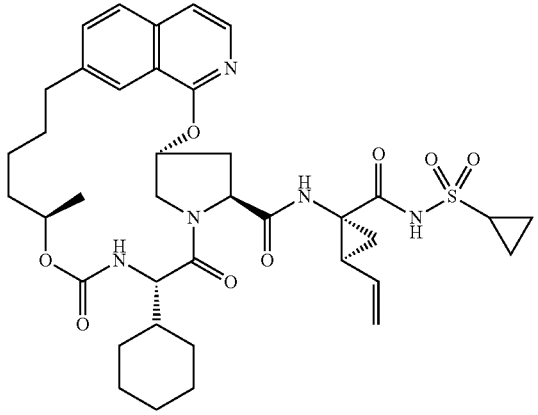
III-77
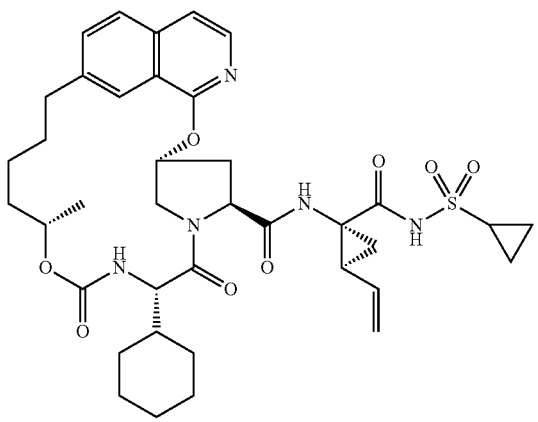
III-78
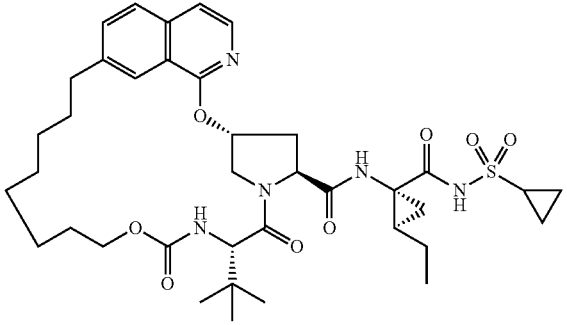
III-79
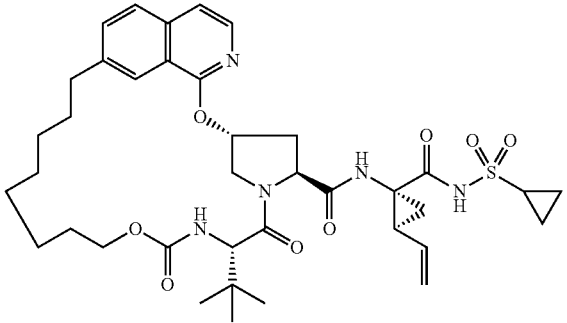

III-80
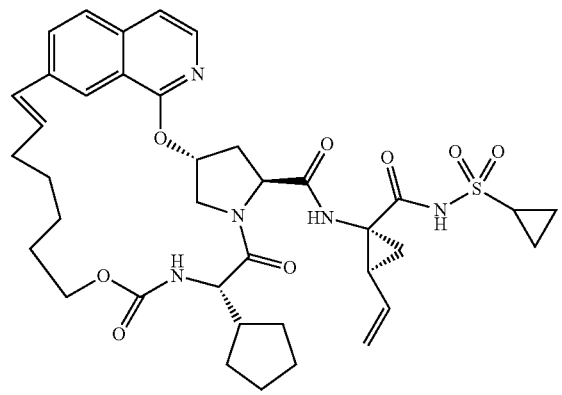
III-84
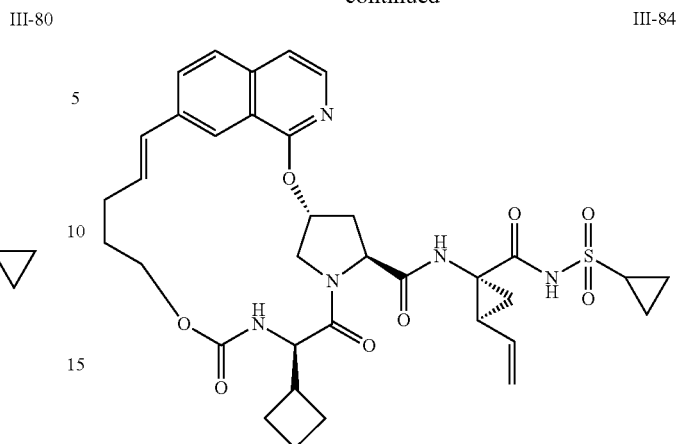
III-81
III-85
III-82
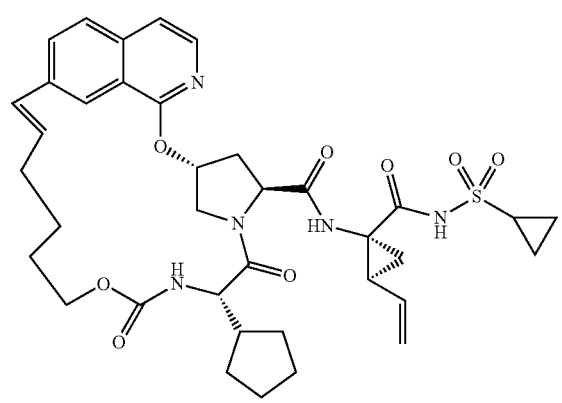
III-83
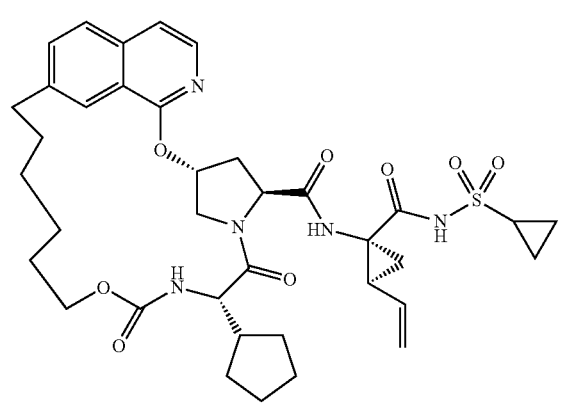
III-86

III-87
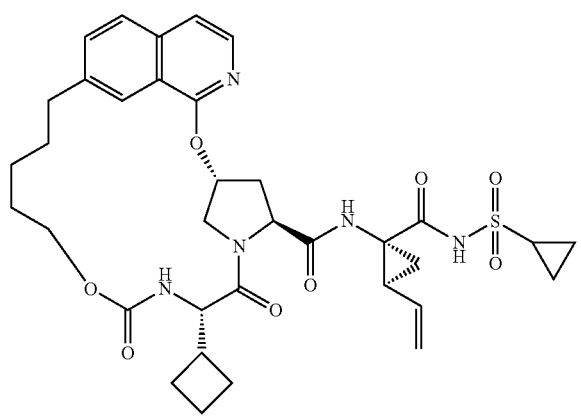
III-90
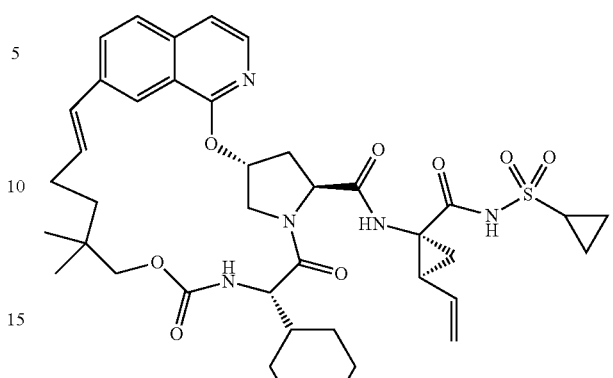
III-88
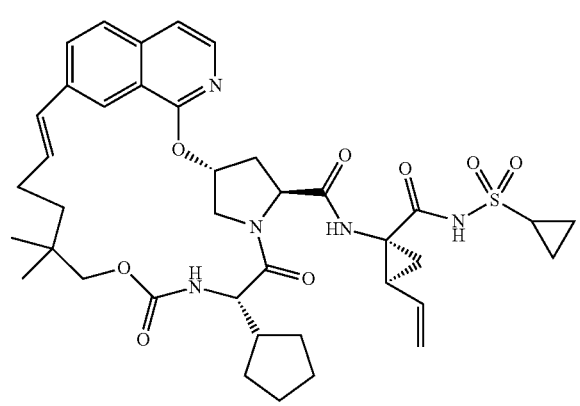
III-91
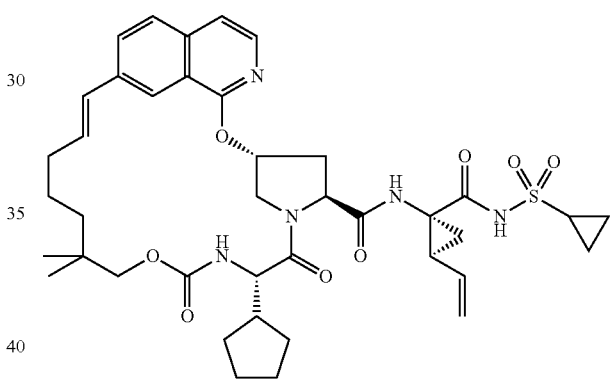
III-89
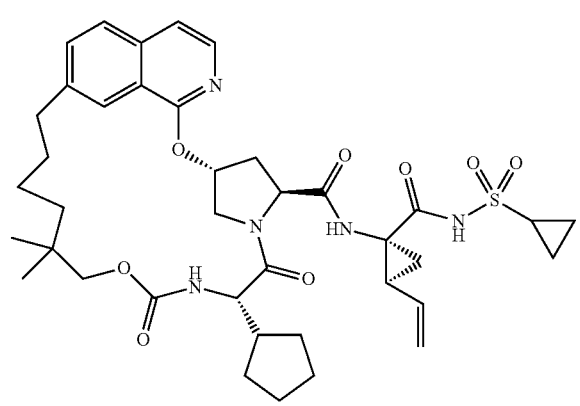
III-92
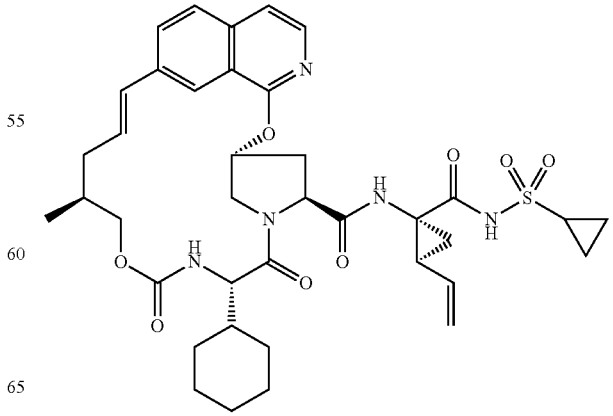

III-93
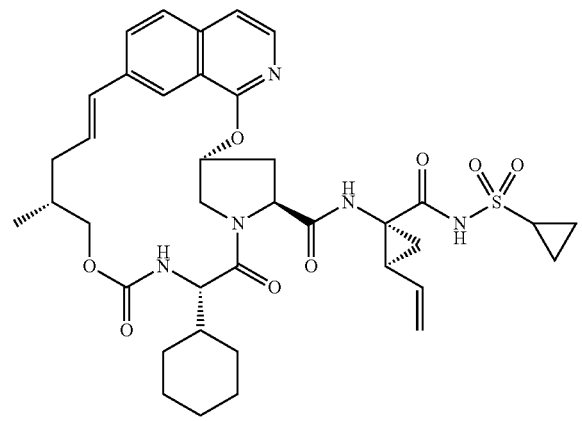
III-97
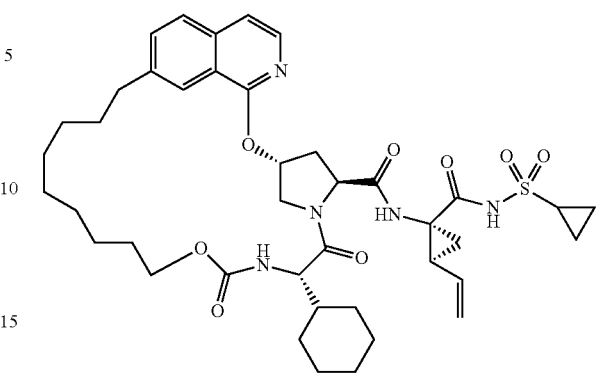
III-94
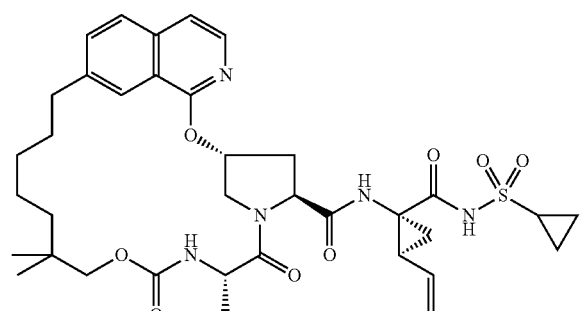
III-98
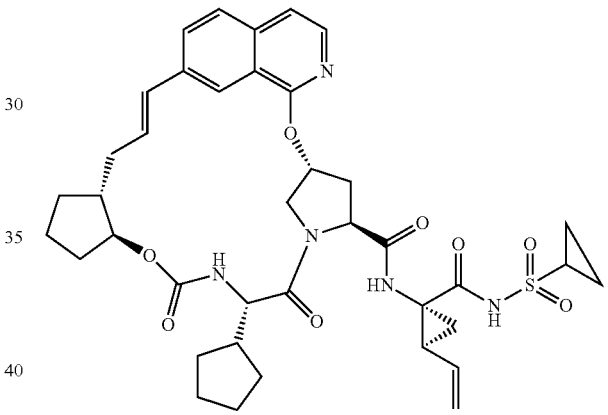
III-95
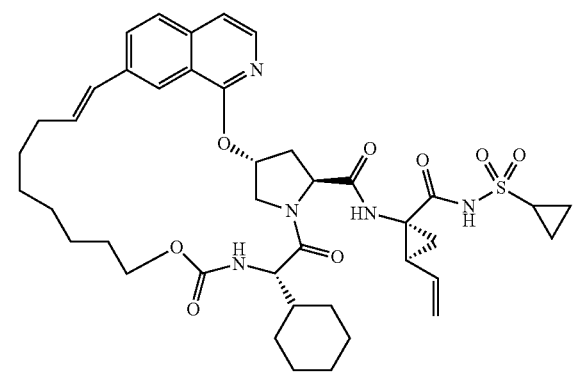
III-96
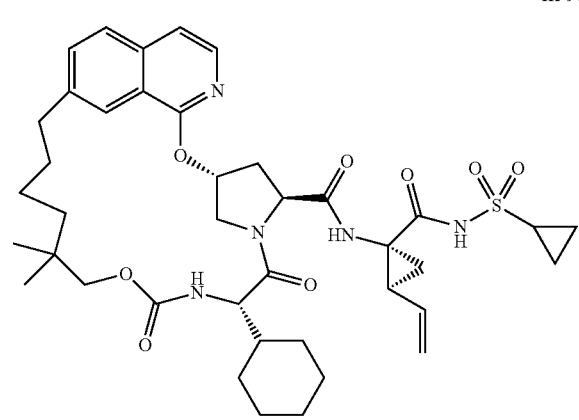
III-99
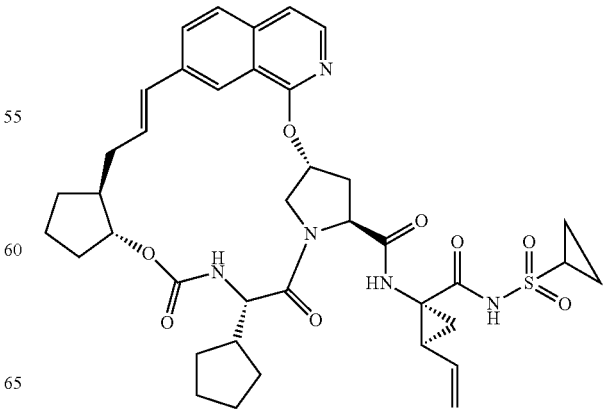

III-100
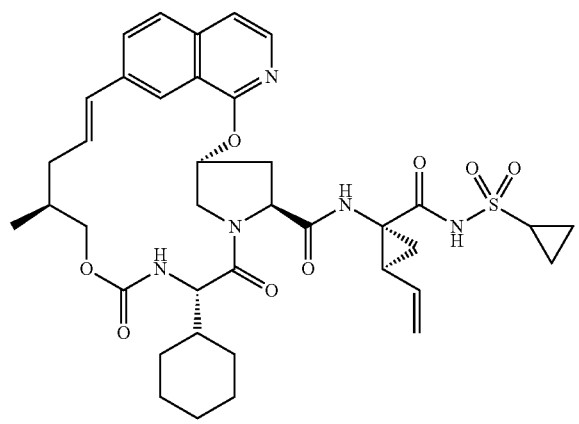
III-103
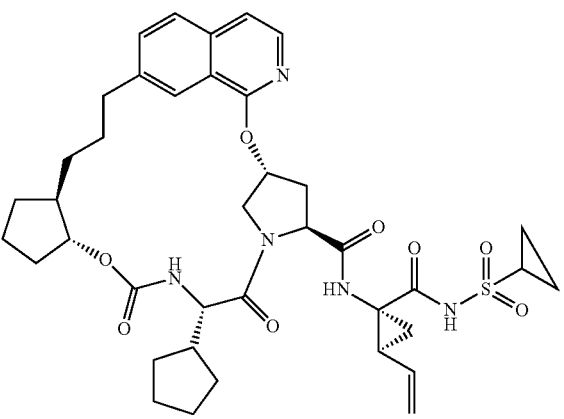
III-101
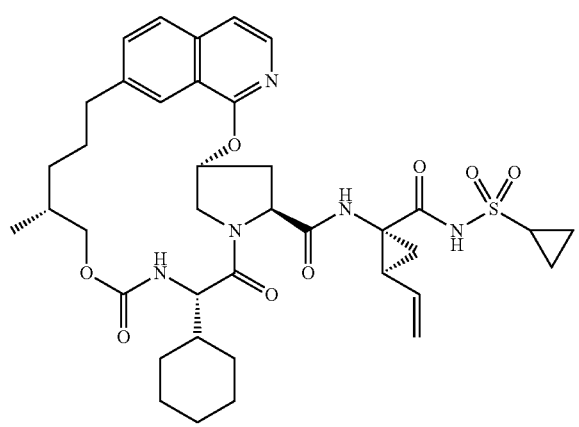
III-104
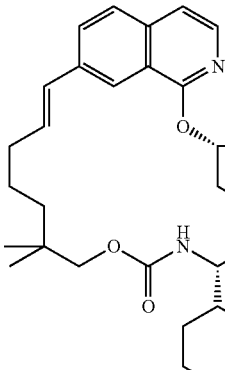
III-102
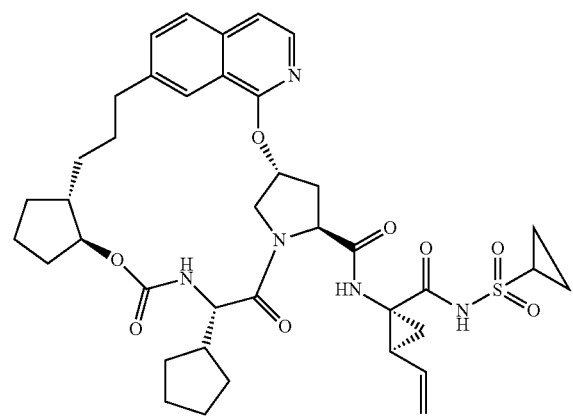
III-105
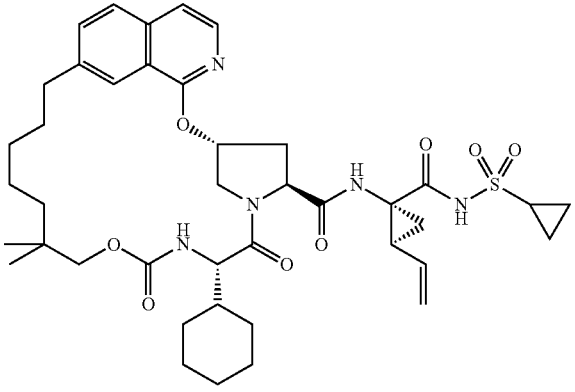

III-106
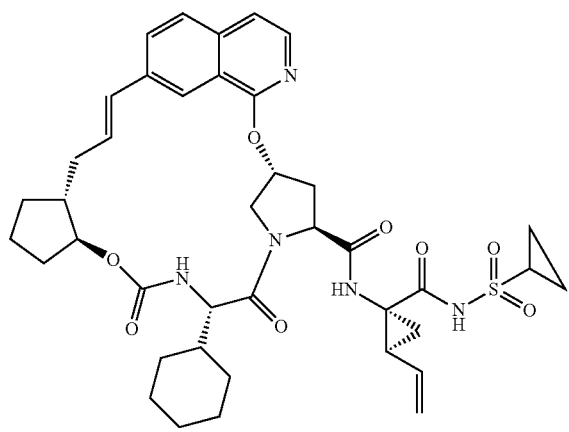
III-107
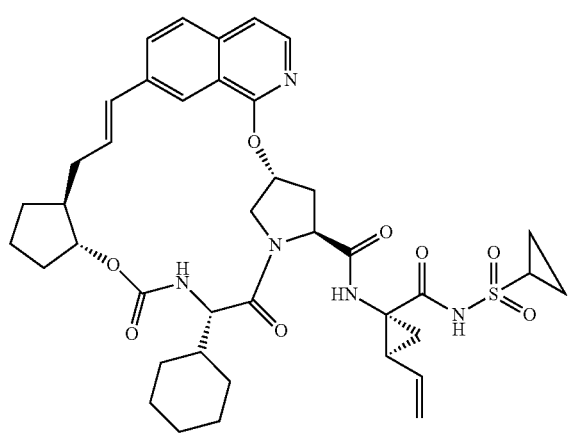
III-108
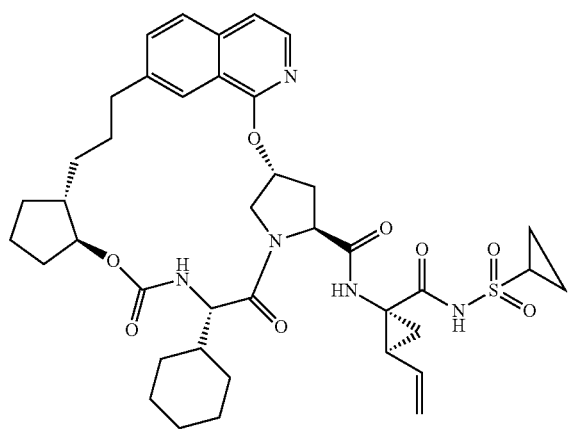
III-109
III-110
III-111
III-112
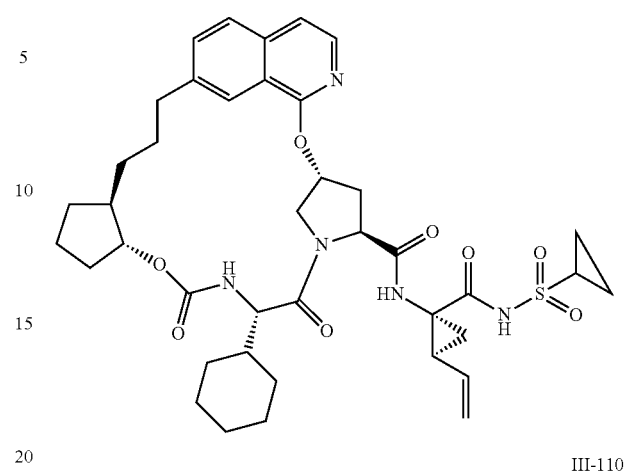
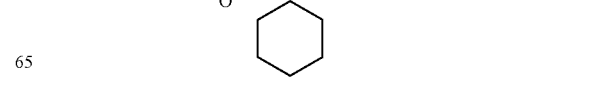

III-113
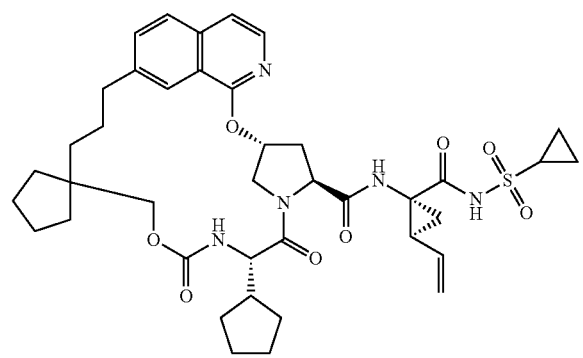
III-117
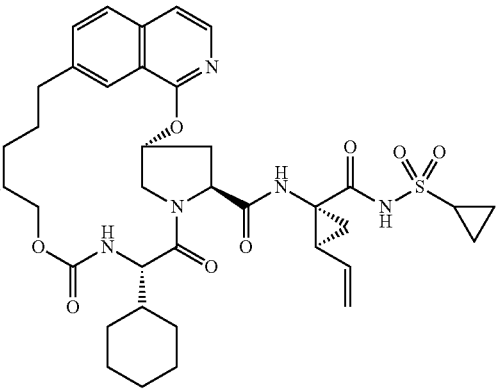
III-114
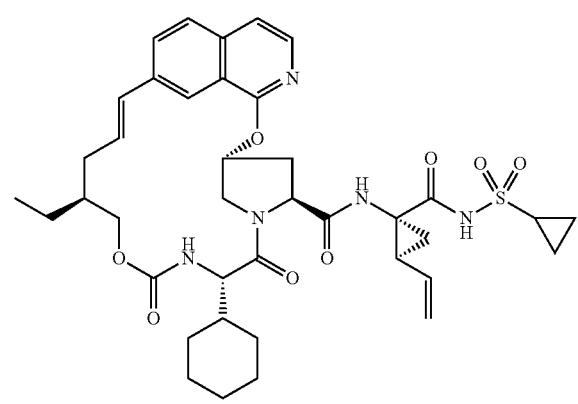
III-118
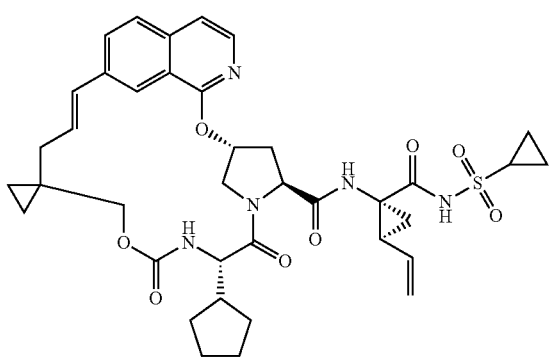
III-115
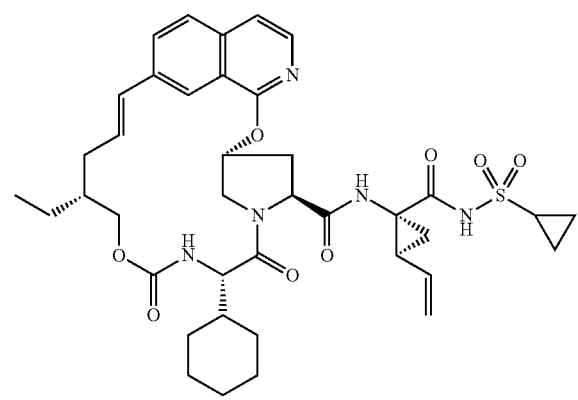
III-119
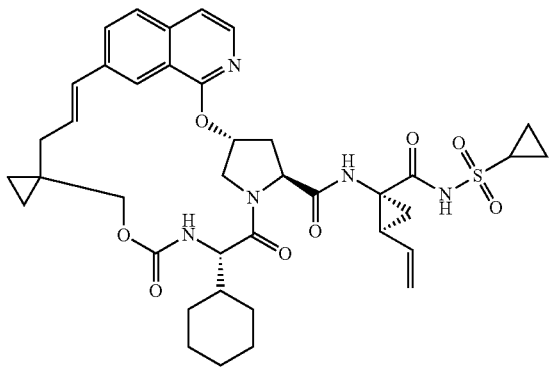
III-116
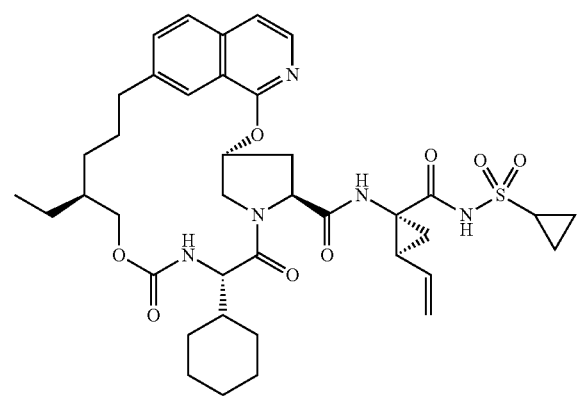
III-120
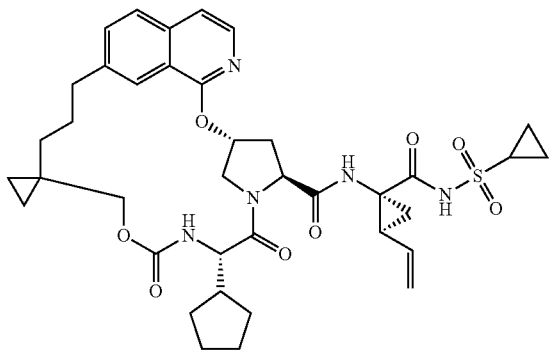

III-121
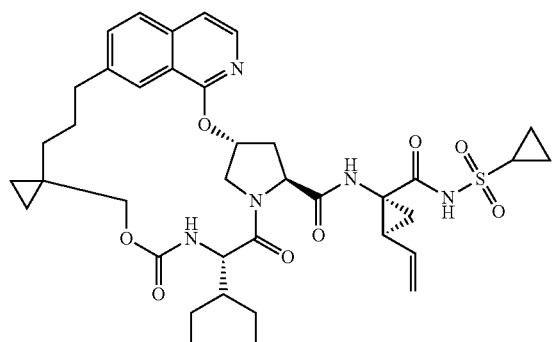
III-124
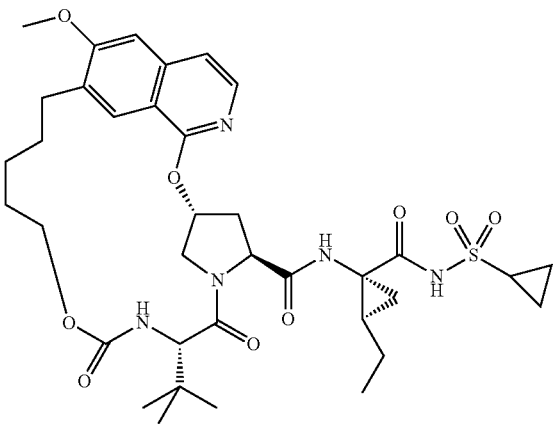
III-122
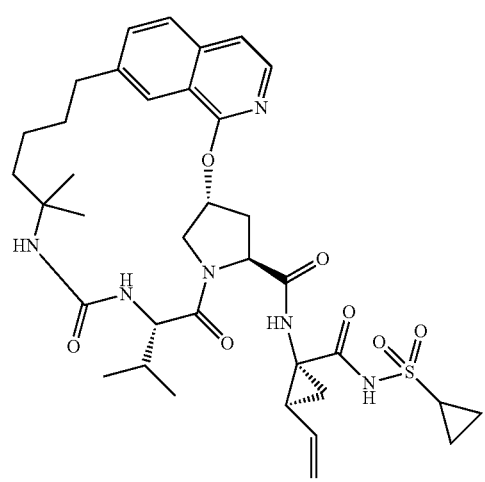
III-125
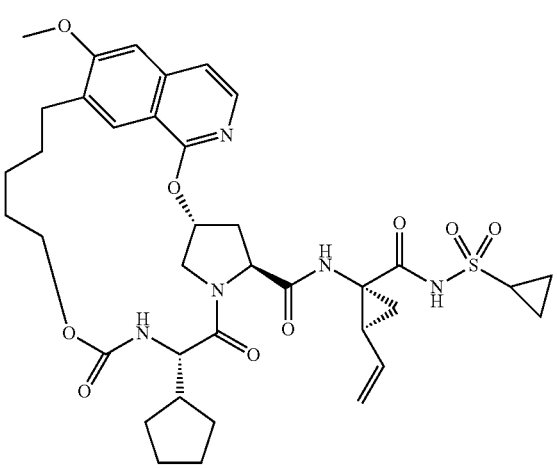
III-123
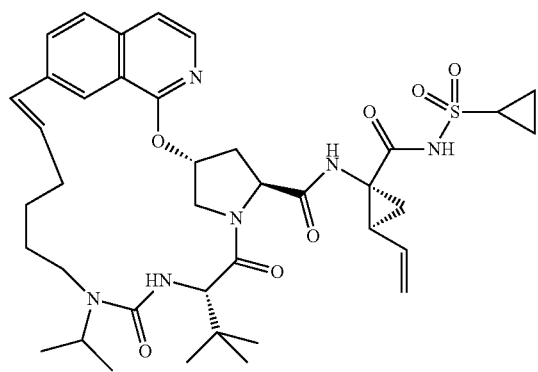
III-126
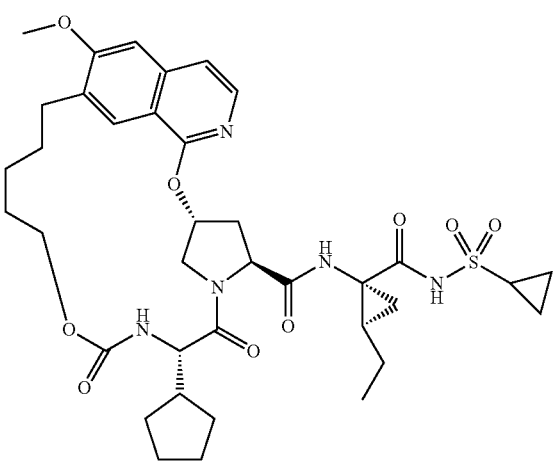

III-127
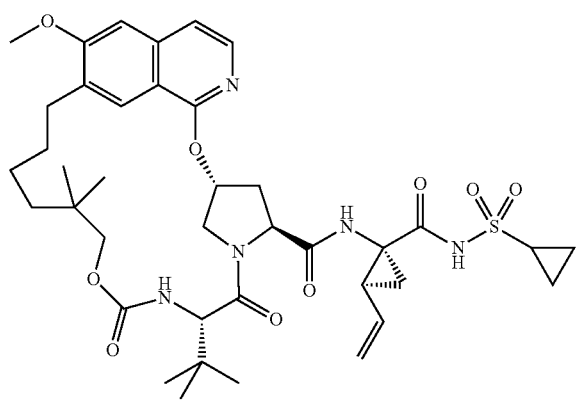
III-128
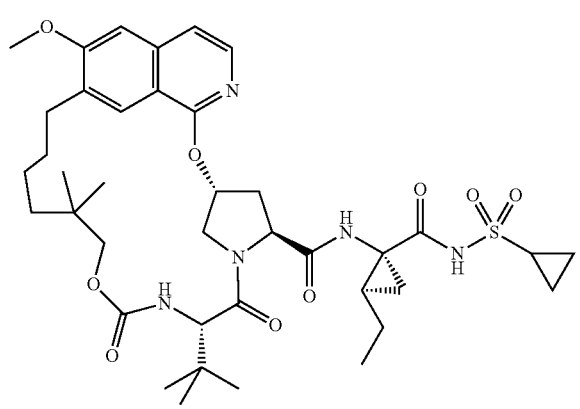
III-129
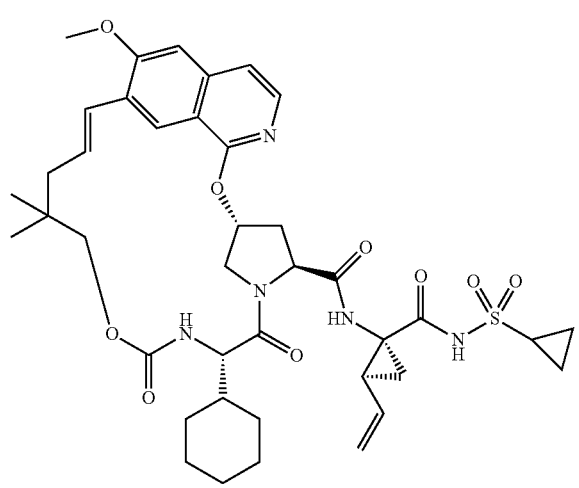
III-130
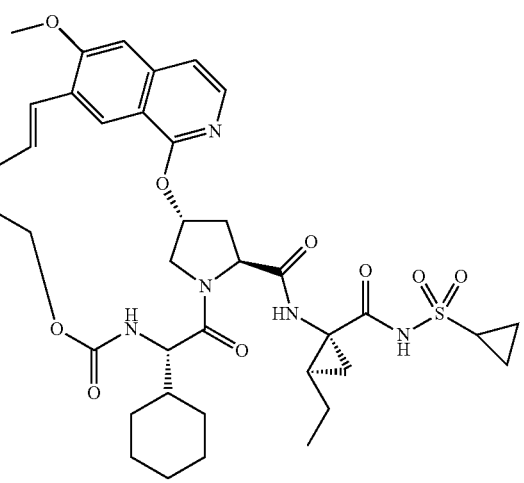
III-131
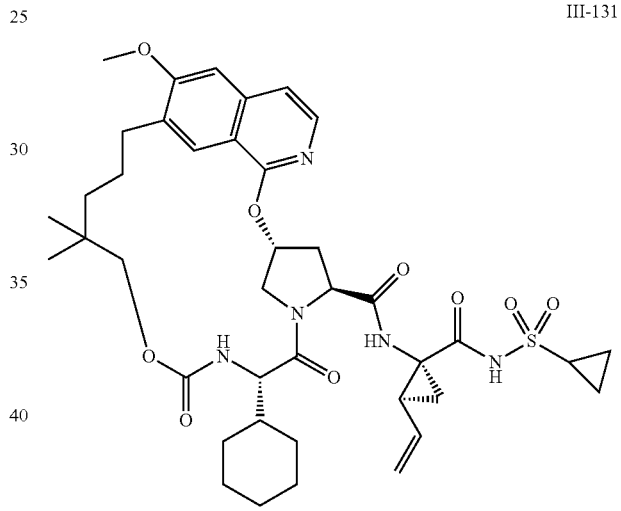
III-132
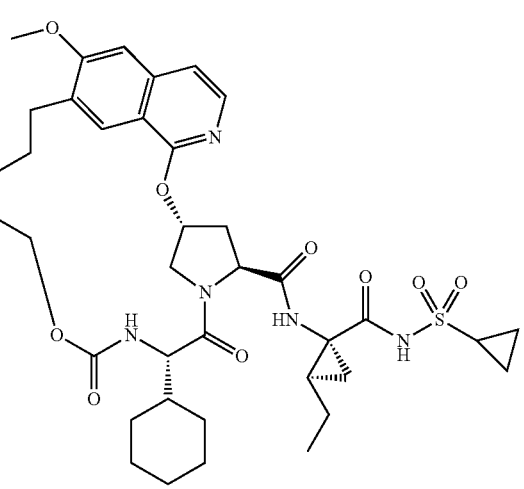

III-133
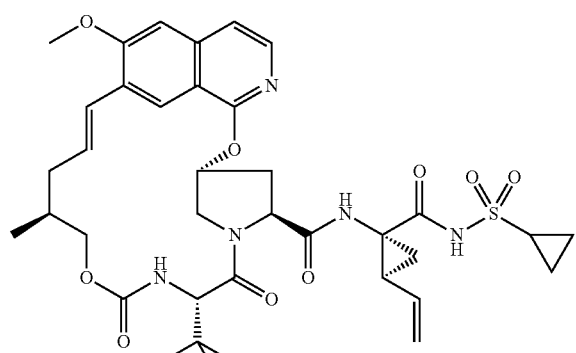
III-137
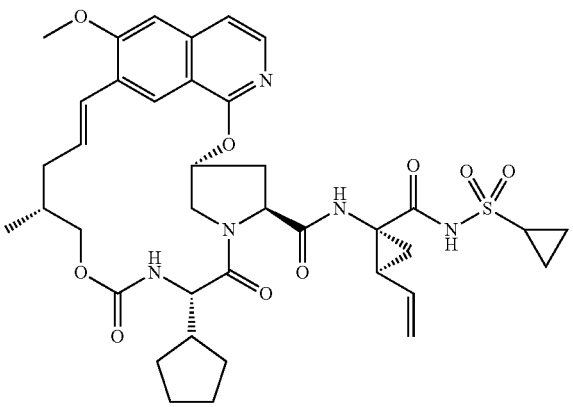
III-134
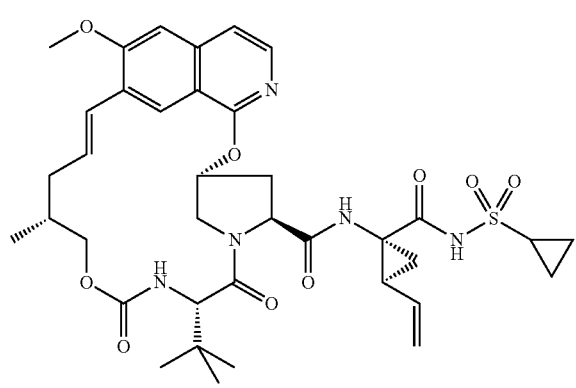
III-135
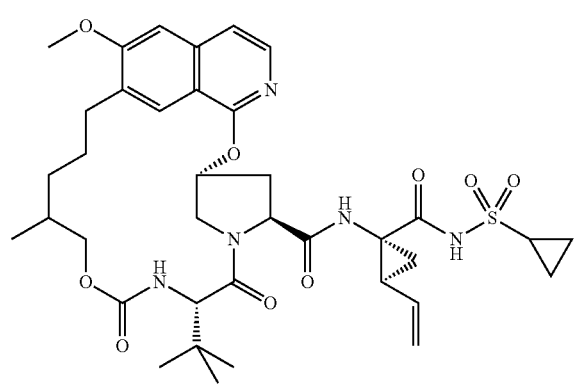
III-138
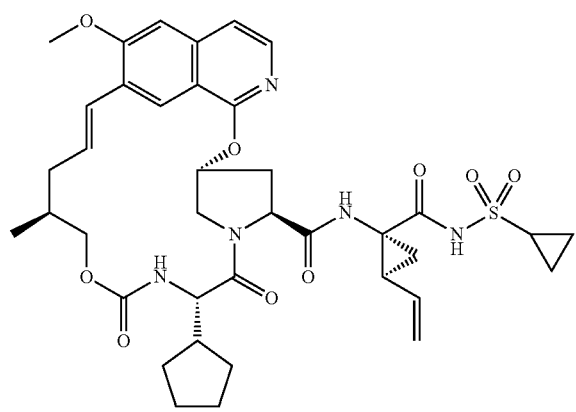
III-136
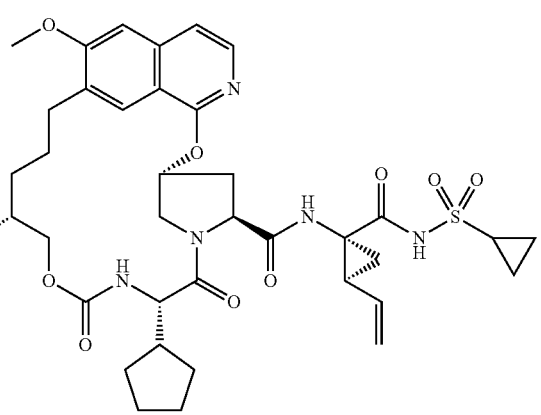
III-139

III-140
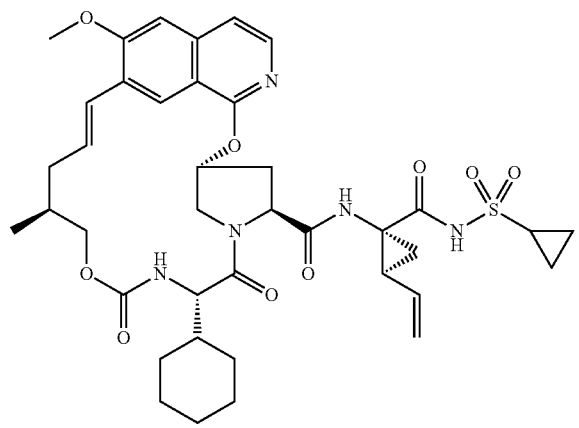
III-141
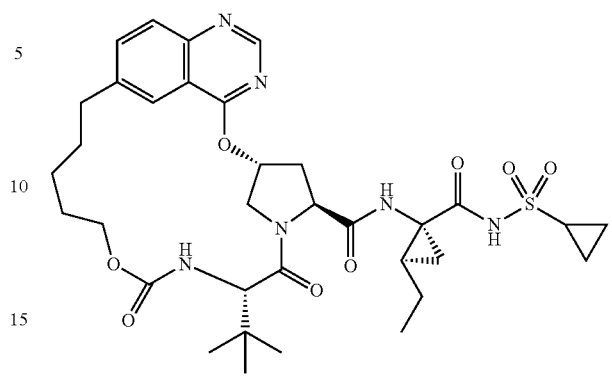
III-142
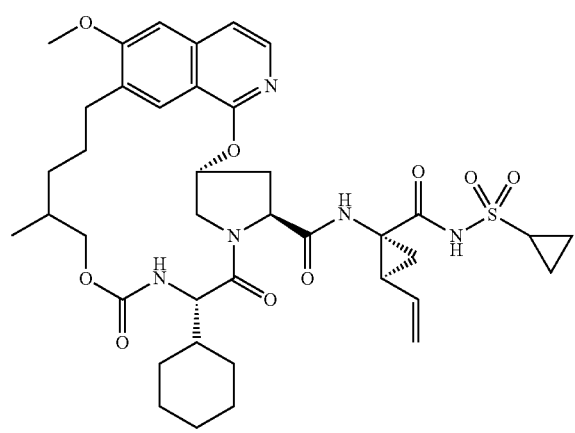
III-143
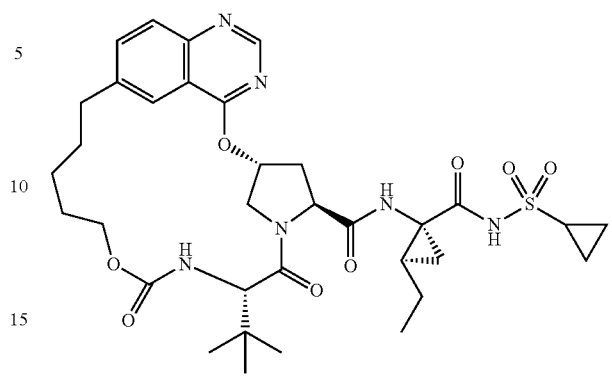
III-144
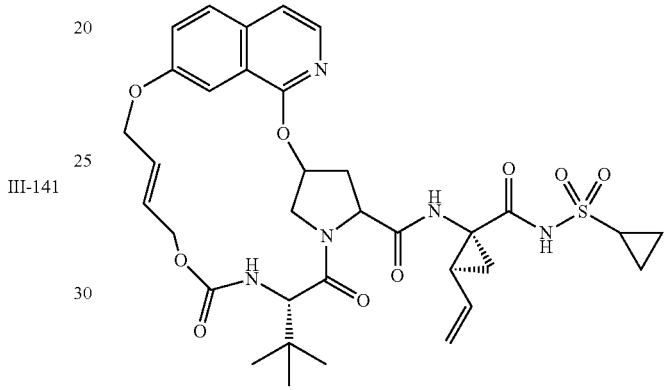
III-145
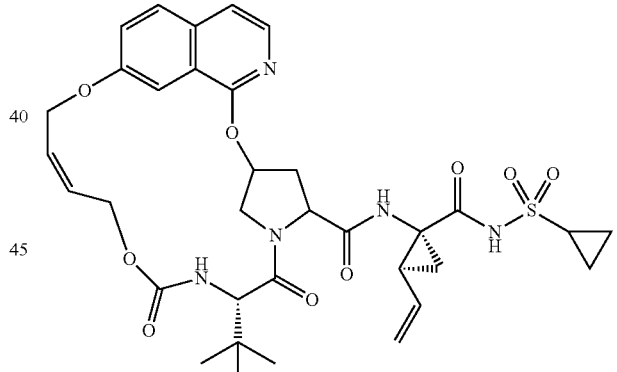
III-146
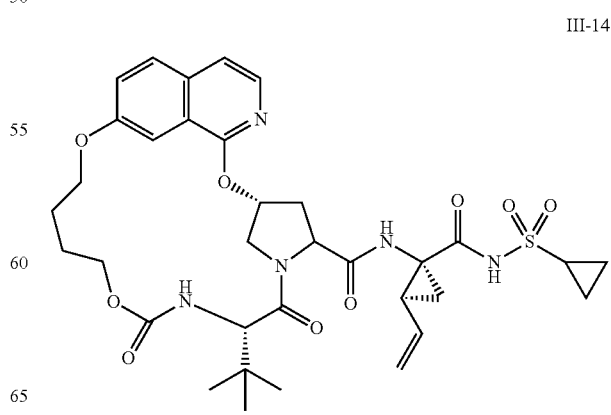

III-147
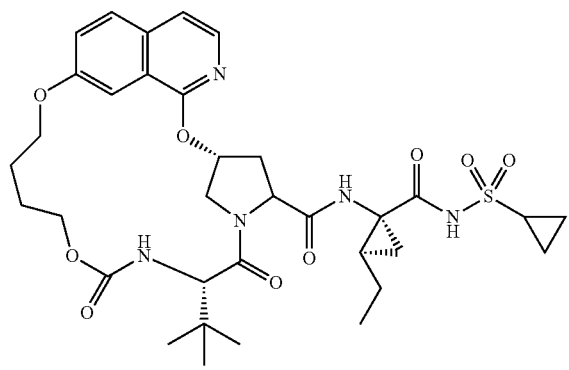
III-150
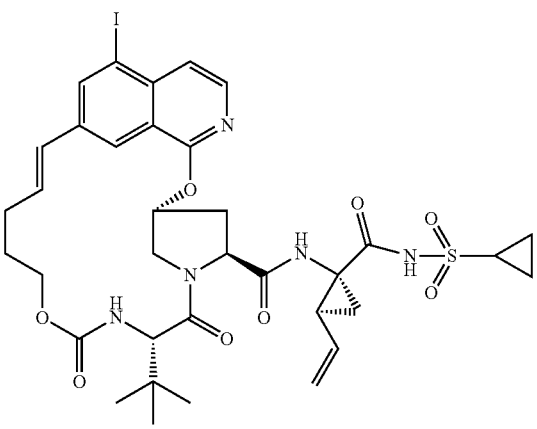
III-148
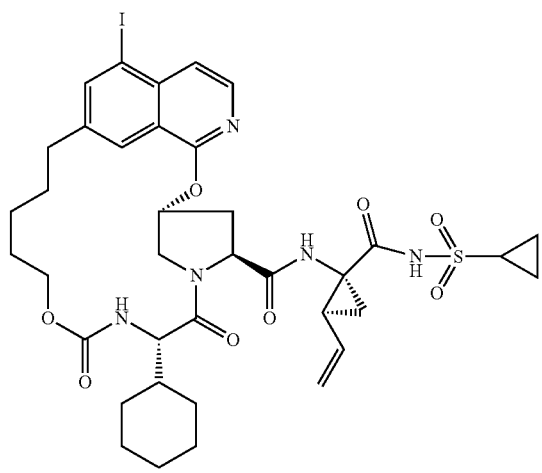
III-151
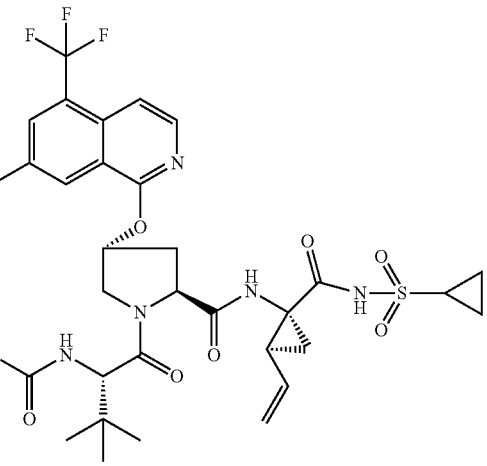
III-149
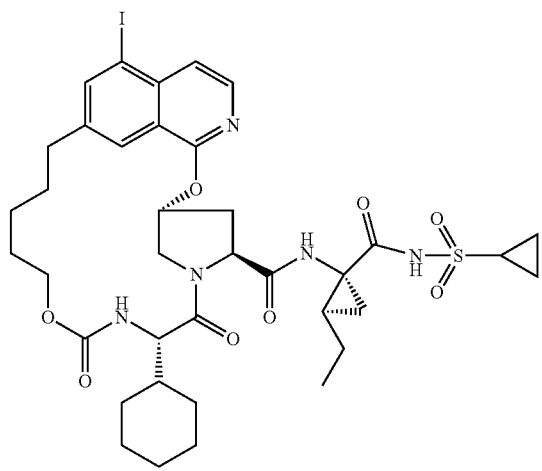
III-152
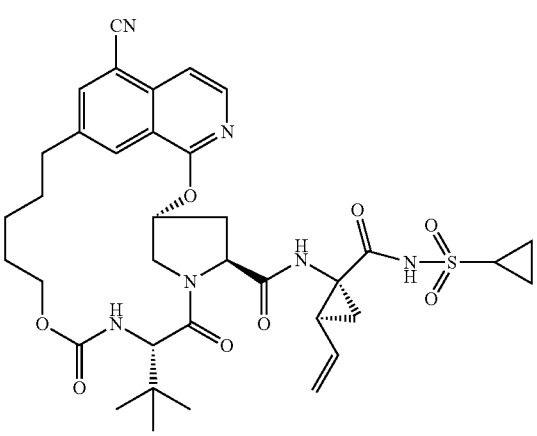

-continued
III-153
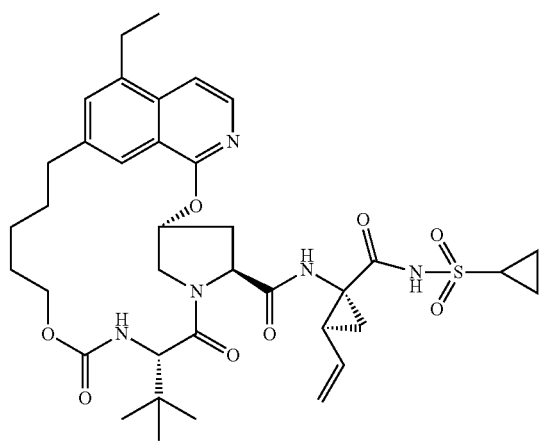
III-154
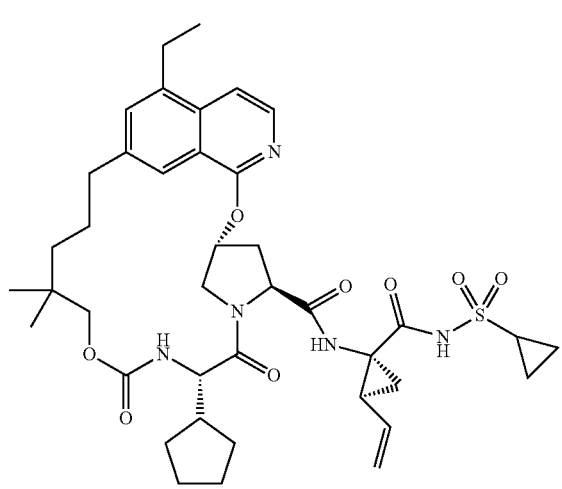
III-155
-continued
III-156
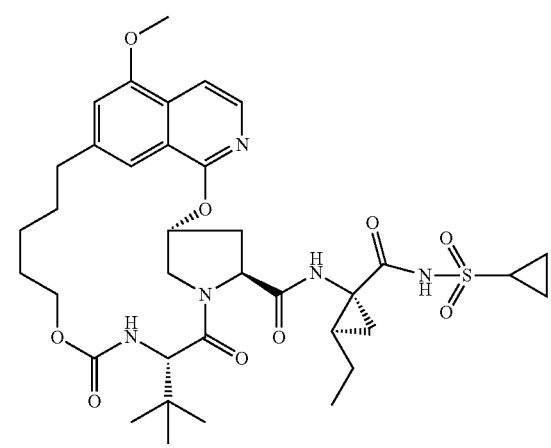
III-157
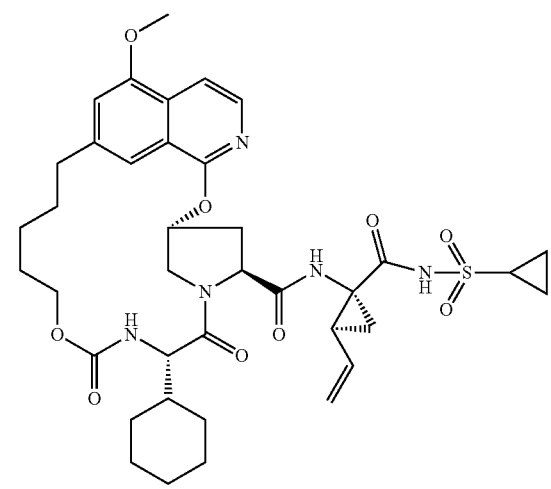
III-158
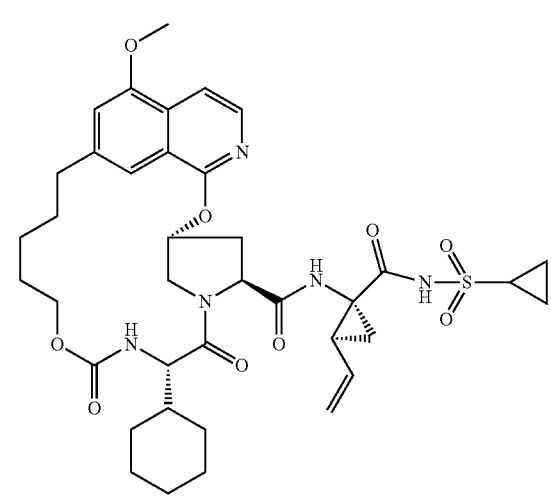

III-159
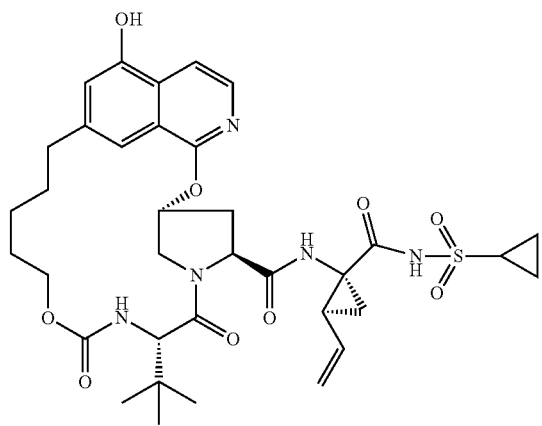
III-160
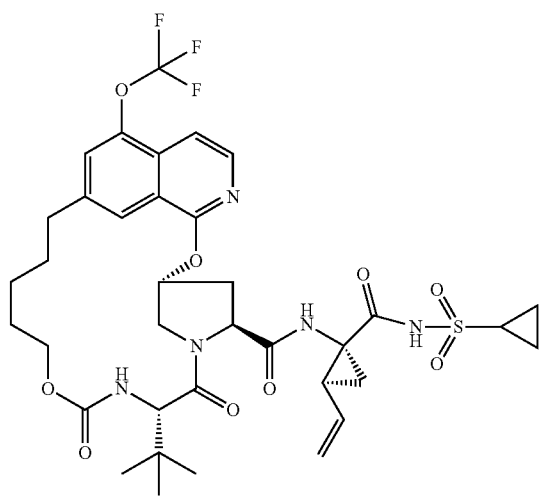
III-161
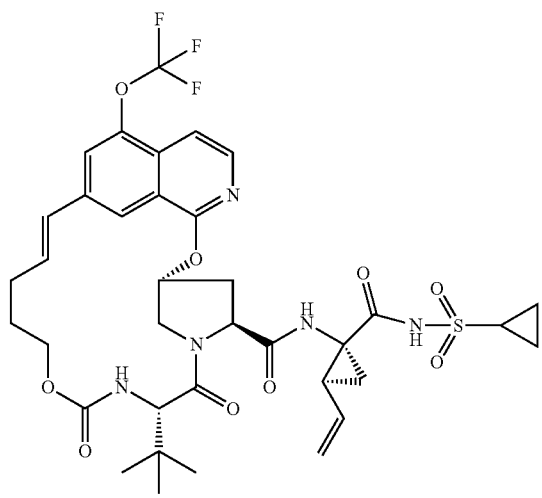
III-162
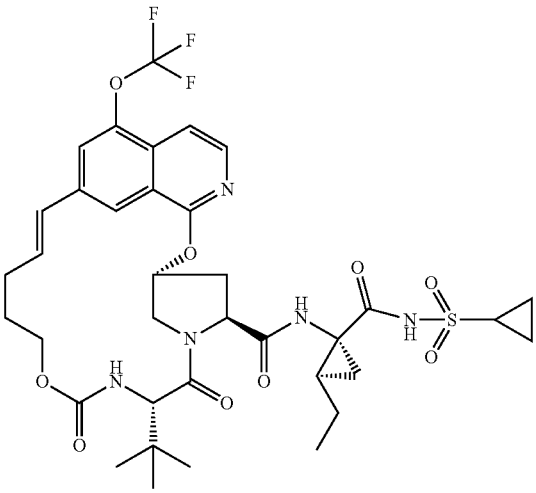
III-163
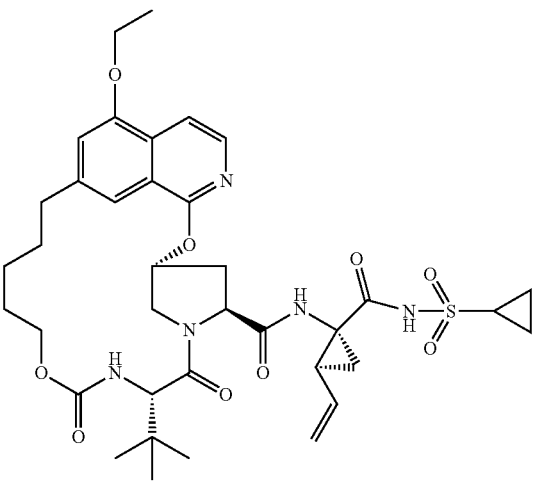
III-164
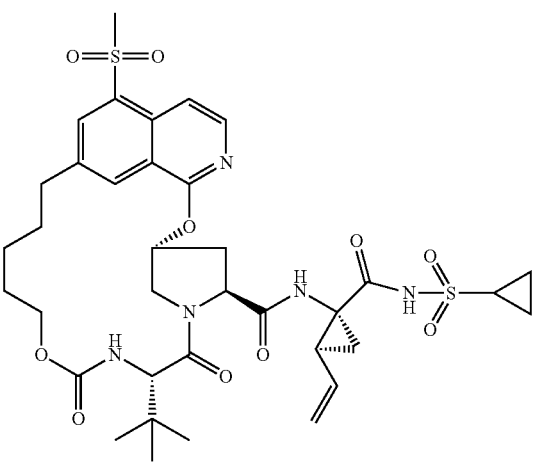

III-165
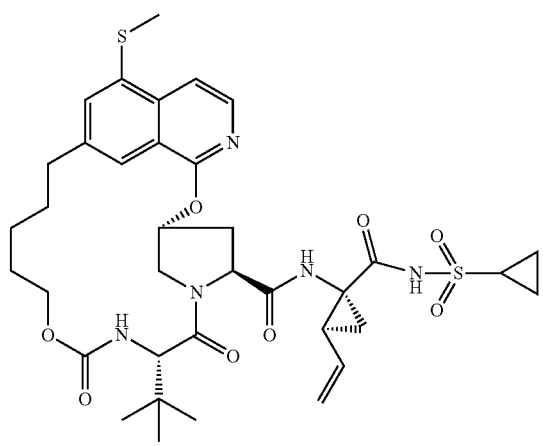
III-166
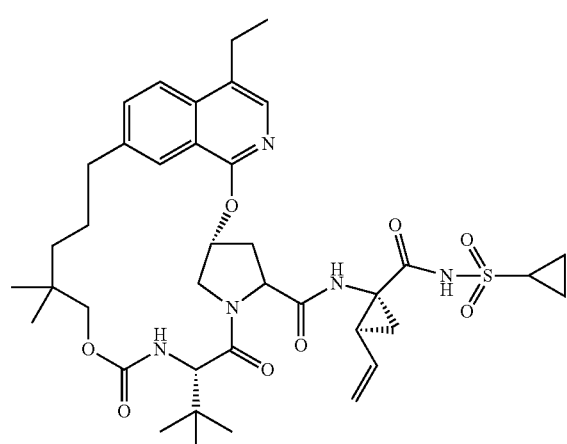
III-167
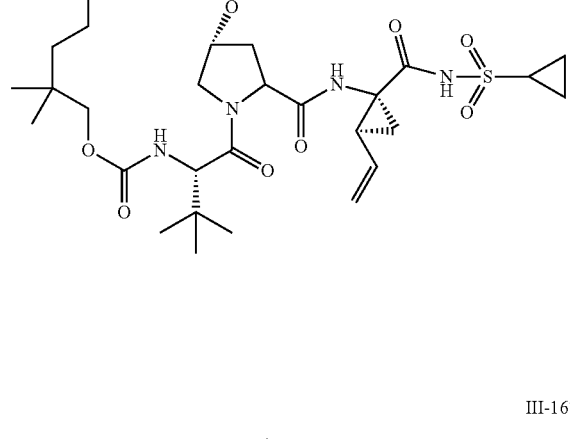
III-168
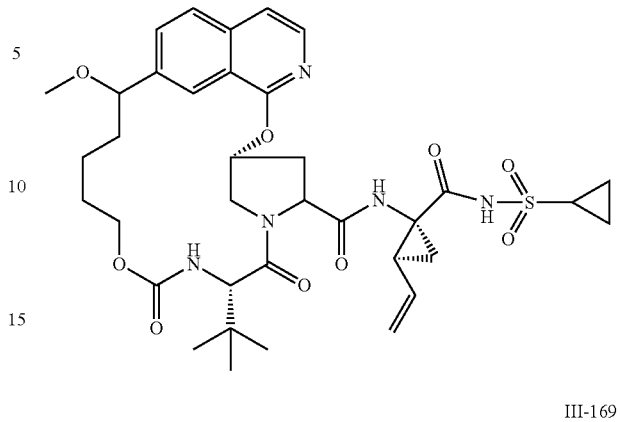
III-169
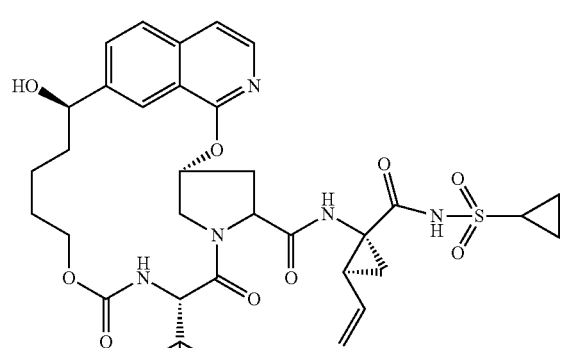
III-170
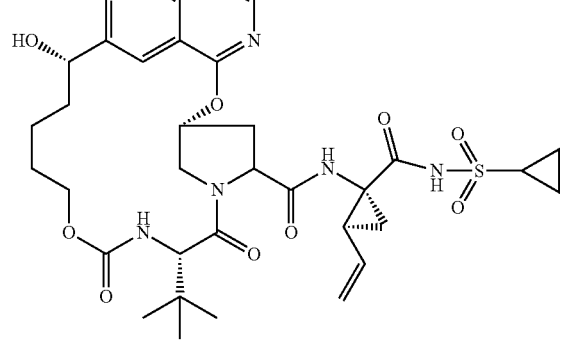
III-171
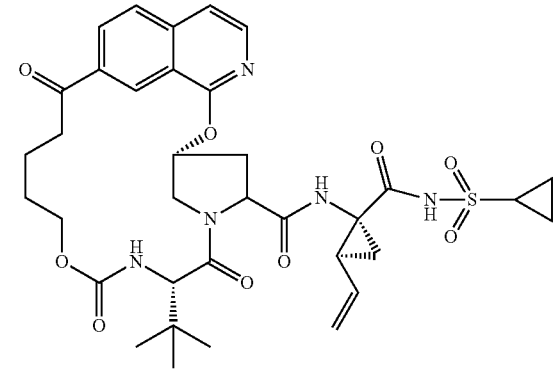

III-172
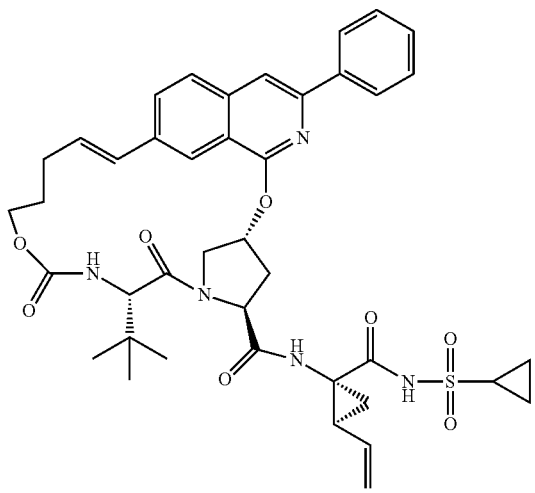
III-176
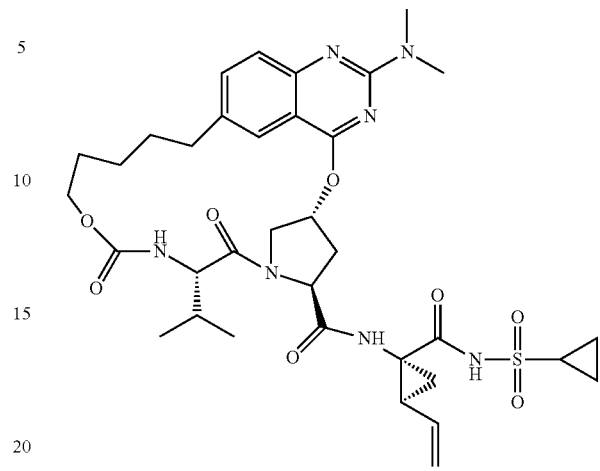
III-174
III-177
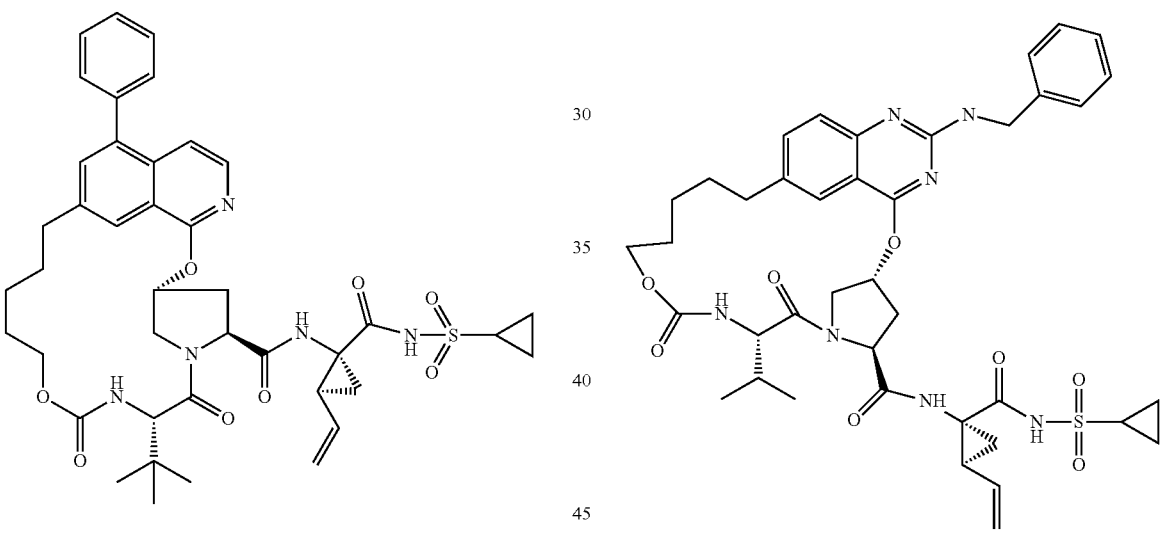
III-175
III-178
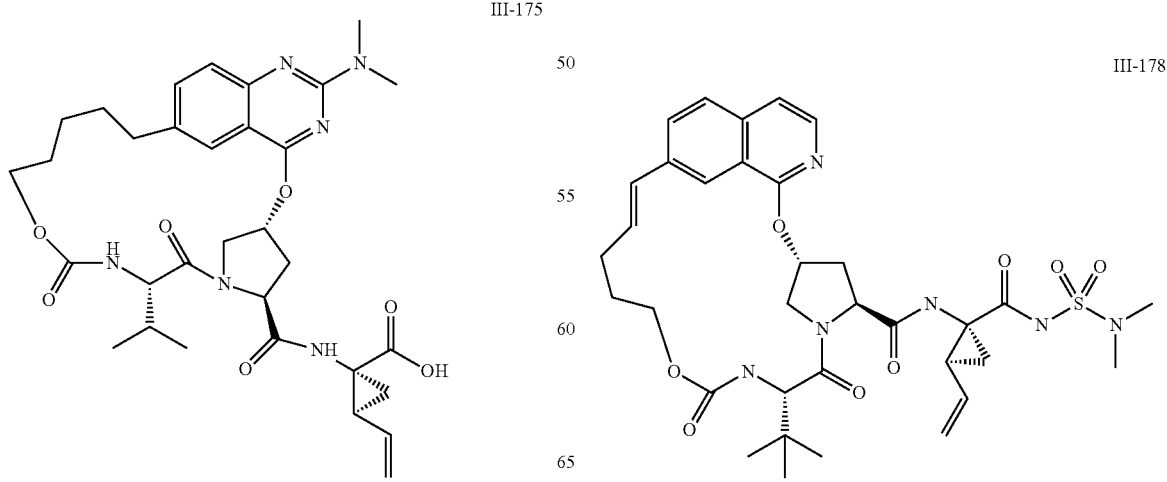

III-179
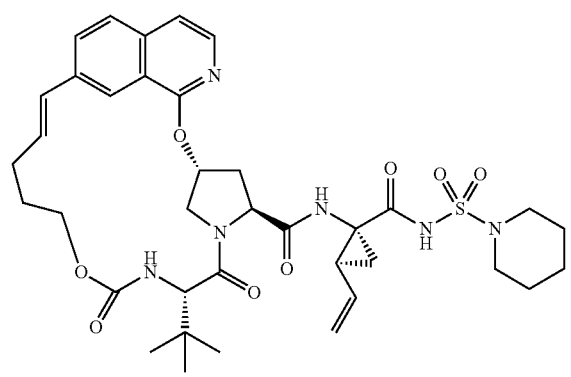
III-180
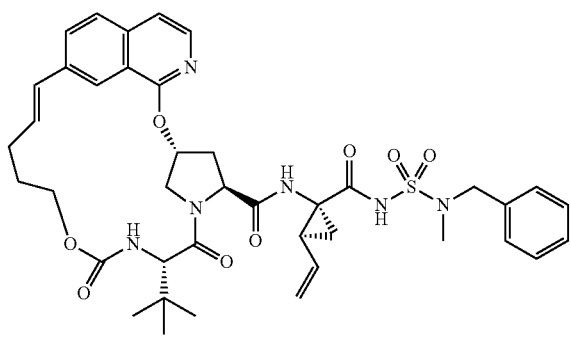
III-181
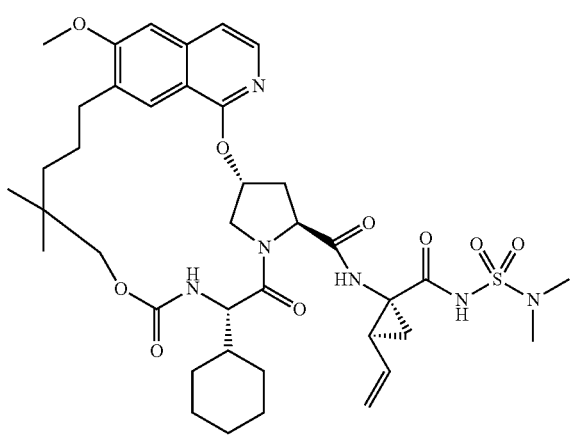
III-182
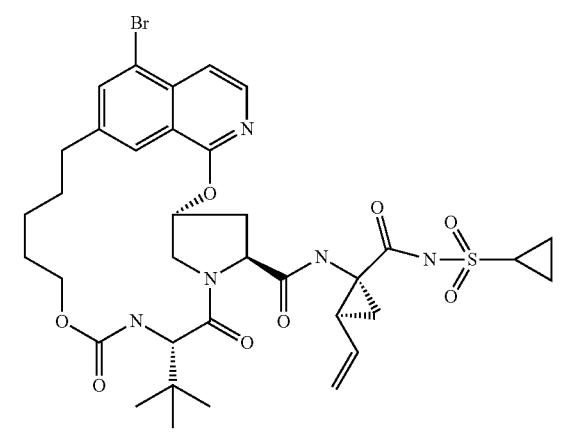
III-183
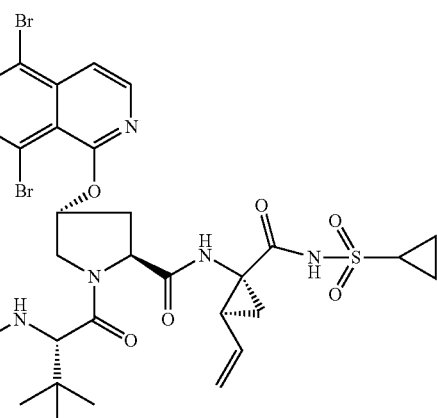
III-184
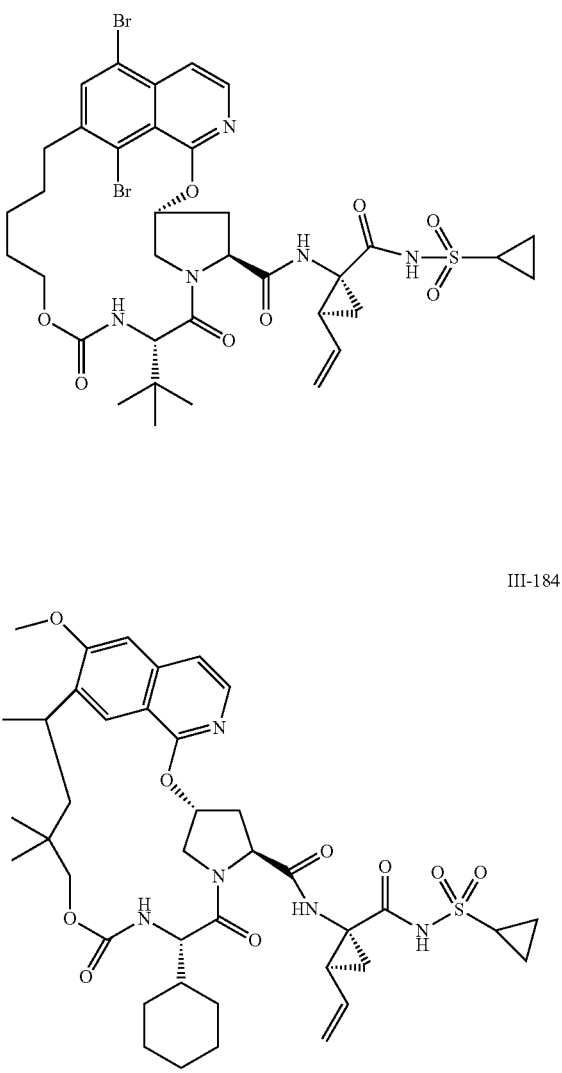
III-185
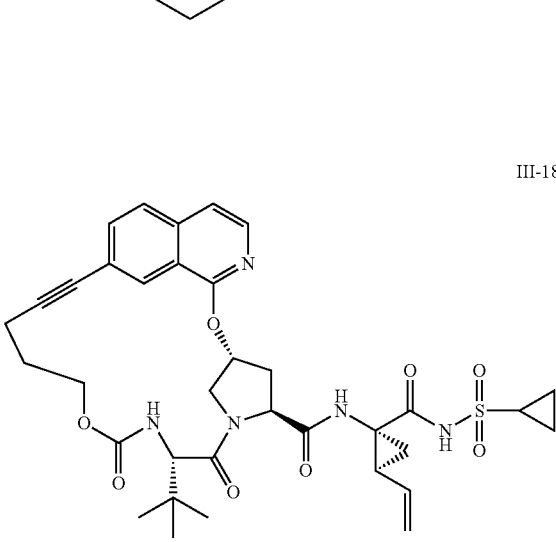
A twenty-first embodiment of the present invention is a compound of formula (I) and/or a pharmaceutically acceptable salt and/or hydrate thereof:

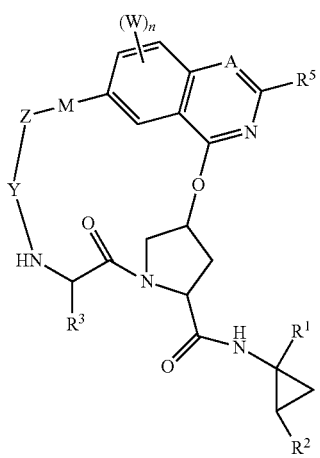

wherein:

n is 1 or 2;

R$^1$ is CO$_2$R$^{10}$, CONR$^{10}$SO$_2$R$^6$, CONR$^{10}$SO$_2$NR$^8$R$^9$, or tetrazolyl;

R$^2$ is C$_1$-C$_6$ alkyl, C$_2$-C$_6$ alkenyl or C$_3$-C$_8$ cycloalkyl, wherein said alkyl, alkenyl or cycloalkyl is optionally substituted with 1 to 3 halo;

R$^3$ is C$_1$-C$_8$ alkyl, C$_3$-C$_8$ cycloalkyl, C$_3$-C$_8$ cycloalkyl(C$_1$-C$_8$) alkyl, aryl(C$_1$-C$_8$)alkyl, or Het, wherein aryl is phenyl or naphthyl and said alkyl, cycloalkyl, or aryl is optionally substituted with 1 to 3 substituents selected from the group consisting of halo, OR$^{10}$, SR$^{10}$, N(R$^{10}$)$_2$, N(C$_1$-C$_6$ alkyl)O (C$_1$-C$_6$ alkyl), C$_1$-C$_6$ alkyl, C$_1$-C$_6$ haloalkyl, halo(C$_1$-C$_6$ alkoxy), NO$_2$, CN, CF$_3$, SO$_2$(C$_1$-C$_6$ alkyl), S(O)(C$_1$-C$_6$ alkyl), NR$^{10}$SO$_2$R$^6$, SO$_2$N(R$^6$)$_2$, NHCOOR$^6$, NHCOR$^6$, NHCONHR$^6$, CO$_2$R$^{10}$, C(O)R$^{10}$, and CON(R$^{10}$)$_2$;

Het is a 5-6 membered saturated cyclic ring having 1, 2 or 3 heteroatoms selected from N, O and S, wherein said ring is optionally substituted with 1 to 3 substituents selected from the group consisting of halo, OR$^{10}$, SR$^{10}$, N(R$^{10}$)$_2$, N(C$_1$-C$_6$ alkyl)O(C$_1$-C$_6$ alkyl), C$_1$-C$_6$ alkyl, C$_1$-C$_6$ haloalkyl, halo(C$_1$-C$_6$ alkoxy), NO$_2$, CN, CF$_3$, SO$_2$(C$_1$-C$_6$ alkyl), S(O)(C$_1$-C$_6$ alkyl), NR$^{10}$SO$_2$R$^6$, SO$_2$N(R$^6$)$_2$, NHCOOR$^6$, NHCOR$^6$, NHCONHR$^6$, CO$_2$R$^{10}$, C(O)R$^{10}$, and CON(R$^{10}$)$_2$;

R$^4$ is H, C$_1$-C$_8$ alkyl, C$_3$-C$_8$ cycloalkyl(C$_1$-C$_8$)alkyl, or aryl (C$_1$-C$_8$)alkyl; wherein aryl is phenyl or naphthyl and said alkyl, cycloalkyl, or aryl is optionally substituted with 1 to 3 substituents selected from the group consisting of halo, OR$^{10}$, SR$^{10}$, N(R$^{10}$)$_2$, N(C$_1$-C$_6$ alkyl)O(C$_1$-C$_6$ alkyl), C$_1$-C$_6$ alkyl, C$_1$-C$_6$ haloalkyl, halo(C$_1$-C$_6$ alkoxy), NO$_2$, CN, CF$_3$, SO$_2$(C$_1$-C$_6$ alkyl), S(O)(C$_1$-C$_6$ alkyl), NR$^{10}$SO$_2$R$^6$, SO$_2$N(R$^6$)$_2$, NHCOOR$^6$, NHCOR$^6$, NHCONHR$^6$, CO$_2$R$^{10}$, C(O)R$^{10}$, and CON(R$^{10}$)$_2$;

R$^5$ is H, halo, OH, C$_1$-C$_6$ alkoxy, C$_1$-C$_6$ alkyl, CN, CF$_3$, SR$^{10}$, SO$_2$(C$_1$-C$_6$ alkyl), C$_3$-C$_8$ cycloalkyl, C$_3$-C$_8$ cycloalkoxy, C$_1$-C$_6$ haloalkyl, N(R$^7$)$_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, OR$^{10}$, SR$^{10}$, N(R$^7$)$_2$, N(C$_1$-C$_6$ alkyl)O(C$_1$-C$_6$ alkyl), C$_1$-C$_6$ alkyl, C$_1$-C$_6$ haloalkyl, halo(C$_1$-C$_6$ alkoxy), C$_3$-C$_6$ cycloalkyl, C$_3$-C$_6$ cycloalkoxy, NO$_2$, CN, CF$_3$, SO$_2$(C$_1$-C$_6$ alkyl), NR$^{10}$SO$_2$R$^6$, SO$_2$N(R$^6$)$_2$, S(O)(C$_1$-C$_6$ alkyl), NHCOOR$^6$, SO$_2$N(R$^6$)$_2$, S(O)(C$_1$-C$_6$ alkyl), NHCOOR$^6$, NHCOR$^6$, NHCONHR$^6$, CO$_2$R$^{10}$, C(O)R$^{10}$, and CON (R$^{10}$)$_2$; wherein the 2 adjacent substituents of said cycloalkyl, cycloalkoxy, aryl, heteroaryl or heterocyclyl are optionally taken together to form a 3-6 membered cyclic ring containing 0-3 heteroatoms selected from N, O and S;

R$^6$ is C$_1$-C$_8$ alkyl, C$_3$-C$_8$ cycloalkyl, C$_3$-C$_8$ cycloalkyl(C$_1$-C$_5$) alkyl, aryl, aryl(C$_1$-C$_4$)alkyl, heteroaryl, heteroaryl(C$_1$-C$_4$ alkyl), heterocyclyl, or heterocyclyl(C$_1$-C$_8$ alkyl), wherein said alkyl, cycloalkyl, aryl, heteroaryl, or heterocyclyl is optionally substituted with 1 to 2 W' substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

Y is C(=O), SO$_2$, or C(=N—CN);

Z is C(R$^{10}$)$_2$, O, or N(R$^4$);

M is C$_1$-C$_{12}$ alkylene or C$_2$-C$_{12}$ alkenylene, wherein said alkylene or alkenylene is optionally substituted with 1 or 2 substituents selected from the group consisting of C$_1$-C$_8$ alkyl, C$_3$-C$_8$ cycloalkyl(C$_1$-C$_8$ alkyl), and aryl(C$_1$-C$_8$ alkyl); and the 2 substituents on adjacent carbon atoms of M are optionally taken together to form a 3-6 membered cyclic ring containing 0-3 heteroatoms selected from N, O and S;

A is C(R$^{11}$) or N;

when R$^5$ is other than H, R$^{11}$ is H, C$_1$-C$_6$ alkyl, halo, OR$^{10}$, SR$^{10}$, or N(R$^{10}$)$_2$;

when R$^5$ is H, R$^{11}$ is H, C$_1$-C$_6$ alkyl, halo, OH, C$_1$-C$_6$ alkoxy, CN, CF$_3$, SR$^{10}$, SO$_2$(C$_1$-C$_6$ alkyl), C$_3$-C$_8$ cycloalkyl, C$_3$-C$_8$ cycloalkoxy, C$_1$-C$_6$ haloalkyl, N(R$^7$)$_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, OR$^{10}$, SR$^{10}$, N(R$^7$)$_2$, N(C$_1$-C$_6$ alkyl)O(C$_1$-C$_6$ alkyl), C$_1$-C$_6$ alkyl, C$_1$-C$_6$ haloalkyl, halo(C$_1$-C$_6$ alkoxy), C$_3$-C$_6$ cycloalkyl, C$_3$-C$_6$ cycloalkoxy, NO$_2$, CN, CF$_3$, SO$_2$(C$_1$-C$_6$ alkyl), NR$^{10}$SO$_2$R$^6$, SO$_2$N(R$^6$)$_2$, S(O)(C$_1$-C$_6$ alkyl), NHCOOR$^6$, NHCOR$^6$, NHCONHR$^6$, CO$_2$R$^{10}$, C(O)R$^{10}$, and CON(R$^{10}$)$_2$; wherein the 2 adjacent substituents of said cycloalkyl, cycloalkoxy, aryl, heteroaryl or heterocyclyl are optionally taken together to form a 3-6 membered cyclic ring containing 0-3 heteroatoms selected from N, O and S;

or R$^5$ and R$^{11}$ are optionally taken together to form a 5- to 6-membered saturated, unsaturated non-aromatic, or aromatic cyclic ring having 0-2 heteroatoms selected from N, O and S;

each R$^7$ is independently H, C$_1$-C$_6$ alkyl, C$_3$-C$_6$ cycloalkyl, C$_3$-C$_6$ cycloalkyl(C$_1$-C$_5$)alkyl, aryl, aryl(C$_1$-C$_4$)alkyl, heteroaryl, heteroaryl(C$_1$-C$_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W' substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently halo, $OR^7$, $C_1$-$C_6$ alkyl, CN, $CF_3$, $NO_2$, $SR^7$, $CO_2R^7$, $CON(R^7)_2$, $C(O)R^7$, $N(R^{10})C(O)R^7$, $SO_2(C_1$-$C_6$ alkyl), $S(O)(C_1$-$C_6$ alkyl), $C_3$-$C_8$ cycloalkyl, $C_3$-$C_8$ cycloalkoxy, $C_1$-$C_6$ haloalkyl, $N(R^7)_2$, $N(C_1$-$C_6$ alkyl)$O(C_1$-$C_6$ alkyl), halo($C_1$-$C_6$ alkoxy), $NR^{10}SO_2R^7$, $SO_2N(R^7)_2$, $NHCOOR^7$, $NHCONHR^7$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein 2 adjacent W moieties are optionally taken together with the atoms to which they are attached to form a 5- to 6-membered saturated, unsaturated non-aromatic, or aromatic cyclic ring having 0-2 heteroatoms selected from N, O and S;

each W' is independently halo, $OR^{10}$, $C_1$-$C_6$ alkyl, CN, $CF_3$, $NO_2$, $SR^{10}$, $CO_2R^{10}$, $CON(R^{10})_2$, $C(O)R^{10}$, $N(R^{10})C(O)R^{10}$, $SO_2(C_1$-$C_6$ alkyl), $S(O)(C_1$-$C_6$ alkyl), $C_3$-$C_8$ cycloalkyl, $C_3$-$C_8$ cycloalkoxy, $C_1$-$C_6$ haloalkyl, $N(R^{10})_2$, $N(C_1$-$C_6$ alkyl)$O(C_1$-$C_6$ alkyl), halo($C_1$-$C_6$ alkoxy), $NR^{10}SO_2R^{10}$, $SO_2N(R^{10})_2$, $NHCOOR^{10}$, $NHCONHR^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein 2 adjacent W' moieties are optionally taken together with the atoms to which they are attached to form a 5- to 6-membered saturated, unsaturated non-aromatic, or aromatic cyclic ring having 0-2 heteroatoms selected from N, O and S;

$R^8$ is $C_1$-$C_8$ alkyl, $C_3$-$C_8$ cycloalkyl, $C_3$-$C_8$ cycloalkyl($C_1$-$C_8$ alkyl), aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein said alkyl, cycloalkyl, aryl, heteroaryl or heterocyclyl is optionally substituted with 1 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3-6 membered cyclic ring containing 0-3 heteroatoms selected from N, O and S;

$R^9$ is $C_1$-$C_8$ alkyl, $C_3$-$C_8$ cycloalkyl, $C_3$-$C_8$ cycloalkyl($C_1$-$C_8$ alkyl), $C_1$-$C_8$ alkoxy, $C_3$-$C_8$ cycloalkoxy, aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein said alkyl, cycloalkyl, alkoxy, cycloalkoxy, aryl, heteroaryl or heterocyclyl is optionally substituted with 1 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3-6 membered cyclic ring containing 0-3 heteroatoms selected from N, O and S;

or $R^8$ and $R^9$ are optionally taken together, with the nitrogen atom to which they are attached, to form a 4-8 membered monocyclic ring containing 0-2 additional heteroatoms selected from N, O and S; and each $R^{10}$ is independently H or $C_1$-$C_6$ alkyl.

A twenty-second embodiment of the present invention is a compound, or a pharmaceutically acceptable salt or hydrate thereof, which is compound III-23 ((1R,2S)-1-({[(2R,4S,7S)-7-tert-Butyl-6,9-dioxo-3,4,6,7,8,9,12,13-octahydro-2H,11H-16,18-ethanediylidene-2,5-methanopyrido[2,3-k][1,10,3,6]dioxadiazacyclononadecin-4-yl]carbonyl}amino)-2-vinylcyclopropanecarboxylic acid).

Other embodiments of the present invention include the following:

(a) A pharmaceutical composition comprising an effective amount of a compound of formula I, II, II-A, II-B, III, III-A, or III-B and a pharmaceutically acceptable carrier.

(b) The pharmaceutical composition of (a), further comprising a second therapeutic agent selected from the group consisting of a HCV antiviral agent, an immunomodulator, and an anti-infective agent.

(c) The pharmaceutical composition of (b), wherein the HCV antiviral agent is an antiviral selected from the group consisting of a HCV protease inhibitor and a HCV NS5B polymerase inhibitor.

(d) A pharmaceutical combination which is (i) a compound of formula I, II, II-A, II-B, III, III-A, or III-B and (ii) a second therapeutic agent selected from the group consisting of a HCV antiviral agent, an immunomodulator, and an anti-infective agent; wherein the compound of formula I, II-A, II-B, III, III-A, or III-B and the second therapeutic agent are each employed in an amount that renders the combination effective for inhibiting HCV NS3 protease, or for treating or preventing infection by HCV.

(e) The combination of (d), wherein the HCV antiviral agent is an antiviral selected from the group consisting of a HCV protease inhibitor and a HCV NS5B polymerase inhibitor.

(f) A method of inhibiting HCV NS3 protease in a subject in need thereof which comprises administering to the subject an effective amount of a compound of formula I, II, II-A, II-B, III, III-A, or III-B.

(g) A method of preventing or treating infection by HCV in a subject in need thereof which comprises administering to the subject an effective amount of a compound of formula II, II, II-A, II-B, III, III-A, or III-B.

(h) The method of (g), wherein the compound of formula I, II, II-A, II-B, III, III-A, or III-B is administered in combination with an effective amount of at least one second therapeutic agent selected from the group consisting of a HCV antiviral agent, an immunomodulator, and an anti-infective agent.

(i) The method of (h), wherein the HCV antiviral agent is an antiviral selected from the group consisting of a HCV protease inhibitor and a HCV NS5B polymerase inhibitor.

(j) A method of inhibiting HCV NS3 protease in a subject in need thereof which comprises administering to the subject the pharmaceutical composition of (a), (b), or (c) or the combination of (d) or (e).

(k) A method of preventing or treating infection by HCV in a subject in need thereof which comprises administering to the subject the pharmaceutical composition of (a), (b), or (c) or the combination of (d) or (e).

The present invention also includes a compound of the present invention (i) for use in, (ii) for use as a medicament for, or (iii) for use in the preparation of a medicament for: (a) inhibiting HCV NS3 protease, or (b) preventing or treating infection by HCV. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "haloalkyl" refers to an alkyl group wherein a hydrogen has been replaced by a halogen. The term "alkoxy" refers to an "alkyl-O—" group.

The term "alkylene" refers to any linear or branched chain alkylene group (or alternatively "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—.

The terms "cycloalkyl" refers to any cyclic ring of an alkane or alkene having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl. The term "cycloalkoxy" refers to a "cycloalkyl-O—" group.

The term "halogen" (or "halo") refers to fluorine, chlorine, bromine and iodine (alternatively referred to as fluoro, chloro, bromo, and iodo).

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

When any variable (e.g., $R^7$ and $R^{10}$) occurs more than one time in any constituent or in formula I, II, II-A, II-B, III, III-A, or III-B or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

Terms referring to 2 substituents "on adjacent carbon atoms" which "optionally taken together" form specified cyclic rings, and 2 substituents "on the same carbon atom" which "optionally taken together" form specified cyclic rings, mean that the 2 substituents can form a ring that includes both of the adjacent carbon atoms, or can form a ring that includes the same carbon atom. For example, ring 1 shown below is formed by two single carbon substituents each attached to adjacent carbon atoms, and ring 2 shown below is formed by two single carbon substituents each attached to the same carbon atom:

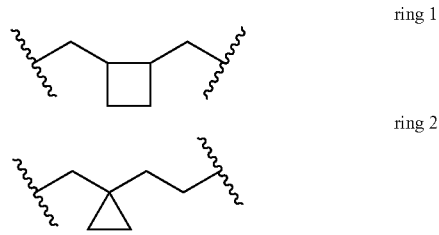

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

As would be recognized by one of ordinary skill in the art, certain of the compounds of the present invention can exist as tautomers. For the purposes of the present invention a reference to a compound of formula I, II-B, III, III-A, or III-B is a reference to the compound per se, or to any one of its tautomers per se, or to mixtures of two or more tautomers.

The compounds of the present inventions are useful in the inhibition of HCV protease (e.g., HCV NS3 protease) and the prevention or treatment of infection by HCV. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HCV protease, e.g., by competitive inhibition. Thus the compounds of this invention are commercial products to be sold for these purposes.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HCV infection), "administration" and its variants are each understood to include concurrent and sequential provision of the compound or salt (or hydrate) and other agents.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HCV NS3 protease and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HCV NS3 protease and preventing or treating HCV infection, the compounds of the present invention, optionally in the form of a salt or a hydrate, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18$^{th}$ edition, edited by A. R. Gennaro, Mack Publishing Co., 1990.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention also relates to a method of inhibiting HCV NS3 protease, inhibiting HCV replication, or preventing or treating HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include, but are not limited to, ribavirin, levovirin, viramidine, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as ROFERON interferon available from Hoffmann-LaRoche, Nutley, N.J.), pegylated interferon-α2a (PEGASYS), interferon-α2b (such as INTRON-A interferon available from Schering Corp., Kenilworth, N.J.), pegylated interferon-α2b (PEGINTRON), a recombinant consensus interferon (such as interferon alphacon-1), and a purified interferon-α product. Amgen's recombinant consensus interferon has the brand name INFERGEN. Levovirin is the L-enantiomer of ribavirin which has shown immunomodulatory activity similar to ribavirin. Viramidine represents an analog of ribavirin disclosed in WO 01/60379 (assigned to ICN Pharmaceuticals). In accordance with the method of the present invention, the individual components of the combination can be administered separately at different times during the course of therapy or concurrently in divided or single combination forms.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in WO 98/22496, WO 98/46630, WO 99/07733, WO 99/07734, WO 99/38888, WO 99/50230, WO 99/64442, WO 00/09543, WO 00/59929, GB-2337262, WO 02/48116, WO 02/48172, and U.S. Pat. No. 6,323,180.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in WO 97/41211 and WO 01/00622 (assigned to Vertex); another IMPDH inhibitor, such as that disclosed in WO 00/25780 (assigned to Bristol-Myers Squibb); or mycophenolate mofetil [see A. C. Allison and E. M. Eugui, *Agents Action*, 44 (Suppl.): 165 (1993)].

For the treatment of HCV infection, the compounds of the present invention may also be administered in combination with the antiviral agent amantadine (1-aminoadamantane) [for a comprehensive description of this agent, see J. Kirschbaum, *Anal. Profiles Drug Subs.* 12: 1-36 (1983)].

The compounds of the present invention may also be combined for the treatment of HCV infection with antiviral 2'-C-branched ribonucleosides disclosed in R. E. Harry-O'kuru, et al., *J. Org. Chem.*, 62: 1754-1759 (1997); M. S. Wolfe, et al., *Tetrahedron Lett.*, 36: 7611-7614 (1995); U.S. Pat. No. 3,480,613 (Nov. 25, 1969); International Publication Number WO 01/90121 (29 Nov. 2001); International Publication Number WO 01/92282 (6 Dec. 2001); and International Publication Number WO 02/32920 (25 Apr. 2002); and International Publication Number WO 04/002999 (8 Jan. 2004); and International Publication Number WO 04/003000 (8 Jan. 2004); and International Publication Number WO 04/002422 (8 Jan. 2004); the contents of each of which are incorporated by reference in their entirety. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-di-aminopurine, and the corresponding amino acid ester of the ribose C-2', C-3', and C-5' hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in WO 02/51425 (4 Jul. 2002), assigned to Mitsubishi Pharma Corp.; WO 01/79246, WO 02/32920, and WO 02/48165 (20 Jun. 2002), assigned to Pharmasset, Ltd.; WO 01/68663 (20 Sep. 2001), assigned to ICN Pharmaceuticals; WO 99/43691 (2 Sep. 1999); WO 02/18404 (7 Mar. 2002), assigned to Hoffmann-LaRoche; U.S. 2002/0019363 (14 Feb. 2002); WO 02/100415 (19 Dec. 2002); WO 03/026589 (3 Apr. 2003); WO 03/026675 (3 Apr. 2003); WO 03/093290 (13 Nov. 2003); US 2003/0236216 (25 Dec. 2003); US 2004/0006007 (8 Jan. 2004); WO 04/011478 (5 Feb. 2004); WO 04/013300 (12 Feb. 2004); US 2004/0063658 (1 Apr. 2004); and WO 04/028481 (8 Apr. 2004); the content of each is incorporated herein by reference in its entirety.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in WO 02/057287, U.S. Pat. No. 6,777,395, WO 02/057425, US 2004/0067901, WO 03/068244, WO 2004/000858, WO 04/003138 and WO 2004/007512; the content of each is incorporated herein by reference in its entirety. Other such HCV polymerase inhibitors include, but are not limited to, valopicitabine (NM-283; Idenix) and 2'-F-2'-beta-methyl-cytidine (see also WO 2005/003147, assigned to Pharmasset, Ltd.).

In one embodiment, nucleoside HCV NS5B polymerase inhibitors that are used in combination with the present HCV NS3 protease inhibitors are selected from the following compounds: 4-amino-7-(2-C-methyl-β-D-arabinofuranosyl)-

7H-pyrrolo[2,3-d]pyrimidine; 4-amino-7-(2-C-methyl-β-D-ribofuranosyl)-7H-pyrrolo[2,3-d]pyrimidine; 4-methylamino-7-(2-C-methyl-β-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3-d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C-ethyl-β-D-ribofuranosyl)-7H-pyrrolo[2,3-d]pyrimidine; 4-amino-7-(2-C,2-O-dimethyl-β-D-ribofuranosyl)-7H-pyrrolo[2,3-d]pyrimidine; 7-(2-C-methyl-β-D-ribofuranosyl)-7H-pyrrolo[2,3-d]pyrimidin-4(3H)-one; 2-amino-5-methyl-7-(2-C,2-O-dimethyl-β-D-ribofuranosyl)-7H-pyrrolo[2,3-d]pyrimidin-4(3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl-β-D-arabinofuranosyl)-7H-pyrrolo[2,3-d]pyrimidine; 4-amino-2-fluoro-7-(2-C-methyl-β-D-ribofuranosyl)-7H-pyrrolo[2,3-d]pyrimidine; 4-amino-7-(3-C-methyl-β-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methyl-β-D-ribofuranosyl)-7H-pyrrolo[2,3-d]pyrimidine; and the corresponding 5'-triphosphates; or a pharmaceutically acceptable salt thereof.

The compounds of the present invention may also be combined for the treatment of HCV infection with non-nucleoside inhibitors of HCV polymerase such as those disclosed in WO 01/77091 (18 Oct. 2001), assigned to Tularik, Inc.; WO 01/47883 (5 Jul. 2001), assigned to Japan Tobacco, Inc.; WO 02/04425 (17 Jan. 2002), assigned to Boehringer Ingelheim; WO 02/06246 (24 Jan. 2002), assigned to Istituto di Ricerche di Biologia Moleculare P. Angeletti S.P.A.; WO 02/20497 (3 Mar. 2002); WO 2005/016927 (in particular JTK003), assigned to Japan Tobacco, Inc.; the content of each is incorporated herein by reference in its entirety; and HCV-796 (Viropharma Inc.).

In one embodiment, non-nucleoside HCV NS5B polymerase inhibitors that are used in combination with the present HCV NS3 protease inhibitors are selected from the following compounds: 14-cyclohexyl-6-[2-(dimethylamino)ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5]benzodiazocine-11-carboxylic acid; 14-cyclohexyl-6-[2-(dimethylamino)ethyl]-3-methoxy-5,6,7,8-tetrahydroindolo[2,1-a][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl]amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[(dimethylamino)sulfonyl]-3-methoxy-6-methyl-5,6,7,8-tetrahydroindolo[2,1-a][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; N'-(11-carboxy-14-cyclohexyl-7,8-dihydro-6H-indolo[1,2-e][1,5]benzoxazocin-7-yl)-N,N-dimethylethane-1,2-diaminium bis(trifluoroacetate); 14-cyclohexyl-7,8-dihydro-6H-indolo[1,2-e][1,5]benzoxazocine-11-carboxylic acid; 14-cyclohexyl-6-methyl-7-oxo-5,6,7,8-tetrahydroindolo[2,1-a][2,5]benzodiazocine-11-carboxylic acid; 14-cyclohexyl-3-methoxy-6-methyl-7-oxo-5,6,7,8-tetrahydroindolo[2,1-a][2,5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5,6,7,8-tetrahydroindolo[2,1-a][2,5]benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-a][2,5]benzodiazocine-11-carboxylic acid; 14-cyclohexyl-6-[2-(diethylamino)ethyl]-7-oxo-5,6,7,8-tetrahydroindolo[2,1-a][2,5]benzodiazocine-11-carboxylic acid; 14-cyclohexyl-6-(1-methylpiperidin-4-yl)-7-oxo-5,6,7,8-tetrahydroindolo[2,1-a][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5]benzodiazocine-11-carboxamide; 14-cyclohexyl-6-[2-(dimethylamino)ethyl]-N-[(dimethylamino)sulfonyl]-7-oxo-5,6,7,8-tetrahydroindolo[2,1-a][2,5]benzodiazocine-11-carboxamide; 14-cyclopentyl-6-[2-(dimethylamino)ethyl]-7-oxo-5,6,7,8-tetrahydroindolo[2,1-a][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-a][2,5]benzodiazocine-11-carboxylic acid; 14-cyclohexyl-6-[2-(dimethylamino)ethyl]-5,6,7,8-tetrahydroindolo[2,1-a][2,5]benzodiazocine-11-carboxylic acid; 13-cyclohexyl-5-methyl-4,5,6,7-tetrahydrofuro[3',2':6,7][1,4]diazocino[1,8-a]indole-10-carboxylic acid; 15-cyclohexyl-6-[2-(dimethylamino)ethyl]-7-oxo-6,7,8,9-tetrahydro-5H-indolo[2,1-a][2,6]benzodiazonine-12-carboxylic acid; 15-cyclohexyl-8-oxo-6,7,8,9-tetrahydro-5H-indolo[2,1-a][2,5]benzodiazonine-12-carboxylic acid; 13-cyclohexyl-6-oxo-6,7-dihydro-5H-indolo[1,2-d][1,4]benzodiazepine-10-carboxylic acid; and pharmaceutically acceptable salts thereof.

The above tetracyclic indole-based HCV NS5B polymerase inhibitors may be obtained following methods A-E as outlined below, wherein different variables may be selected in accordance with the specific tetracyclic indole compound to be prepared:

Method A

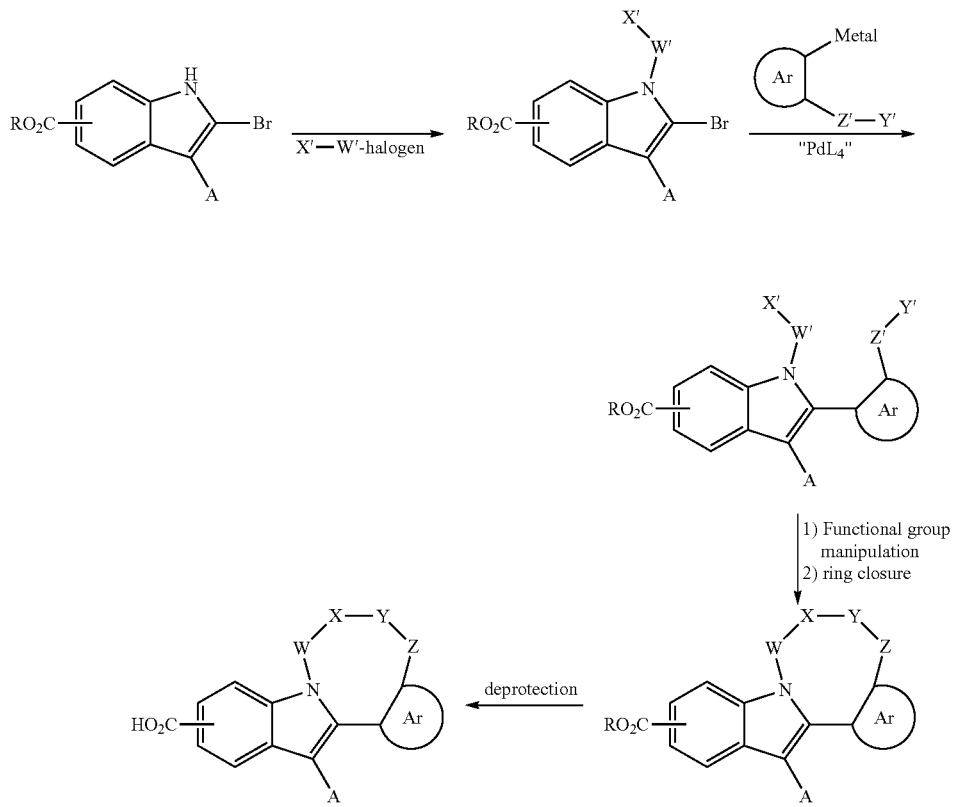

2-Bromoindole intermediate (prepared as described in published International patent application WO2004087714) was functionalized on the indole nitrogen to introduce pre-cursor functionality W'/X' to either or both of the elements W/X of the tether. Pd-mediated cross-coupling methodology (e.g., Suzuki, Stille etc.) then brought in the C2 aromatic bearing pre-cursor functionality Z'/Y' to either or both of the elements Z/Y of the tether. Functional group manipulation followed by ring closure afforded the tetracyclic system. Ester deprotection then yielded the target indole carboxylic acids, with the C2 aromatic tethered to the indole nitrogen.

Method B

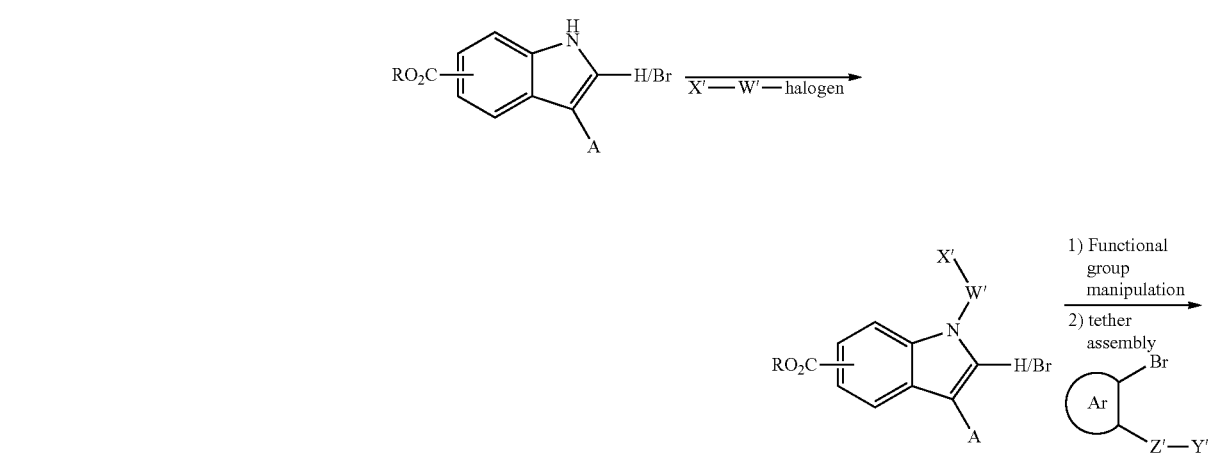

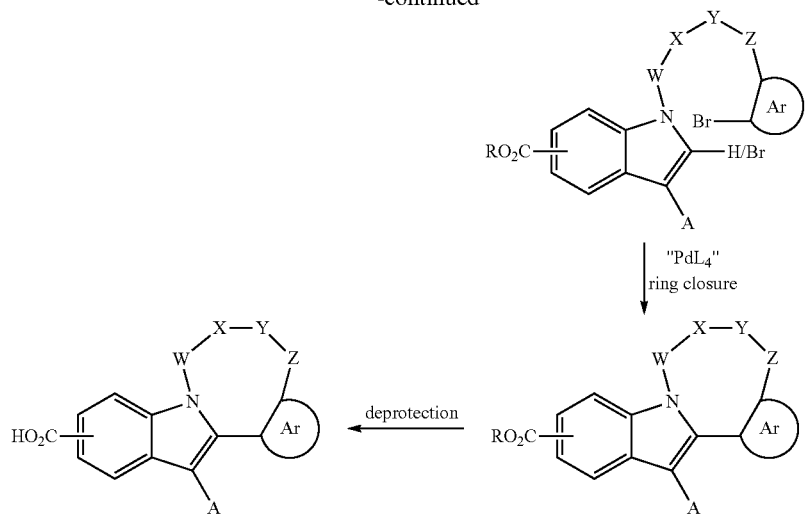
Following tether assembly out to the appropriate 2-haloaromatic, Pd-mediated ring closure afforded the fused tetracyclic system. Ester deprotection then yielded the target indole carboxylic acids, with the C2 aromatic tethered to the indole nitrogen.
Method C
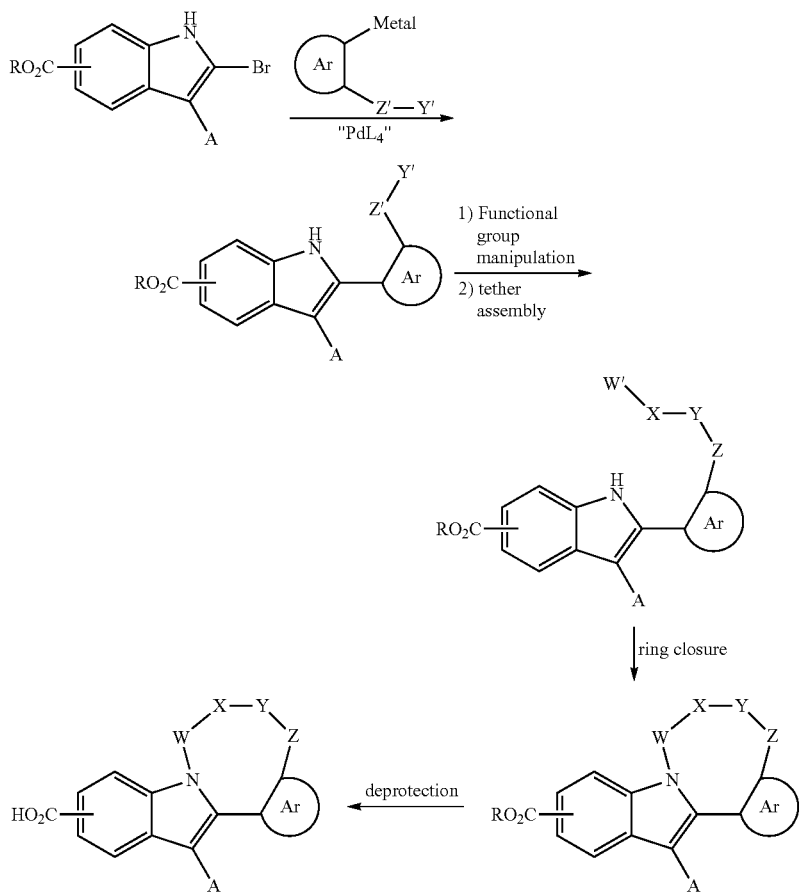

The C2 aromatic was introduced at the outset via Pd-mediated cross-coupling methodology (Suzuki, Stille etc). The tether was then built up, with cyclisation onto the indole nitrogen finally closing the ring. Ester deprotection then yielded the target indole carboxylic acids, with the C2 aromatic tethered to the indole nitrogen.

Method D

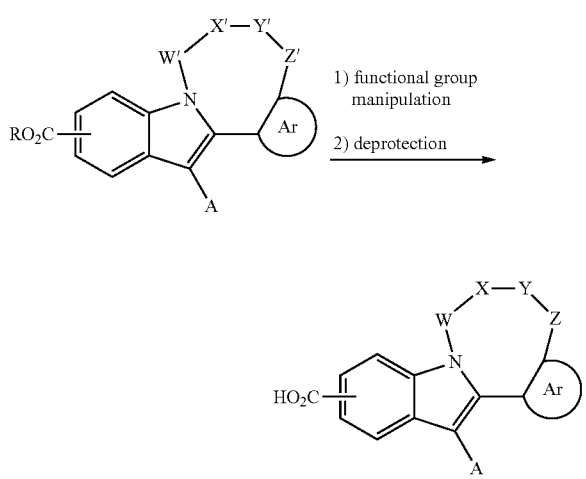

Fused tetracyclic intermediates arising from Methods A-C underwent manipulation of the functionality in the tether prior to ester deprotection to yield the target C2-tethered indole carboxylic acids.

Method E

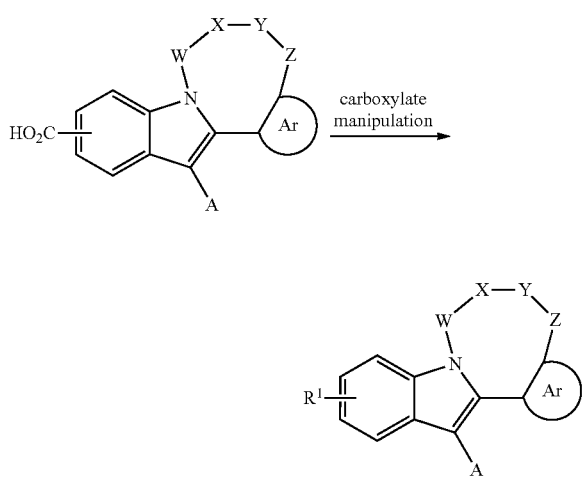

C2-tethered indole carboxylic acids arising from Methods A-D were further derivatised through manipulation of the carboxylate functionality to give compounds bearing a carboxylate replacement or carboxamide. During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The HCV NS3 protease inhibitory activity of the present compounds may be tested using assays known in the art. One such assay is HCV NS3 protease time-resolved fluorescence (TRF) assay as described in Example 9. Other examples of such assays are described in e.g., International patent publication WO2005/046712. Compounds useful as HCV NS3 protease inhibitors would have a Ki less than 50 µM, more preferably less than 10 µM, and even more preferably less than 100 nM.

The present invention also includes processes for making compounds of formula I, II, II-A, II-B, III, III-A, or III-B. The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice. The examples are not to be construed as limitations on the scope or spirit of the invention.

General Description of Synthesis:

The compounds of the present invention may be synthesized as outlined in the general Schemes 1, 2 and 3.

SCHEME 1

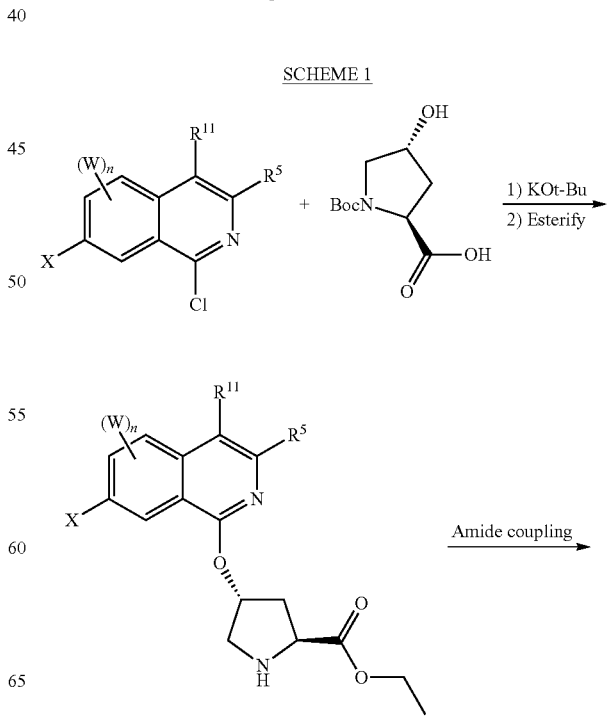

93
-continued

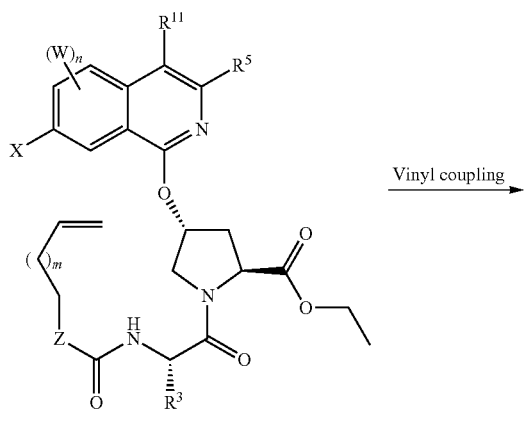

Vinyl coupling →

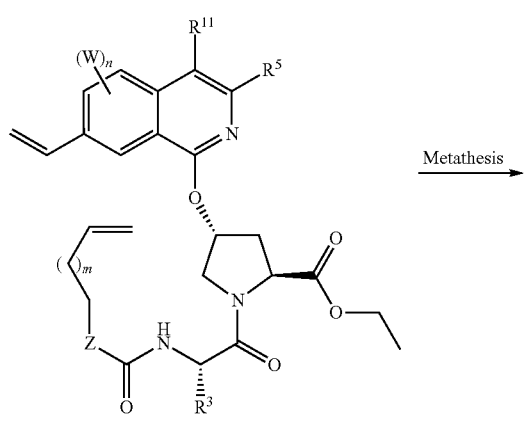

Metathesis →

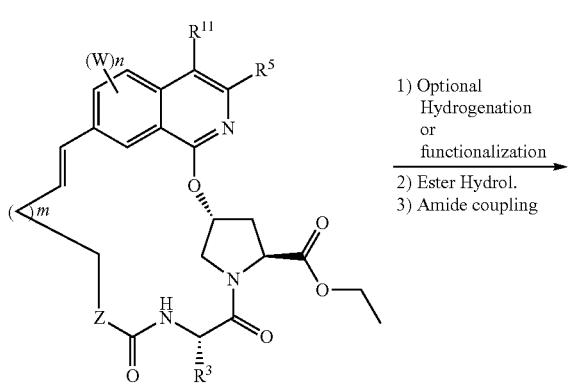

1) Optional Hydrogenation or functionalization
2) Ester Hydrol.
3) Amide coupling 94
-continued

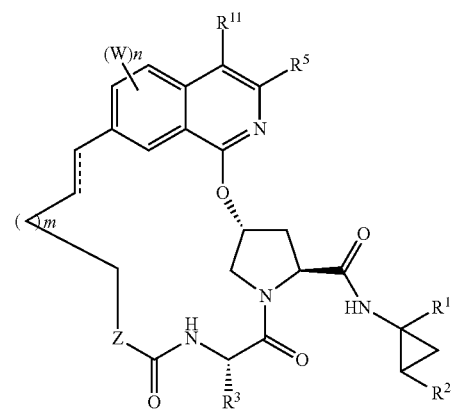

Scheme 1 (m=0-9) outlines the synthesis of a representative molecule. An appropriately protected 4-hydroxyproline derivative (for example, a carbamate protected nitrogen) can be reacted with potassium t-butoxide or equivalent reagent and then reacted with an appropriately substituted chloro-isoquinoline. The acid can then be esterified with acid in an appropriate alcohol solvent. These conditions also remove the BOC protecting group on the proline nitrogen.

Scheme 2 describes the synthesis of the olefin containing amino acid portion. An amino acid (either commercially available or may be prepared readily using known methods in the art) in which the acid functionality is protected as an ester (for example, R=methyl) can be converted to amides A by coupling an olefinic carboxylic acid utilizing a wide range of peptide coupling agents known to those skilled in the art such as DCC, EDC, BOP, TBTU, etc. Preparation of the sulfonamides B can be accomplished by reaction with the appropriate sulfonyl chloride in an organic solvent (e.g., THF) with an amine base as scavenger. Urea derivatives C may be prepared by reacting the aminoester with a reagent such as carbonyldiimidazole, to form an intermediate isocyanate (Catalano et al., WO 03/062192) followed by addition of a second olefin containing amine. Alternatively, phosgene, diphosgene or triphosgene may be used in place of carbonyldiimidazole. Cyanoguanidine derivatives D can be prepared by reaction of the amino acid ester with diphenyl C-cyanocarbonimidate in an organic solvent, followed by addition of a second olefin containing amine. Carbamate derivatives E may be prepared by reacting an olefin containing alcohol with carbonyldiimidazole (or phosgene, triphosgene or diphosgene) in an organic solvent, followed by addition of the amino ester.

SCHEME 2

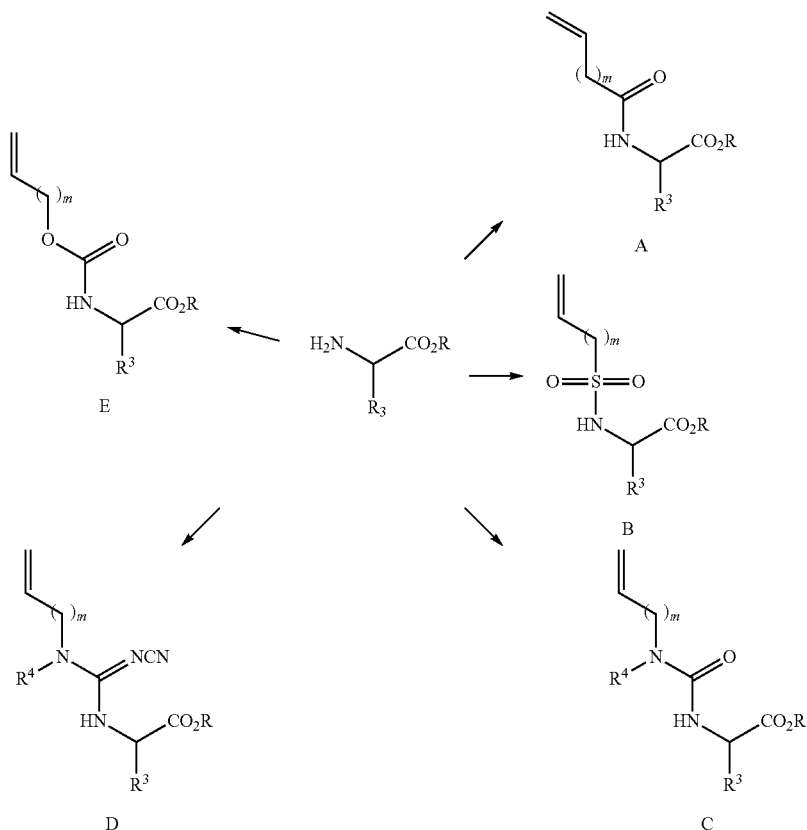

Following functionalization of the amine, the ester can be hydrolyzed under a range of basic conditions known to those skilled in the art (Theodora W. Greene, Protective Groups in Organic Synthesis, Third Edition, John Wiley and Sons, 1999).

Deprotection of the carbamate protecting group on the proline portion may be carried out by a variety of methods known to persons skilled in the art (Theodora W. Greene, Protective Groups in Organic Synthesis, Third Edition, John Wiley and Sons, 1999). To complete the synthesis of the compounds of this invention, the amino acid derivative can be coupled to the proline derivative via a wide range of peptide coupling reagents such as DCC, EDC, BOP, TBTU etc (see Scheme 1). The alkenyl functionality may be introduced at this stage by palladium catalyzed reaction of a halide substituent such as bromide or iodide, or other functionality such as a triflate with an organometallic reagent such as a vinyl or allyltrialkyltin. Macrocyclization is then achieved by an olefin metathesis using a range of catalysts that have been described in the literature for this purpose. At this stage the olefinic bond produced in the ring closing metathesis may be optionally hydrogenated to give a saturated linkage or functionalized in alternative ways such as cyclopropanation. The proline ester is then hydrolyzed under basic conditions and coupled with the cyclopropylamino acid ester (the appropriate alkenyl or alkylcyclopropane portion of the molecule can be prepared as described previously (Llinas-Brunet et al., U.S. Pat. No. 6,323,180) and subjected to an additional basic hydrolysis step to provide the final compounds. The proline ester can also be hydrolyzed and directly coupled to an appropriately functionalized cyclopropylamino acid acyl sulfonamide (which can be prepared according to Wang X. A. et al. WO2003/099274) to provide the final compounds.

Molecules with 3-substituted isoquinolines or 2-substituted quinazolines may be prepared according to Scheme 3 (wherein V is, for example, halo such as chloro). An appropriately substituted 3-halo isoquinoline or 2-halo quinazoline can be employed in a sequence similar to the route shown in Scheme 1. In a final additional step, an $R^5$ group can be installed via displacement reactions or metal-mediated coupling reactions.

SCHEME 3

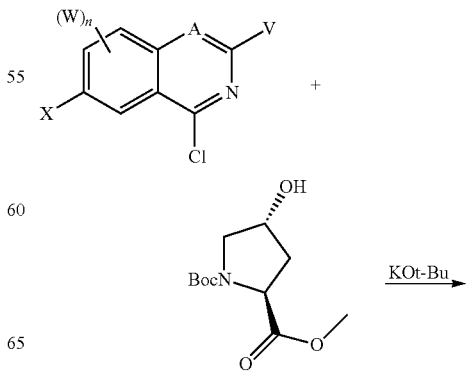

97

-continued

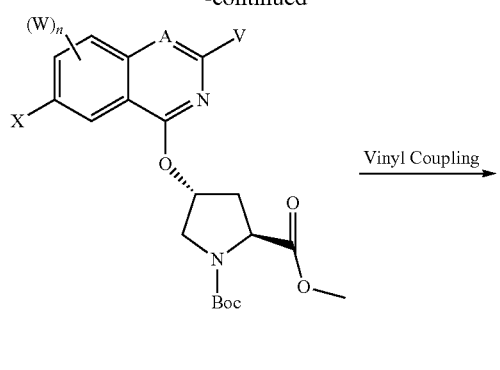

Vinyl Coupling →

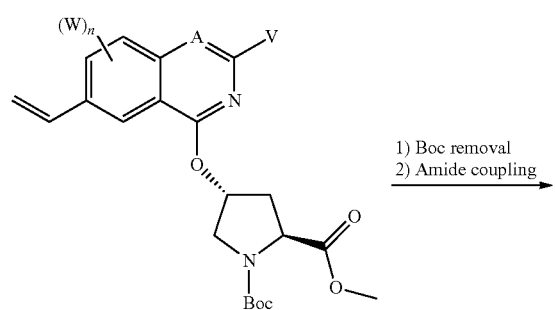

1) Boc removal
2) Amide coupling →

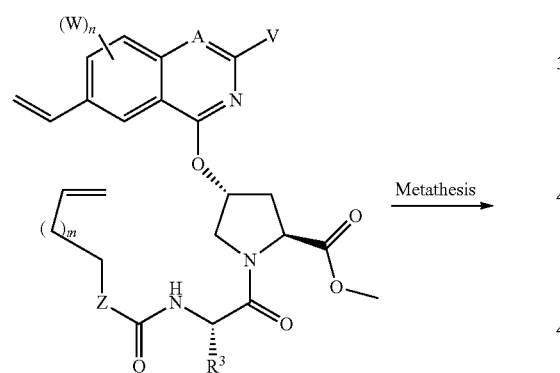

Metathesis →

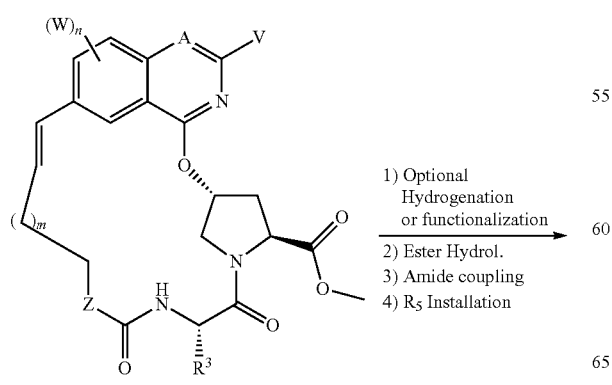

1) Optional Hydrogenation or functionalization
2) Ester Hydrol.
3) Amide coupling
4) R₅ Installation →

98

-continued

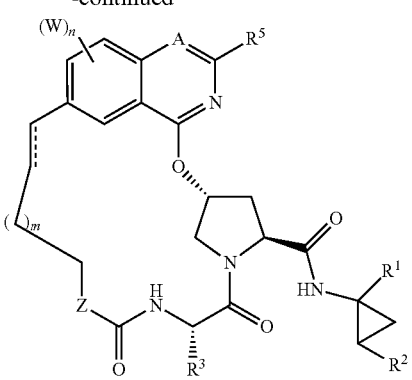

Olefin metathesis catalysts include the following Ruthenium based species: F: Miller et al *J. Am. Chem. Soc* 1996, 118, 9606; G: Kingsbury et al *J. Am. Chem. Soc* 1999, 121, 791; H: Scholl et al Org. Lett. 1999, 1, 953; Hoveyda et al US2002/0107138; K: Furstner et al. J. Org. Chem. 1999, 64, 8275. The utility of these catalysts in ring closing metathesis is well known in the literature (e.g. Trnka and Grubbs, *Acc. Chem. Res.* 2001, 34, 18).

F

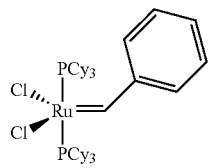

G

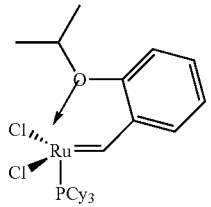

H

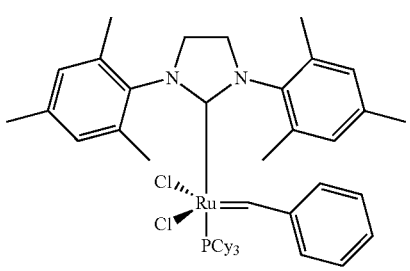

J

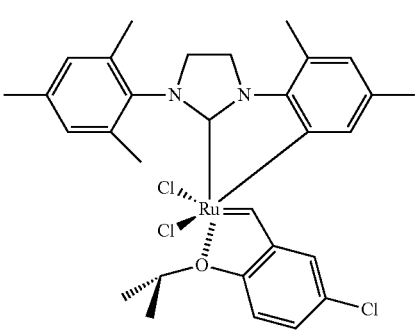

-continued

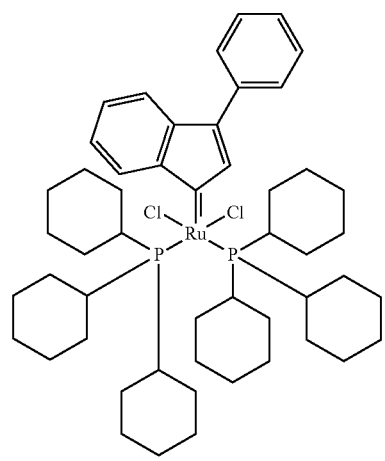

K

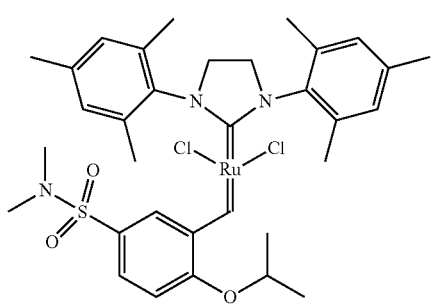

L

Structure L is the Zhan ruthenium metathesis catalyst RC-303 (Zhan catalyst 1B, RC-303, Zannan Pharma Ltd.)

List of Abbreviations
BOP   Benzotriazole-1-yl-oxy-tris-(dimethylamino)-phosphonium hexafluorophosphate
Brosyl chloride 4-Bromophenyl sulfonylchloride
CH$_3$CN Acetonitrile
DABCO 1,4-Diazabicyclo[2.2.2]octane
DBU 1,8-Diazabicyclo[5.4.0]undec-7-ene
DCC Dicyclohexylcarbodiimide
DCE Dichloroethane
DCM Dichloromethane
DMAP 4-Dimethylamino pyridine
DIPEA Diisoproylethylamine
DMF Dimethylformamide
DMSO Dimethyl Sulfoxide
EDC N-(3-Dimethylaminopropyl)-N'-ethylcarbodiimide
Et$_3$N Triethylamine
Et$_2$O Diethyl ether
EtOAc Ethyl Acetate
EtOH Ethanol
HATU O-(7-Azabenzotriazol-1-yl)-N,N,N',N'-tetramethyluronium hexafluorophosphate
HBr Hydrobromic acid
HCl Hydrochloric acid
HOAc Acetic acid
HOAt 1-Hydroxy-7-azabenzotriazole
LiOH Lithium hydroxide
MeOH Methanol
MgSO$_4$ Magnesium Sulfate
Na$_2$SO$_4$ Sodium sulfate
NaHCO$_3$ Sodium bicarbonate
NaOH Sodium hydroxide
NH$_4$Cl Ammonium chloride
NH$_4$OH Ammonium hydroxide
Nle Norleucine
Pd/C Palladium on carbon
PhMe Toluene
PPh$_3$ Triphenylphosphine
RT Room temperature
TBAF Tetrabutylammonium fluoride
TBTU O-Benzotriazol-1-yl-N,N,N',N'-tetramethyluronium tetrafluoroborate
THF Tetrahydrofuran
Synthesis of Intermediates

| Synthesis of Intermediates A | | | |
|---|---|---|---|
| Intermediate # | Structure | Name | Lit. Reference |
| A1 | | (1R,2S)-1-Amino-N-(cyclopropylsulfonyl)-2-vinylcyclopropanecarboxamide hydrochloride | Wang et al, U.S. Pat. No. 6,995,174 |
| A2 | | Ethyl (1R,2S)-1-amino-2-vinylcyclopropanecarboxylate hydrochloride | Llinas-Brunet et al, U.S. Pat. No. 6,323,180 |

Intermediate A3: (1R,2R)-1-amino-N-(cyclopropylsulfonyl)-2-ethylcyclopropanecarboxamide hydrochloride

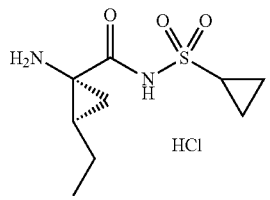

Step 1: tert-butyl ((1R,2R)-1-{[(cyclopropylsulfonyl)amino]carbonyl}-2-ethylcyclopropyl)carbamate

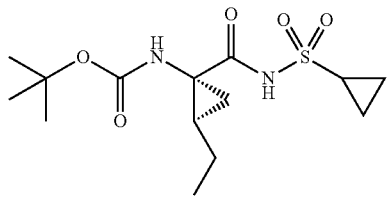

A hydrogenaton vessel was charged with a methanol (1000 mL) slurry of tert-butyl ((1R,2S)-1-{[(cyclopropylsulfonyl)amino]carbonyl}-2-vinylcyclopropyl)carbamate (164 g, 0.50 mol) (Wang et al., U.S. Pat. No. 6,995,174) and 5% Ru/C (dry, 7.5 wt %, 12.4 g) and set stirring. The vessel was placed under nitrogen (20 psig) and vented to atmospheric pressure three times to remove residual oxygen. The vessel was then placed under hydrogen (50 psig). After 20 hours, the vessel was vented to atmospheric pressure. The reaction slurry was then transferred out of the reaction and filtered through SOLKA FLOK (34 grams, wetted w/100 mL methanol) to yield a clear, light brown solution. The SOLKA FLOK was rinsed with methanol (200 mL×2). The combined methanol solutions were concentrated under reduced pressure to yield crude product as a white solid (153 g). The crude product was slurried in ethyl acetate (800 mL), warmed to 40° C. and aged 30 minutes. The solution was then seeded and aged 30 minutes, and heptane (500 mL) was added via addition funnel over 30 minutes. The partially crystallized solid was cooled to room temperature and aged overnight after which additional heptane (500 mL) was added. After one hour, additional heptane (250 mL) was added via addition funnel, and the white slurry aged for one hour. The solution was filtered, and the solid was rinsed with heptane/EtOAc (500 mL, 4:1) and dried under reduced pressure to give tert-butyl ((1R,2R)-1-{[(cyclopropylsulfony)amino]carbonyl}-2-ethylcyclopropyl)carbamate (125.9 g).

Step 2: (1R,2R)-1-amino-N-(cyclopropylsulfonyl)-2-ethylcyclopropanecarboxamide hydrochloride (Intermediate A3)

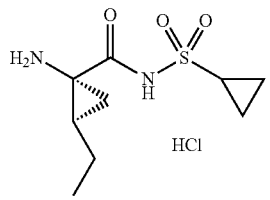

A solution of the product from Step 1 above (92 g, 0.28 mol) in DCM (1200 mL) was cooled to 0° C. and HCl bubbled through the solution for 10 min, the cooling bath removed and the reaction mixture stirred for 2 h. Nitrogen was bubbled through the reaction mixture for 5 min and the volatiles evaporated. The residue was azeotroped with DCM (×3) to give an off white powder (75 g). LRMS (M+H)$^+$ Calcd.=233; found 233

Alternative preparation of and name for Intermediate A3 (1R,2R)-1-{[(cyclopropylsulfonyl)amino]carbonyl}-2-ethylcyclopropanaminium chloride

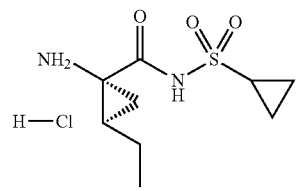

A mixture of (1R,2S)-1-{[(cyclopropylsulfonyl)amino]carbonyl}-2-vinylcyclopropanaminium chloride (0.05 g, 0.187 mmol) and palladium on carbon (10% wt., 0.01 g) in EtOAc (5 mL) was vigorously stirred under hydrogen atmosphere provided by a hydrogen balloon for 1 hour. The reaction mixture was filtered and concentrated to give (1R,2R)-1-{[(cyclopropylsulfonyl)amino]carbonyl}-2-ethylcyclopropanaminium chloride (0.045 g, 89% yield).

Preparation of Intermediates B

Preparation of Intermediate B1: N-[(pent-4-en-1-yloxy)carbonyl]-L-norleucine

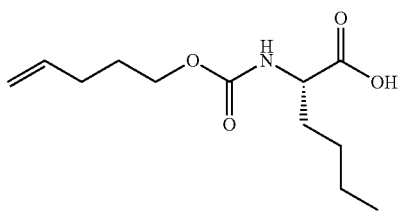

To a solution of 1-penten-4-ol (0.95 g, 11.0 mmol) in DMF (15 mL) at 0° C. was added carbonyldiimidazole (1.79 g, 11.0 mmol). The reaction mixture was warmed to room temperature and stirred for 30 min. L-norleucine methyl ester hydrochloride (2.0 g, 11.0 mmol) was then added, the reaction mixture was heated to 50° C. and stirred for 15 min. Upon cooling, the reaction mixture was diluted with ethyl ether and washed twice with water. The organic layer was dried over sodium sulfate, filtered and concentrated. The crude product was purified by silica gel chromatography (gradient elution 10 to 90% ethyl acetate in hexanes) to afford 2.1 g (74%) methyl N-[(pent-4-en-1-yloxy)carbonyl]-L-norleucinate as a clear oil.

To a stirred solution of methyl N-[(pent-4-enyloxy)carbonyl]-L-norleucinate (8.50 g, 33.03 mmol) in THF (20 mL) was added 1N NaOH (20 mL). This reaction solution was stirred at r.t. for 3 h, then acidified to pH 3 with 1N HCl and extracted with (3×250 mL) EtOAc. The combined EtOAc layer was washed with 50 mL water, 50 mL brine, dried over sodium sulfate, filtered and concentrated to give 7.09 g (88%)

Preparation of Intermediate B2 (2S)-3,3-dimethyl-2-{[(pent-4-en-1-yloxy)carbonyl]amino}butanoic acid

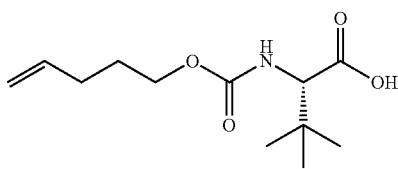

Diisopropylethyl amine (9.85 g, 76.2 mmol) was added dropwise to a 0° C. solution of 4-penten-1-ol (7.22 g, 83.9 mmol) and triphosgene (11.3 g, 38.1 mmol) in 160 mL dioxane. The resulting white suspension was stirred for 5 min at 0° C., then allowed to warm to 25° C. over 1 h. The suspension was cooled to 0° C. with an ice bath and 1 N NaOH (76.2 mL) and L-tert-butylglycine (10.0 g, 76.2 mmol) were added. The reaction mixture was warmed to 25° C. and stirred for 18 h. The dioxane was removed in vacuo and the reaction mixture was basified to pH 12 with 1 N NaOH. The aqueous layer was extracted with dichloromethane (3×150 mL), then acidified to pH~1 with 6 N HCl. The aqueous layer was extracted with dichloromethane (3×150 mL). The combined organic layers were dried over $MgSO_4$ and concentrated to give the compound as a tan oil (13.7 g, 73.9% yield). LRMS (ESI) m/z 244 [(M+H)$^+$; calcd for $C_{12}H_{22}NO_4$ 244].

The following carbamate intermediates (B3-B49) were prepared using the chemistry described for the preparation of (2S)-3,3-dimethyl-2-{[(pent-4-en-1-yloxy)carbonyl]amino}butanoic acid (B2), by utilizing the appropriate amino acid and alcohol or the preparation of N-[(Pent-4-en-1-yloxy)carbonyl]-L-norleucine (B1) by utilizing the appropriate alcohol and amino ester.

| Int | Amino Acid | Alcohol | Structure | Name | LRMS (M + H)$^+$ |
|---|---|---|---|---|---|
| B1 | L-Norleucine | 4-Penten-1-ol | 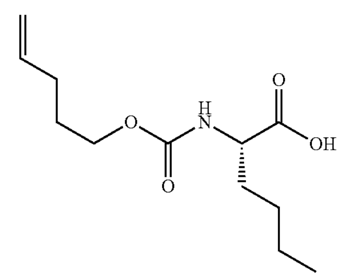 | N-[(Pent-4-en-1-yloxy)carbonyl]-L-norleucine (Intermediate 1) | 244.3 |
| B2 | L-t-Butyl-glycine | 4-Penten-1-ol | 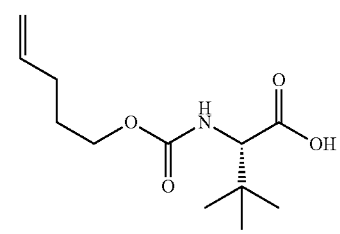 | (2S)-3,3-Dimethyl-2-{[(pent-4-en-1-yloxy)carbonyl]amino}butanoic acid | 244.2 |
| B3 | L-Valine | 4-Penten-1-ol | 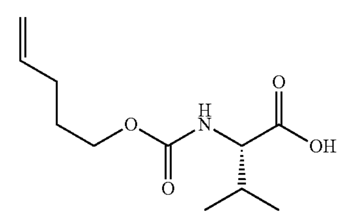 | N-[(Pent-4-en-1-yloxy)carbonyl]-L-valine | 230.3 |
| B4 | L-t-Butyl-glycine | 3,3-Dimethyl-4-penten-1-ol Ref: *Tetrahedron Lett.* (2004), 45, 2939. | 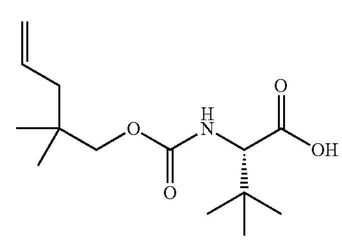 | N-{[(2,2-Dimethylpent-4-en-1-yl)oxy]carbonyl}-3-methyl-L-valine | 272.3 |

-continued

| Int | Amino Acid | Alcohol | Structure | Name | LRMS (M + H)+ |
|---|---|---|---|---|---|
| B5 | L-t-Butyl-glycine | 5-Hexen-1-ol | 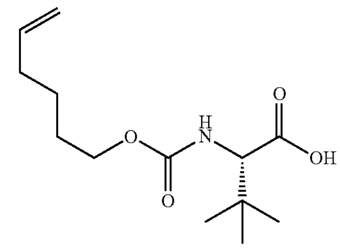 | N-[(Hex-5-en-1-yloxy)carbonyl]-3-methyl-L-valine | 258.3 |
| B6 | L-Phenyl-glycine | 4-Penten-1-ol | 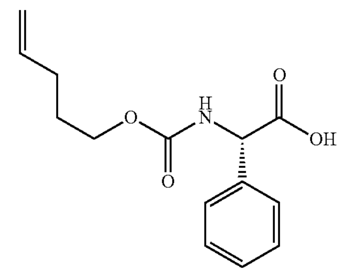 | (2S)-{[(Pent-4-en-1-yloxy)carbonyl]amino}(phenyl)acetic acid | 264.3 |
| B7 | L-t-Butyl-glycine | 6-Hepten-1-ol | 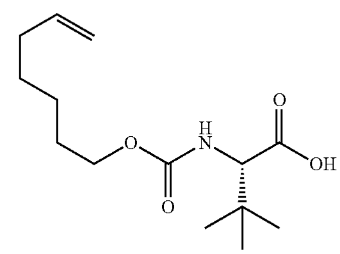 | N-[(Hept-6-en-1-yloxy)carbonyl]-3-methyl-L-valine | 272.3 |
| B8 | L-Cyclohexyl-glycine | 4-Penten-1-ol | 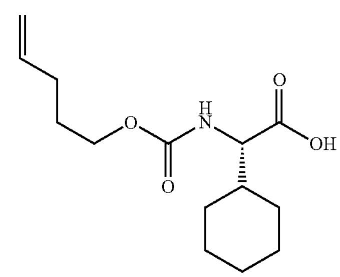 | (2S)-Cyclohexyl{[(pent-4-en-1-yloxy)carbonyl]amino}acetic acid | 270.3 |
| B9 | L-Phenyl alanine | 4-Penten-1-ol | 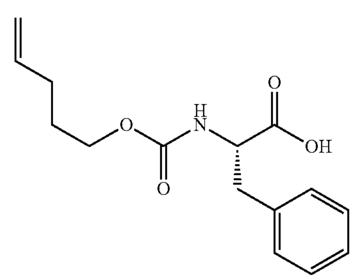 | N-{(Pent-4-en-1-yloxy)carbonyl]-L-phenylalanine | 278.2 |
| B10 | 3,3,3-Trifluoroalanine | 4-Penten-1-ol | 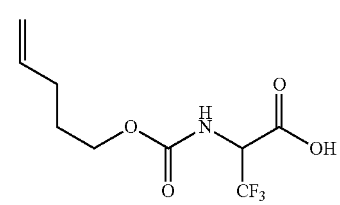 | 3,3,3-trifluoro-N-[(pent-4-en-1-yloxy)carbonyl]alanine | 256.2 |

-continued

| Int | Amino Acid | Alcohol | Structure | Name | LRMS (M + H)+ |
|---|---|---|---|---|---|
| B11 | L-t-Butyl-glycine | 4-Pentyn-1-ol | 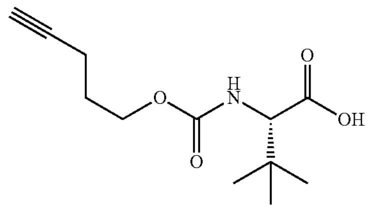 | 3-Methyl-N-[(pent-4-yn-1-yloxy)carbonyl]-L-valine | 242.2 |
| B12 | L-Norvaline | 4-Penten-1-ol | 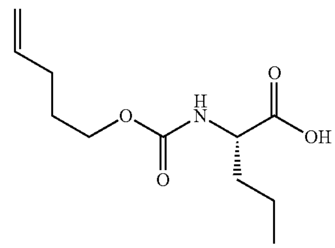 | N-[(Pent-4-en-1-yloxy)carbonyl]-L-norvaline | 230.3 |
| B13 | L-Cyclopentyl-glycine | 4-Penten-1-ol | 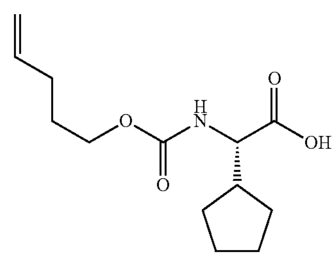 | (2S)-Cyclopentyl{[(pent-4-en-1-yloxy)carbonyl]amino}acetic acid | 256.3 |
| B14 | 2-Amino-4,4,4-trifluorobutanoic acid | 5-Hexen-1-ol | 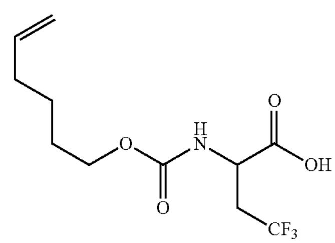 | 4,4,4-Trifluoro-2-{[(hex-5-en-1-yloxy)carbonyl]amino}butanoic acid | 305.2 (M + Na)+ |
| B15 | L-Leucine | 4-Penten-1-ol | 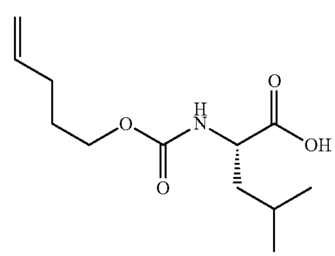 | N-[(Pent-4-en-1-yloxy)carbonyl]-L-leucine | 244.3 |
| B16 | L-Tryptophan | 4-Penten-1-ol | 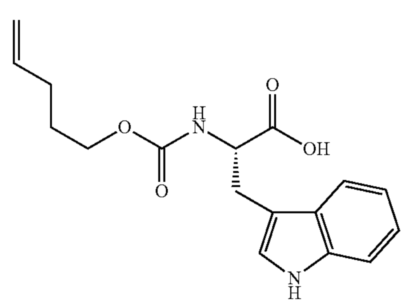 | N-[(Pent-4-en-1-yloxy)carbonyl]-L-tryptophan | 317.4 |

-continued

| Int | Amino Acid | Alcohol | Structure | Name | LRMS (M + H)+ |
|---|---|---|---|---|---|
| B17 | O-(tert-Butyl)-L-serine | 4-Penten-1-ol | 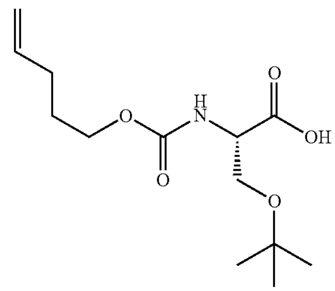 | O-(tert-Butyl)-N-[(pent-4-en-1-yloxy)carbonyl]-L-serine | 218.3 (M − tBu)+ |
| B18 | 6,6,6-trifluoronorleucine | 5-Hexen-1-ol | 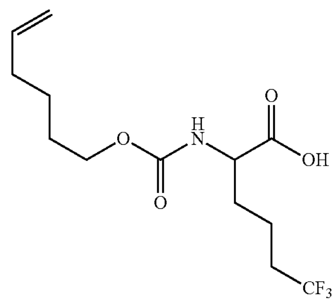 | 6,6,6-Trifluoro-N-[(hex-5-en-1-yloxy)carbonyl]norleucine | 353.2 (M + MeCN)+ |
| B19 | Amino(2,3-dihydro-1H-inden-2-yl)acetic acid | 4-Penten-1-ol | 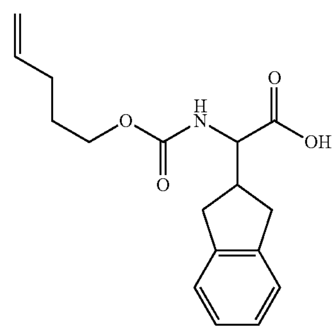 | 2,3-Dihydro-1H-inden-2-yl{[(pent-4-en-1-yloxy)carbonyl]amino}acetic acid | 304.3 |
| B20 | L-t-Butyl-glycine | (trans)-2-allylcyclohexanol Ref: *Tetrahedron* (2004), 60, 4837. | 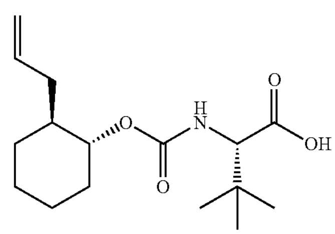 | N-({[(trans)-2-Allylcyclohexyl]oxy}carbonyl)-3-methyl-L-valine | 298.4 |
| B21 | L-Cyclohexyl-glycine | 3-Buten-1-ol | 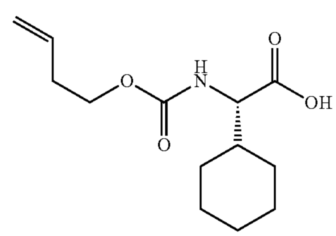 | (2S)-{[(But-3-en-1-yloxy)carbonyl]amino}(cyclohexyl)acetic acid | 256.2 |
| B22 | L-t-Butyl-glycine | 3-Buten-1-ol | 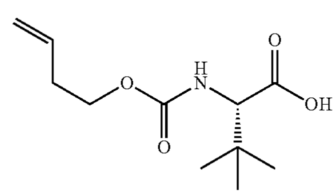 | N-[(But-3-en-1-yloxy)carbonyl]-3-methyl-L-valine | 230.3 |

-continued

| Int | Amino Acid | Alcohol | Structure | Name | LRMS (M + H)+ |
|---|---|---|---|---|---|
| B23 | L-Cyclohexyl-glycine | 2,2-Dimethyl-4-penten-1-ol Ref: *Tetrahedron Lett.* (2004), 45, 2939. | 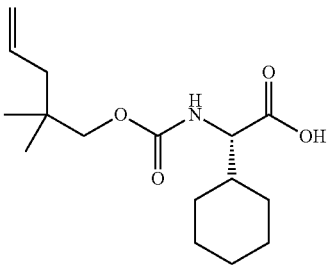 | (2S)-Cyclohexyl({[(2,2-dimethylpent-4-en-1-yl)oxy]carbonyl}amino) acetic acid | 298.3 |
| B24 | L-Cyclopentyl-glycine | 2,2-Dimethyl-4-penten-1-ol Ref: *Tetrahedron Lett.* (2004), 45, 2939. | 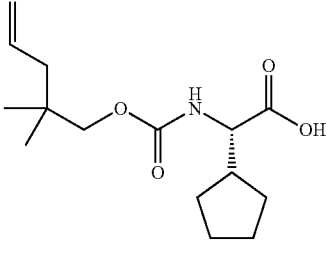 | (2S)-Cyclopentyl({[(2,2-dimethylpent-4-en-1-yl)oxy]carbonyl}amino) acetic acid | 284.3 |
| B25 | L-t-Butyl-glycine | 2,2-Dimethylhex-5-en-1-ol Ref: *J. Org. Chem.* (1991), 56, 1623. | 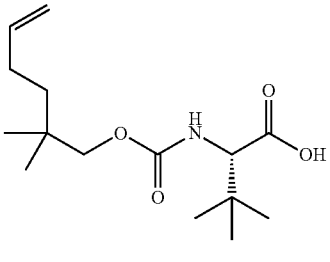 | N-{[(2,2-Dimethylhex-5-en-1-yl)oxy]carbonyl}-3-methyl-L-valine | 286.3 |
| B26 | L-Cyclohexyl-glycine | 6-Hepten-1-ol | 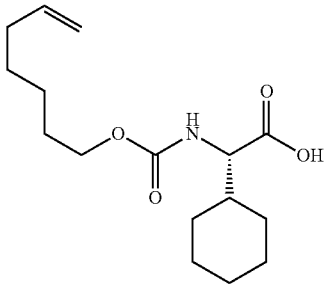 | (2S)-Cyclohexyl{[(hept-6-en-1-yloxy)carbonyl]amino} acetic acid | 298.3 |
| B27 | L-t-Butyl-glycine | 7-Octen-1-ol | 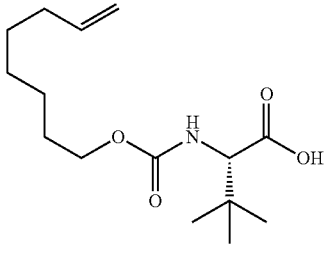 | 3-Methyl-N-[(oct-7-en-1-yloxy)carbonyl]-L-valine | 286.3 |

-continued

| Int | Amino Acid | Alcohol | Structure | Name | LRMS (M + H)+ |
|---|---|---|---|---|---|
| B28 | L-Cyclohexyl-glycine | 5-Hexen-1-ol | 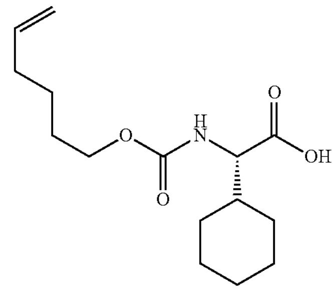 | (2S)-Cyclohexyl{[(hex-5-en-1-yloxy)carbonyl]amino} acetic acid | 284.4 |
| B29 | L-t-Butyl-glycine | (trans)-2-Allyl cyclopentanol Ref: *J. Chem. Soc., Perkin Trans 1* (1994), 11, 1377. | 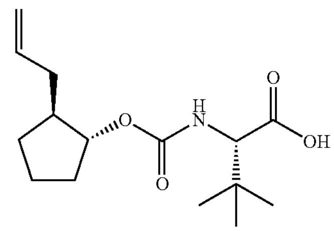 | N-({[(trans)-2-Allylcyclopentyl]oxy} carbonyl)-3-methyl-L-valine | 284.2 |
| B30 | L-Cyclohexyl-glycine | 1-Methylpent-4-en-1-ol Ref: *Tetrahedron Assym.* (1998), 9, 657. | 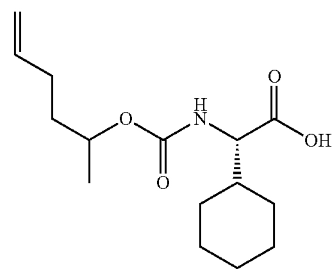 | (2S)-Cyclohexyl({[(1-methylpent-4-en-1-yl)oxy]carbonyl}amino) acetic acid | 284.2 |
| B31 | L-Cyclopentyl-glycine | 5-Hexen-1-ol | 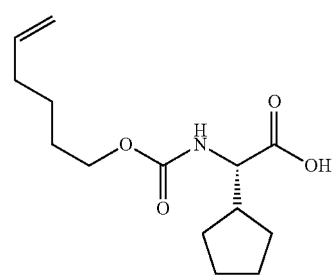 | (2S)-Cyclopentyl{[(hex-5-en-1-yloxy)carbonyl]amino} acetic acid | 270.3 |
| B32 | L-Cyclopentyl-glycine | 6-Hepten-1-ol | 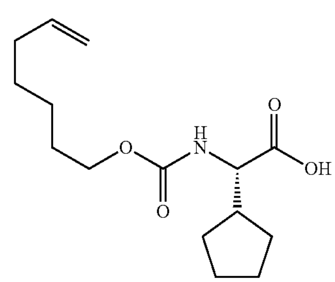 | (2S)-Cyclopentyl{[(hept-6-en-1-yloxy)carbonyl]amino} acetic acid | 284.4 |

-continued

| Int | Amino Acid | Alcohol | Structure | Name | LRMS (M + H)+ |
|---|---|---|---|---|---|
| B33 | L-Cyclobutyl-glycine | 4-Penten-1-ol | 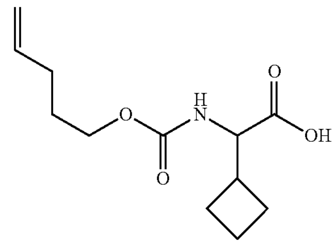 | Cyclobutyl{[(pent-4-en-1-yloxy)carbonyl]amino}acetic acid | 242.3 |
| B34 | L-Cyclopentyl-glycine | 2,2-Dimethylhex-5-en-1-ol Ref: *J Org. Chem.* (1991), 56, 1623. | 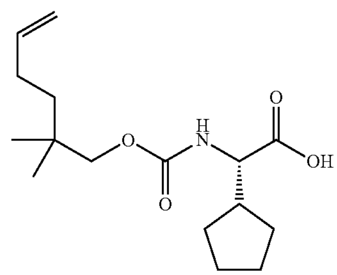 | (2S)-Cyclopentyl({[(2,2-dimethylhex-5-en-1-yl)oxy]carbonyl}amino)acetic acid | 298.3 |
| B35 | L-Cyclohexyl-glycine | 2,2-Dimethylhex-5-en-1-ol Ref: *J Org. Chem.* (1991), 56, 1623. | 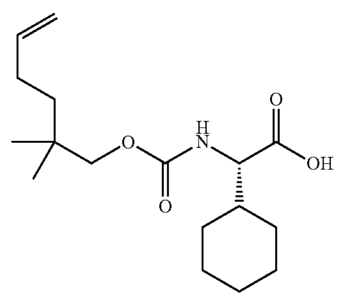 | (2S)-Cyclohexyl({[(2,2-dimethylhex-5-en-1-yl)oxy]carbonyl}amino)acetic acid | 312.3 |
| B36 | L-Cyclopentyl-glycine | 2,2-Dimethylhept-6-en-1-ol Ref: *J. Org. Chem.* (1980), 45, 2685. | 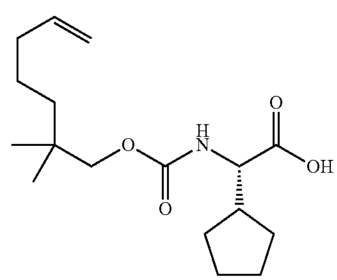 | (2S)-Cyclopentyl({[(2,2-dimethylhept-6-en-1-yl)oxy]carbonyl}amino)acetic acid | 312.2 |
| B37 | L-Cyclohexyl-glycine | 8-Nonen-1-ol | 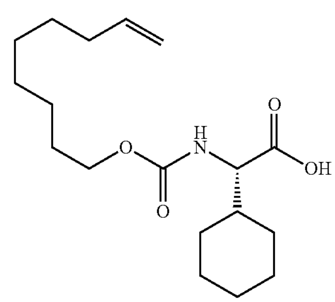 | (2S)-Cyclohexyl{[(non-8-en-1-yloxy)carbonyl]amino}acetic acid | 326.3 |

-continued

| Int | Amino Acid | Alcohol | Structure | Name | LRMS (M + H)+ |
|---|---|---|---|---|---|
| B38 | L-Cyclopentyl-glycine | (trans)-2-Allyl cyclopentanol Ref: *J. Chem. Soc., Perkin Trans 1* (1994), 11, 1377. | 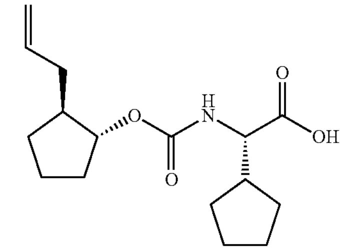 | (2S)-[({[(trans)-2-Allylcyclopentyl]oxy}carbonyl)amino](cyclopentyl)acetic acid | 296.4 |
| B39 | L-Cyclohexyl-glycine | 2-Methylpent-4-en-1-ol Ref: *Tetrahedron* (1993), 49, 947. | 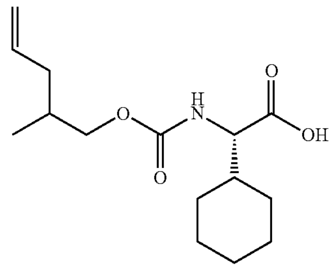 | (2S)-Cyclohexyl({[(2-methylpent-4-en-1-yl)oxy]carbonyl}amino)acetic acid | 284.4 |
| B40 | L-Cyclohexyl-glycine | 2,2-Dimethylhept-6-en-1-ol Ref: *J. Org. Chem.* (1980), 45, 2685. | 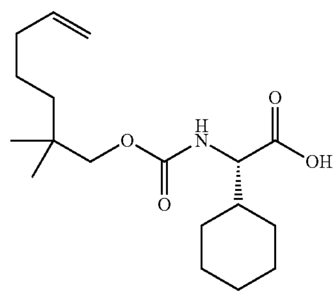 | (2S)-Cyclohexyl({[(2,2-dimethylhept-6-en-1-yl)oxy]carbonyl}amino)acetic acid | 326.4 |
| B41 | L-Cyclohexyl-glycine | (trans)-2-Allyl cyclopentanol Ref: *J. Chem. Soc., Perkin Trans 1* (1994), 11, 1377. | 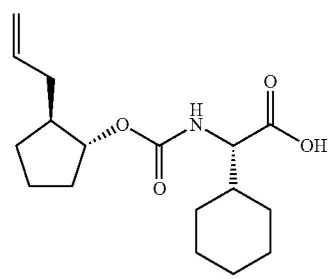 | (2S)-[({[(trans)-2-Allylcyclopentyl]oxy}carbonyl)amino](cyclohexyl) acetic acid | 310.5 |
| B42 | L-Cyclohexyl-glycine | (1-Allyl cyclopentyl) methanol) Ref: *J. Org. Chem.* (1992), 57, 1727. | 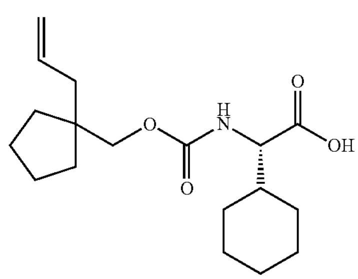 | (2S)-({[(1-Allylcyclopentyl)methoxy]carbonyl}amino)(cyclohexyl)acetic acid | 324.3 |

-continued

| Int | Amino Acid | Alcohol | Structure | Name | LRMS (M + H)+ |
|---|---|---|---|---|---|
| B43 | L-Cyclohexyl-glycine | 2-Ethylpent-4-en-1-ol Ref: *Tetrahedron Lett.* (1985), 26, 6085. | 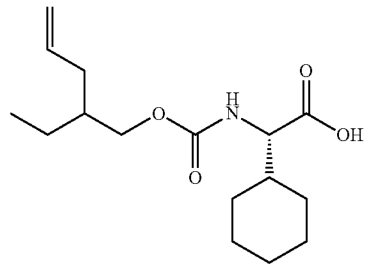 | (2S)-Cyclohexyl({[(2-ethylpent-4-en-1-yl)oxy]carbonyl}amino) acetic acid | 298.2 |
| B44 | L-Cyclopentyl-glycine | (1-Allyl cyclopropyl) methanol Ref: *Helv. Chim. Acta* (1986), 69, 1655. | 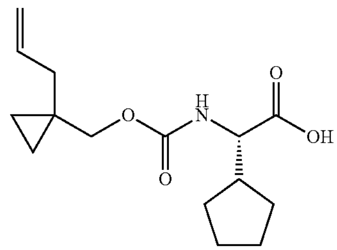 | (2S)-({[(1-Allylcyclopropyl) methoxy]carbonyl} amino)(cyclopentyl) acetic acid | 282.3 |
| B45 | L-Cyclohexyl-glycine | (1-Allyl cyclopropyl) methanol Ref: *Helv. Chim. Acta* (1986), 69, 1655. | 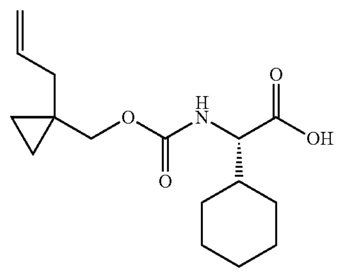 | (2S)-({[(1-Allylcyclopropyl) methoxy]carbonyl} amino)(cyclohexyl) acetic acid | 296.3 |
| B46 | L-t-Butyl-glycine | 2-Methylpent-4-en-1-ol Ref: *Tetrahedron* (1993), 49, 947. | 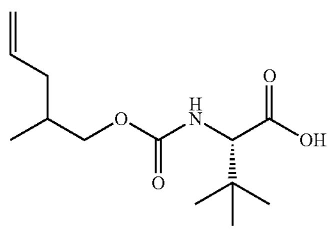 | 3-Methyl-N-{[(2-methylpent-4-en-1-yl)oxy]carbonyl}-L-valine | 258.3 |
| B47 | L-Cyclopentyl-glycine | (1-Allyl cyclopentyl) methanol Ref: *J. Org. Chem.* (1992), 57, 1727. | 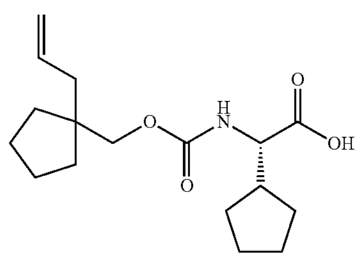 | (2S)-({[(1-Allylcyclopentyl) methoxy]carbonyl} amino)(cyclopentyl) acetic acid | 310.3 |
| B48 | L-Cyclopentyl-glycine | 2-Methylpent-4-en-1-ol Ref: *Tetrahedron* (1993), 49, 947. | 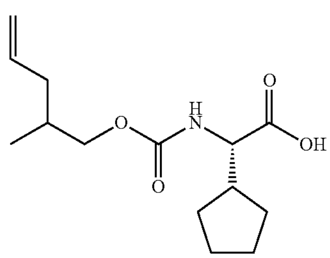 | (2S)-Cyclopentyl({[(2-methylpent-4-en-1-yl)oxy]carbonyl}amino) acetic acid | 270.2 |

| Int | Amino Acid | Alcohol | Structure | Name | LRMS (M + H)+ |
|---|---|---|---|---|---|
| B49 | L-t-Butyl-glycine | Allyl alcohol | 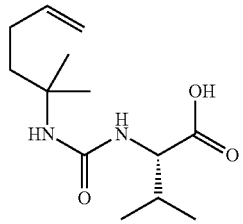 | N-[(allyloxy)carbonyl]-3-methyl-L-valine | 215.2 |

Intermediate B50: N-{[(1,1-dimethylpent-4-en-1-yl)amino]carbonyl}-L-valine

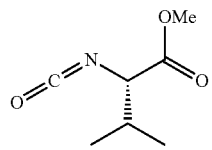

Step 1: methyl N-(oxomethylene)-L-valinate

A mixture of L-valine methyl ester hydrochloride (10.0 g, 59.9 mmol), DCM (300 mL), and pyridine (19.3 mL, 240 mmol) was cooled in an ice/salt bath and a solution of 20% phosgene in toluene (35.6 mL, 719 mmol) added dropwise, maintaining the reaction temperature below 5° C. during the addition. A white suspension resulted and after 1.5 h, the reaction mixture was poured into ice cold 1M hydrochloric acid and extracted with DCM (2×500 mL). The combined organic phases were washed with brine, dried over anhydrous MgSO$_4$, and evaporated. Flash column chromatography on silica (95 hexane/5 ethyl acetate) gave the title compound as a colorless oil (6.43 g). $^1$H NMR (CDCl$_3$ 500 MHz) δ 3.94 (d, J=4.0 Hz, 1 H), 3.82 (s, 3 H), 2.24 (m, 1 H), 1.03 (d, J=7.0 Hz, 3 H), 0.90 (d, J=6.5 Hz, 3 H) ppm.

Step 2: methyl N-{[(1,1-dimethylpent-4-en-1-yl)amino]carbonyl}-L-valinate

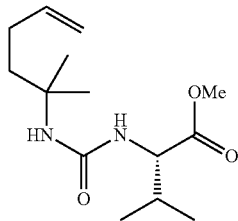

Methyl N-(oxomethylene)-L-valinate (2.80 g, 17.7 mmol) was added to 2-methylhex-5-en-2-amine [*J. Org. Chem.* (1976) 41(5) 855-863.] (2.00 g, 17.7 mmol) in THF (15 mL). After 5 minutes, the reaction mixture was evaporated to give the title compound as a solid which was triturated with hexane and isolated by filtration (2.71 g). LRMS (M+H)+=271.4.

Step 3: N-{[(1,1-dimethylpent-4-en-1-yl)amino]carbonyl}-L-valine (Intermediate B50)

1M lithium hydroxide (54 mL, 54 mmol) was added to N-{[(1,1-dimethylpent-4-en-1-yl)amino]carbonyl}-L-valine (2.94 g, 10.9 mmol) in THF (20 mL). The reaction mixture was stirred at RT under nitrogen for 18 hours then heated to reflux for 2 hours, cooled to room temperature and THF removed by evaporation. Water was then added and the mixture extracted with DCM (4×). The aqueous layer was made acidic with 1M hydrochloric acid and extracted with DCM (3×70 mL). The combined organic extracts were dried over anhydrous Na$_2$SO$_4$ and the solvent evaporated to give the title compound as a white foam (2.25 g). LRMS (M+H)+=257.3.

The following urea intermediates (B51-B52) were prepared using the chemistry described for the preparation of N-{[(1,1-dimethylpent-4-en-1-yl)amino]carbonyl}-L-valine (as described in Intermediate B50), by utilizing the appropriate amino acid and amine.

| Int | Amino Acid | Amine | Structure | Name | LRMS (M + H)+ |
|---|---|---|---|---|---|
| B51 | L-t-Butyl-glycine | N-Methylpent-4-en-1-amine | 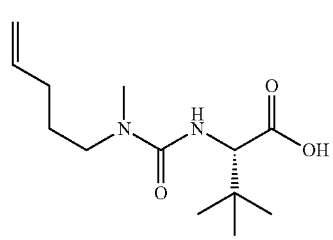 | 3-Methyl-N-{[methyl(pent-4-en-1-yl)amino]carbonyl-L-valine | 257.3 |

| Int | Amino Acid | Amine | Structure | Name | LRMS (M + H)+ |
|---|---|---|---|---|---|
| B52 | L-t-Butyl-glycine | N-Isopropylhex-5-en-1-amine | 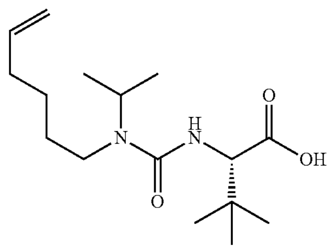 | N-{[Hex-5-en-1-yl(isopropyl)amino]carbonyl}-3-methyl-L-valine | 299.3 |

Intermediate B53: N-hept-6-enoyl-3-methyl-L-valine

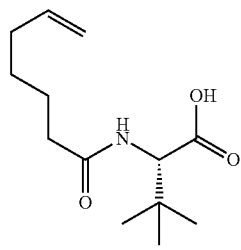

Step 1: Methyl N-hept-6-enoyl-3-methyl-L-valinate

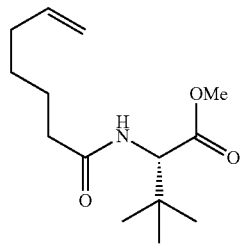

A solution of L-tert-leucine methyl ester (1.00 g, 6.89 mmol), 6-heptenoic acid (1.06 g, 8.26 mmol), EDC (1.58 g, 8.26 mmol) and HOAt (1.23 g, 8.26 mmol) in DMF (10 mL) was stirred at 22° C. for 2 h. The reaction mixture was diluted with aqueous saturated NaHCO$_3$ (30 mL), and extracted with EtOAc (3×50 mL). The combined organic layers were washed with water (3×30 mL), brine (20 mL), dried over Na$_2$SO$_4$, filtered and concentrated. The residue was chromatographed on silica gel, eluting with 5-50% EtOAc/hexane, to give the title product (1.42 g, 81%). LRMS (ESI) m/z 256.3 [(M+H)+; calcd for C$_{14}$H$_{26}$NO$_3$: 256.2].

Step 2: N-hept-6-enoyl-3-methyl-L-valine (Intermediate B53)

A solution of methyl N-hept-6-enoyl-3-methyl-L-valinate (1.40 g, 5.48 mmol) in THF (10 mL) and 1N NaOH (10 mL) was stirred at 22° C. for 2 h. The reaction mixture was acidified to pH 3 with 1 N HCl and extracted with EtOAc (3×150 mL). The combined EtOAc layers were washed with water (50 mL), brine (50 mL), dried over Na$_2$SO$_4$, filtered and concentrated to give the title product (1.12 g, 84%). LRMS (ESI) m/z 242.3 [(M+H)+; calcd for C$_{13}$H$_{24}$NO$_3$: 242.2].

Preparation of Intermediates C

Intermediate C1: Ethyl (4R)-4-[(7-bromo-6-methoxyisoquinolin-1-yl)oxy]-L-prolinate hydrochloride

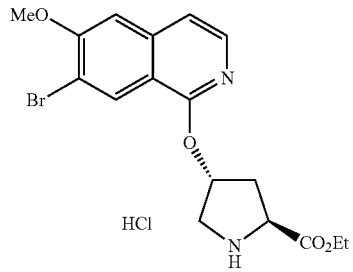

Step 1: (2E)-3-(4-bromo-3-methoxyphenyl)acrylic acid

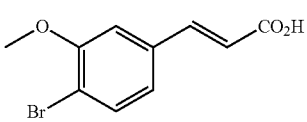

To a solution of 1-bromo-4-iodo-2-methoxybenzene (L. A. Hasvold et al, US 2004/0254159, EXAMPLE 57B) (33.45 g, 107 mmol) in MeCN (100 mL) was added acrylic acid (9.61 g, 133 mmol), triethylamine (37.2 mL, 267 mmol) and palladium acetate (719 mg, 3.2 mmol). The reaction mixture was heated to 90° C. for 40 min, cooled to RT and poured into 2.4 L 1M HCl. After stirring for 30 min, the solid was filtered, heated to reflux in EtOH (230 mL), allowed to cool to RT and stirred overnight. The solid was filtered and washed with 1:1 EtOH hexane (50 mL) to give desired product. LRMS ESI+ (M+H)+ 257.0.

125

Step 2: 7-bromo-6-methoxyisoquinolin-1(2H)-one

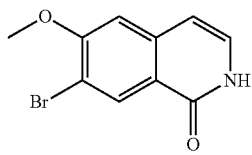

A portion of the product from Step 1 [(2E)-3-(4-bromo-3-methoxyphenyl)acrylic acid] (12.5 g, 48.6 mmol) was azeotroped with benzene and suspended in benzene (94 mL). Triethylamine (9.49 mL, 68.1 mmol) and diphenylphosphoryl azide (10.48 mL, 48.6 mmol) were added and the reaction mixture stirred at RT for 1 h. The mixture was filtered through a pad of silica and eluted with ~1 L of toluene, the volatiles evaporated, the residue resuspended in diphenylmethane (94 mL) and the mixture heated to reflux for three hours (internal temperature 250° C.). The reaction mixture was allowed to cool to RT, stirred overnight, filtered and the solid washed with hexanes (100 mL) to give tan solid (7.4 g). LRMS ESI+ (M+H)+ 254.1.

Step 3: 7-bromo-1-chloro-6-methoxyisoquinoline

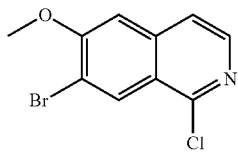

A mixture of the product from Step 2 (7-bromo-6-methoxyisoquinolin-1(2H)-one) (4.7 g, 18.5 mmol) in phosphorus oxychloride (30 mL) was heated to reflux for 2 h, cooled to RT, the volatiles evaporated and the residue partitioned between 3M NaOH and DCM. The organic phase was dried over $Na_2SO_4$, solvent evaporated and the solid triturated with $Et_2O$ (20 mL) and filtered to give a solid (3.75 g). LRMS ESI+ (M+H)+ 274.0.

Step 4: Ethyl (4R)-4-[(7-bromo-6-methoxyisoquinolin-1-yl)oxyl-L-prolinate hydrochloride (Intermediate C1)

The title compound was prepared from the product of Step 3 (7-bromo-1-chloro-6-methoxyisoquinoline), utilizing the procedure described in EXAMPLE 10, Step 1. LRMS ESI+ (M+H)+ 395.0.

Intermediate C2: Methyl (4R)-4-[(6-bromoquinazolin-4-yl)oxy]-L-prolinate hydrochloride

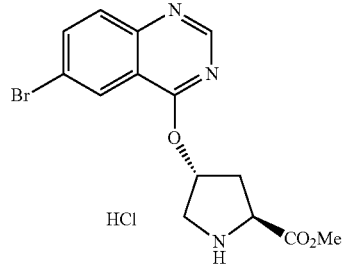

126

Step 1: 4-hydroxy-6-bromoquinazoline

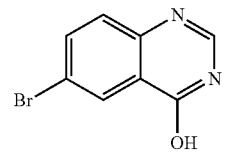

Bromoanthranilic acid (12.0 g, 55.5 mmol) and formamidine acetate (29.2 g, 281 mmol) were combined in acetic acid (96 mL) and heated to reflux for 2 h. The reaction mixture was cooled, concentrated to remove acetic acid and poured into water (500 mL). The reaction mixture was stirred for 0.5 h and resulting solids filtered. The solids were air dried to give a tan solid (12.0 g). LRMS (M+H)+=225.0.

Step 2: 1-tert-butyl 2-methyl (2S,4R)-4-[(6-bromoquinazolin-4-yl)oxy]pyrrolidine-1,2-dicarboxylate

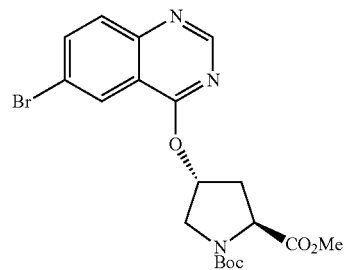

To a solution of N-boc-cis-hydroxyproline methyl ester (2.0 g, 8.15 mmol), 4-hydroxy-6-bromoquinazoline (1.84 g, 8.15 mmol) and triphenylphosphine (2.57 g, 9.79 mmol) at 0° C. in THF (80 mL) was added diisopropylazodicarboxylate (1.98 g, 9.79 mmol) dropwise. The mixture was stirred at 25° C. for 18 h. The reaction was diluted with EtOAc (100 mL), washed with 10% aqueous $Na_2CO_3$ (2×50 mL) and water (2×50 mL). The combined aqueous layers were backextracted with EtOAc (50 mL) and the combined EtOAc extracts dried over $Na_2SO_4$, filtered and concentrated to an oil. The oil was chromatographed on silica using 25 to 60% EtOAc/hexane to give the title compound (3.46 g). LRMS (M+H)+=452.2.

Step 3: Methyl (4R)-4-[(6-bromoquinazolin-4-yl)oxy]-L-prolinate hydrochloride (Intermediate C2)

To a solution of 1-tert-butyl 2-methyl (2S,4R)-4-[(6-bromoquinazolin-4-yl)oxy]pyrrolidine-1,2-dicarboxylate (3.46 g, 6.65 mmol) in dioxane (80 mL) at 0° C. was introduced anhydrous HCl (g) over 30 min. The reaction was complete by HPLC/MS. The reaction mixture was concentrated and the resulting solids were azeotroped with diethyl ether (50 mL) to give the title compound (3.0 g). LRMS (M+H)+=352.2.

Intermediate C3: Ethyl (4R)-4-[(7-bromo-3-chloroisoquinolin-1-yl)oxy]-L-prolinate hydrochloride

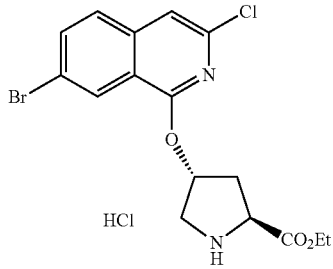

Step 1: 7-bromo-1-chloroisoquinoline 2-oxide

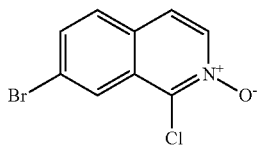

To a solution of 7-bromo-1-chloroisoquinoline (4.0 g, 15.8 mmol) in DCM (100 mL) at 0° C. was added mCPBA (~77%, 7.46 g, 33.3 mmol). The reaction was allowed to stir at room temperature for 24 hours, diluted with DCM (100 mL) and washed with 1N NaOH and brine. The DCM extracts were dried over $Na_2SO_4$, filtered, concentrated and chromatographed on silica eluting with 5 to 15% acetone/DCM to give the title compound (1.43 g). LRMS $(M+H)^+$=258.0.

Step 2: 7-bromo-1,3-dichloroisoquinoline

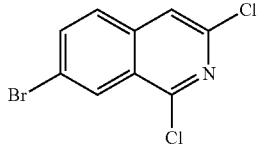

7-Bromo-1-chloroisoquinoline 2-oxide (1.43 g, 5.56 mmol) and $POCl_3$ (20 mL) were heated at reflux for 2 h. The reaction mixture was cooled and carefully poured onto a mixture of ice/water (500 g), stirred for 1 h and the pH adjusted to 10.0 with 10M NaOH. The mixture was extracted with chloroform (2×100 mL) and the chloroform extracts washed with brine, dried over $MgSO_4$, filtered and concentrated to give the title compound (1.40 g). LRMS $(M+H)^+$= 276.0.

Step 3: Ethyl (4R)-4-[(7-bromo-3-chloroisoquinolin-1-yl)oxy]-L-prolinate hydrochloride (Intermediate C3)

Ethyl (4R)-4-[(7-bromo-3-chloroisoquinolin-1-yl)oxy]-L-prolinate hydrochloride was prepared from 7-bromo-1,3-dichloroisoquinoline according to the procedure for EXAMPLE 10, Step 1. LRMS $(M+H)^+$=399.1.

Intermediate C4: Methyl (4R)-4-{[7-(allyloxy)isoquinolin-1-yl]oxy}-L-prolinate

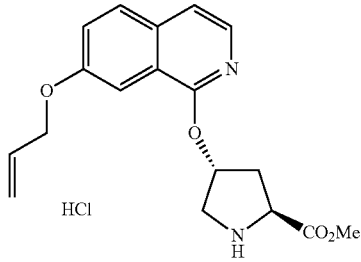

Step 1: 1-chloroisoquinolin-7-ol

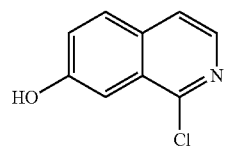

7-Bromo-1-chloroisoquinoline (2.0 g, 8.25 mmol), bis(pinacolato)diboron (2.20 g, 8.66 mmol), potassium acetate (2.43 g, 24.7 mmol) and $PdCl_2$(dppf)DCM adduct (0.337 g, 0.412 mmol) were combined under nitrogen in dioxane (40 mL) and heated in an oil bath at 100° C. for 24 h. The reaction mixture was cooled, diluted with EtOAc (100 mL) and washed with 10% aqueous $KHSO_4$. The organic phase was dried over $Na_2SO_4$, filtered and concentrated to an oil. The oil was dissolved in acetone (100 mL) and a solution of OXONE (5.07 g, 8.25 mmol) in water (20 mL) added over 2 min. The reaction mixture was stirred for 10 min, diluted with aqueous sodium bisulfate solution and stirred for an additional 20 min. and then concentrated to remove acetone. The resulting mixture was filtered to give the title compound (1.4 g) which was used without further purification. LRMS $(M+H)^+$=180.1.

Step 2: 7-(allyloxy)-1-chloroisoquinoline

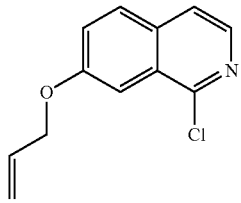

1-Chloroisoquinolin-7-ol (4.87 gm, 20.34 mmol) and cesium carbonate (6.63 g, 20.34 mmol) were combined in acetonitrile (100 mL) and stirred for 2 min. Allyl bromide (1.76 mL, 20.34 mmol) was added and the reaction mixture stirred for 30 min. The reaction mixture was diluted with aqueous $KHSO_4$ (40 mL) and EtOAc (100 mL) and stirred. The organic extract was removed, dried over $Na_2SO_4$, concentrated and chromatographed on silica gel using 20-50% EtOAc/hexanes to give 0.85 g of an oil which solidified upon storing in the freezer. LRMS (M+H)$^+$=220.1.

Step 3: Methyl (4R)-4-{[7-(allyloxy)isoquinolin-1-yl]oxy}-L-prolinate (Intermediate C4)

Intermediate C4 was prepared according to the procedure described in Example 10 Step 1, using 7-(allyloxy)-1-chloroisoquinoline. LRMS (M+H)$^+$=329.3.

Preparation of Intermediates D

Intermediate D1: (2R,4 S,7S)-7-tert-butyl-22-iodo-6,9-dioxo-3,4,6,7,8,9,12,13-octahydro-2H,11H-16,18-ethanediylidene-2,5-methanopyrido[2,3-k][1,10,3,6]dioxadiazacyclononadecine-4-carboxylic acid

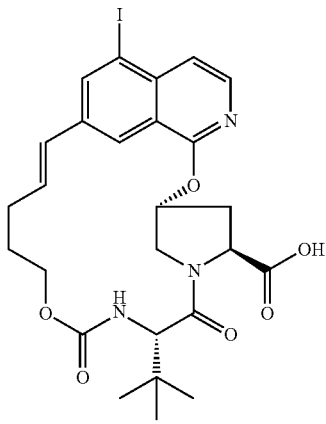

Step 1: Ethyl (2R,4S,7S)-15-bromo-7-tert-butyl-22-iodo-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate

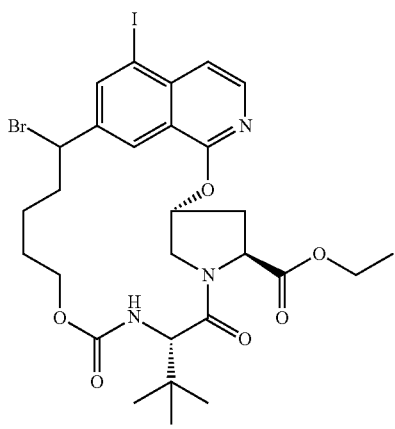

Ethyl (2R,4S,7S)-7-tert-butyl-22-iodo-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate (EXAMPLE 13, Step 1) (120 mg, 0.188 mmol) was dissolved in carbon tetrachloride (3 mL), followed by the addition of N-bromosuccinimide (37 mg, 0.207 mmol) and catalytic benzoyl peroxide (4 mg). The reaction mixture was heated to reflux under N$_2$ for 3 h, cooled and concentrated and the resulting residue was purified on silica gel (10-60% EtOAc in hexanes) to yield the title compound as a white foam (113 mg). LRMS (M+H)$^+$=716.4.

Step 2: (2R,4S,7S)-7-tert-butyl-22-iodo-6,9-dioxo-3,4,6,7,8,9, 12,13-octahydro-2H, 11H-16,18-ethanediylidene-2,5-methanopyrido[2,3-k][1,10,3,6]dioxadiazacyclononadecine-4-carboxylic acid (Intermediate D1)

To a solution of the product from Step 1 (43 mg, 0.06 mmol) in THF (2 mL), under nitrogen, was added 1M potassium t-butoxide in THF (0.09 mL, 0.09 mmol), the reaction mixture stirred for 30 min and then a second portion of potassium t-butoxide (0.03 mL, 0.03 mmol) added. The reaction mixture was stirred for 45 min, diluted with water, acidified with 1N HCl and extracted with EtOAc (×2). The combined organics were washed with brine, dried over Na$_2$SO$_4$, filtered, concentrated, and azeotroped from Et$_2$O to yield the crude title compound as a dark yellow solid (36 mg). LRMS (M+H)$^+$=608.4.

Intermediate D2: (2R,4S,7S)-7-tert-butyl-15-methoxy-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylic acid

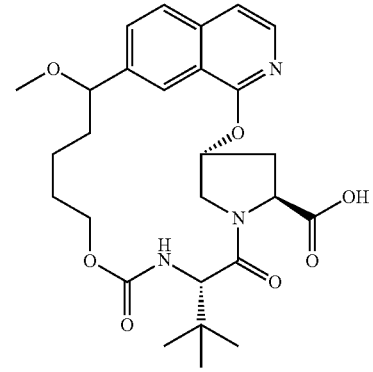

Step 1: Ethyl (2R,4S,7S)-15-bromo-7-tert-butyl-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate

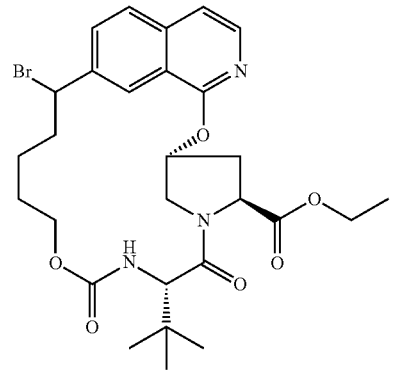

Ethyl (2R,4S,7S)-15-bromo-7-tert-butyl-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate was prepared according to the procedure described for Intermediate D1, Step 1, starting with ethyl (2R,4S,7S)-7-tert-butyl-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate (EXAMPLE 11, Step 1). LRMS (M+H)$^+$=590.5.

Step 2: (2R,4S,7S)-7-tert-Butyl-15-methoxy-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylic acid (Intermediate D2)

A solution of the product from Step 1 (78 mg, 0.132 mmol) in MeOH (4 mL) was heated at 60 C for 6 h. Sodium hydroxide (1N, 0.528 mL, 0.528 mmol) was added and the reaction mixture was stirred for 4 h. The reaction mixture was concentrated and the resulting residue was partitioned between EtOAc and 1N HCl (×2). The organic layers were combined, washed with brine, dried over Na$_2$SO$_4$, filtered, and concentrated to yield the title compound as a white foam (68 mg). LRMS (M+H)$^+$=514.3.

Intermediate D3: Ethyl (2R,4S,7S)-7-tert-butyl-15-hydroxy-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate

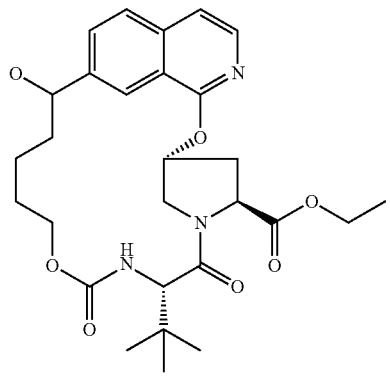

To a solution of ethyl(2R,4S,7S)-15-bromo-7-tert-butyl-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate (Intermediate D2, Step 1) (89 mg, 0.151 mmol) in acetone (1 mL) was added a solution of silver nitrate (38 mg, 0.226 mmol) in H$_2$O (1 mL). The reaction mixture was stirred in the dark for 16 h filtered, concentrated, and the resulting residue partitioned between DCM and H$_2$O (×3). The combined organic phases were washed with brine, dried over Na$_2$SO$_4$, filtered, and concentrated. The crude product was purified on silica gel (15% to 60% EtOAc in hexanes) to yield the title compound as a white foam (37 mg). LRMS (M+H)$^+$=528.8.

Intermediate D4: Ethyl (2R,4S,7S)-7-tert-butyl-6,9,15-trioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate

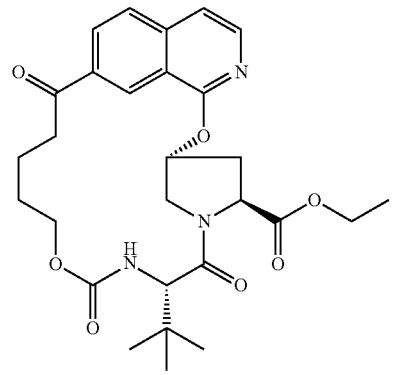

To a solution of ethyl (2R,4S,7S)-7-tert-butyl-15-hydroxy-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate (Intermediate D3) (70 mg, 0.133 mmol) in DCM (3 mL) was added PCC (41 mg, 0.191 mmol) and the reaction mixture stirred for 4 h, filtered, concentrated, and the resulting residue purified on silica gel (0% to 5% acetone in DCM) to yield the title compound as a white solid (59 mg). LRMS (M+H)$^+$=526.5.

Intermediate D5: Ethyl (2R,4S,7S)-7-tert-butyl-6,9-dioxo-22-(trifluoromethyl)-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate

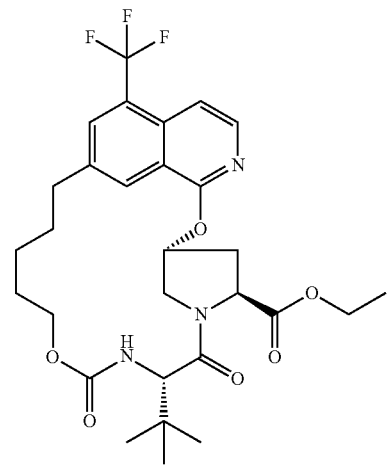

To a solution of ethyl (2R,4S,7S)-7-tert-butyl-22-iodo-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate (EXAMPLE 13, Step 1) (25 mg, 0.039 mmol) in DMF (1.5 mL) was added methyl fluorosulphonyldifluoroacetate (0.015 mL, 0.118 mmol) and copper (I) iodide (22 mg, 0.118 mmol). The mixture was heated to 150° C. in a microwave for 10 min, cooled, filtered, concentrated, and the resulting residue purified on silica gel (10% to 50% EtOAc in hexanes) to yield the title compound as a white solid (20 mg). LRMS (M+H)$^+$=580.5.

Intermediate D6: Ethyl (2R,4S,7S)-7-tert-butyl-22-cyano-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate

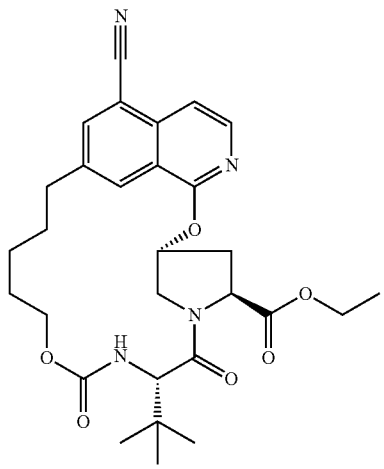

To a solution of ethyl (2R,4S,7S)-7-tert-butyl-22-iodo-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate (EXAMPLE 13, Step 1) (75 mg, 0.118 mmol) in DMF (1.5 mL) was added copper (I) cyanide (32 mg, 0.353 mmol) and the mixture heated to 150° C. in a sealed tube for 4 h. The reaction mixture was partitioned between EtOAc and saturated NaHCO$_3$ (×3). The combined organic layers were washed with brine, dried over Na$_2$SO$_4$, filtered, and concentrated. The resulting crude material was purified on silica gel (10% to 50% EtOAc in hexanes) to yield the title compound as a white foam (40 mg). LRMS (M+H)$^+$=537.4.

Intermediate D7: Ethyl (2R,4S,7S)-7-tert-butyl-22-ethyl-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate

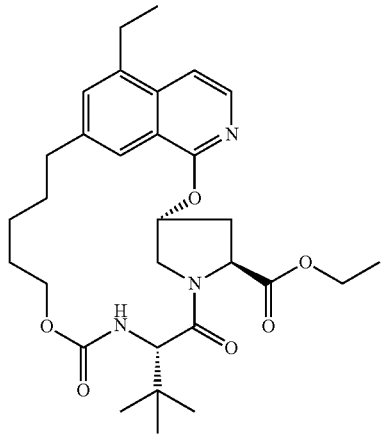

Step 1: Ethyl (2R,4S,7S)-7-tert-butyl-6,9-dioxo-22-vinyl-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate

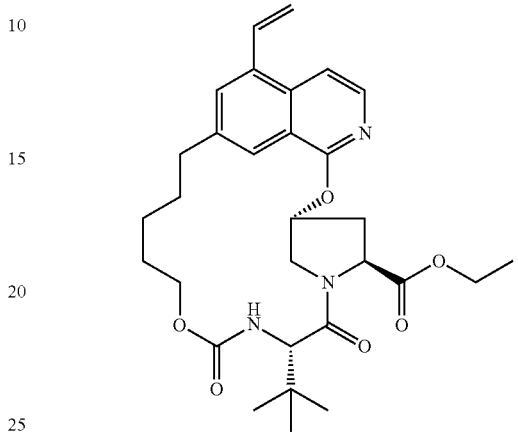

Nitrogen was bubbled through a solution of ethyl (2R,4S,7S)-7-tert-butyl-22-iodo-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate (EXAMPLE 13, Step 1) (90 mg, 0.141 mmol) in toluene (2 mL) for 30 min. Tributyl(vinyl)tin (0.049 mL, 0.169 mmol) and tetrakis(triphenylphosphine) palladium (0) (16 mg, 0.014 mmol) were added and the reaction mixture heated to reflux for 2 h. The cooled reaction mixture was concentrated and the residue purified by chromatography on silica gel (10% to 60% EtOAc in hexanes) to yield the title compound as a clear oil (58 mg). LRMS (M+H)$^+$=538.5.

Step 2: Ethyl (2R,4S,7S)-7-tert-butyl-22-ethyl-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate (Intermediate D7)

To a solution of ethyl (2R,4S,7S)-7-tert-butyl-6,9-dioxo-22-vinyl-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate (58 mg, 0.108 mmol) in ethanol (5 mL) was added 10% palladium on carbon catalyst (20 mg). The reaction mixture was placed under a hydrogen balloon and stirred for 16 h. The reaction mixture was filtered, concentrated, and the title compound was obtained as white foam (46 mg). LRMS (M+H)$^+$=540.5.

Intermediate D8: Ethyl (2R,4S,7S)-7-cyclopentyl-22-ethyl-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate

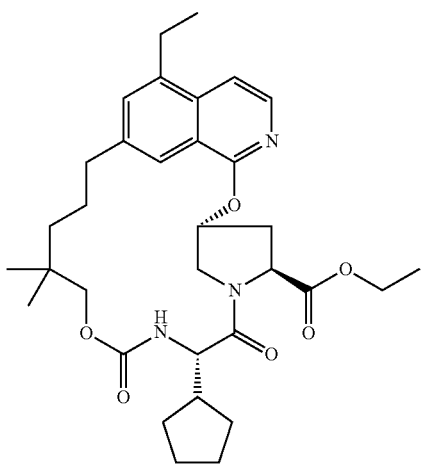

Step 1: Ethyl (2R,4S,7S)-7-cyclopentyl-22-iodo-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate

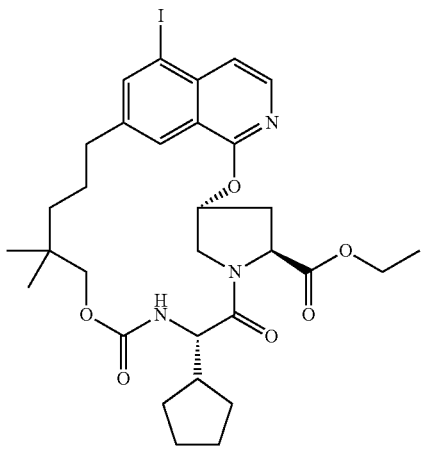

Ethyl (2R,4S,7S)-7-cyclopentyl-22-iodo-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate was prepared according to the procedure described for EXAMPLE 13, Step 1 using ethyl (2R,4S,7S)-7-cyclopentyl-12,12-dimethyl-6,9-dioxo-3,4,6,7,8,9,12,13,14,15-decahydro-2H,11H-16,18-etheno-2,5-methanopyrido[2,3-k][1,10,3,6]dioxadiazacyclononadecine-4-carboxylate (EXAMPLE 15, Step 1). LRMS (M+H)$^+$=678.3.

Step 2: Ethyl (2R,4S,7S)-7-cyclopentyl-22-ethyl-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate (Intermediate D8)

Ethyl (2R,4S,7S)-7-cyclopentyl-22-ethyl-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate (Intermediate D8) was prepared according to the procedure described for Intermediate D7 using ethyl (2R,4S,7S)-7-cyclopentyl-22-iodo-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate. LRMS (M+H)$^+$=580.3.

Intermediate D9: (2R,4S,7S)-7-tert-butyl-22-methoxy-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylic acid

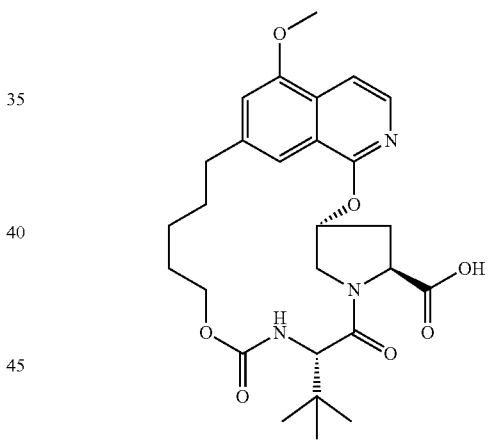

To a solution of ethyl(2R,4S,7S)-7-tert-butyl-22-iodo-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate (EXAMPLE 13, Step 1) (195 mg, 0.306 mmol) in MeOH (4 mL) was added sodium methoxide (30% in MeOH, 0.17 mL, 0.918 mmol) and copper (I) iodide (9 mg, 0.046 mmol). The reaction mixture was heated to 100° C. in the microwave for 20 min, cooled, sodium hydroxide (1N, 1.0 mL, 1.0 mmol) added and the reaction mixture was stirred for 4 h. The mixture was filtered, concentrated, and the residue partitioned between EtOAc and 1N HCl (×3). The combined organics were washed with brine, dried over Na$_2$SO$_4$, filtered, and concentrated to yield the crude title compound as a yellow oil. LRMS (M+H)$^+$=514.4.

Intermediate D10: (2R,4S,7S)-7-cyclohexyl-22-methoxy-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylic acid

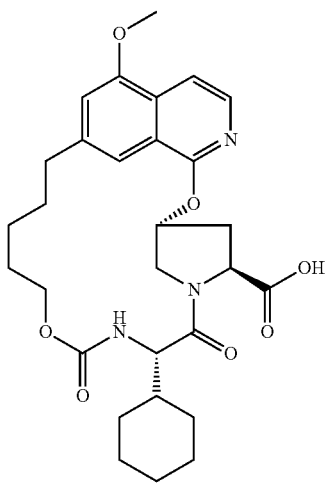

Step 1: Ethyl (2R,4S,7S)-7-cyclohexyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate

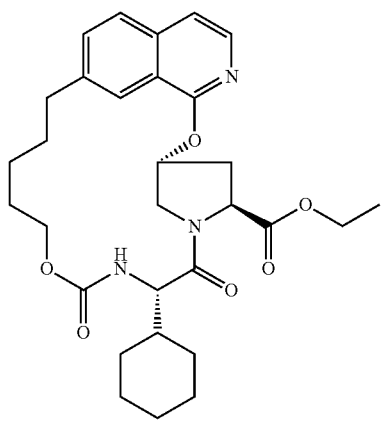

Ethyl (2R,4S,7S)-7-cyclohexyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate was prepared using the procedures described in EXAMPLE 14, Steps 1-3 using Intermediate B8 in Step 1, followed by hydrogenation according to the procedure given in EXAMPLE 15, Step 1. LRMS (M+H)$^+$=538.4.

Step 2: Ethyl (2R,4S,7S)-7-cyclohexyl-22-iodo-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate

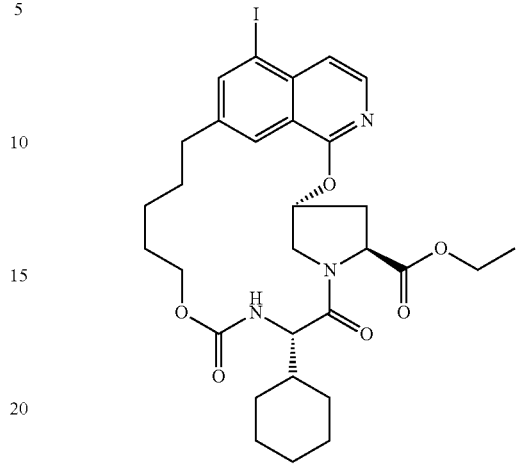

Ethyl (2R,4S,7S)-7-cyclohexyl-22-iodo-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate was prepared according to the procedure described for EXAMPLE 13, Step 1 using ethyl (2R,4S,7S)-7-cyclohexyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate. LRMS (M+H)$^+$=664.4.

Step 3: (2R,4S,7S)-7-cyclohexyl-22-methoxy-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylic acid (Intermediate D10)

Intermediate D10 was prepared according to the procedure described for Intermediate D9 using ethyl (2R,4S,7S)-7-cyclohexyl-22-iodo-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate. LRMS (M+H)$^+$=540.4.

Intermediate D11: (2R,4S,7S)-7-tert-butyl-22-hydroxy-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylic acid

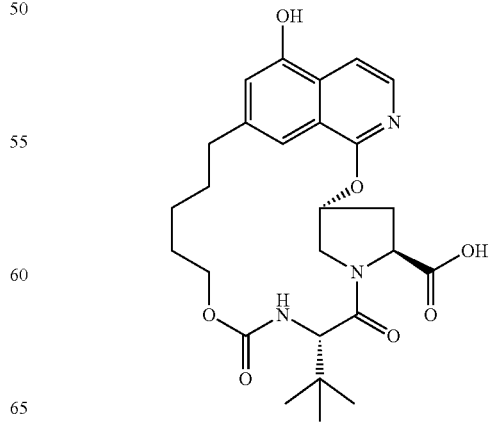

To a solution of (2R,4S,7S)-7-tert-butyl-22-methoxy-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylic acid (Intermediate D9) (53 mg, 0.103 mmol) in DCM (2 mL) was added boron tribromide (1M in DCM, 0.31 mL, 0.31 mmol) at −78° C. and the reaction mixture stirred for 1 h, then slowly warmed to RT and stirred for 1 h. The reaction mixture was quenched with several drops of MeOH and H$_2$O and then concentrated. The residue was partitioned between EtOAc and 1N HCl (×3). The combined organics were washed with brine, dried over Na$_2$SO$_4$, filtered, and concentrated to yield the crude title compound as a gray solid (33 mg). LRMS (M+H)$^+$=500.3.

Intermediate D12: Methyl (2R,4S,7S)-7-tert-butyl-22-ethoxy-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate

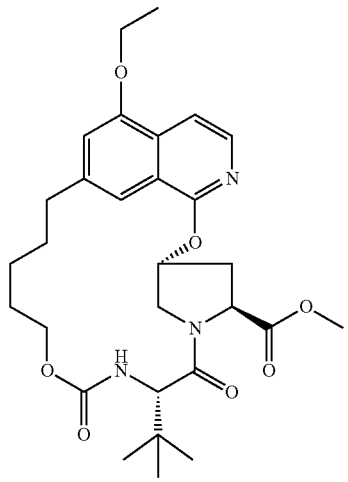

Step 1: Methyl (2R,4S,7S)-7-tert-butyl-22-hydroxy-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate

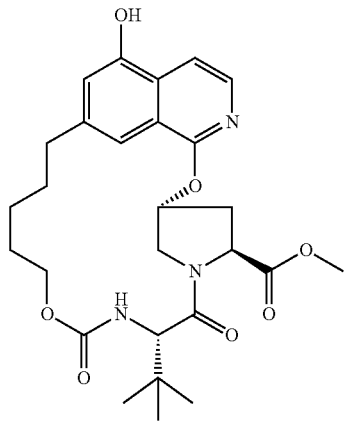

To a solution of (2R,4S,7S)-7-tert-butyl-22-methoxy-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylic acid (Intermediate D9) (53 mg, 0.103 mmol) in DCM (2 mL) was added boron tribromide (1M in DCM, 0.31 mL, 0.31 mmol) at −78 C and the reaction mixture was stirred for 1 h. Slowly warmed to RT and stirred for 1 h. The reaction was quenched with excess MeOH and then concentrated. The resulting residue was partitioned between EtOAc and 1N HCl. The layers were separated and the aqueous layer was extracted with EtOAc (2×). The combined organics were washed with brine, dried over Na$_2$SO$_4$, filtered, and concentrated to yield the crude title compound as a gray solid (33 mg). LRMS (M+H)$^+$=514.3.

Step 2: Methyl (2R,4S,7S)-7-tert-butyl-22-ethoxy-6,9-dioxo-3,4,6,7,8,9,12,13,14,15-decahydro-2H,11H-16,18-ethanediylidene-2,5-methanopyrido[2,3-k[1,10,3,6]dioxadiazacyclononadecine-4-carboxylate (Intermediate D12)

To a solution of methyl (2R,4S,7S)-7-tert-butyl-22-hydroxy-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate (254 mg, 0.495 mmol) in DMF (5 mL) was added iodoethane (0.079 mL, 0.989 mmol) and DBU (0.185 mL, 1.24 mmol) and the reaction mixture stirred for 16 h. The reaction mixture was partitioned between EtOAc and 1N HCl. The layers were separated and the organic layer was washed with 1N HCl (2×), brine, dried over Na$_2$SO$_4$, filtered, and concentrated. The resulting crude compound was purified on silica gel (gradient elution 15% to 35% EtOAc in hexanes) to yield the title compound as a white foam (82 mg). LRMS (M+H)$^+$=5423.

Intermediate D13: Ethyl (2R,4S,7S)-7-tert-butyl-22-(methylsulfonyl)-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate

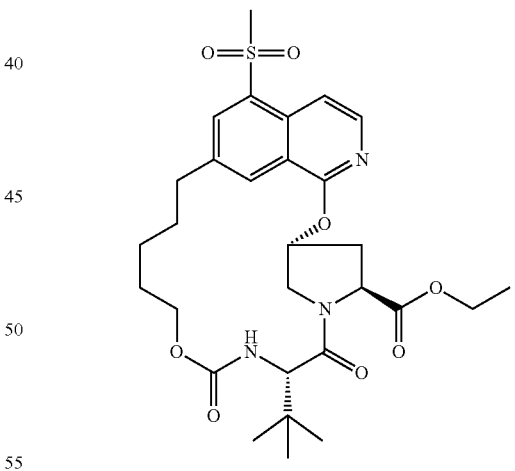

To a solution of ethyl(2R,4S,7S)-7-tert-butyl-22-iodo-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate (EXAMPLE 13, Step 1) (50 mg, 0.078 mmol) in DMSO (1 mL) was added sodium methanesulfinate (10 mg, 0.094 mmol), copper (I) trifluoromethanesulfonate toluene complex (1 mg, 0.004 mmol) and N,N'-dimethylethylendiamine (1 mg, 0.008 mmol). The reaction mixture was heated in a sealed tube at 110° C. for 16 h, cooled and partitioned between EtOAc and H$_2$O. The organic layer was washed with H$_2$O (2×), brine, dried over Na₂SO₄, filtered, and concentrated. The crude product was purified on silica gel (25% to 60% EtOAc in hexanes) to yield the title compound as a white solid (23 mg). LRMS (M+H)⁺= 590.3.

Intermediate D14: Ethyl (2R,4S,7S)-7-tert-butyl-22-(methylthio)-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate

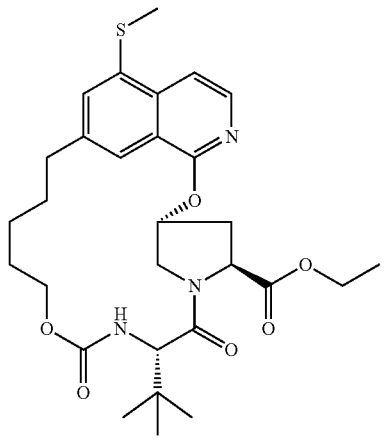

To a solution of ethyl (2R,4S,7S)-7-tert-butyl-22-iodo-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate (EXAMPLE 13, Step 1) (50 mg, 0.078 mmol) in pyridine (1 mL) was added dimethyldisulfide (0.004 mL, 0.039 mmol), and copper dust (1 mg, 0.016 mmol) and the mixture heated in a sealed tube at 100° C. for 16 h. The cooled reaction mixture was partitioned between EtOAc and 1N HCl and the layers were separated. The organic layer was washed with 1N HCl (2×), brine, dried over Na₂SO₄, filtered, and concentrated to yield the crude title compound as a yellow oil. LRMS (M+H)⁺=558.4.

Intermediate D15: Ethyl (2R,4S,7S,14E)-7-tert-butyl-6,9-dioxo-22-(trifluoromethoxy)-3,4,6,7,8,9,12,13-octahydro-2H,11H-16,18-(ethanediylidene)-2,5-methanopyrido[2,3-k][1,10,3,6]dioxadiazacyclononadecine-4-carboxylate

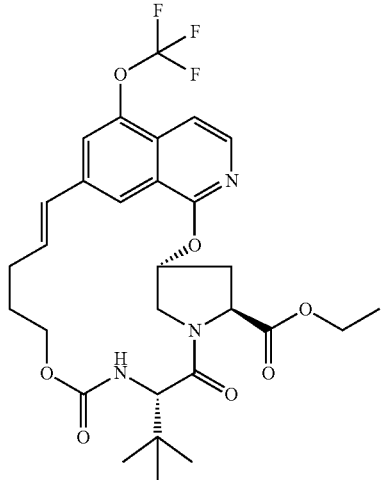

Ethyl (2R,4S,7S,14E)-7-tert-butyl-6,9-dioxo-22-(trifluoromethoxy)-3,4,6,7,8,9,12,13-octahydro-2H,11H-16,18-(ethanediylidene)-2,5-methanopyrido[2,3-k][1,10,3,6]dioxadiazacyclononadecine-4-carboxylate was prepared according to the procedures described for Intermediate C1 using 4-bromo-2-(trifluoromethoxy)iodobenzene in Step 1, followed by the procedures described in EXAMPLE 14, Steps 1-3 using Intermediate B2 in Step 1. LRMS (M+H)⁺= 596.3.

Intermediate D16: Ethyl (2R,4S,7S)-7-tert-butyl-19-ethyl-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate

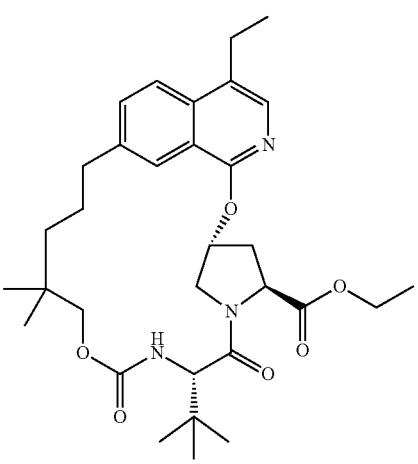

Step 1: Ethyl (2R,4S,7S)-7-tert-butyl-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate

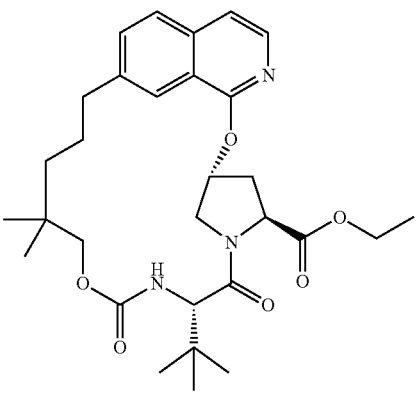

Ethyl (2R,4S,7S)-7-tert-butyl-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate was prepared using the procedure described for EXAMPLE 14, Steps 1-3 using Intermediate B4 in Step 1, followed by the hydrogenation procedure described in EXAMPLE 15, Step 1. LRMS (M+H)$^+$=540.3.

Step 2: Ethyl (2R,4S,7S)-7-tert-butyl-19-iodo-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate

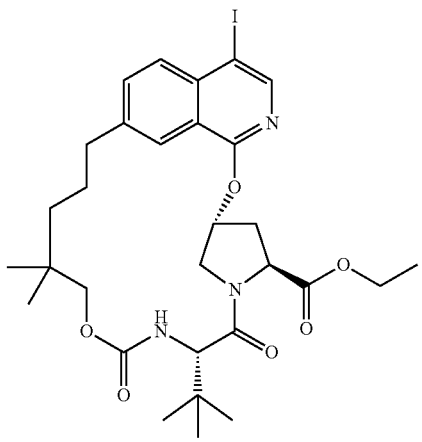

To a solution of ethyl (2R,4S,7S)-7-tert-butyl-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate (0.5 g, 0.93 mmol) in DCM (5 mL) was added triflic acid (0.165 ml, 1.853 mmol) and N-iodosuccinimide (208 mg, 0.93 mmol) and the mixture stirred under $N_2$ for 16 h. An additional portion of NIS (208 mg, 0.93 mmol) was added and the reaction mixture was stirred for an additional 24 h. The reaction mixture was poured into saturated $NaHCO_3$ and extracted with DCM (2×). The combined organic layers were washed with brine, dried over $Na_2SO_4$, filtered, and concentrated. The resulting crude compound was purified on silica gel (20% to 40% EtOAc in hexanes) to yield the title compound as a white foam (170 mg). LRMS (M+H)$^+$=666.4.

Step 3: Ethyl (2R,4S,7S)-7-tert-butyl-19-ethyl-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate (Intermediate D16)

Ethyl (2R,4S,7S)-7-tert-butyl-19-ethyl-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate was prepared using the procedure described for Intermediate D7, Steps 1 and 2 using ethyl (2R,4S,7S)-7-tert-butyl-19-iodo-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate. LRMS (M+H)$^+$=568.4.

EXAMPLE 1

(1R,2S)-1-({[(2R,4S,7S)-7-butyl-6,9-dioxo-3,4,6,7,8,9,12,13-octahydro-2H,11H-16,18-ethanediylidene-2,5-methanopyrido[2,3-k][1,10,3,6]dioxadiazacyclononadecin-4-yl]carbonyl}amino)-2-vinylcyclopropanecarboxylic acid (III-1)

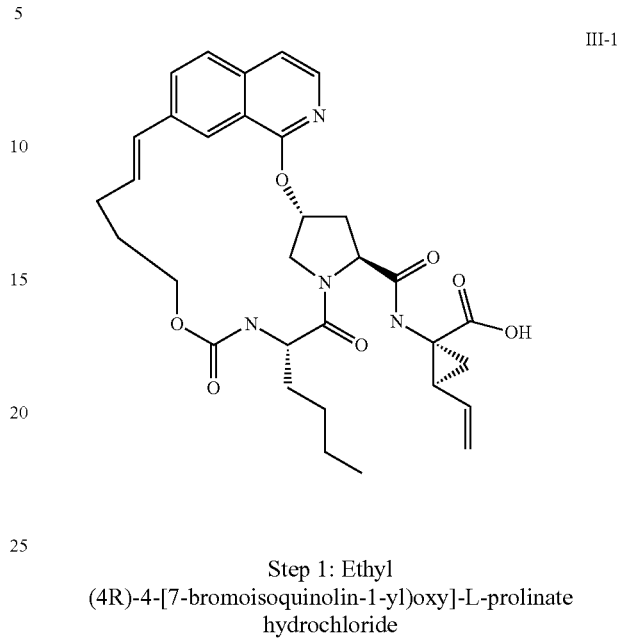

Step 1: Ethyl (4R)-4-[7-bromoisoquinolin-1-yl)oxy]-L-prolinate hydrochloride

To a solution of trans 4-hydroxy L-BOC-proline (4.83 g, 20.9 mmol) in 100 mL DMSO at room temperature was added potassium t-butoxide (7.03 g, 62.66 mmol) in a single portion. The reaction mixture was stirred at r.t. for 30 min, cooled to 17° C. and 7-bromo-1-chloroisoquinoline (5.06 g, 20.9 mmol) added, the reaction allowed to warm to r.t. and stirred overnight. The reaction mixture was quenched with ice-cold 10% citric acid solution and partitioned with ethyl acetate. The organic layer was washed with aqueous citric acid solution, water and brine and the aqueous phases back extracted with ethyl acetate. The combined organic phases were dried over anhydrous sodium sulfate and the solvent evaporated to dark solid. The solid was dissolved in ethanol (120 mL), cooled to 0° C. and HCl bubbled through until the solution was saturated. The reaction mixture was then stirred at room temperature for 48 h and the volatiles evaporated under reduced pressure. The remaining solid was azeotroped with ethanol (4×100 mL) to give 11.95 g (>100% crude) of a gray solid used directly in the next step. LRMS (ESI) m/z 365 [(M+H)$^+$; calcd for $C_{16}H_{18}BrN_2O_3$: 365].

Step 2: Ethyl N-[(pent-4-en-1-yloxy)carbonyl]-1-norleucyl-(4R)-4-[(7-bromoisoquinolin-1-yl)oxy]-L-prolinate

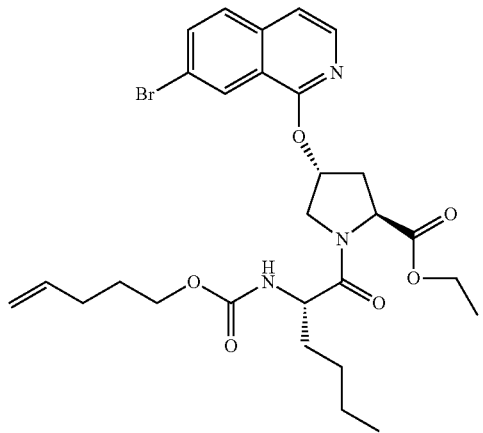

To a solution of crude ethyl (4R)-4-[7-bromoisoquinolin-1-yl)oxy]-L-prolinate hydrochloride (4 g, ~11 mmol) in DMF (30 mL) was added N-[(pent-4-en-1-yloxy)carbonyl]-L-norleucine (Intermediate B1) (4.0 g, 16.4 mmol), diisopropylethylamine (4.9 mL, 27 mmol) and TBTU (5.13 g, 16 mmol). The reaction mixture was stirred at room temperature overnight and partitioned between water and ethyl acetate. The organic layer was washed with water, saturated sodium bicarbonate solution, brine, dried over anhydrous sodium sulfate and the solvent was then evaporated. The crude product was purified by chromatography on silica (10-100% EtOAc hexane) to give desired product (3.3 g). LRMS (ESI) m/z 590 [(M+H)$^+$; calcd for $C_{28}H_{37}BrN_3O_6$: 590].

Step 3: Ethyl N-[(pent-4-en-1-yloxy)carbonyl]-L-norleucyl-(4R)-4-[(7-vinylisoquinolin-1-yl)oxy]-L-prolinate

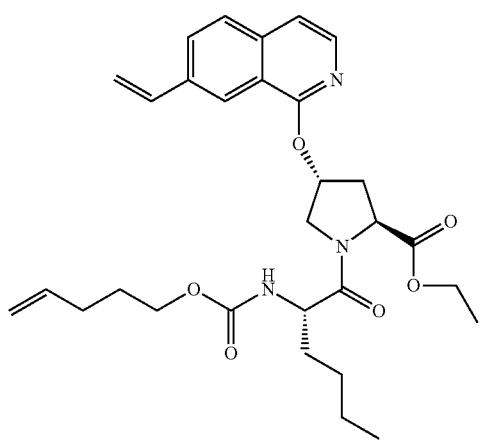

The bromide from step 2 (62 mg, 0.105 mmol) was dissolved in 5 mL toluene and nitrogen bubbled through for 15 min. Tributylvinyltin (0.037 mL, 0.126 mmol) and tetrakis(triphenylphosphine)palladium(0) (6 mg, 0.005 mmol) were added and the reaction mixture heated to 100° C. under nitrogen. After 5 h, the reaction was complete, the volatiles were evaporated and the residue purified by silica gel chromatography (10-75% EtOAc/hexane) to give a clear oil. LRMS (ESI) m/z 538 [(M+H)$^+$; calcd for $C_{30}H_{40}N_3O_6$: 538].

Step 4: Ethyl (2R,4S,7S)-7-butyl-6,9-dioxo-3,4,6,7,8,9,12,13-octahydro-2H,11H-16,18-ethanediylidene-2,5-methanopyrido[2,3-k][1,10,3,6]dioxodiazacyclononadecine-4-carboxylate

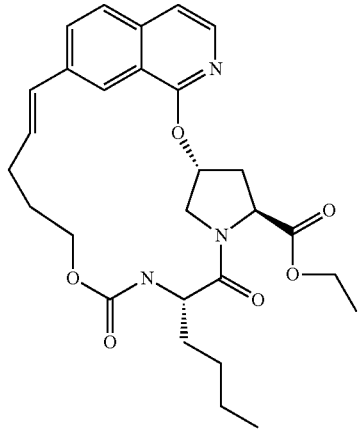

The olefin from Step 3 (40 mg, 0.074 mmol) was dissolved in dichloroethane (10 mL) and nitrogen bubbled through the solution for 15 min. Dichloro(5-chloro-2-isopropoxybenzylidene)(1,3-dimesitylimidazolidin-2-ylidene)ruthenium (Zhan ruthenium metathesis catalyst RC-301, Zhan Catalyst I (as depicted as J on page 35), RC-301, Zannan Pharma Ltd.) (5 mg, 0.007 mmol) was added and the reaction mixture heated in an 80° C. oil bath for 2 h, after which reaction was complete. Volatiles were evaporated and the residue purified by silica gel chromatography (10-75% EtOAc/hexane) to give the title compound (24 mg). LRMS (ESI) m/z 510 [(M+H)$^+$; calcd for $C_{28}H_{36}N_3O_6$: 510].

Step 5: (1R,2S)-1-({[(2R,4S,7S)-7-butyl-6,9-dioxo-3,4,6,7,8,9,12,13-octahydro-2H,11H-16,18-ethanediylidene-2,5-methanopyrido[2,3-k][1,10,3,6]dioxadiazacyclononadecin-4-yl]carbonyl}amino)-2-vinylcyclopropanecarboxylic acid The ester from Step 4 (24 mg, 0.047 mmol) was dissolved in THF (0.5 mL) and EtOH (0.5 mL) and a solution of LiOH in water (5 mg in 0.5 mL) was added. The reaction mixture was stirred at room temperature for 1.5 h after which HPLC analysis indicated complete reaction and 1M HCl (0.2 mL) was added and the mixture was evaporated to a solid. The solid was dissolved in DMF (2 mL) and (1R,2S)-1-amino-2-vinylcyclopropanecarboxylic acid ethyl ester hydrochloride (Intermediate A2)(Llinas-Brunet et al U.S. Pat. No. 6,323,180 and Wang et al WO 03/099274) ((4 mg, 0.019 mmol), diisopropylethylamine (0.017 mL, 0.095 mmol), and TBTU (6 mg, 0.019 mmol) was added and the reaction mixture was stirred at room temperature overnight. The reaction mixture was purified directly by reverse phase HPLC to yield a white foam which was dissolved in THF (0.25 mL) and ethanol (0.25 mL) and a solution of LiOH in water (4.5 mg in 0.25 mL) was added. The reaction mixture was heated to 40° C. for 2 h, cooled to room temperature, 3M HCl (0.06 mL) and DMF (0.5 mL) were added and the reaction mixture was purified by reverse phase HPLC to give the desired product as solid. LRMS (ESI) m/z 591 [(M+H)$^+$; calcd for $C_{32}H_{39}N_4O_7$: 591].

EXAMPLE 2

(1R,2S)-1-({[(2R,4S,7S)-7-Butyl-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecin-4-yl]carbonyl}amino)-2-vinylcyclopropanecarboxylic acid (III-2)

III-2

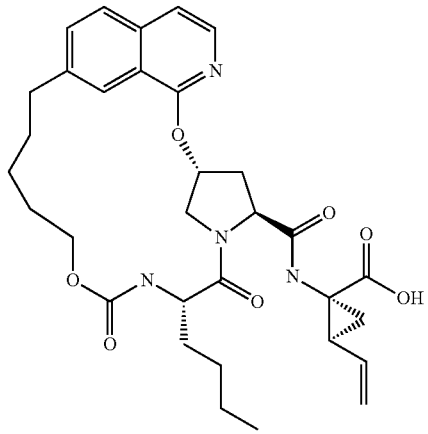

A solution of the olefin prepared as described in Example 1, Step 4 (180 mg, 0.353 mmol) in ethyl acetate (10 mL) was treated with 10% Pd/C and hydrogenated under a balloon of hydrogen for 18 h. The catalyst was removed by filtration and the filtrate was evaporated to give an oil. The oil was treated as described in Example 1, Step 5 to afford the title compound. LRMS (ESI) m/z 593 [(M+H)$^+$; calcd for $C_{32}H_{40}N_4O_7$: 593].

EXAMPLE 3

(2R,4S,7S)-7-butyl-N-((1R,2S)-1-{[(cyclopropylsulfonyl)amino]carbonyl}-2-vinylcyclopropyl)-6,9-dioxo-3,4,6,7,8,9,12,13,15,16-decahydro-2H,11H-16,18-ethanediylidene-2,5-methanopyrido[2,3-k][1,10,3,6]dioxadiazacyclononadecine-4-carboxamide (III-3)

III-3

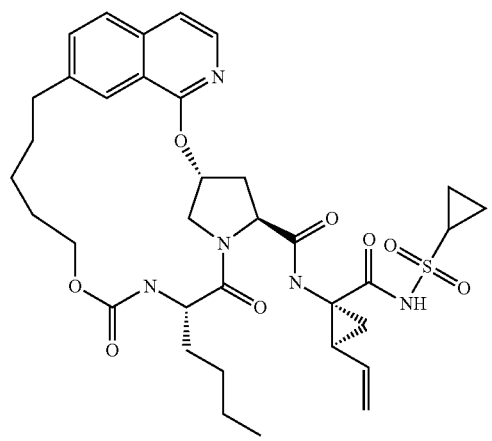

The title compound was prepared as described for Example 2, by using (1R,2S)-1-amino-N-(cyclopropylsulfonyl)-2-vinylcyclopropanecarboxamide hydrochloride (Intermediate A1)(Wang et al WO 03/099274) in place of (1R,2S)-1-amino-2-vinylcyclopropanecarboxylic acid ethyl ester hydrochloride in the coupling step. LRMS (ESI) m/z 696 [(M+H)$^+$; calcd for $C_{35}H_{45}N_5O_8S$: 696]. $^1$H NMR (500 MHz, CD$_3$OD, ppm) δ 9.28 (s, 1 H), 7.97 (s, 1 H), 7.88 (d, J=5.9 Hz, 1 H), 7.72 (d, J=8.3 Hz, 1 H), 7.56 (dd, J=8.3 and 1.7 Hz, 1 H), 7.28 (d, J=5.9 Hz, 1 H), 6.13 (m, 1 H), 5.74 (m, 1 H), 5.27 (dd, J=17.1 and 1.2 Hz, 1 H), 5.10 (dd, J=10.3 and 1.5 Hz, 1 H), 4.65 (d, J=11.2 Hz, 1 H), 4.53 (m, 1 H), 4.44 (t, J=7.6 Hz, 1 H), 4.32 (m, 1 H), 3.99 (dd, J=11.7 and 3.2 Hz, 1 H), 3.73 (m, 1 H), 2.96 (m, 1 H), 2.87 (m, 1 H), 2.71 (m, 1 H), 2.54 (m, 1 H), 2.28 (m, 1 H), 2.20 (m, 1 H), 1.60-1.90 (m, 6 H), 1.51 (m, 1 H), 1.12-1.40 (m, 10 H), 0.94 (t, J=6.8 Hz, 3 H).

EXAMPLE 4

(2R,4S,7S)-7-butyl-N-((1R,2S)-1-{[(phenylsulfonyl)amino]carbonyl}-2-vinylcyclopropyl)-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxamide (III-4)

III-4

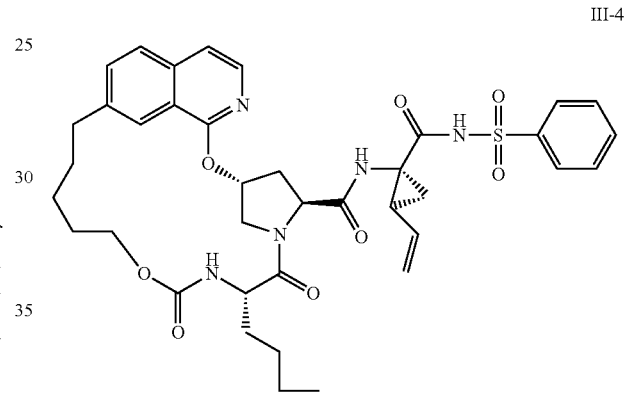

Step 1: (1R,2S)-1-({[(2R,4S,7S)-7-butyl-6,9-dioxo-3,4,6,7,8,9,12,13,14,15-decahydro-2H,11H-16,18-ethanediylidene-2,5-methanopyridine[2,3-k][1,10,3,6]dioxadiazacyclononadecin-4-yl]carbonyl}amino)-2-vinylcyclopropanecarboxylic acid

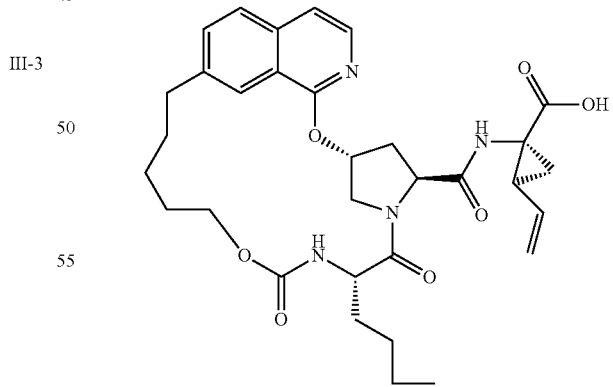

To a solution of the ethyl ester (initial hydrogenation product from Example 2) (400 mg, 0.65 mmol) in tetrahydrofuran (10 mL), ethanol (5 mL) and water (5 mL) were added lithium hydroxide (155 mg, 6.45 mmol) and the mixture let stir at 40° C. for 24 h. The reaction was cooled, concentrated in vacuo to remove tetrahydrofuran and ethanol and diluted with 3N HCL (2.5 mL). The reaction was allowed to stir for 30 min and the resulting solids filtered and washed with water (1 mL). The solid was air dried to give the title compound as a white solid (0.44 g). LRMS (ESI) m/z 593 [(M+H)+; calcd for C$_{32}$H$_{41}$N$_4$O$_7$: 593].

Step 2: (2R,4S,7S)-7-butyl-6,9-dioxo-N-((1R,2S)-1-{[(phenylsulfonyl)amino]carbonyl}-2-vinylcyclopropyl)-3,4,6,7,8,9,12,13,14,15-decahydro-2H,11H-16,18-ethanediylidene-2,5-methanopyridine[2,3-k][1,10,3,6]dioxadiazacyclononadecine-4-carboxamide

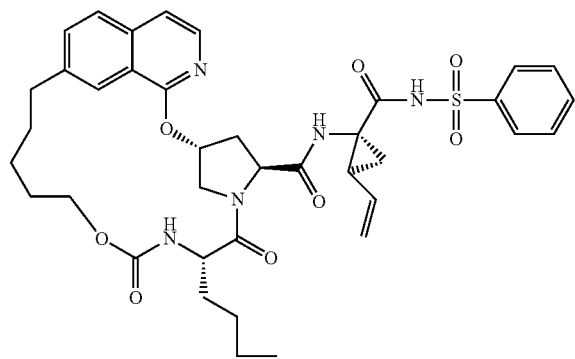

To a solution of the acid from Step 1 (30 mg, 0.05 mmol) in DMF (0.34 mL), under nitrogen, was added carbonyldiimidazole (13 mg, 0.078 mmol) and the mixture stirred at 40° C. for 2 hr. Benzenesulfonamide (12 mg, 0.078 mmol) was added and the reaction stirred overnight at 40° C. The reaction was directly purified by reverse phase chromatography and the resulting product was concentrated in vacuo to give the title compound as a white solid (18 mg). LRMS (ESI) m/z 732 [(M+H)+; calcd for C$_{38}$H$_{46}$N$_5$O$_8$S: 732].

EXAMPLE 5

(2R,4S,7S)-N-((1R,2S)-1-{[(2-methylphenylsulfonyl)amino]carbonyl}-2-vinylcyclopropyl)-7-butyl-6,9-dioxo-3,4,6,7,8,9,12,13,14,15-decahydro-2H,11H-16,18-ethanediylidene-2,5-methanopyridine[2,3-k][1,10,3,6]dioxadiazacyclononadecine-4-carboxamide (III-5)

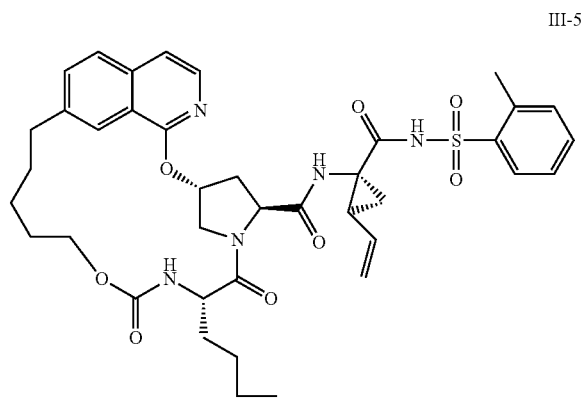

The title compound was prepared in a similar manner to that described in Example 4, replacing benzenesulfonamide with 2-methylphenylsulfonamide. LRMS (ESI) m/z 746 [(M+H)+; calcd for C$_{39}$H$_{48}$N$_5$O$_8$S: 746].

EXAMPLE 6

(2R,4S,7S)-7-butyl-N-((1R,2S)-1-{[(methylsulfonyl)amino]carbonyl}-2-vinylcyclopropyl)-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxamide (III-6)

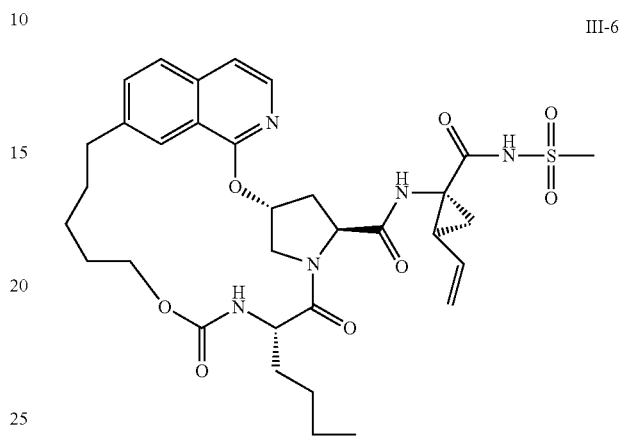

The title compound was prepared in a similar manner to that described in Example 4, replacing benzenesulfonamide with methanesulfonamide. LRMS (ESI) m/z 670 [(M+H)+; calcd for C$_{33}$H$_{43}$N$_5$O$_8$S: 670].

EXAMPLE 7

(2R,4S,7S)-7-butyl-N-((1R,2S)-1-{[(ethylsulfonyl)amino]carbonyl}-2-vinylcyclopropyl)-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxamide (III-7)

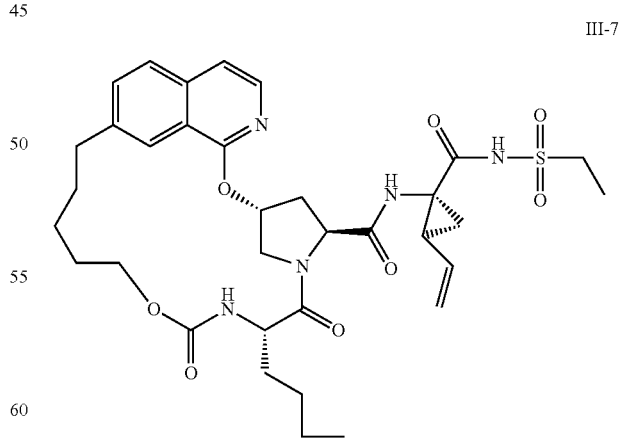

The title compound was prepared in a similar manner to that described in Example 4, replacing benzenesulfonamide with ethanesulfonamide. LRMS (ESI) m/z 684 [(M+H)+; calcd for C$_{34}$H$_{46}$N$_5$O$_8$S: 684].

151
EXAMPLE 8

(2R,4S,7S)-7-butyl-N-((1R,2S)-1-{[(t-butylsulfonyl)amino]carbonyl}-2-vinylcyclopropyl)-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxamide (III-8)

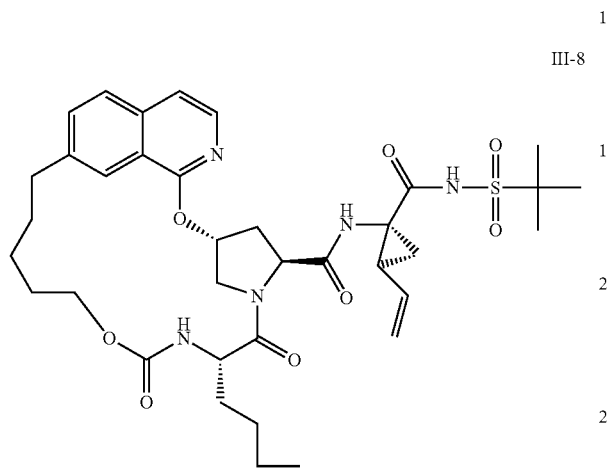

The title compound was prepared in a similar manner to that described in Example 4, replacing benzenesulfonamide with t-butylsulfonamide. LRMS (ESI) m/z 712 [(M+H)$^+$; calcd for $C_{36}H_{50}N_5O_8S$: 712].

EXAMPLE 9

HCV NS3 Protease Time-Resolved Fluorescence (TRF) Assay

The NS3 protease TRF assay was performed in a final volume of 100 µl in assay buffer containing 50 mM HEPES, pH 7.5, 150 mM NaCl, 15% glycerol, 0.15% Triton X-100, 10 mM DTT, and 0.1% PEG 8000. The NS3 protease was pre-incubated with various concentrations of inhibitors for 10-30 minutes. The peptide substrate for the assay is Ac—C(Eu)-DDMEE-Abu-[COO]-XSAK(QSY7)-NH2, where Eu is an europium-labeled group, Abu is 1-aminobutanoic acid which connects an ester linkage with 2-hydroxy propanoic acid (X). Hydrolysis of the peptide by NS3 protease activity causes in separation of the fluorophore from the quencher, resulting in an increase in fluorescence. Activity of the protease was initiated by adding the TRF peptide substrate (final concentration 50-100 nM). The reaction was quenched after 1 hour at room temperature with 100 µl of 500 mM MES, pH 5.5. Product fluorescence was detected using either a Victor V2 or Fusion fluorimeter (Perkin Elmer Life and Analytical Sciences) with excitation at 340 nm and emission at 615 nm with 50-400 µs delay. Testing concentrations of different enzyme forms was selected with a signal to background ratio of 10-30. The inhibition constants were derived using a four-parameter fit.

Compounds III-1 and III-3 to III-9, III-10, III-12, III-14, III-15, III-20, III-23, III-24, III-25, III-28, III-29, III-31, III-32, III-34, III-37, III-38, III-39 to III-46 and III-48 to III-185 were tested to have a Ki value of less than 100 nM in the NS3 protease TRF assay as described above.

152
EXAMPLE 10

(1R,2S)-1-({[(2R,4S,7S)-7-tert-butyl-6,9-dioxo-3,4,6,7,8,9,12,13-octahydro-2H,11H-16,18-ethanediylidene-2,5-methanopyrido[2,3-k][1,10,3,6]dioxadiazacyclononadecin-4-yl]carbonyl}amino)-2-vinylcyclopropanecarboxylic acid (III-23)

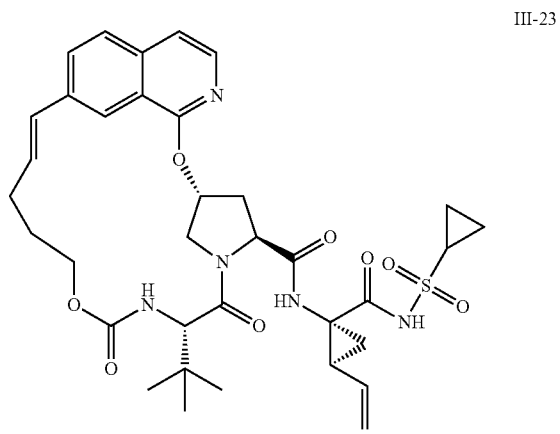

Step 1: Ethyl (4R)-4-[7-bromoisoquinolin-1-yl)oxy]-L-prolinate hydrochloride

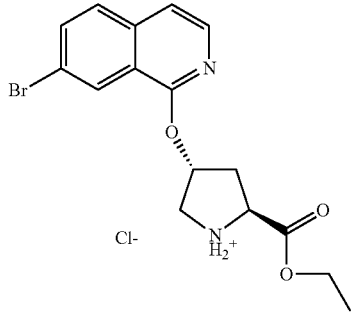

To a solution of trans 4-hydroxy L-BOC-proline (4.83 g, 20.9 mmol) in 100 mL DMSO at room temperature was added potassium t-butoxide (7.03 g, 62.66 mmol) in a single portion. The reaction mixture was stirred at r.t. for 30 min, cooled to 17° C. and 7-bromo-1-chloroisoquinoline (5.06 g, 20.9 mmol) added, the reaction allowed to warm to r.t. and stirred overnight. The reaction mixture was quenched with ice-cold 10% citric acid solution and partitioned with ethyl acetate. The organic layer was washed with aqueous citric acid solution, water and brine and the aqueous phases back extracted with ethyl acetate. The combined organic phases were dried over anhydrous sodium sulfate and the solvent evaporated to dark solid. The solid was dissolved in ethanol (120 mL), cooled to 0° C. and HCl bubbled through until the solution was saturated. The reaction mixture was then stirred at room temperature for 48 h and the volatiles evaporated under reduced pressure. The remaining solid was azeotroped with ethanol (4×100 mL) to give 11.95 g (>100% crude) of a gray solid used directly in the next step. LRMS (ESI) m/z 365 [(M+H)$^+$; calcd for $C_{16}H_{18}BrN_2O_3$: 365].

Step 2: Ethyl N-[(pent-4-en-1-yloxy)carbonyl]-1-tert-butyl-(4R)-4-[(7-bromoisoquinolin-1-yl)oxy]-L-prolinate

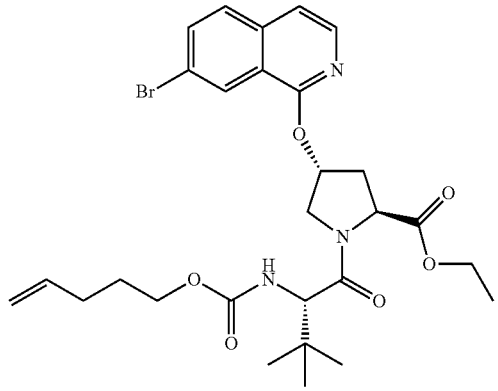

To a solution of crude ethyl (4R)-4-[7-bromoisoquinolin-1-yl)oxy]-L-prolinate hydrochloride (1.03 g, ~2.6 mmol) in DMF (10 mL) was added N-[(pent-4-en-1-yloxy)carbonyl]-L-tert-butylglycine (Intermediate B2) (0.44 g, 1.81 mmol), diisopropylethylamine (1.8 mL, 10.4 mmol) and TBTU (1.25 g, 3.9 mmol). The reaction mixture was stirred at room temperature overnight and partitioned between water and ethyl acetate. The organic layer was washed with water, saturated sodium bicarbonate solution, brine, dried over anhydrous sodium sulfate and the solvent was then evaporated. The crude product was purified by chromatography on silica (20-60% EtOAc hexane) to give desired product (0.9 g). LRMS (ESI) m/z 590 [(M+H)$^+$; calcd for $C_{28}H_{37}BrN_3O_6$: 590].

Step 3: Ethyl N-[(pent-4-en-1-yloxy)carbonyl]-L-tert-butylglycine-(4R)-4-[(7-vinylisoquinolin-1-yl)oxy]-L-prolinate

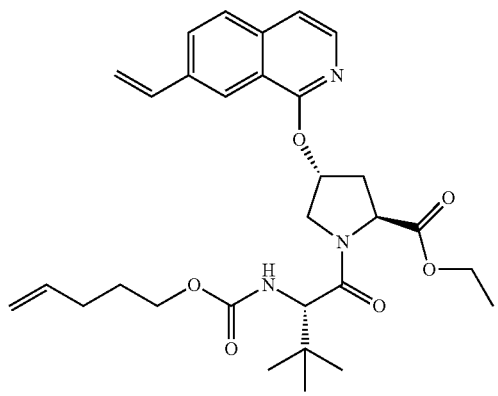

The bromide from step 2 (0.90 gm, 1.53 mmol) was dissolved in toluene (20 mL) and nitrogen bubbled through for 15 min. Tributylvinyltin (0.54 mL, 1.83 mmol) and tetrakis(triphenylphosphine)palladium(0) (178.0 mg, 0.153 mmol) were added and the reaction mixture heated to 100° C. under nitrogen. After 3 h, the reaction was complete, the volatiles were evaporated and the residue purified by silica gel chromatography (20-50% EtOAc/hexane) to give a clear oil. LRMS (ESI) m/z 538 [(M+H)$^+$; calcd for $C_{30}H_{40}N_3O_6$: 538].

Step 4: Ethyl (2R,4S,7S)-7-tert-butyl-6,9-dioxo-3,4,6,7,8,9,12,13-octahydro-2H,11H-16,18-ethanediylidene-2,5-methanopyrido[2,3-k][1,10,3,6]dioxodiazacyclononadecine-4-carboxylate

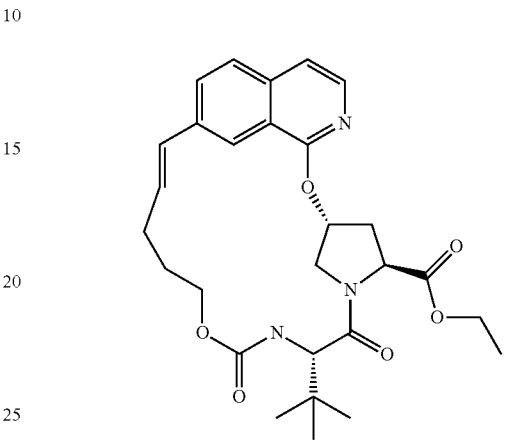

The olefin from Step 3 (1.0 gm, 1.86 mmol) was dissolved in dichloromethane (200 mL) and nitrogen bubbled through the solution for 30 min. Bis(tricyclohexylphosphine)-3-phenyl-1H-indene-1ylideneruthenium dichloride (Neolyst M1 catalyst, Stem Chemicals, CAS#250220-36-1) (300 mg, 0.30 mmol) dissolved in degassed dichloromethane was added over 30 minutes and the reaction let stir 24 hrs or until complete. Volatiles were evaporated and the residue purified by silica gel chromatography (20-60% EtOAc/hexane) to give the title compound (0.73 gm). LRMS (ESI) m/z 510 [(M+H)$^+$; calcd for $C_{28}H_{36}N_3O_6$: 510].

Step 5: (1R,2S)-1-({[(2R,4S,7S)-7-tert-butyl-6,9-dioxo-3,4,6,7,8,9,12,13-octahydro-2H,11H-16,18-ethanediylidene-2,5-methanopyrido[2,3-k][1,10,3,6]dioxadiazacyclononadecin-4-yl]carbonyl}amino)-2-vinylcyclopropanecarboxylic acid The ester from Step 4 (0.73 gm, 0.1.43 mmol) was dissolved in THF (20 mL) and EtOH (10 mL) and a solution of LiOH in water (257 mg in 10 mL) was added. The reaction mixture was stirred at room temperature for 1.5 h after which HPLC analysis indicated complete reaction and 3M HCl (5.0 mL) was added and the mixture was evaporated to a solid. The solid was dissolved in ethyl acetate (20 mL) and water (20 mL) (pH~2.0) and ethyl acetate layer separated, dried over sodium sulfate, filtered and concentrated to a foam. The foam was dissolved in dichloromethane (40 mL) and cyclopropanesulfonic acid (1-(R)-amino-2-(S)-vinyl-cyclopropanecarbonyl)-amide hydrochloride salt (A1)(0.419 mg, 1.58 mmol) (Llinas-Brunet et al US03/15755 and Wang et al WO 03/099274), diisopropylethylamine (0.75 mL, 4.30 mmol), dimethylaminopyridine (0.087 gm, 0.72 mmol) and HATU (0.65 gm, 1.72 mmol) was added and the reaction mixture was stirred at room temperature overnight. The reaction mixture was purified directly by reverse phase HPLC to yield the desired product as a solid. LRMS (ESI) m/z 694 [(M+H)$^+$; calcd for $C_{35}H_{44}N_5O_8S$: 694]. $^1$H NMR. (500 MHz, ppm) (d$_6$-DMSO) δ 10.40 (s, 1 H), 8.70 (s, 1 H), 8.45 (s, 1 H), 7.95 (d, J=5.9 Hz, 1 H), 7.81 (d, J=8.3 Hz, 1 H), 7.61 (dd, J=8.6 and 1.7 Hz, 1 H), 7.35 (d, J=5.9 Hz, 1 H), 7.25 (d, J=7.32 Hz, 1 H), 6.62 (d, J=15.9 Hz, 1 H), 6.39 (m, 1 H), 5.68 (s, 1 H), 5.56 (m, 1 H), 5.17 (d, J=18.1 Hz, 1 H), 5.06 (d, J=11.5 Hz, 1 H), 4.52 (d, J=11.2 Hz, 1 H), 4.31 (m, 3 H), 3.95 (m, 1 H), 3.86 (dd, 1 H, J=11.5 and 2.9 Hz), 2.92 (m, 1 H), 2.61 (m, 1 H), 2.95 (m, 2 H), 2.10 (m, 2 H), 1.85 (m, 1 H), 1.75 (m, 1 H), 1.66 (m, 1 H), 1.28 (m, 1 H), 1.00-1.15 (m, 4 H), 1.04 (s, 9 H).

EXAMPLE 11

(2R,4S,7S)-7-tert-butyl-N-((1R,2S)-1-{[(cyclopropylsulfonyl)amino]carbonyl}-2-vinylcyclopropyl)-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxamide (III-9)

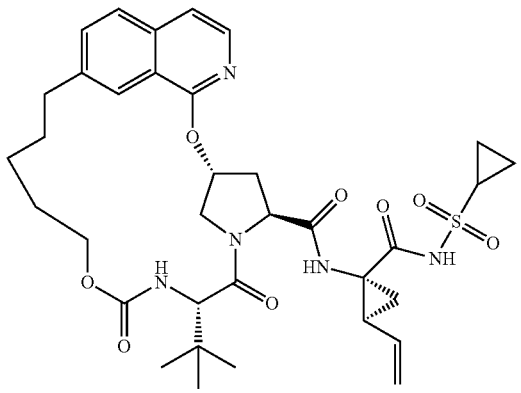

III-9

Step 1: Ethyl (2R,4S,7S)-7-tert-butyl-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate

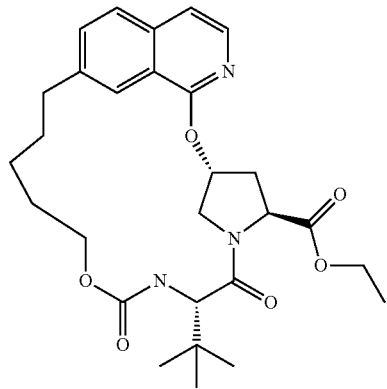

The ester from Example 10, Step 4 (512 mg, 1.00 mmol) was dissolved in ethyl acetate (40 mL) degassed with nitrogen and 10% palladium on carbon added (50 mg). The mixture was then purged with hydrogen 3 times and let stir under a hydrogen balloon for 24 h. The reaction was filtered, concentrated in vacuo to give the compound (493 mg) as a foam. LRMS (ESI) m/z 512 [(M+H)$^+$; calcd for $C_{28}H_{38}N_3O_6$: 512].

Step 2: (2R,4S,7S)-7-tert-butyl-N-((1R,2S)-1-{[(cyclopropylsulfonyl)amino]carbonyl}-2-vinylcyclopropyl)-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxamide The title compound was prepared in a similar manner as described for the preparation of Example 10 Step 5 utilizing the ester from Step 1. LRMS (ESI) m/z 696 [(M+H)$^+$; calcd for $C_{35}H_{46}N_5O_8S$: 696].

$^1$H NMR (500 MHz, ppm, CDCl$_3$) δ 9.88 (s, 1 H), 7.92 (d, J=7.1 Hz, 1 H), 7.78 (s, 1 H), 7.65 (d, J=10.6 Hz, 1 H), 7.49 (dd, J=10.7 and 1.6 Hz, 1 H), 7.30 (d, J=7.1 Hz, 1 H), 7.19 (s, 1 H), 6.22 (m, 1 H), 5.76 (m, 1 H), 5.65 (d, J=11.7, 1 H), 5.26 (d, J=18.8 Hz, 1 H), 5.15 (d, J=11.2 Hz, 1 H), 4.62 (m, 1 H), 4.46 (m, 3 H), 3.92 (dd, 1 H, J=11.2 and 2.9 Hz), 3.73 (m, 1 H), 2.90 (m, 2 H), 2.70 (m, 1 H), 2.62 (m, 1 H), 2.51 (m, 1 H), 2.10 (m, 1 H), 1.96 (m, 1 H), 1.72 (m, 3 H), 1.48 (m, 2 H), 1.20-1.35 (m, 4 H), 1.07 (s, 9 H), 1.01 (m, 2 H).

EXAMPLE 12

2R,4S,7S-7-tert-butyl-N-((1R,2R)-1-{[(cyclopropylsulfonyl)amino]carbonyl}-2-ethylcyclopropyl)-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxamide (III-37)

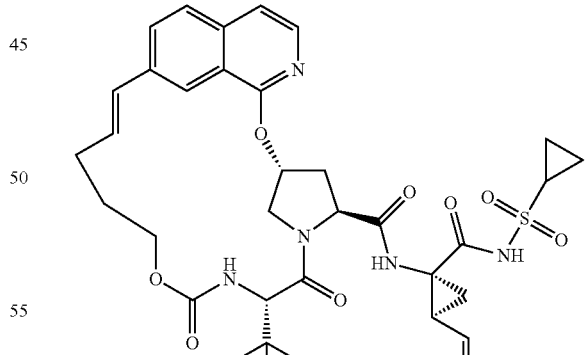

III-37

The title compound was prepared in a similar manner as described for the preparation of Example 10 Step 5 utilizing (1R,2R)-1-{[(cyclopropylsulfonyl)amino]carbonyl}-2-ethylcyclopropanaminium chloride (Intermediate A3). LRMS (ESI) m/z 696 [(M+H)$^+$; calcd for $C_{35}H_{46}N_5O_8S$: 696]. $^1$H NMR (500 MHz, ppm) (d$_6$-DMSO) δ 10.28 (s, 1 H), 8.66 (s, 1 H), 8.45 (s, 1 H), 7.94 (d, J=5.9 Hz, 1 H), 7.81 (d, J=8.3 Hz, 1 H), 7.62 (dd, J=8.3 and 1.7 Hz, 1 H), 7.35 (d, J=5.9 Hz, 1 H), 7.23 (d, J=7.32 Hz, 1 H), 6.62 (d, J=15.6 Hz, 1 H), 6.39 (m, 1 H), 5.68 (m, 1 H), 4.52 (d, J=11.0 Hz, 1 H), 4.31 (m, 3 H), 3.95 (m, 1 H), 3.86 (dd, J=11.7 and 3.2 Hz, 1 H), 2.93 (m, 1 H), 2.55 (m, 1 H), 2.28 (m, 2 H), 2.08 (m, 1 H), 1.84 (m, 1 H), 1.75 (m, 1 H), 1.46 (m, 1 H), 1.24-1.38 (m, 3 H), 1.00-1.15 (m, 5 H), 1.04 (s, 9 H), 0.85 (t, J=7.3 Hz, 3 H).

EXAMPLE 13

(2R,4S,7S)-7-tert-butyl-N-((1R,2S)-1-{[(cyclopropylsulfonyl)amino]carbonyl}-2-vinylcyclopropyl)-22-iodo-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxamide (III-38)

III-38

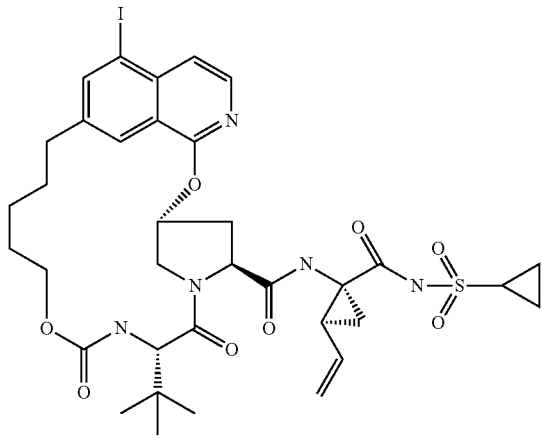

Step 1: Ethyl (2R,4S,7S)-7-tert-butyl-22-iodo-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxylate

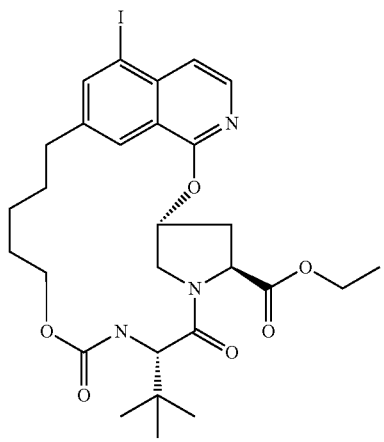

The ester from Example 11, Step 1 (0.79 gm, 1.55 mmol) was dissolved in triflic acid (5 mL) and added N-iodosuccinimide (0.90 gm, 4.0 mmol) in 4 portions over 4 h. Reaction was poured into a cold mixture of ethyl acetate and saturated sodium bicarbonate solution. Layers were separated and the organic layer was washed with saturated sodium bicarbonate solution and brine. Organics were dried over anhydrous sodium sulfate and the solvent was then evaporated to yield a crude oil. The crude product was purified by chromatography on silica (10-50% EtOAc hexane) to give the title compound (0.76 gm). LRMS (ESI) m/z 638 [(M+H)$^+$; calcd for $C_{28}H_{37}IN_3O_6$: 638].

Step 2: (2R,4S,7S)-7-tert-butyl-N-((1R,2S)-1-{[(cyclopropylsulfonyl)amino]carbonyl}-2-vinylcyclopropyl)-22-iodo-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxamide The title compound was prepared in a similar manner as described for the preparation of Example 10 Step 5 utilizing the ester from step 1. LRMS (ESI) m/z 822 [(M+H)$^+$; calcd for $C_{35}H_{45}IN_5O_8S$: 822]: $^1$H NMR (400 MHz, ppm) (CD$_3$OD) δ 9.17 (s, 1 H), 8.17 (s, 1 H), 8.01 (d, J=6.1 Hz, 1 H), 7.95 (s, 1 H), 7.43 (d, J=6.04 Hz, 1 H), 6.2 (s, 1 H), 5.73 (m, 1 H), 5.28 (d, J=18.7 Hz, 1 H), 5.12 (dd, J=10.2 and 1.6 Hz, 1 H), 4.57 (m, 1 H), 4.41 (m, 3 H), 3.99 (dd, J=11.7 and 3.1 Hz, 1 H), 3.74 (m, 1 H), 2.93 (m, 2 H), 2.64 (m, 1 H), 2.55 (m, 1 H), 2.24 (m, 2 H), 1.88 (m, 1 H), 1.73 (m, 3 H), 1.49 (m, 1 H), 1.43 (m, 1 H), 1.25 (m, 4 H), 1.09 (m, 2 H), and 1.06 (s, 9 H).

EXAMPLE 14

(2R,4S,7S,14E)-7-Cyclopentyl-N-((1R,2S)-1-{[(cyclopropylsulfonyl)amino]carbonyl}-2-vinylcyclopropyl)-12,12-dimethyl-6,9-dioxo-3,4,6,7,8,9,12,13-octahydro-2H,11H-16,18-etheno-2,5-methanopyrido[2,3-k][1,10,3,6]dioxadiazacyclononadecine-4-carboxamide (III-39)

III-39

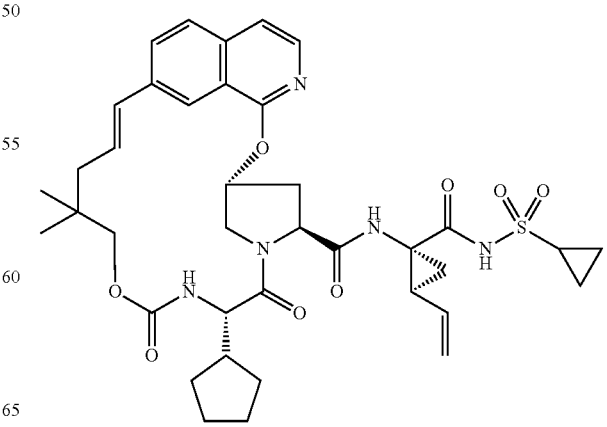

Step 1: Ethyl(4R)-4-[(7-bromoisoquinolin-1-yl)oxy]-1-[(2S)-2-cyclopentyl-2-({[(2,2-dimethylpent-4-en-1-yl)oxy]carbonyl}amino)acetyl]-L-prolinate

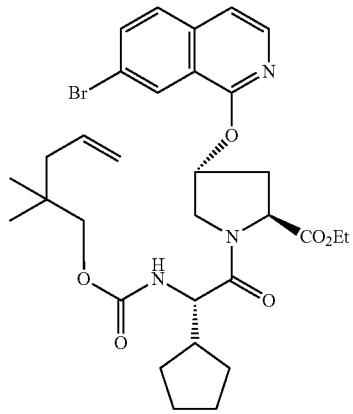

To a solution of ethyl (4R)-4-[7-bromoisoquinolin-1-yl)oxy]-L-prolinate hydrochloride (EXAMPLE 1, Step 1) (500 mg, 1.25 mmol) and (2S)-cyclopentyl({[(2,2-dimethylpent-4-en-1-yl)oxy]carbonyl}amino)acetic acid (Intermediate B24) (353 mg, 1.25 mmol) in DMF (7 mL) at RT was added HATU (710 mg, 1.87 mmol) and DIPEA (0.87 mL, 5.00 mmol). After 2 h, the reaction mixture was poured into EtOAc, and extracted with 1 N HCl. The organic layer was washed with water and brine, dried over $Na_2SO_4$ and the solvent was removed in vacuo. The crude product was purified on silica (gradient elution, 5% to 75% EtOAc in hexanes) to yield 526 mg (67%) of the title compound. LRMS (ESI) m/z 630.3 [(M+H)$^+$; calcd for $C_{31}H_{41}BrN_3O_6$: 630.2].

Step 2: Ethyl(4R)-1-[(2S)-2-cyclopentyl-2-({[(2,2-dimethylpent-4-en-1-yl)oxy]carbonyl}amino)acetyl]-4-[(7-vinylisoquinolin-1-yl)oxy]-L-prolinate

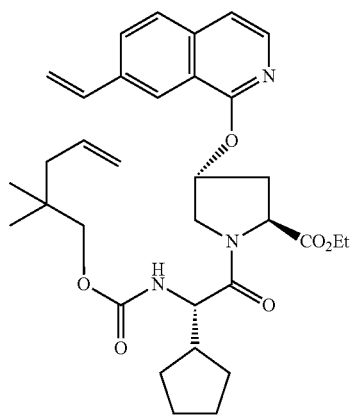

Ethyl(4R)-4-[(7-bromoisoquinolin-1-yl)oxy]-1-[(2S)-2-cyclopentyl-2-({[(2,2-dimethylpent-4-en-1-yl)oxy]carbonyl}amino)acetyl]-L-prolinate (526 mg, 0.83 mmol) was dissolved in ethanol (10 mL) and nitrogen was bubbled through for 15 min. Potassium vinyltrifluoroborate (168 mg, 1.25 mmol) and dichloro[1,1'-bis(diphenylphosphino)ferrocene]palladium(II) DCM adduct (34 mg, 0.04 mmol) were added and the reaction mixture heated to reflux under nitrogen. After 15 h, the reaction was complete and the volatiles were evaporated and the residue purified by silica gel chromatography (gradient elution, 10-75% EtOAc/hexane) to give a clear oil. LRMS (ESI) m/z 578.4 [(M+H)$^+$; calcd for $C_{33}H_{44}N_3O_6$: 578.3].

Step 3: Ethyl(2R,4S,7S,14E)-7-cyclopentyl-12,12-dimethyl-6,9-dioxo-3,4,6,7,8,9,12,13-octahydro-2H,11H-16,18-etheno-2,5-methanopyrido[2,3-k][1,10,3,6]dioxadiazacyclononadecine-4-carboxylate

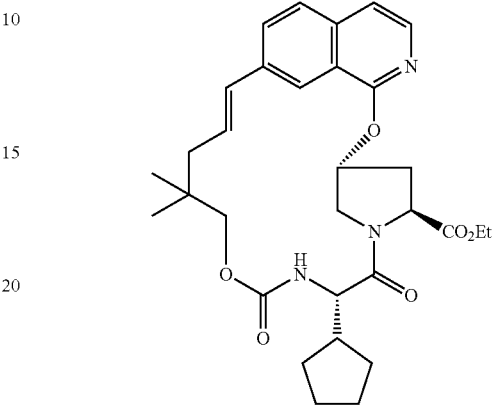

To a solution of the product from Step 2 (413 mg, 0.72 mmol) in degassed (nitrogen bubbling for 30 min) DCE (250 mL) was added Zhan 1B catalyst (Zhan catalyst 1B, RC-303, Zannan Pharma Ltd.) (52 mg, 0.07 mmol). The mixture was then stirred at 70° C. under an $N_2$ atmosphere. After 3 h, the reaction was complete and was concentrated in vacuo. The crude product was then directly purified on silica (gradient elution, 5% to 75% EtOAc in hexanes) to yield 325 mg (83%) of the title compound. LRMS (ESI) m/z 550.4 [(M+H)$^+$; calcd for $C_{31}H_{40}N_3O_6$: 550.3].

Step 4: (2R,4S,7S,14E)-7-Cyclopentyl-12,12-dimethyl-6,9-dioxo-3,4,6,7,8,9,12,13-octahydro-2H,11H-16,18-etheno-2,5-methanopyrido[2,3-k][1,10,3,6]dioxadiazacyclononadecine-4-carboxylic acid

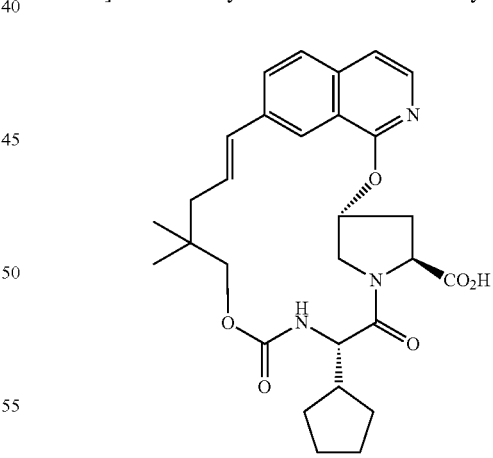

To a solution of the product from Step 3 (160 mg, 0.29 mmol) in THF (5 mL) and EtOH (0.5 mL) at RT was added LiOH (1 M, 2.9 mL, 2.9 mmol). After 1 h, the reaction mixture was partitioned between EtOAc and 1N HCl (×4). The combined organic layers were washed with brine, dried over $Na_2SO_4$ and the solvent was removed in vacuo to yield 144 mg (95%) of the title compound which was used without further purification. LRMS (ESI) m/z 522.3 [(M+H)$^+$; calcd for $C_{29}H_{36}N_3O_6$: 522.3].

Step 5: (2R,4S,7S,14E)-7-Cyclopentyl-N-((1R,2S)-1-{[(cyclopropylsulfonyl)amino]carbonyl}-2-vinylcyclopropyl)-12,12-dimethyl-6,9-dioxo-3,4,6,7,8,9,12,13-octahydro-2H,11H-16,18-etheno-2,5-methanopyrido[2,3-k][1,10,3,6]dioxadiazacyclononadecine-4-carboxamide (III-39)

To a solution of the product from Step 4 (147 mg, 0.28 mmol) and (1R,2S)-1-amino-N-(cyclopropylsulfonyl)-2-vinylcyclopropanecarboxamide hydrochloride (Intermediate A1) (90 mg, 0.34 mmol) in DMF (2 mL) was added DIPEA (0.25 mL, 1.41 mmol), DMAP (3 mg, 0.03 mmol) and HATU (107 mg, 0.28 mmol). After full conversion (15 h), the reaction mixture was purified by reverse-phase HPLC (gradient elution, 30% to 100% CH$_3$CN in 0.15% TFA/water) to yield 122 mg (59%) of the title compound as a white powder. $^1$H NMR (500 MHz, CD$_3$OD) δ 9.16 (s, 1 H), 8.44 (s, 1 H), 7.87 (d, J=5.9 Hz, 1 H), 7.72 (d, J=8.3 Hz, 1 H), 7.56 (d, J=8.3 Hz, 1 H), 7.27 (d, J=6.1 Hz, 1 H), 6.47 (s, 2 H), 5.77 (s, 1 H), 5.70 (m, 1 H), 5.24 (d, J=17.1 Hz, 1 H), 5.07 (d, J=10.3 Hz, 1 H), 4.79 (d, J=11.7 Hz, 1 H), 4.43 (d, J=11.0 Hz, 1 H), 4.34 (m, 2 H), 4.03 (dd, J=11.5 & 2.7 Hz, 1 H), 2.95 (m, 1 H), 2.65 (m, 1 H), 2.42 (m, 2 H), 2.22 (m, 1 H), 2.13 (q, J=8.8 Hz, 1 H), 2.01 (m, 1 H), 1.92 (m, 1 H), 1.86 (m, 1 H), 1.80-1.60 (m, 5 H), 1.43-1.20 (m, 5 H), 1.15 (s, 3 H), 1.10 (m, 2 H), 0.89 (s, 3 H) ppm. LRMS (ESI) m/z 734.4 [(M+H)$^+$; calcd for C$_{38}$H$_{48}$N$_5$O$_8$S: 734.3].

EXAMPLE 15

(2R,4S,7S)-7-Cyclopentyl-N-((1R,2S)-1-{[(cyclopropylsulfonyl)amino]carbonyl}-2-vinylcyclopropyl)-12,12-dimethyl-6,9-dioxo-3,4,6,7,8,9,12,13,14,15-decahydro-2H,11H-16,18-etheno-2,5-methanopyrido[2,3-k][1,10,3,6]dioxadiazacyclononadecine-4-carboxamide (III-40)

III-40

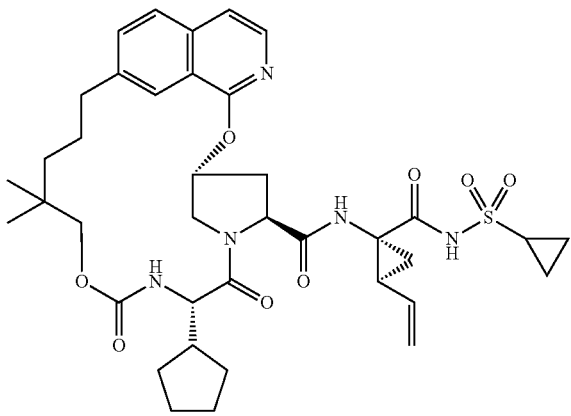

Step 1: Ethyl(2R,4S,7S)-7-cyclopentyl-12,12-dimethyl-6,9-dioxo-3,4,6,7,8,9,12,13,14,15-decahydro-2H,11H-16,18-etheno-2,5-methanopyrido[2,3-k][1,10,3,6]dioxadiazacyclononadecine-4-carboxylate

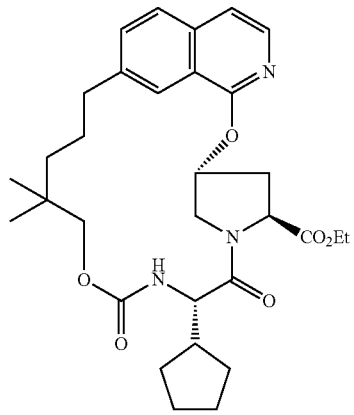

To a solution of ethyl (2R,4S,7S,14E)-7-cyclopentyl-12,12-dimethyl-6,9-dioxo-3,4,6,7,8,9,12,13-octahydro-2H,11H-16,18-etheno-2,5-methanopyrido[2,3-k][1,10,3,6]dioxadiazacyclononadecine-4-carboxylate (EXAMPLE 14, Step 3) (160 mg, 0.29 mmol) in EtOAc (7 mL) at RT was added Pd/C (100 mg). An H$_2$ balloon was then placed on the reaction flask, the flask was evacuated quickly and filled with H$_2$. After 7 h, the reaction mixture was filtered through celite and washed with EtOAc. Concentration of the filtrate gave 147 mg (92%) of the title compound which was used without further purification. LRMS (ESI) m/z 552.4 [(M+H)$^+$; calcd for C$_{31}$H$_{42}$N$_3$O$_6$S: 552.3].

Step 2: (2R,4S,7S)-7-Cyclopentyl-N-((1R,2S)-1-{[(cyclopropylsulfonyl)amino]carbonyl}-2-vinylcyclopropyl)-12,12-dimethyl-6,9-dioxo-3,4,6,7,8,9,12,13,14,15-decahydro-2H,11H-16,18-etheno-2,5-methanopyrido[2,3-k][1,10,3,6]dioxadiazacyclononadecine-4-carboxamide (III-40)

The title compound was prepared from ethyl (2R,4S,7S)-7-cyclopentyl-12,12-dimethyl-6,9-dioxo-3,4,6,7,8,9,12,13,14,15-decahydro-2H,11H-16,18-etheno-2,5-methanopyrido[2,3-k][1,10,3,6]dioxadiazacyclononadecine-4-carboxylate using the procedures described in EXAMPLE 14, Steps 4 and 5. $^1$H NMR (500 MHz, CD$_3$OD) δ 9.26 (s, 1 H), 7.89 (s, 1 H), 7.87 (d, J=5.9 Hz, 1 H), 7.71 (d, J=8.3 Hz, 1 H), 7.55 (d, J=8.3 Hz, 1 H), 7.29 (d, J=5.9 Hz, 1 H), 6.03 (s, 1 H), 5.76 (m, 1 H), 5.28 (d, J=15.6 Hz, 1 H), 5.10 (d, J=8.5 Hz, 1 H), 4.58 (d, J=11.5 Hz, 1 H), 4.46 (m, 1 H), 4.33 (d, J=10.7 Hz, 2 H), 4.01 (dd, J=11.5 & 2.7 Hz, 1 H), 3.28 (d, J=10.7 Hz, 1 H), 2.97 (sep, J=4.6 Hz, 1 H), 2.81 (m, 1 H), 2.64 (m, 1 H), 2.55 (q, J=6.7 Hz, 1 H), 2.44 (m, 1 H), 2.26 (m, 1 H), 2.18 (q, J=9.0 Hz, 1 H), 1.88 (m, 2 H), 1.70 (m, 4 H), 1.56 (m, 3 H), 1.40 (m, 3 H), 1.27 (m, 4 H), 1.07 (m, 4 H), 0.77 (s, 3 H) ppm. LRMS (ESI) m/z 736.4 [(M+H)$^+$; calcd for C$_{38}$H$_{50}$N$_5$O$_8$S: 736.3].

By using the appropriate procedures and the appropriate A and B intermediates in place of (1R,2S)-1-amino-N-(cyclopropylsulfonyl)-2-vinylcyclopropanecarboxamide hydrochloride (Intermediate A1) and (2S)-cyclopentyl({[(2,2-dimethylpent-4-en-1-yl)oxy]carbonyl}amino)acetic acid (Intermediate B24), the following compounds were prepared.

| Ex. | Structure | Name | LRMS (M + H)+ | Prepared using the appropriate Intermediates according to the procedure below. | Int. |
|---|---|---|---|---|---|
| 16, III-41 | 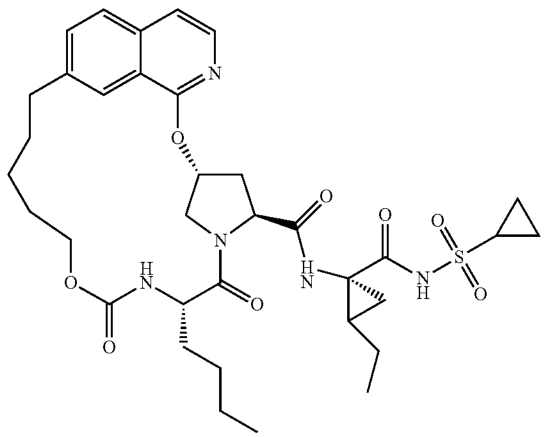 | (2R,4S,7S)-7-butyl-N-((1R)-1-{[(cyclopropylsulfonyl)amino]carbonyl}-2-ethylcyclopropyl)-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 698.5 | See Example 15 | A3, B1 |
| 17, III-15 | 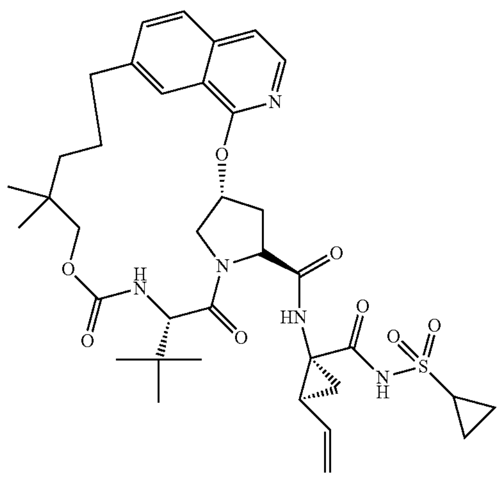 | (2R,4S,7S)-7-tert-butyl-N-((1R,2S)-1-{[(cyclopropylsulfonyl)amino]carbonyl}-2-vinylcyclopropyl)-12,12-dimethyl-6,9-dioxo-3,4,6,7,8,9,12,13,14,15-decahydro-2H,11H-16,18-etheno-2,5-methanopyrido[2,3-k][1,10,3,6]dioxadiazacyclononadecine-4-carboxamide | 724.4 | See Example 15 | A1, B4 |
| 18, III-29 | 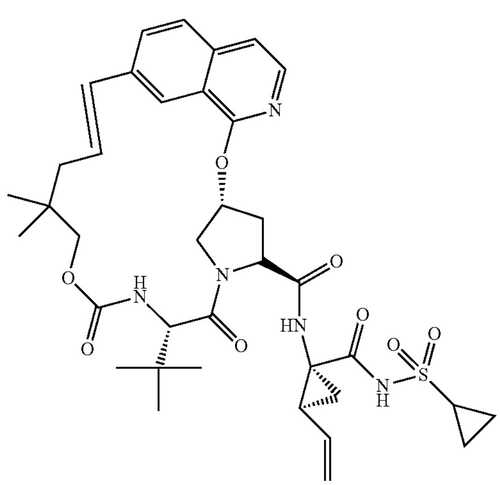 | (2R,4S,7S,14E)-7-tert-butyl-N-((1R,2S)-1-{[(cyclopropylsulfonyl)amino]carbonyl}-2-vinylcyclopropyl)-12,12-dimethyl-6,9-dioxo-3,4,6,7,8,9,12,13-octahydro-2H,11H-16,18-etheno-2,5-methanopyrido[2,3-k][1,10,3,6]dioxadiazacyclononadecine-4-carboxamide | 722.3 | See Example 14 | A1, B4 |

| Ex. | Structure | Name | LRMS (M + H)+ | Prepared using the appropriate Intermediates according to the procedure below. | Int. |
|---|---|---|---|---|---|
| 19, III-42 | 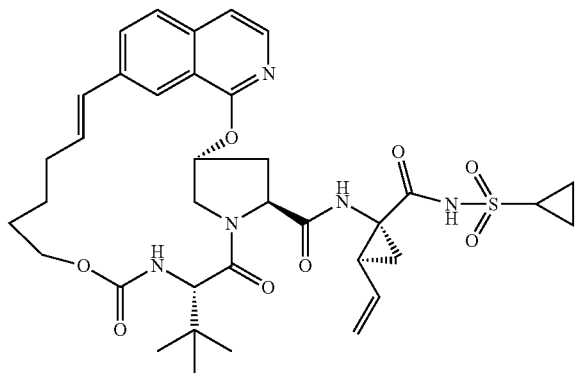 | (2R,4S,7S,15E)-7-tert-butyl-N-((1R,2S)-1-[(cyclopropyl-sulfonyl)amino]carbonyl}-2-vinyl-cyclopropyl)-6,9-dioxo-3,4,6,7,8,9,11,12,13,14-decahydro-2H-17,19-(ethanediylidene)-2,5-methanopyrido[2,3-k][1,10,3,6]dioxadiazacyclo-icosine-4-carboxamide | 708.6 | See Example 14 | A1, B5 |
| 20, III-43 | 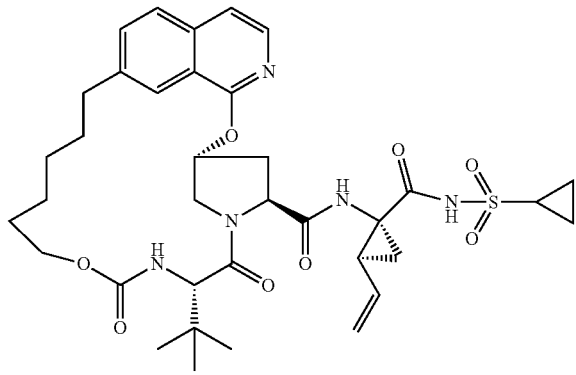 | (2R,4S,7S)-7-tert-butyl-N-((1R,2S)-1-{[(cyclopropyl-sulfonyl)amino]carbonyl}-2-vinyl-cyclopropyl)-6,9-dioxo-3,4,6,7,8,9,11,12,13,14,15,16-dodecahydro-2H-17,19-(ethanediylidene)-2,5-methanopyrido[2,3-k][1,10,3,6]dioxadiazacyclo-icosine-4-carboxamide | 710.6 | See Example 15 | A1, B5 |
| 21, III-44 | 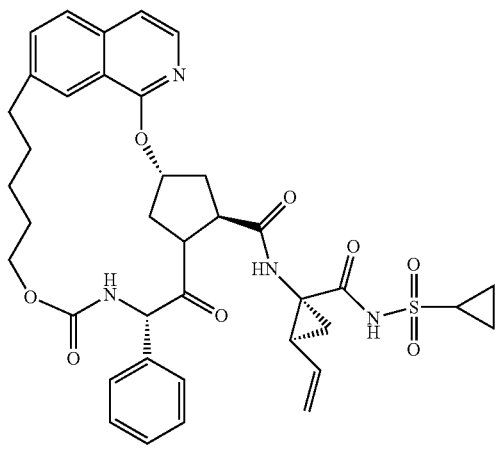 | (2R,4S,7S)-N-((1R,2S)-1-{[(cyclo-propylsulfonyl)amino]carbonyl}-2-vinylcyclopropyl)-6,9-dioxo-7-phenyl-3,4,6,7,8,9,12,13,14,15-decahydro-2H,11H-16,18-(ethanediyhdene)-2,5-methanopyrido[2,3-k][1,10,3,6]dioxadiazacyclonona-decine-4-carboxamide | 716.3 | See Example 15 | A1, B6 |

-continued

| Ex. | Structure | Name | LRMS (M + H)+ | Prepared using the appropriate Intermediates according to the procedure below. | Int. |
|---|---|---|---|---|---|
| 22, III-45 | 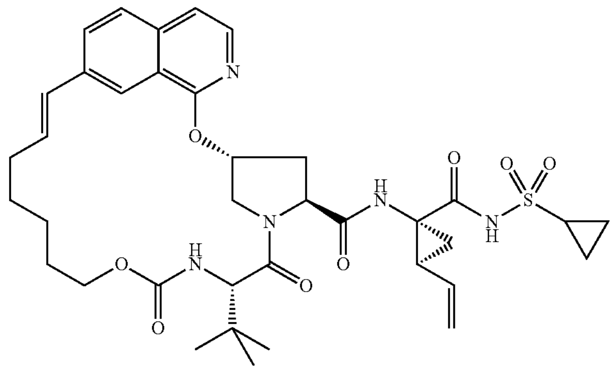 | (2R,4S,7S,16E)-7-tert-butyl-N-((1R,2S)-1-{[[(cyclopropyl-sulfonyl)amino]carbonyl}-2-vinyl-cyclopropyl)-6,9-dioxo-3,4,6,7,8,9,12,13,14,15-decahydro-2H,11H-18,20-etheno-2,5-methanopyrido[2,3-k][1,10,3,6]dioxadiazacyclo-henicosine-4-carboxamide | 722.5 | See Example 14 | A1, B7 |
| 23, III-10 | 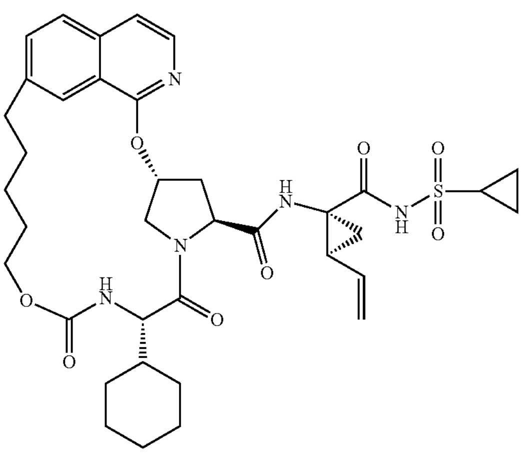 | (2R,4S,7S)-7-cyclohexyl-N-((1R,2S)-1-{[(cyclopropyl-sulfonyl)amino]carbonyl}-2-vinyl-cyclopropyl)-6,9-dioxo-3,4,6,7,8,9,12,13,14,15-decahydro-2H,11H-16,18-(ethanediylidene)-2,5-methanopyrido[2,3-k][1,10,3,6]dioxadiazacyclonona-decine-4-carboxamide | 708.3 | See Example 15 | A1, B8 |
| 24, III-46 | 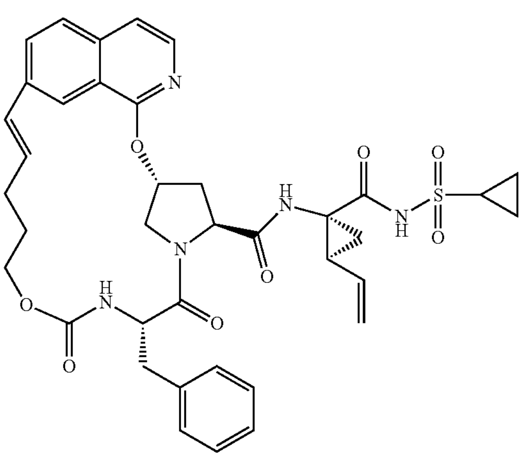 | (2R,4S,7S,14E)-7-benzyl-N-((1R,2S)-1-{[(cyclopropyl-sulfonyl)amino]carbonyl}-2-vinyl cyclopropyl)-6,9-dioxo-3,4,6,7,8,9,12,13-octahydro-2H,11H-16,18-(ethanediylidene)-2,5-methanopyrido[2,3-k][1,10,3,6]dioxadiazacyclonona-decine-4-carboxamide | 728.4 | See Example 14 | A1, B9 |

-continued

| Ex. | Structure | Name | LRMS (M + H)+ | Prepared using the appropriate Intermediates according to the procedure below. | Int. |
|---|---|---|---|---|---|
| 25, III-47 | 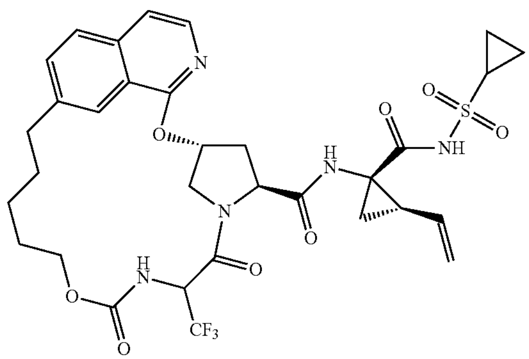 | (2R,4S)-N-((1S)-1-{[(cyclopropyl-sulfonyl)amino]carbonyl}-2-vinylcyclopropyl)-6,9-dioxo-7-(trifluoromethyl)-3,4,6,7,8,9,12,13,14,15-decahydro-2H,11H-16,18-(ethanediylidene)-2,5-methanopyrido[2,3-k][1,10,3,6]dioxadiazacyclonona-decine-4-carboxamide | 708.2 | See Example 15 | A1, B10 |
| 26, III-48 | 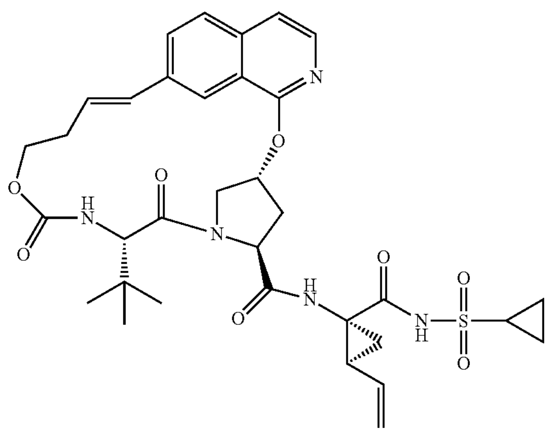 | (2R,4S,7S,13E)-7-tert-butyl-N-((1R,2S)-1-{[(cyclopropylsulfonyl)amino]carbonyl}-2-vinylcyclopropyl)-6,9-dioxo-3,4,6,7,8,9,11,12-octahydro-2H-15,17-(ethanediylidene)-2,5-methanopyrido[2,3-k][1,10,3,6]dioxadiazacycloocta-decine-4-carboxamide | 680.6 | See Example 14 | A1, B22 |
| 27, III-24 | 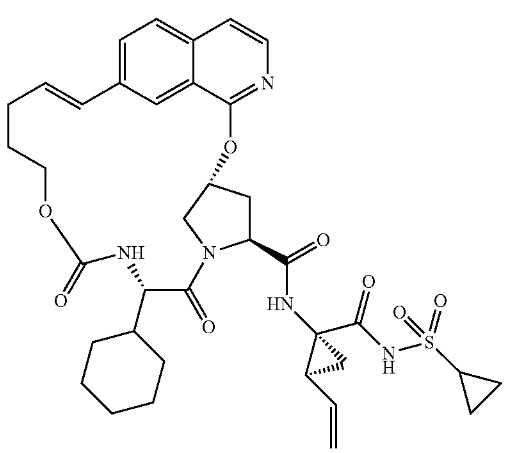 | (2R,4S,7S,14E)-7-cyclohexyl-N-((1R,2S)-1-{[(cyclopropyl-sulfonyl)amino]carbonyl}-2-vinyl-cyclopropyl)-6,9-dioxo-3,4,6,7,8,9,12,13-octahydro-2H,11H-16,18-(ethanediylidene)-2,5-methanopyrido[2,3-k][1,10,3,5]dioxadiazacyclo-ononadecine-4-carboxamide | 720.6 | See Example 14 | A1, B8 |

| Ex. | Structure | Name | LRMS (M + H)+ | Prepared using the appropriate Intermediates according to the procedure below. | Int. |
|---|---|---|---|---|---|
| 28, III-49 | 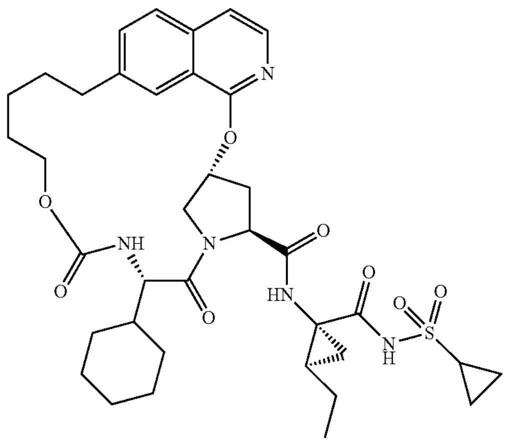 | (2R,4S,7S)-7-cyclohexyl-N-((1R,2R)-1-{[(cyclopropyl-sulfonyl)amino]carbonyl)-2-ethyl-cyclopropyl)-6,9-dioxo-3,4,6,7,8,9,12,13,14,15-decahydro-2H,11H-16,18-(ethanediylidene)-2,5-methanopyrido[2,3-k][1,10,3,6]dioxadiazacyclonona-decine-4-carboxamide | 724.5 | See Example 15 | A3, B8 |
| 29, III-50 | 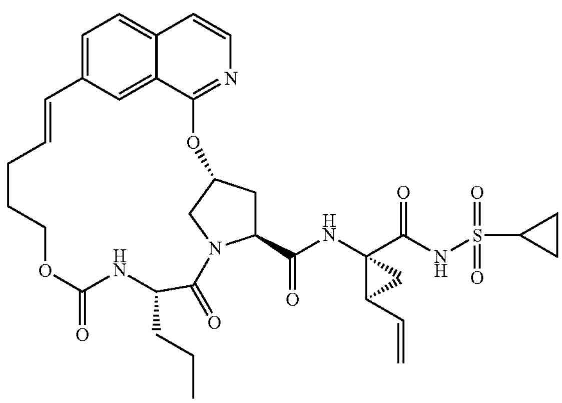 | (2R,4S,7S,14E)-N-((1R,2S)-1-{[(cyclo-propylsulfonyl)amino]carbonyl}-2-vinylcyclopropyl)-6,9-dioxo-7-propyl-3,4,6,7,8,9,12,13-octahydro-2H,11H-16,18-(ethanediylidene)-2,5-methanopyrido[2,3-k][1,10,3,6]dioxadiazacyclonona-decine-4-carboxamide | 680.5 | See Example 14 | A1, B12 |
| 30, III-51 | 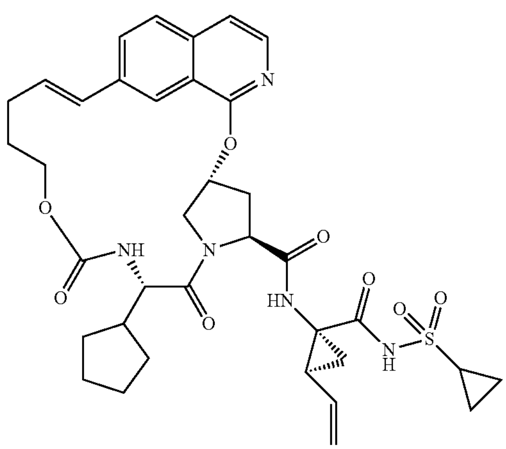 | (2R,4S,7S,14E)-7-cyclopentyl-N-((1R,2S)-1-{[(cyclopropyl-sulfonyl)amino]carbonyl}-2-vinyl-cyclopropyl)-6,9-dioxo-3,4,6,7,8,9,12,13-octahydro-2H,11H-16,18-(ethanediylidene)-2,5-methanopyrido[2,3-k][1,10,3,6]dioxadiazacyclonona-decine-4-carboxamide | 706.5 | See Example 14 | A1, B13 |

-continued

| Ex. | Structure | Name | LRMS (M + H)+ | Prepared using the appropriate Intermediates according to the procedure below. | Int. |
|---|---|---|---|---|---|
| 31, III-52 | 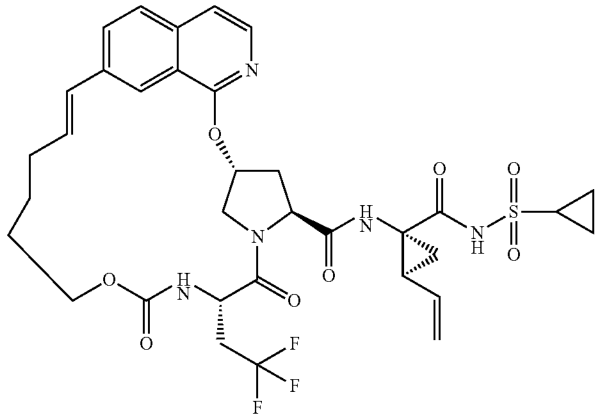 | (2R,4S,7S,15E)-N-((1R,2S)-{[(cyclo-propylsulfonyl)amino]carbonyl}-2-vinylcyclopropyl)-6,9-dioxo-7-(2,2,2-trifluoroethyl)-3,4,6,7,8,9,11,12,13,14-decahydro-2H-17,19-(ethanediylidene)-2,5-methanopyrido[2,3-k][1,10,3,6]dioxadiazacycloicosine-4-carboxamide | 734.4 | See Example 14, separated diastereomers | A1, B14 |
| 32, III-53 | 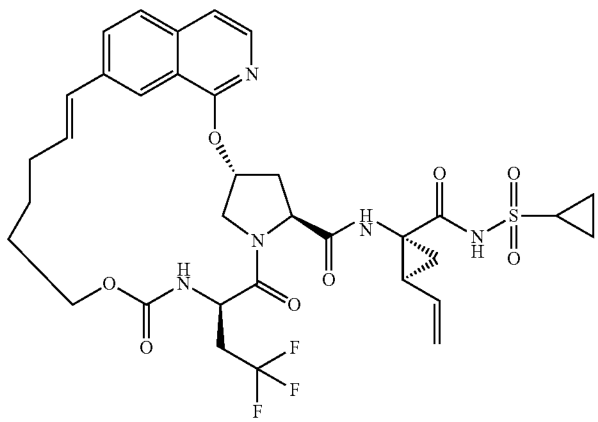 | (2R,4S,7R,15E)-N-((1R,2S)-1-{[(cyclo-propylsulfonyl)amino]carbonyl}-2-vinylcyclopropyl)-6,9-dioxo-7-(2,2,2-trifluoroethyl)-3,4,6,7,8,9,11,12,13,14-decahydro-2H-17,19-(ethanediylidene)-2,5-methanopyrido[2,3-k][1,10,3,6]dioxadiazacycloicosine-4-carboxamide | 734.4 | See Example 14, separated diastereomers | A1, B14 |
| 33, III-54 | 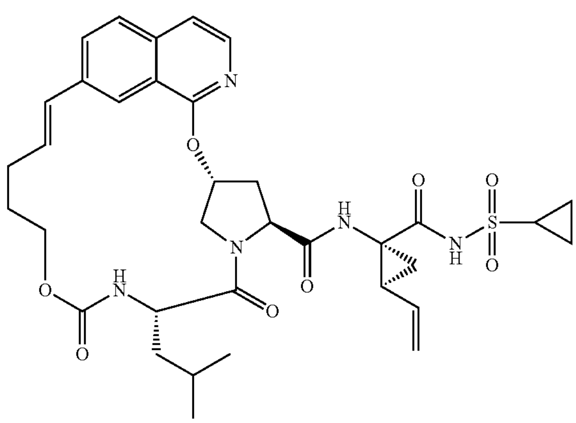 | (2R,4S,7S,14E)-N-((1R,2S)-1-{[(cyclo-propylsulfonyl)amino]carbonyl}-2-vinyl-cyclopropyl)-7-isobutyl-6,9-dioxo-3,4,6,7,8,9,12,13-octahydro-2H,11H-16,18-(ethanediylidene)-2,5-methanopyrido[2,3-k][1,10,3,6]dioxadiazacyclonona-decine-4-carboxamide | 694.5 | See Example 14 | A1, B15 |

| Ex. | Structure | Name | LRMS (M + H)+ | Prepared using the appropriate Intermediates according to the procedure below. | Int. |
|---|---|---|---|---|---|
| 34, III-55 | 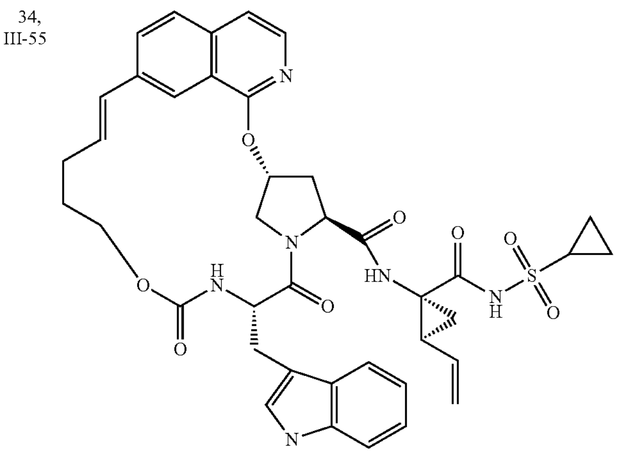 | (2R,4S,7S,14E)-N-((1R,2S)-1-{[(cyclo-propylsulfonyl)amino]carbonyl}-2-vinyl-cyclopropyl)-7-(1H-indol-3-ylmethyl)-6,9-dioxo-3,4,6,7,8,9,12,13-octahydro-2H,11H-16,18-etheno-2,5-methanopyrido[2,3-k][1,10,3,6]dioxadiazacyclonona-decine-4-carboxamide | 767.3 | See Example 14 | A1, B16 |
| 35, III-56 | 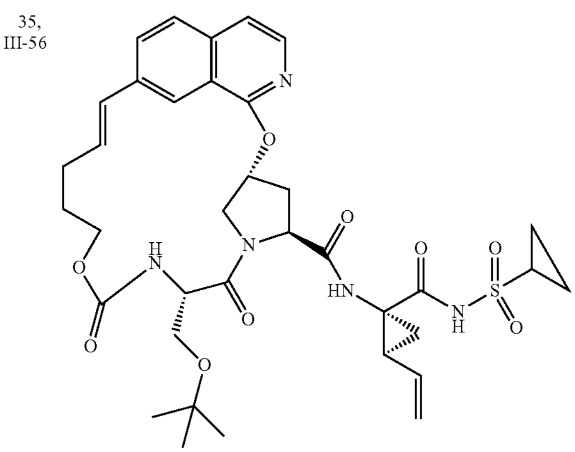 | (2R,4S,7S,14E)-7-(tert-butoxymethyl)-N-((1R,2S)-1-{[(cyclo-propylsulfonyl)amino]carbonyl}-2-vinyl-cyclopropyl)-6,9-dioxo3,4,6,7,8,9,12,13-octahydro-2H,11H-16,18-etheno-2,5-methanopyrido[2,3-k][1,10,3,6]dioxadiazacyclonona-decine-4-carboxamide | 724.4 | See Example 14 | A1, B17 |
| 36, III-57 | 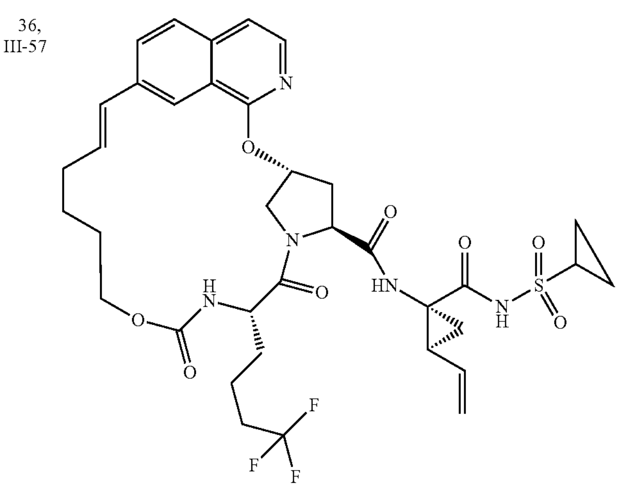 | (2R,4S,7S,15E)-N-((1R,2S)-1-{[(cyclo-propylsulfonyl)amino]carbonyl}-2-vinylcyclo-propyl)-6,9-dioxo-7-(4,4,4-trifluorobutyl)-3,4,6,7,8,9,11,12,13,14-decahydro-2H-17,19-etheno-2,5-methanopyrido[2,3-k][1,10,3,6]dioxadiazacycloicosine-4-carboxamide | 762.3 | See Example 14, separated diastereomers | A1, B18 |

-continued

| Ex. | Structure | Name | LRMS (M + H)+ | Prepared using the appropriate Intermediates according to the procedure below. | Int. |
|---|---|---|---|---|---|
| 37, III-58 | 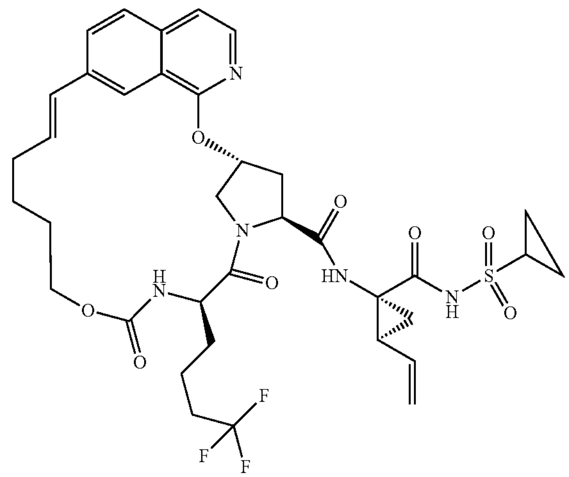 | (2R,4S,7R,15E)-N-((1R,2S)-1-{[(cyclo-propylsulfonyl)amino]carbonyl}-2-vinylcyclopropyl)-6,9-dioxo-7-(4,4,4-trifluorobutyl)-3,4,6,7,8,9,11,12,13,14-decahydro-2H-17,19-etheno-2,5-methanopyrido[2,3-k][1,10,3,6]dioxadiazacycloicosine-4-carboxamide | 762.3 | See Example 14, separated diastereomers | A1, B18 |
| 38, III-59 | 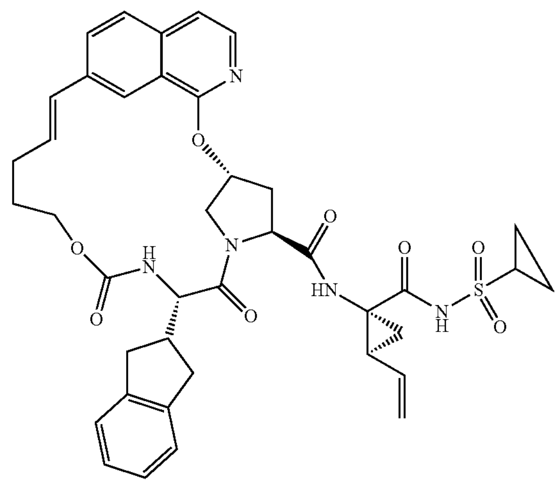 | (2R,4S,7S,14E)-N-((1R,2S)-1-{[(cyclo-propylsulfonyl)amino]carbonyl}-2-vinylcyclo-propyl)-7-(2,3-dihydro-1H-inden-2-yl)-6,9-dioxo-3,4,6,7,8,9,12,13-octahydro-2H,11H-16,18-etheno-2,5-methanopyrido[2,3-k][1,10,3,6]dioxadiazacyclonona-decine-4-carboxamide | 754.3 | See Example 14, separated diastereomers | A1, B19 |
| 39, III-60 | 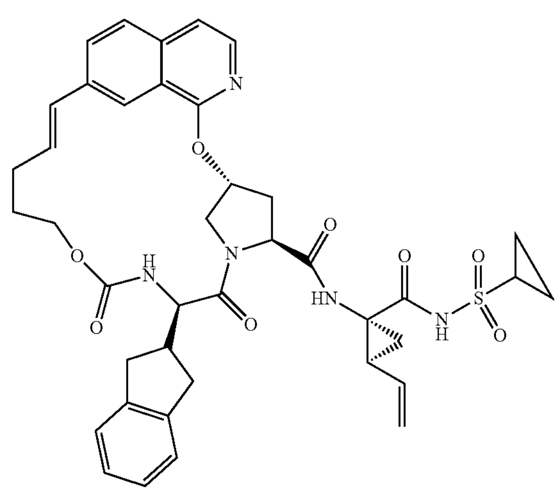 | (2R,4S,7R,14E)-N-((1R,2S)-1-{[(cyclo-propylsulfonyl)amino]carbonyl}-2-vinyl-cyclopropyl)-7-(2,3-dihydro-1H-inden-2-yl)-6,9-dioxo-3,4,6,7,8,9,12,13-octahydro-2H,11H-16,18-etheno-2,5-methanopyrido[2,3-k][1,10,3,6]dioxadiazacyclonona-decine-4-carboxamide | 754.3 | See Example 14, separated diastereomers | A1, B19 |

| Ex. | Structure | Name | LRMS (M + H)+ | Prepared using the appropriate Intermediates according to the procedure below. | Int. |
|---|---|---|---|---|---|
| 40, III-61 | 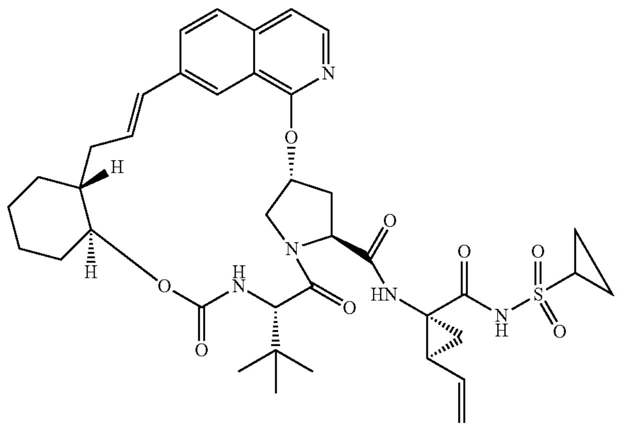 | (6R,8S,11S,14aS,18aR, 20E)-11-tert-butyl-N-((1R,2S)-1-{[(cyclopropylsulfonyl)amino]carbonyl}-2-vinylcyclopropyl)-10,13-dioxo-7,8,10,11,12,13,15,16,17,18,18a,19-dodecahydro-6H,14aH-1,22-etheno-6,9-methanopyrido[2,3-k][1,10,3,6]benzodioxadiaza-cyclononadecine-8-carboxamide | 748.3 | See Example 14, separated diastereomers | A1, B20 |
| 41, III-62 | 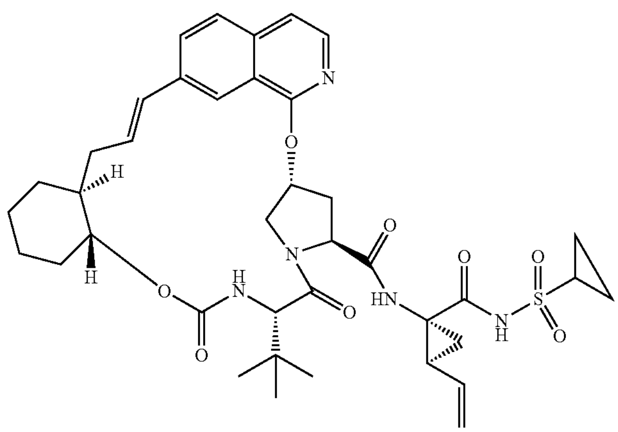 | (6R,8S,11S,14aR,18aS, 20E)-11-tert-butyl-N-((1R,2S)-1-{[(cyclopropylsulfonyl)amino]carbonyl}-2-vinylcyclopropyl)-10,13-dioxo-7,8,10,11,12,13,15,16,17,18,18a,19-dodecahydro-6H,14aH-1,22-etheno-6,9-methanopyrido[2,3-k][1,10,3,6]benzodioxadiaza-cyclononadecine-8-carboxamide | 748.3 | See Example 14, separated diastereomers | A1, B20 |
| 42, III-63 | 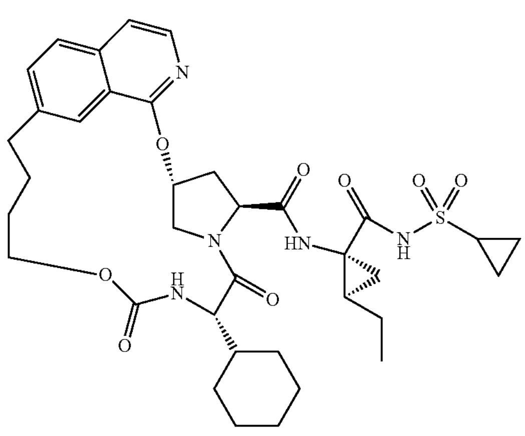 | (2R,4S,7S)-7-cyclohexyl-N-((1R,2R)-{[(cyclopropylsulfonyl)amino]carbonyl}-2-ethylcyclopropyl)-6,9-dioxo-3,4,6,7,8,9,11,12,13,14-decahydro-2H-5,17-(ethanediylidene)-2,5-methanopyrido[2,3-k][1,10,3,6]dioxadiazacycloocta-decine-4-carboxamide | 710.5 | See Example 15 | A3, B21 |

-continued

| Ex. | Structure | Name | LRMS (M + H)+ | Prepared using the appropriate Intermediates according to the procedure below. | Int. |
|---|---|---|---|---|---|
| 43, III-64 | 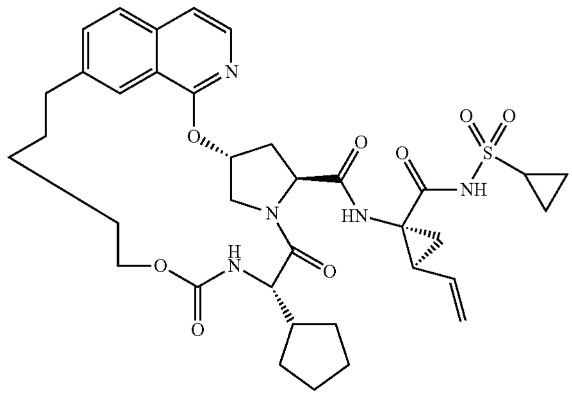 | (2R,4S,7S)-7-cyclopentyl-N-((1R,2S)-1-{[(cyclopropyl-sulfonyl)amino]carbonyl}-2-vinyl-cyclopropyl)-6,9-dioxo-3,4,6,7,8,9,12,13,14,15-decahydro-2H,11H-16,18-(ethanediylidene)-2,5-methanopyrido[2,3-k][1,10,3,6]dioxadiazacyclonona-decine-4-carboxamide | 708.4 | See Example 15 | A1, B13 |
| 44, III-65 | 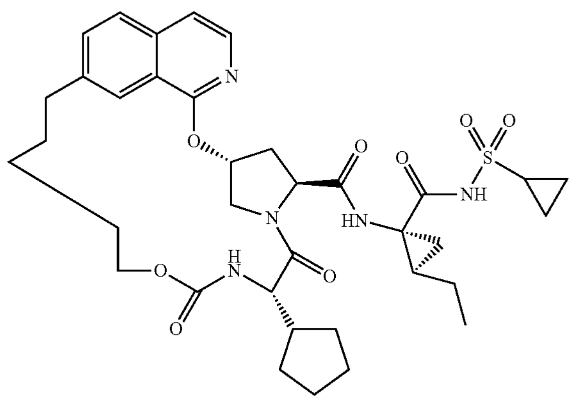 | (2R,4S,7S)-7-cyclopentyl-N-((1R,2R)-1-{[(cyclopropyl-sulfonyl)amino]carbonyl}-2-ethyl-cyclopropyl)-6,9-dioxo-3,4,6,7,8,9,12,13,14,15-decahydro-2H,11H-16,18-(ethanediylidene)-2,5-methanopyrido[2,3-k][1,10,3,6]dioxadiazacyclonona-decine-4-carboxamide | 710.5 | See Example 15 | A3, B13 |
| 45, III-66 | 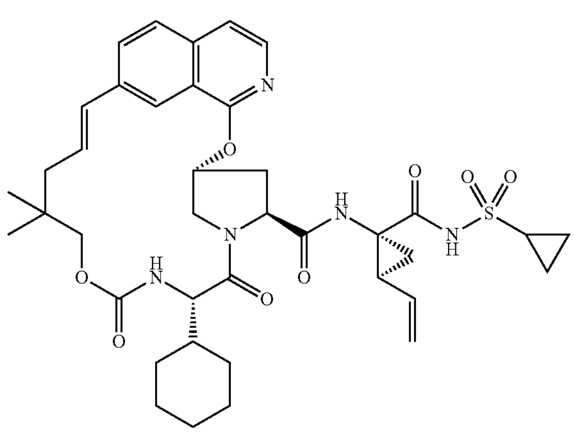 | (2R,4S,7S,14E)-7-cyclohexyl-N-((1R,2S)-1-[(cyclopropyl-{sulfonyl)amino]carbonyl}-2-vinyl-cyclopropyl)-12,12-dimethyl-6,9-dioxo-3,4,6,7,8,9,12,13-octahydro-2H,11H-16,18-etheno-2,5-methanopyrido[2,3-k][1,10,3,6]dioxadiazacyclonona-decine-4-carboxamide | 748.5 | See Example 14 | A1, B23 |

| Ex. | Structure | Name | LRMS (M + H)+ | Prepared using the appropriate Intermediates according to the procedure below. | Int. |
|---|---|---|---|---|---|
| 46, III-67 | 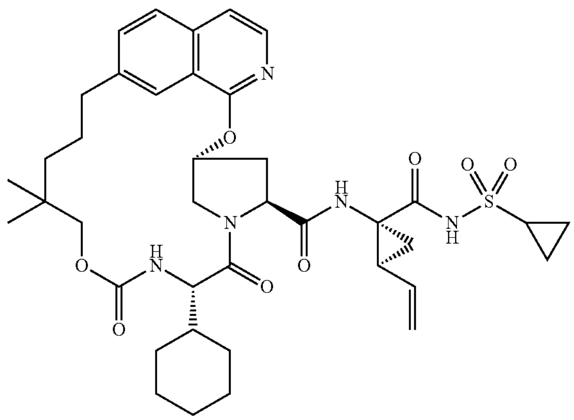 | (2R,4S,7S)-7-cyclohexyl-N-((1R,2S)-1-{[(cyclopropyl-sulfonyl)amino]carbonyl}-2-vinyl-cyclopropyl)-12,12-dimethyl-6,9-dioxo-3,4,6,7,8,9,12,13,14,15-decahydro-2H,11H-16,18-etheno-2,5-methanopyrido[2,3-k][1,10,3,6]dioxadiazacyclonona-decine-4-carboxamide | 750.5 | See Example 15 | A1, B23 |
| 47, III-68 | 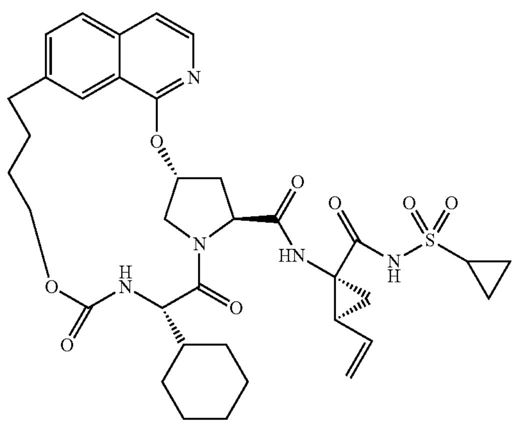 | (2R,4S,7S)-7-cyclohexyl-N-((1R,2S)-1-{[(cyclopropyl-sulfonyl)amino]carbonyl}-2-vinyl-cyclopropyl)-6,9-dioxo-3,4,6,7,8,9,11,12,13,14-decahydro-2H-15,17-(ethanediylidene)-2,5-methanopyrido[2,3-k][1,10,3,6]dioxadiazacycloocta-decine-4-carboxamide | 708.3 | See Example 15 | A1, B21 |
| 48, III-69 | 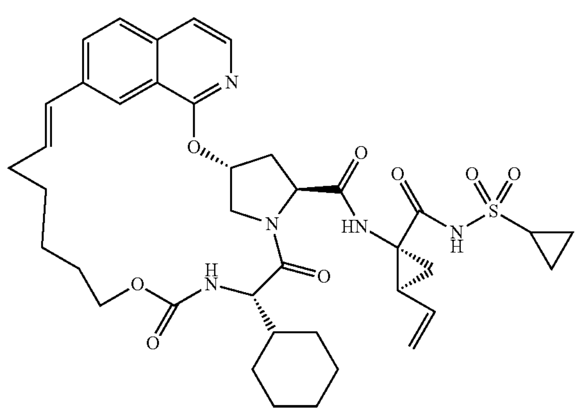 | (2R,4S,7S,16E)-7-cyclohexyl-N-((1R,2S)-1-{[(cyclopropyl-sulfonyl)amino]carbonyl}-2-vinyl-cyclopropyl)-6,9-dioxo-3,4,6,7,8,9,12,13,14,15-decahydro-2H,11H-18,20-(ethanediylidene)-2,5-methanopyrido[2,3-k][1,10,3,6]dioxadiazacyclo-henicosine-4-carboxamide | 748.3 | See Example 14 | A1, B26 |

| Ex. | Structure | Name | LRMS (M + H)+ | Prepared using the appropriate Intermediates according to the procedure below. | Int. |
|---|---|---|---|---|---|
| 49, III-70 | 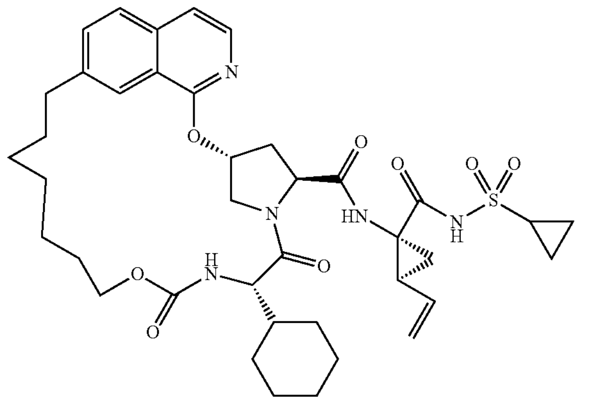 | (2R,4S,7S)-7-cyclohexyl-N-((1R,2S)-1-{[(cyclopropylsulfonyl)amino]carbonyl}-2-vinylcyclopropyl)-6,9-dioxo-3,4,6,7,8,9,12,13,14,15,16,17-dodecahydro-2H,11H-18,20-(ethanediylidene)-2,5-methanopyrido[2,3-k][1,10,3,6]dioxadiazacyclohenicosine-4-carboxamide | 750.5 | See Example 15 | A1, B26 |
| 50, III-71 | 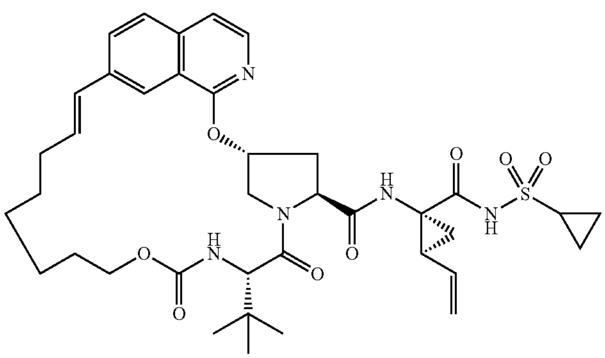 | (2R,4S,7S,17E)-7-tert-butyl-N-((1R,2S)-1-{[(cyclopropylsulfonyl)amino]carbonyl}-2-vinylcyclopropyl)-6,9-dioxo-3,4,6,7,8,9,11,12,13,14,15,16-dodecahydro-2H-19,21-etheno-2,5-methanopyrido[2,3-k][1,10,3,6]dioxadiazacyclodocosine-4-carboxamide | 736.5 | See Example 14 | A1, B27 |
| 51, III-72 | 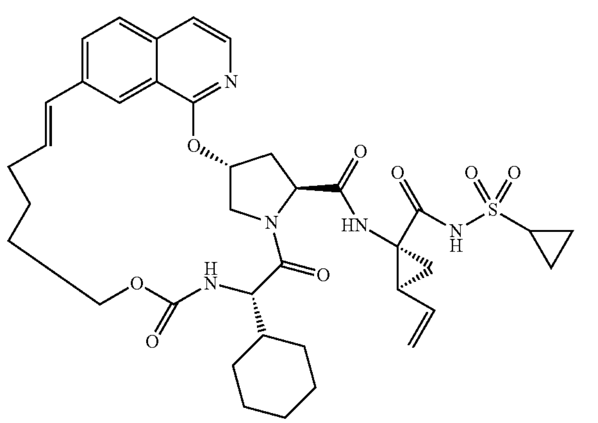 | (2R,4S,7S,15E)-7-cyclohexyl-N-((1R,2S)-1-{[(cyclopropylsulfonyl)amino]carbonyl}-2-vinylcyclopropyl)-6,9-dioxo-3,4,6,7,8,9,11,12,13,14-decahydro-2H-17,19-(ethanediylidene)-2,5-methanopyrido[2,3-k][1,10,3,6]dioxadiazacycloicosine-4-carboxamide | 734.4 | See Example 14 | A1, B28 |

-continued

| Ex. | Structure | Name | LRMS (M + H)+ | Prepared using the appropriate Intermediates according to the procedure below. | Int. |
|---|---|---|---|---|---|
| 52, III-73 | 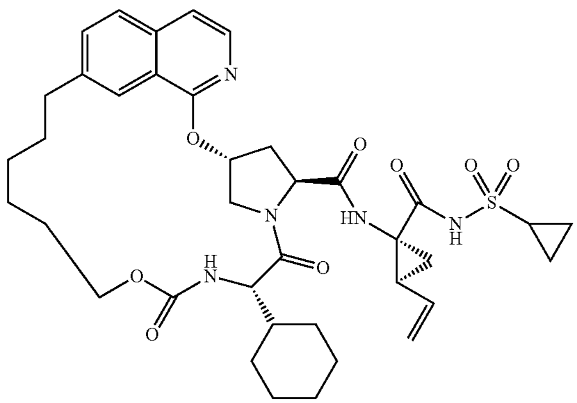 | (2R,4S,7S)-7-cyclohexyl-N-((1R,2S)-1-{[(cyclopropyl-sulfonyl)amino]carbonyl}-2-vinyl-cyclopropyl)-6,9-dioxo-3,4,6,7,8,9,11,12,13,14,15,16-dodecahydro-2H-17,19-ethanediylidene-2,5-methanopyrido[2,3-k][1,10,3,6]dioxadiazacycloicosine-4-carboxamide | 736.5 | See Example 15 | A1, B28 |
| 53, III,74 | 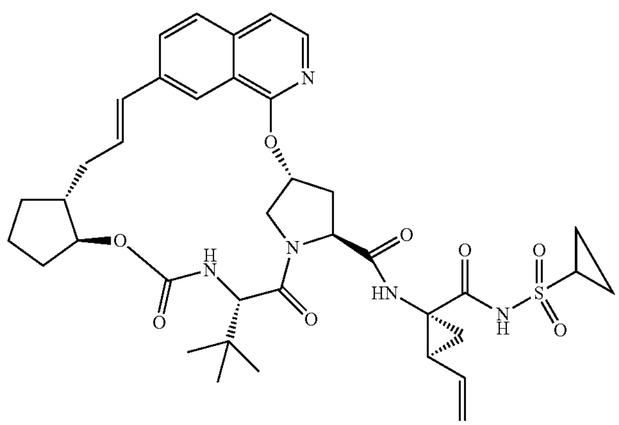 | (6R,8S,11S,14aS,17aR,19E)-11-tert-butyl-N-((1R,1S)-1-{[(cyclo-propylsulfonyl)amino]carbonyl}-2-vinylcyclo-propyl)-10,13-dioxo-7,8,10,11,12,13,14a,15,16,17,17a,18-dodecahydro-6H-1,21-etheno-6,9-methanocyclopenta[r]pyrido[2,3-k][1,10,3,6]dioxadiazacyclonona-decine-8-carboxamide | 734.3 | See Example 14, separated diastereomers | A1, B29 |
| 54, III-75 | 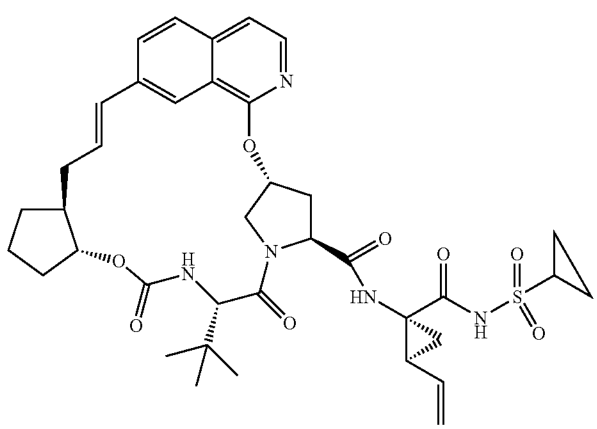 | (6R,8S,11S,14aR,17aS,19E)-11-tert-butyl-N-((1R,2S)-1-{[(cyclo-propylsulfonyl)amino]carbonyl}-2-vinylcyclo-propyl)-10,13-dioxo-7,8,10,11,12,13,14a,15,16,17,17a,18-dodecahydro-6H-1,21-etheno-6,9-methanocyclopenta[r]pyrido[2,3-k][1,10,3,6]dioxadiazacyclonona-decine-8-carboxamide | 734.3 | See Example 14, separated diastereomers | A1, B29 |

| Ex. | Structure | Name | LRMS (M + H)+ | Prepared using the appropriate Intermediates according to the procedure below. | Int. |
|---|---|---|---|---|---|
| 55, III-76 | 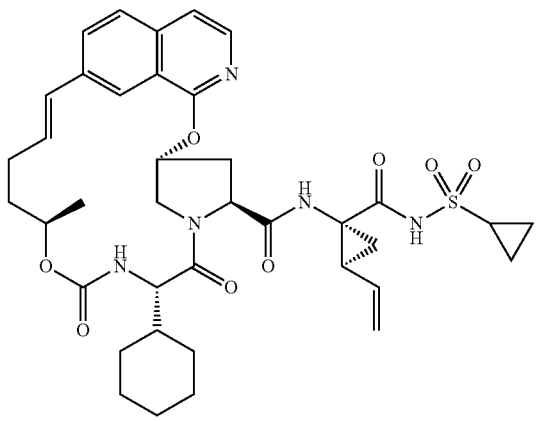 | (2R,4S,7S,11R)-7-cyclohexyl-N-((1R,2S)-1-{[(cyclopropyl-sulfonyl)amino]carbonyl}-2-vinyl-cyclopropyl)-11-methyl-6,9-dioxo-3,4,6,7,8,9,2,13,14,15-decahydro-2H,11H-16,18-etheno-2,5-methanopyrido[2,3-k][1,10,3,6]dioxadiazacyclonona-decine-4-carboxamide | 736.5 | See Example 15, separated diastereomers | A1, B30 |
| 56, III-77 | 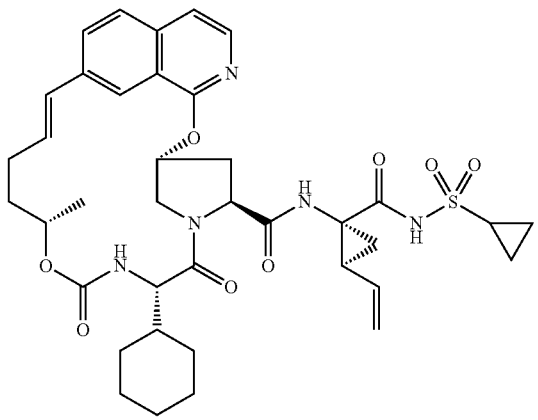 | (2R,4S,7S,11S)-7-cyclohexyl-N-((1R,2S)-1-{[(cyclo-propylsulfonyl)amino]carbonyl}-2-vinyl-cyclopropyl)-11-methyl-6,9-dioxo-3,4,6,7,8,9,12,13,14,15-decahydro-2H,11H-16,18-etheno-2,5-methanopyrido[2,3-k][1,10,3,6]dioxadiazacyclonona-decine-4-carboxamide | 736.4 | See Example 15, separated diastereomers | A1, B30 |
| 57, III-78 | 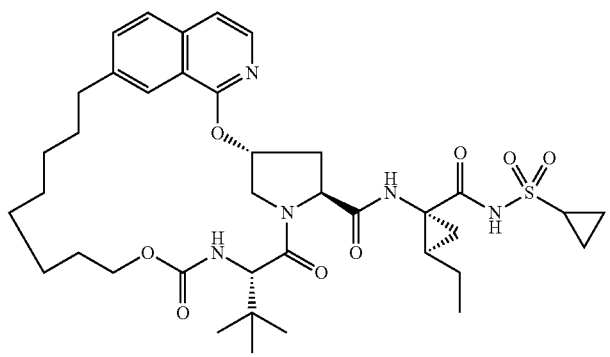 | (2R,4S,7S)-7-tert-butyl-N-((1R,2R)-1-{[(cyclopropyl-sulfonyl)amino]carbonyl}-2-ethyl-cyclopropyl)-6,9-dioxo-3,4,6,7,8,9,11,12,13,14,15,16,17,18-tetradecahydro-2H-19,21-etheno-2,5-methanopyrido[2,3-k][1,10,3,6]dioxadiazacyclo-docosine-4-carboxamide | 740.6 | See Example 15 | A3, B27 |

-continued

| Ex. | Structure | Name | LRMS (M + H)⁺ | Prepared using the appropriate Intermediates according to the procedure below. | Int. |
|---|---|---|---|---|---|
| 58, III-79 | 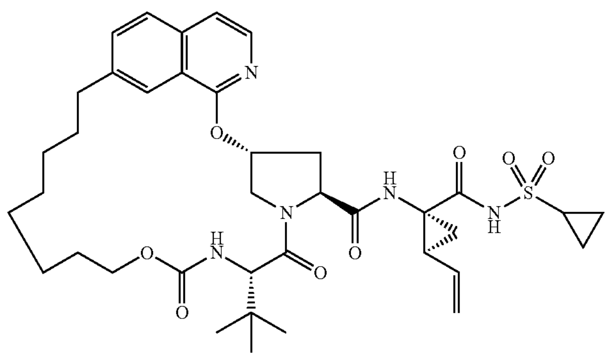 | (2R,4S,7S)-7-tert-butyl-N-((1R,2S)-1-{[(cyclopropyl-sulfonyl)amino]carbonyl}-2-vinyl-cyclpropyl)-6,9-dioxo-3,4,6,7,8,9,11,12,13,14,15,16,17,18-tetradecahydro-2H-19,21-etheno-2,5-methanopyrido[2,3-k][1,10,3,6]dioxadiazacyclo-docosine-4-carboxamide | 738.5 | See Example 15 | A1, B27 |
| 59, III-80 | 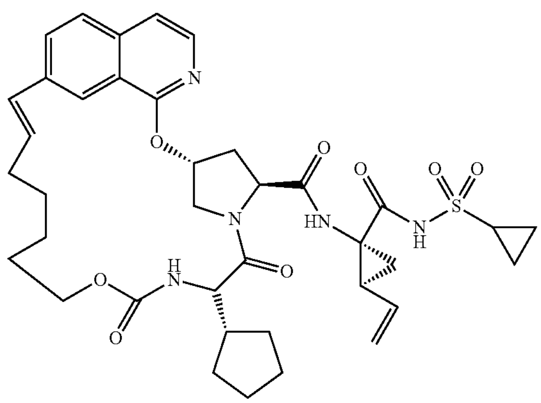 | (2R,4S,7S,15E)-7-cyclopentyl-N-((1R,2S)-1-{[(cyclo-propylsulfonyl)amino]carbonyl}-2-vinylcyclopropyl)-6,9-dioxo-3,4,6,7,8,9,11,12,13,14-decahydro-2H-17,19-(ethanediylidene)-2,5-methanopyrido[2,3-k][1,10,3,6]dioxadiazacycloicosine-4-carboxamide | 720.4 | See Example 14 | A1, B32 |
| 60, III-81 | 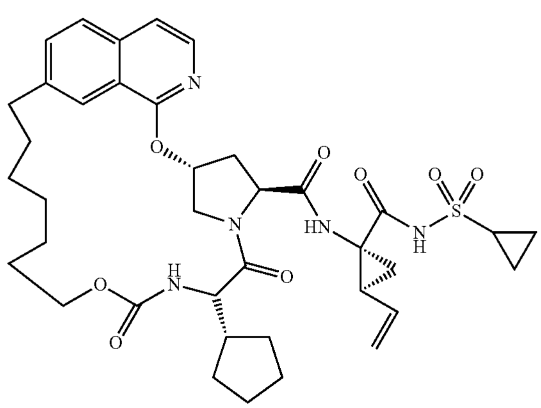 | (2R,4S,7S)-7-cyclopentyl-N-((1R,2S)-1-{[(cyclo-propylsulfonyl)amino]carbonyl}-2-vinylcyclopropyl)-6,9-dioxo-3,4,6,7,8,9,12,13,14,15,16,17-dodecahydro-2H,11H-18,20-ethanediylidene-2,5-methanopyrido[2,3-k][1,10,3,6]dioxadiazacyclo-henicosine-4-carboxamide | 722.4 | See Example 15 | A1, B32 |

-continued

| Ex. | Structure | Name | LRMS (M + H)+ | Prepared using the appropriate Intermediates according to the procedure below. | Int. |
|---|---|---|---|---|---|
| 61, III-82 | 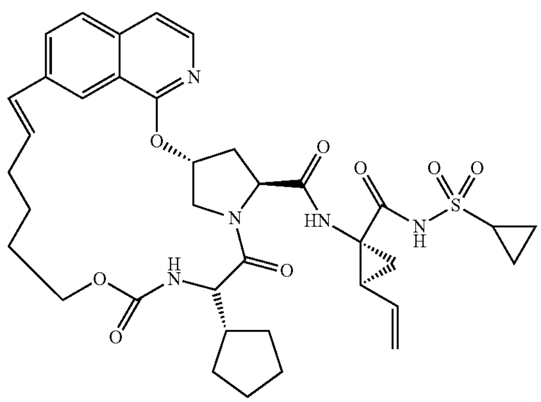 | (2R,4S,7S)-7-cyclopentyl-N-((1R,2S)-1-{[(cyclopropyl-sulfonyl)amino]carbonyl}-2-vinyl-cyclopropyl)-6,9-dioxo-3,4,6,7,8,9,12,13,14,15-decahydro-2H,11H-18,20-(ethanediylidene)-2,5-methanopyrido[2,3-k][1,10,3,6]dioxadiazacyclo-henicosine-4-carboxamide | 734.4 | See Example 14 | A1, B31 |
| 62, III-83 | 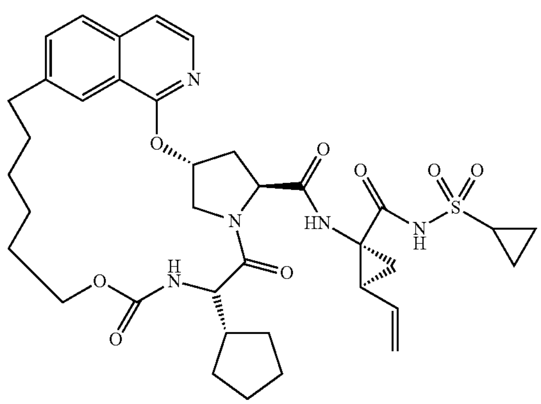 | (2R,4S,7S)-7-cyclopentyl-N-((1R,2S)-1-{[(cyclopropyl-sulfonyl)amino]carbonyl}-2-vinyl-cyclopropyl)-6,9-dioxo-3,4,6,7,8,9,12,13,14,15,16,17-dodecahydro-2H,11H-18,20-(ethanediylidene)-2,5-methanopyrido[2,3-k][1,10,3,6]dioxadiazacyclo-henicosine-4-carboxamide | 736.4 | See Example 15 | A1, B31 |
| 63, III-84 | 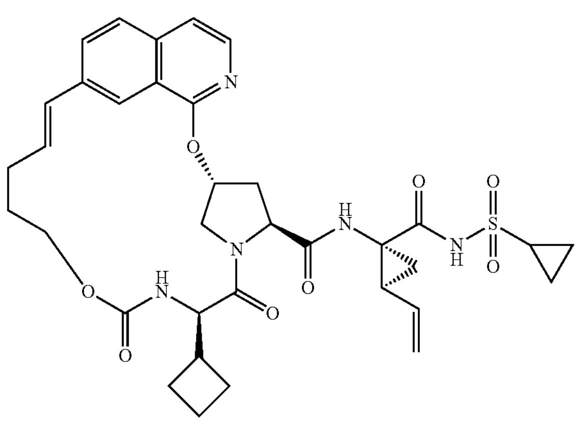 | (2R,4S,7R,14E)-7-cyclobutyl-N-((1R,2S)-1-{[(cyclopropyl-sulfonyl)amino]carbonyl}-2-vinyl-cyclopropyl)-6,9-dioxo-3,4,6,7,8,9,12,13-octahydro-2H,11H-16,18-etheno-2,5-methanopyrido[2,3-k][1,10,3,6]dioxadiazacyclonona-decine-4-carboxamide | 692.3 | See Example 14, separated diastereomers | A1, B33 |

-continued

| Ex. | Structure | Name | LRMS (M + H)+ | Prepared using the appropriate Intermediates according to the procedure below. | Int. |
|---|---|---|---|---|---|
| 64, III-85 | 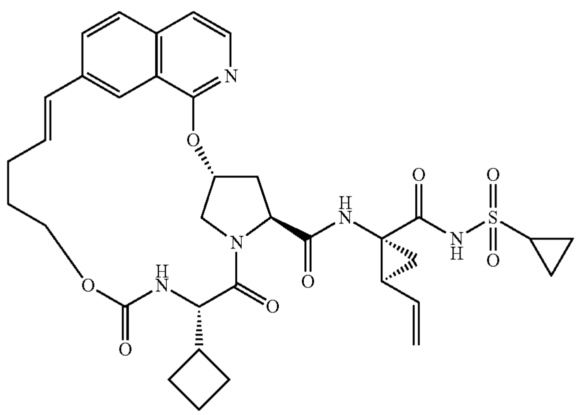 | (2R,4S,7S,14E)-7-cyclobutyl-N-((1R,2S)-1-{[(cyclopropyl-sulfonyl)amino]carbonyl}-2-vinylcyclo-propyl)-6,9-dioxo-3,4,6,7,8,9,12,13-octahydro-2H,11H-16,18-etheno-2,5-methanopyrido[2,3-k][1,10,3,6]dioxadiazacyclonona-decine-4-carboxamide | 692.4 | See Example 14, separated diastereomers | A1, B33 |
| 65, III-86 | 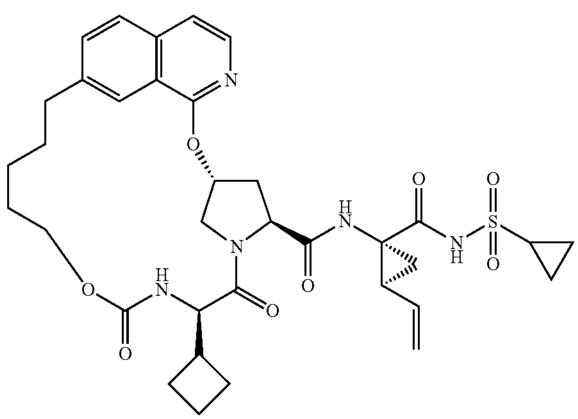 | (2R,4S,7R)-7-cyclobutyl-N-((1R,2S)-1-{[(cyclopropyl-sulfonyl)amino]carbonyl}-2-vinyl-cyclopropyl)-6,9-dioxo-3,4,6,7,8,9,12,13,14,15-decahydro-2H,11H-16,18-etheno-2,5-methanopyrido[2,3-k][1,10,3,6]dioxadiazacyclonona-decine-4-carboxamide | 694.3 | See Example 15, separated diastereomers | A1, B33 |
| 66, III-87 | 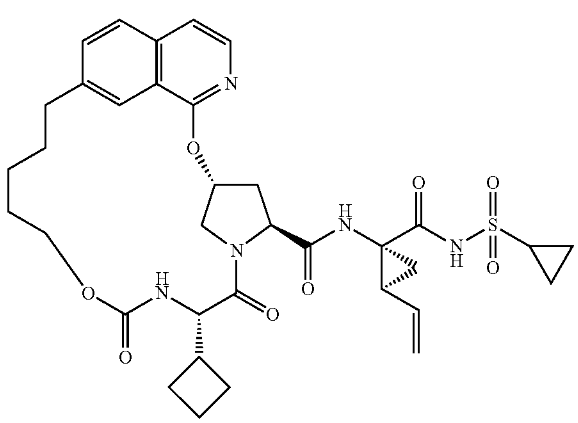 | (2R,4S,7S)-7-cyclobutyl-N-((1R,2S)-1-{[(cyclopropyl-sulfonyl)amino]carbonyl}-2-vinyl-cyclopropyl)-6,9-dioxo-3,4,6,7,8,9,12,13,14,15-decahydro-2H,11H-16,18-etheno-2,5-methanopyrido[2,3-k][1,10,3,6]dioxadiazacyclonona-decine-4-carboxamide | 694.3 | See Example 15, separated diastereomers | A1, B33 |

-continued

| Ex. | Structure | Name | LRMS (M + H)+ | Prepared using the appropriate Intermediates according to the procedure below. | Int. |
|---|---|---|---|---|---|
| 67, III-88 | 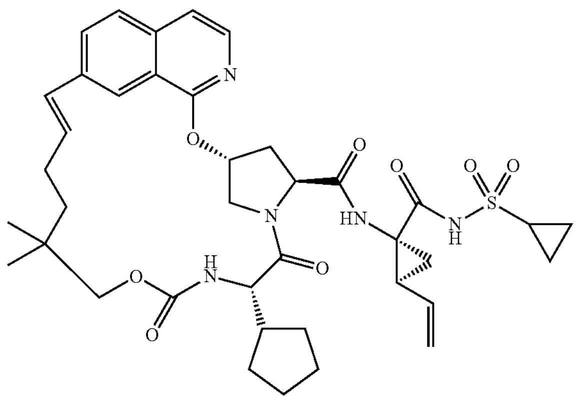 | (2R,4S,7S,15E)-7-cyclopentyl-N-((1R,2S)-1-{[(cyclopropyl-sulfonyl)amino]carbonyl}-2-vinyl-cyclpropyl)-12,12-dimethyl-6,9-dioxo-3,4,6,7,8,9,11,12,13,14-decahydro-2H-17,19-(ethanediylidene)-2,5-methanopyrido[2,3-k][1,10,3,6]dioxadiazacycloicosine-4-carboxamide | 748.4 | See Example 14 | A1, B34 |
| 68, III-89 | 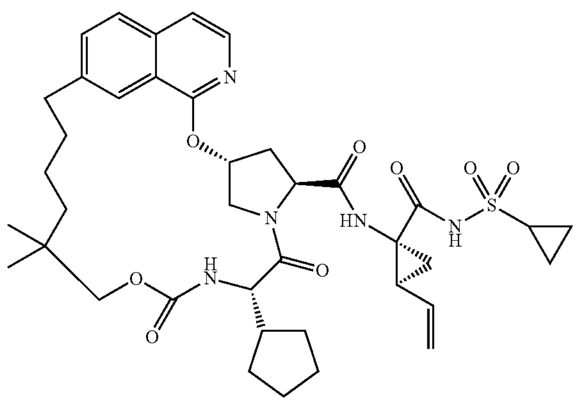 | (2R,4S,7S)-7-cyclopentyl-N-((1R,2S)-1-{[(cyclopropyl-sulfonyl)amino]carbonyl}-2-vinyl-cyclopropyl)-12,12-dimethyl-6,9-dioxo-3,4,6,7,8,9,11,12,13,14,15,16-dodecahydro-2H-17,19-(ethanediylidene)-2,5-methanopyrido[2,3-k][1,10,3,6]dioxadiazacycloicosine-4-carboxamide | 750.4 | See Example 15 | A1, B34 |
| 69, III-90 | 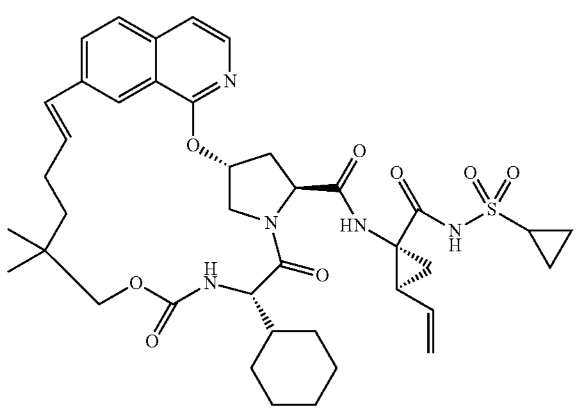 | (2R,4S,7S,15E)-7-cyclohexyl-N-((1R,2S)-1-{[(cyclopropyl-sulfonyl)amino]carbonyl}-2-vinyl-cyclopropyl)-12,12-dimethyl-6,9-dioxo-3,4,6,7,8,9,11,12,13,14-decahydro-2H-17,19-(ethanediylidene)-2,5-methanopyrido[2,3-k][1,10,3,6]dioxadiazacycloicosine-4-carboxamide | 762.4 | See Example 14 | A1, B35 |

-continued

| Ex. | Structure | Name | LRMS (M + H)+ | Prepared using the appropriate Intermediates according to the procedure below. | Int. |
|---|---|---|---|---|---|
| 70, III-91 | 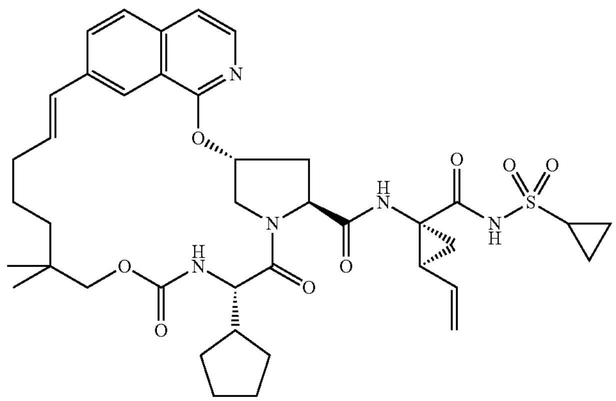 | (2R,4S,7S,16E)-7-cyclopentyl-N-((1R,2S)-1-{[(cyclopropyl-sulfonyl)amino]carbonyl}-2-vinyl-cyclopropyl)-12,12-dimethyl-6,9-dioxo-3,4,6,7,8,9,12,13,14,15-decahydro-2H,11H-18,20-etheno-2,5-methanopyrido[2,3-k][1,10,3,6]dioxadiazacyclo-henicosine-4-carboxamide | 762.5 | See Example 14 | A1, B36 |
| 71, III-92 | 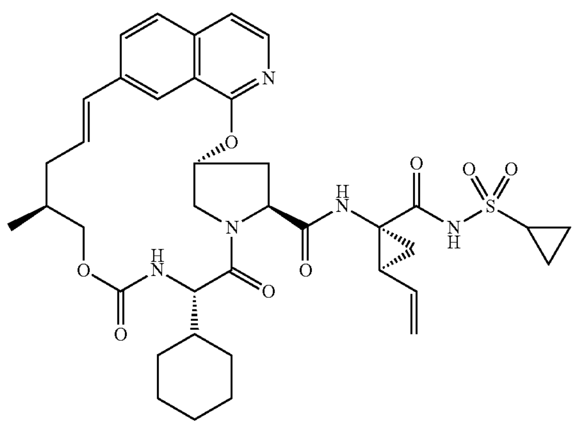 | (2R,4S,7S,12S,14E)-7-cyclohexyl-N-((1R,2S)-1-{[(cyclopropyl-sulfonyl)amino]carbonyl}-2-vinyl-cyclopropyl)-12-methyl-6,9-dioxo-3,4,6,7,8,9,12,13-octahydro-2H,11H-16,18-etheno-2,5-methanopyrido[2,3-k][1,10,3,6]dioxadiazacyclonona-decine-4-carboxamide | 734.4 | See Example 14, separated diastereomers | A1, B39 |
| 72, III-93 | 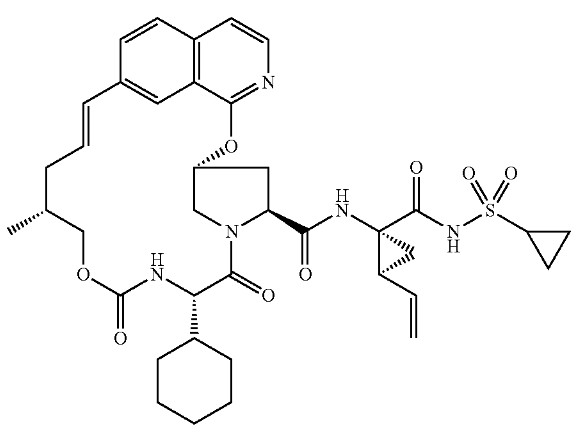 | (2R,4S,7S,12R,14E)-7-cyclohexyl-N-((1R,2S)-1-{[(cyclo-propylsulfonyl)amino]carbonyl}-2-vinylcyclopropyl)-12-methyl-6,9-dioxo-3,4,6,7,8,9,12,13-octahydro-2H,11H-16,18-etheno-2,5-methanopyrido[2,3-k][1,10,3,6]dioxadiazacyclonona-decine-4-carboxamide | 734.4 | See Example 14, separated diastereomers | A1, B39 |

| Ex. | Structure | Name | LRMS (M + H)+ | Prepared using the appropriate Intermediates according to the procedure below. | Int. |
|---|---|---|---|---|---|
| 73, III-94 | 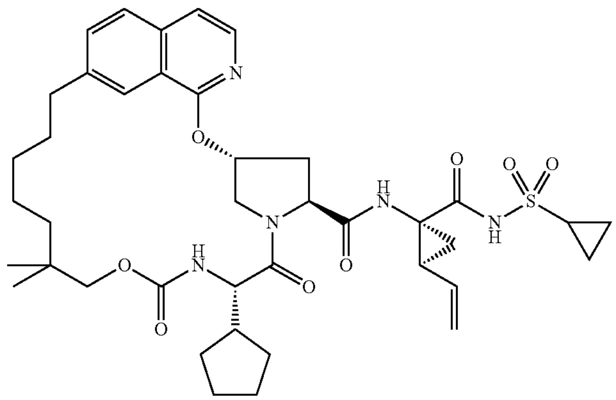 | (2R,4S,7S)-7-cyclopentyl-N-((1R,2S)-1-{[(cyclopropylsulfonyl)amino]carbonyl}-2-vinylcyclopropyl)-12,12-dimethyl-6,9-dioxo-3,4,6,7,8,9,12,13,14,15,16,17-dodecahydro-2H,11H-18,20-etheno-2,5-methanopyrido[2,3-k][1,10,3,6]dioxadiazacyclohenicosine-4-carboxamide | 764.6 | See Example 15 | A1, B36 |
| 74, III-95 | 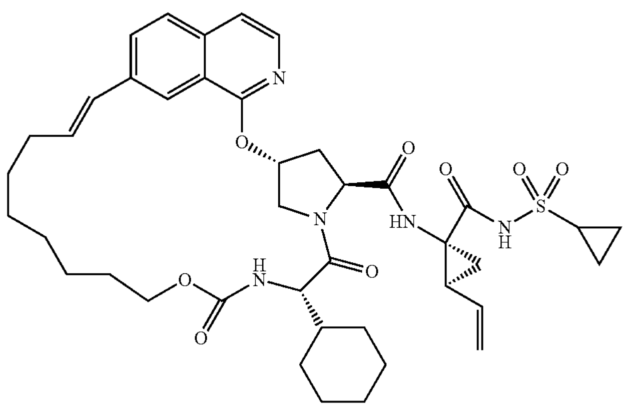 | (2R,4S,7S,18E)-7-cyclohexyl-N-((1R,2S)-1-{[(cyclopropylsulfonyl)amino]carbonyl}-2-vinylcyclopropyl)-6,9-dioxo-3,4,6,7,8,9,12,13,14,15,16,17-dodecahydro-2H,11H-20,22-(ethanediylidene)-2,5-methanopyrido[2,3-k][1,10,3,6]dioxadiazacyclotricosine-4-carboxamide | 776.5 | See Example 14 | A1, B37 |
| 75, III-96 | 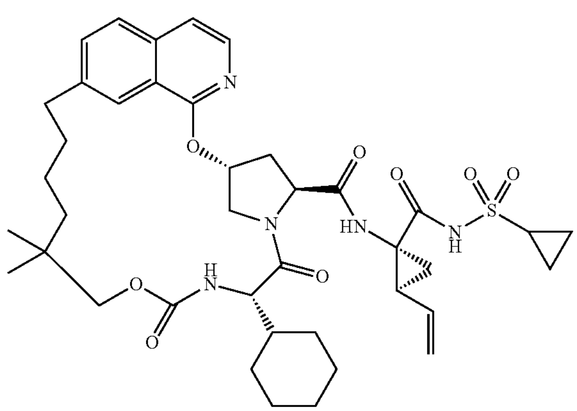 | (2R,4S,7S)-7-cyclohexyl-N-((1R,2S)-1-{[(cyclopropylsulfonyl)amino]carbonyl}-2-vinylcyclopropyl)-12,12-dimethyl-6,9-dioxo-3,4,6,7,8,9,11,12,13,14,15,16-dodecahydro-2H-17,19-(ethanediylidene)-2,5-methanopyrido[2,3-k][1,10,3,6]dioxadiazacycloicosine-4-carboxamide | 764.4 | See Example 15 | A1, B35 |

-continued

| Ex. | Structure | Name | LRMS (M + H)+ | Prepared using the appropriate Intermediates according to the procedure below. | Int. |
|---|---|---|---|---|---|
| 76, III-97 | 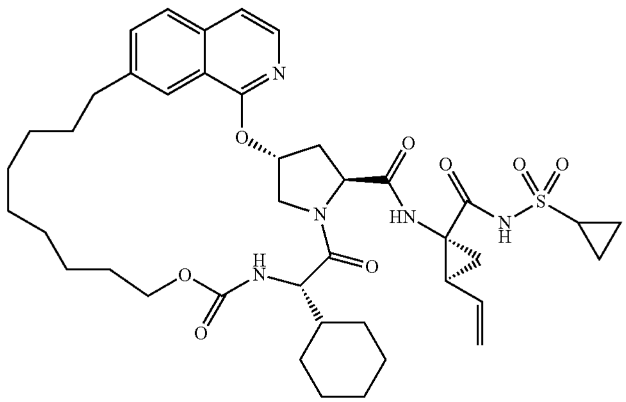 | (2R,4S,7S)-7-cyclohexyl-N-((1R,2S)-1-{[(cyclopropyl-sulfonyl)amino]carbonyl}-2-vinyl-cyclopropyl)-6,9-dioxo-3,4,6,7,8,9,12,13,14,15,16,17,18,19-tetradecahydro-2H,11H-20,22-(ethanediylidene)-2,5-methanopyrido[2,3-k][1,10,3,6]dioxadiazacyclo-tricosine-4-carboxamide | 778.5 | See Example 15 | A1, B37 |
| 77, III-98 | 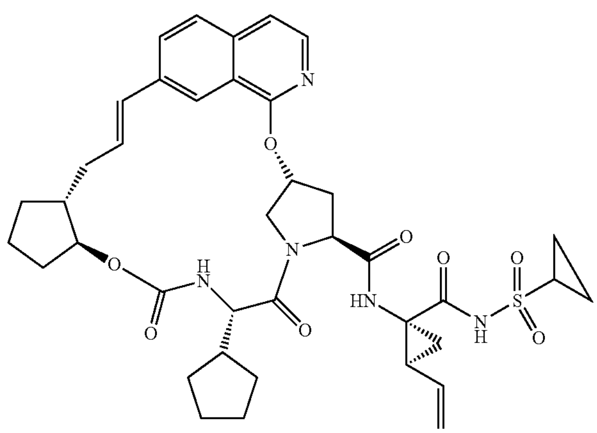 | (6R,8S,11S,14aS,17aR,19E)-11-cyclopentyl-N-((1R,2S)-1-{[(cyclo-propylsulfonyl)amino]carbonyl}-2-vinyl-cyclopropyl)-10,13-dioxo-7,8,10,11,12,13,14a,15,16,17,17a,18-dodecahydro-6H-1,21-etheno-6,9-methanocyclopenta[r]pyrido[2,3-k][1,10,3,6]dioxadiazacyclonona-decine-8-carboxamide | 746.4 | See Example 14, separated diastereomers | A1, B38 |
| 78, III-99 | 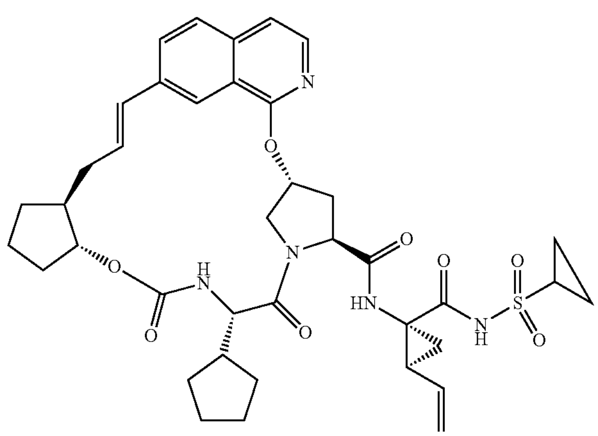 | (6R,8S,11S,14aR,17aS,19E)-11-cyclopentyl-N-((1R,2S)-1-{[(cyclo-propylsulfonyl)amino]carbonyl}-2-vinyl-cyclopropyl)-10,13-dioxo-7,8,10,11,12,13,14a,15,16,17,17a,18-dodecahydro-6H-1,21-etheno-6,9-methanocyclopenta[r]pyrido[2,3-k][1,10,3,6]dioxadiazacyclonona-decine-8-carboxamide | 746.4 | See Example 14, separated diastereomers | A1, B38 |

-continued

| Ex. | Structure | Name | LRMS (M + H)+ | Prepared using the appropriate Intermediates according to the procedure below. | Int. |
|---|---|---|---|---|---|
| 79, III-100 | 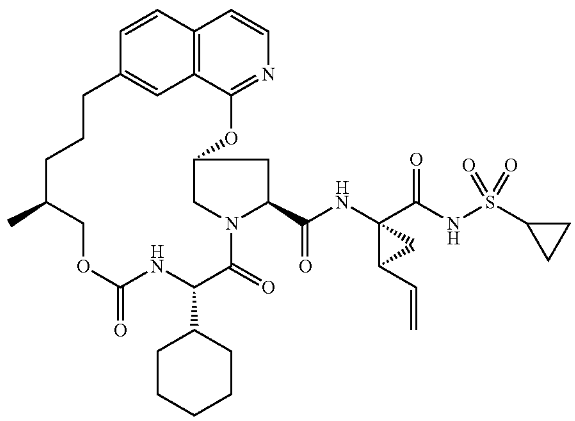 | (2R,4S,7S,12S)-7-cyclohexyl-N-((1R,2S)-1-{[(cyclopropyl-sulfonyl)amino]carbonyl}-2-vinyl-cyclopropyl)-12-methyl-6,9-dioxo-3,4,6,7,8,9,12,13,14,15-decahydro-2H,11H-16,18-etheno-2,5-methanopyrido[2,3-k][1,10,3,6]dioxadiazacyclonona-decine-4-carboxamide | 736.3 | See Example 15, separated diastereomers | A1, B39 |
| 80, III-101 | 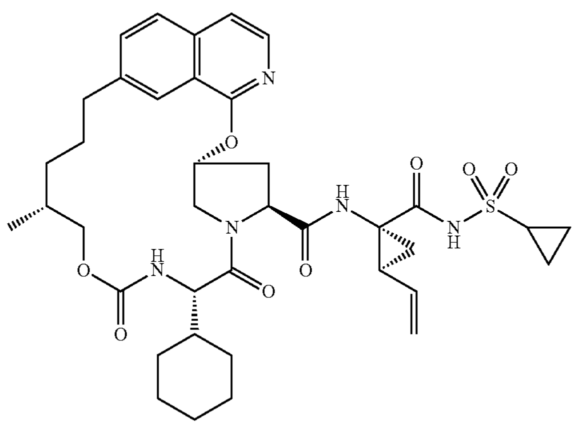 | (2R,4S,7S,12R)-7-cyclohexyl-N-((1R,2S)-1-{[(cyclopropyl-sulfonyl)amino]carbonyl}-2-vinyl-cyclopropyl)-12-methyl-6,9-dioxo-3,4,6,7,8,9,12,13,14,15-decahydro-2H,11H-16,18-etheno-2,5-methanopyrido[2,3-k][1,10,3,6]dioxadiazacyclonona-decine-4-carboxamide | 736.3 | See Example 15, separated diastereomers | A1, B39 |
| 81, III-102 | 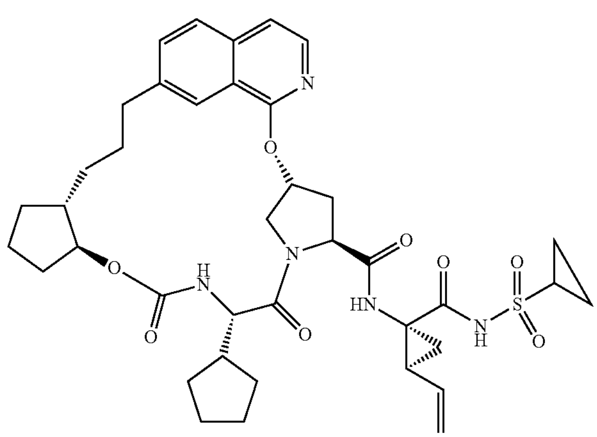 | (6R,8S,11S,14aS,17aS)-11-cyclopentyl-N-((1R,2S)-1-{[(cyclopropylsulfonyl)amino]carbonyl}-2-vinylcyclopropyl)-10,13-dioxo-7,8,10,11,12,13,14a,15,16,17,17a,18,19,20-tetradecahydro-6H-1,21-etheno-6,9-methanocyclopenta[r]pyrido[2,3-k][1,10,3,6]dioxadiazacyclonona-decine-8-carboxamide | 748.3 | See Example 15, separated diastereomers | A1, B38 |

-continued

| Ex. | Structure | Name | LRMS (M + H)+ | Prepared using the appropriate Intermediates according to the procedure below. | Int. |
|---|---|---|---|---|---|
| 82, III-103 | 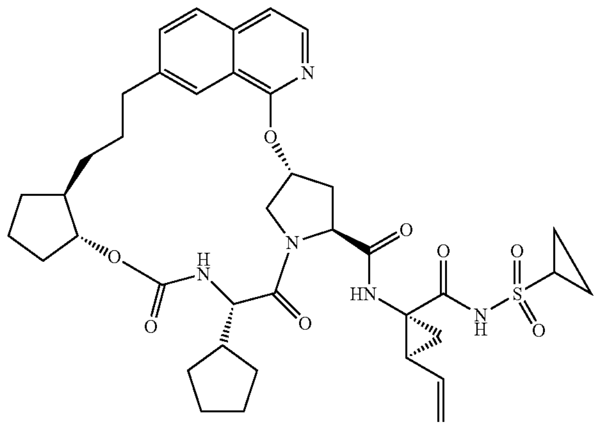 | (6R,8S,11S,14aR,17aR)-11-cyclopentyl-N-((1R,2S)-1-{[(cyclopropylsulfonyl)amino]carbonyl}-2-vinylcyclopropyl)-10,13-dioxo-7,8,10,11,12,13,14a,15,16,17,17a,18,19,20-tetradecahydro-6H-1,21-etheno-6,9-methanocyclopenta[r]pyrido[2,3-k][1,10,3,6]dioxadiazacyclononadecine-8-carboxamide | 748.3 | See Example 15, separated diastereomers | A1, B38 |
| 83, III-104 | 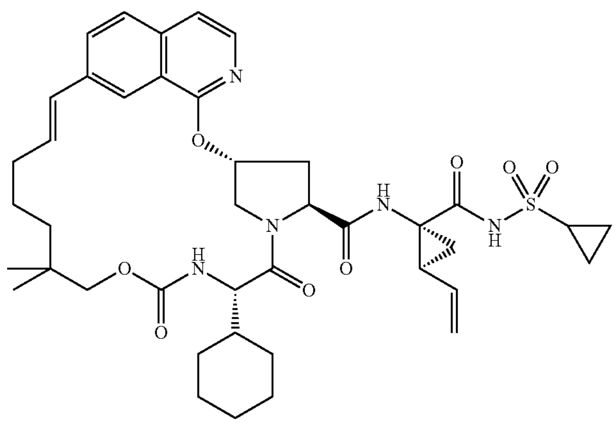 | (2R,4S,7S,16E)-7-cyclohexyl-N-((1R,2S)-1-{[(cyclopropylsulfonyl)amino]carbonyl}-2-vinylcyclopropyl)-12,12-dimethyl-6,9-dioxo-3,4,6,7,8,9,12,13,14,15-decahydro-2H,11H-18,20-etheno-2,5-methanopyrido[2,3-k][1,10,3,6]dioxadiazacyclohenicosine-4-carboxamide | 776.3 | See Example 14 | A1, B40 |
| 84, III-105 | 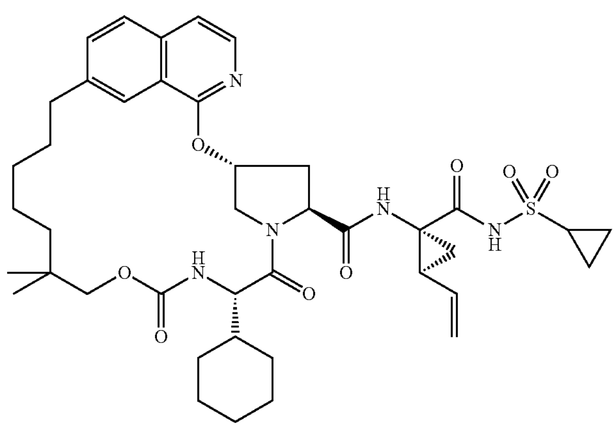 | (2R,4S,7S)-7-cyclohexyl-N-((1R,2S)-1-{[(cyclopropylsulfonyl)amino]carbonyl}-2-vinylcyclopropyl)-12,12-dimethyl-6,9-dioxo-3,4,6,7,8,9,12,13,14,15,16,17-dodecahydro-2H,11H-18,20-etheno-2,5-methanopyrido[2,3-k][1,10,3,6]dioxadiazacyclohenicosine-4-carboxamide | 778.4 | See Example 15 | A1, B40 |

| Ex. | Structure | Name | LRMS (M + H)+ | Prepared using the appropriate Intermediates according to the procedure below. | Int. |
|---|---|---|---|---|---|
| 85, III-106 | 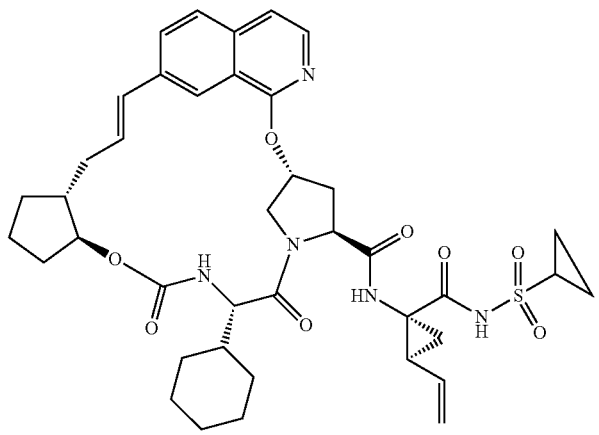 | (6R,8S,11S,14aS,17aR, 19E)-11-cyclohexyl-N-((1R,2S)-1-{[(cyclo-propylsulfonyl)amino] carbonyl}-2-vinyl-cyclopropyl)-10,13-dioxo-7,8,10,11,12,13, 14a,15,16,17,17a,18-dodecahydro-6H-1,21-etheno-6,9-methanocyclopenta[r] pyrido[2,3-k][1,10,3,6] dioxadiazacyclonona-decine-8-carboxamide | 760.5 | See Example 14, separated diastereomers | A1, B41 |
| 86, III-107 | 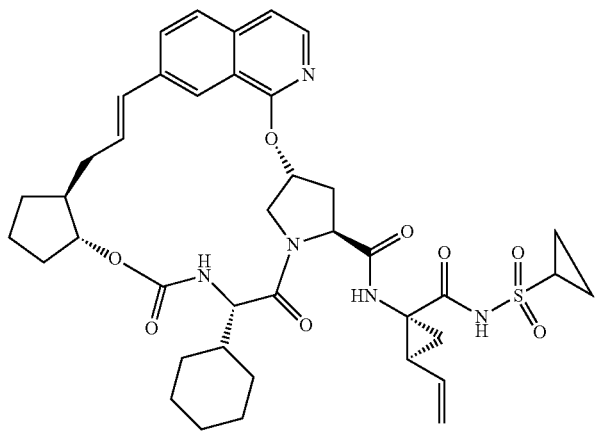 | (6R,8S,11S,14aR,17aS, 19E)-11-cyclohexyl-N-((1R,2S)-1-{[(cyclo-propylsulfonyl)amino] carbonyl}-2-vinyl-cyclopropyl)-10,13-dioxo-7,8,10,11,12,13, 14a,15,16,17,17a,18-dodecahydro-6H-1, 21-etheno-6,9-methanocyclopenta[r] pyrido[2,3-k][1,10,3,6] dioxadiazacyclonona-decine-8-carboxamide | 760.5 | See Example 14, separated diastereomers | A1, B41 |
| 87, III-108 | 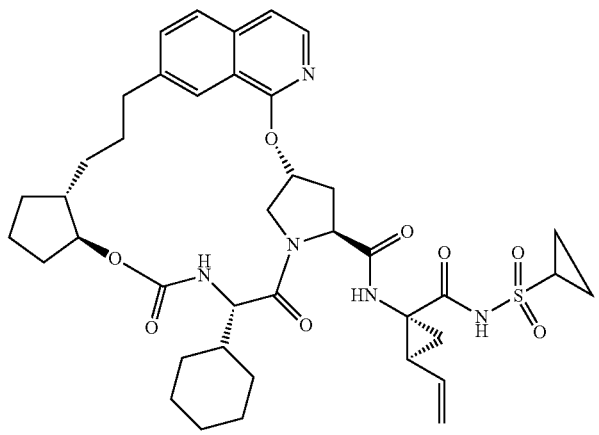 | (6R,8S,11S,14aS, 17aS)-11-cyclohexyl-N-((1R,2S)-1-{[(cyclo-propylsulfonyl)amino] carbonyl}-2-vinyl-cyclopropyl)-10,13-dioxo-7,8,10,11,12,13, 14a,15,16,17,17a,18, 19,20-tetradecahydro-6H-1,21-etheno-6,9-methanocyclopenta[r] pyrido[2,3-k][1,10,3,6] dioxadiazacyclonona-decine-8-carboxamide | 762.6 | See Example 15, separated diastereomers | A1, B41 |

| Ex. | Structure | Name | LRMS (M + H)+ | Prepared using the appropriate Intermediates according to the procedure below. | Int. |
|---|---|---|---|---|---|
| 88, III-109 | 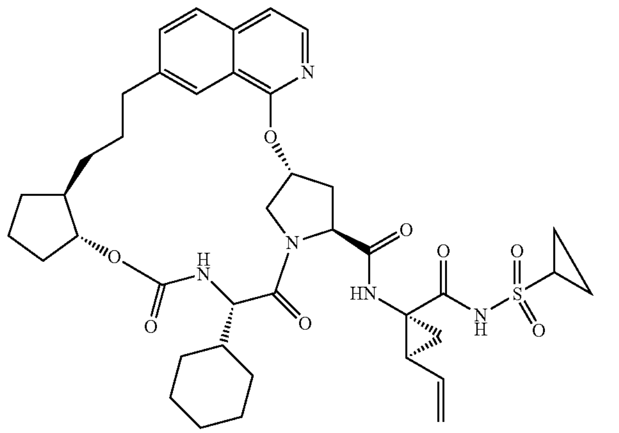 | (6R,8S,11S,14aR,17aR)-11-cyclohexyl-N-((1R,2S)-1-{[(cyclopropylsulfonyl)amino]carbonyl}-2-vinylcyclopropyl)-10,13-dioxo-7,8,10,11,12,13,14a,15,16,17,17a,18,19,20-tetradecahydro-6H-1,21-etheno-6,9-methanocyclopenta[r]pyrido[2,3-k][1,10,3,6]dioxadiazacyclononadecine-8-carboxamide | 762.6 | See Example 15, separated diastereomers | A1, B41 |
| 89, III-110 | 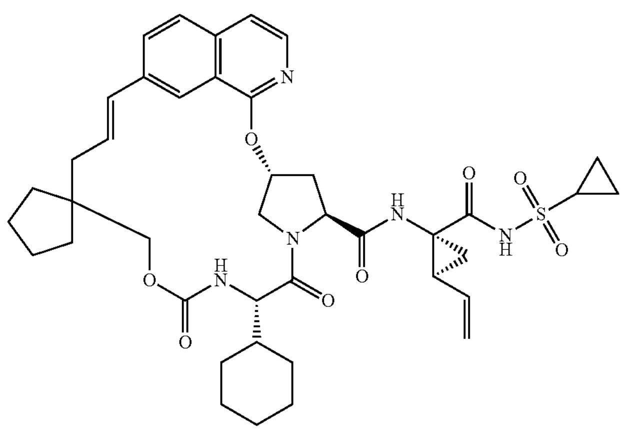 | (2'R,4'S,7'S,14'E)-7'-cyclohexyl-N-((1R,2S)-1-{[(cyclopropylsulfonyl)amino]carbonyl}-2-vinylcyclopropyl)-6',9'-dioxo-3',4',6',7',8',9'-hexahydro-2'H,13'H-spiro[cyclopentane-1,12'-[1,10]dioxa[5,8,21]triaza[16,18]etheno[2,5]methanopyrido[2,3-k][1,10,3,6]dioxadiazacyclononadecine]-4'-carboxamide | 774.2 | See Example 14 | A1, B42 |
| 90, III-111 | 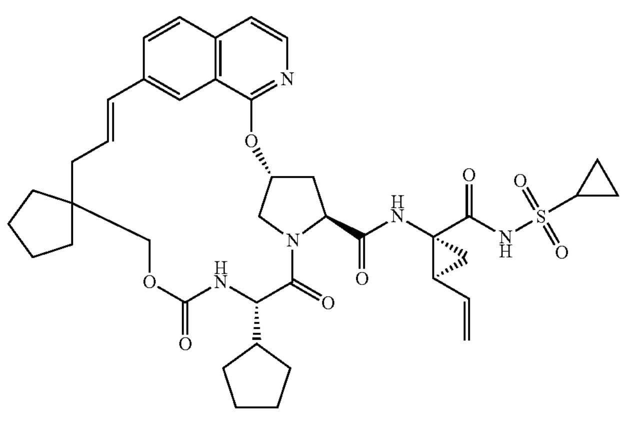 | (2'R,4'S,7'S,14'E)-7'-cyclopentyl-N-((1R,2S)-1-{[(cyclopropylsulfonyl)amino]carbonyl}-2-vinylcyclopropyl)-6',9'-dioxo-3',4',6',7',8',9'-hexahydro-2'H,13'H-spiro[cyclopentane-1,12'-[1,10]dioxa[5,8,21]triaza[16,18]etheno[2,5]methanopyrido[2,3-k][1,10,3,6]dioxadiazacyclononadecine]-4'-carboxamide | 760.3 | See Example 14 | A1, B47 |

| Ex. | Structure | Name | LRMS (M + H)+ | Prepared using the appropriate Intermediates according to the procedure below. | Int. |
|---|---|---|---|---|---|
| 91, III-112 | 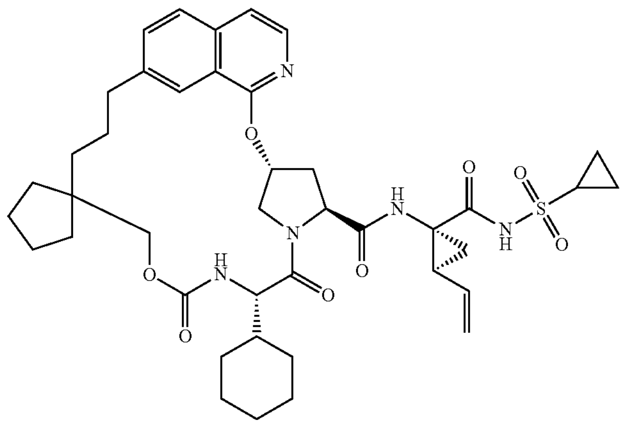 | (2'R,4'S,7'S)-7'-cyclohexyl-N-((1R,2S)-1-{[(cyclopropyl-sulfonyl)amino]carbonyl}-2-vinyl-cyclopropyl)-6',9'-dioxo-3',4',6',7',8',9',14',15'-octahydro-2'H,13'H-spiro[cyclopentane-1,12'-[1,10]dioxa[5,8,21]triaza[16,18]etheno[2,5]methanopyrido[2,3-k][1,10,3,6]dioxadiazacyclonona-decine]-4'-carboxamide | 776.4 | See Example 15 | A1, B42 |
| 92, III-113 | 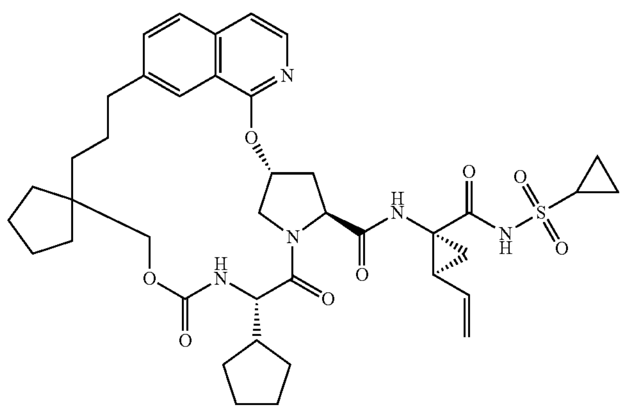 | (2'R,4'S,7'S)-7'-cyclopentyl-N-((1R,2S)-1-{[(cyclopropyl-sulfonyl)amino]carbonyl}-2-vinyl-cyclopropyl)-6',9'-dioxo-3',4',6',7',8',9',14',15'-octahydro-2'H,13'H-spiro[cyclopentane-1,12'-[1,10]dioxa[5,8,21]triaza[16,18]etheno[2,5]methanopyrido[2,3-k][1,10,3,6]dioxadiazacyclonona-decine]-4'-carboxamide | 762.3 | See Example 15 | A1, B47 |
| 93, III-114 | 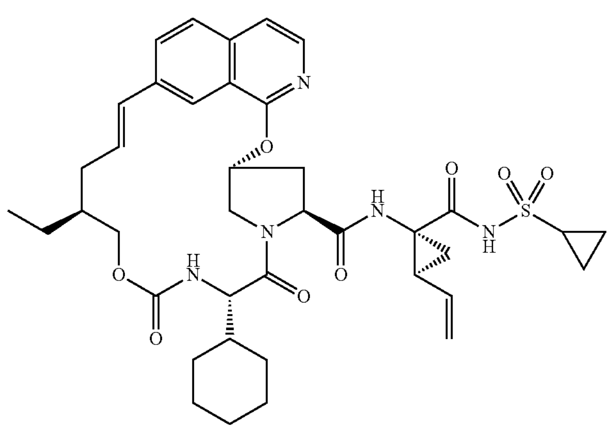 | (2R,4S,7S,12S,14E)-7-cyclohexyl-N-((1R,2S)-1-{[(cyclopropyl-sulfonyl)amino]carbonyl}-2-vinyl-cyclopropyl)-12-ethyl-6,9-dioxo-3,4,6,7,8,9,12,13-octahydro-2H,11H-16,18-etheno-2,5-methanopyrido[2,3-k][1,10,3,6]dioxadiazacyclonona-decine-4-carboxamide | 748.4 | See Example 14, separated diastereomers | A1, B43 |

-continued

| Ex. | Structure | Name | LRMS (M + H)+ | Prepared using the appropriate Intermediates according to the procedure below. | Int. |
|---|---|---|---|---|---|
| 94, III-115 | 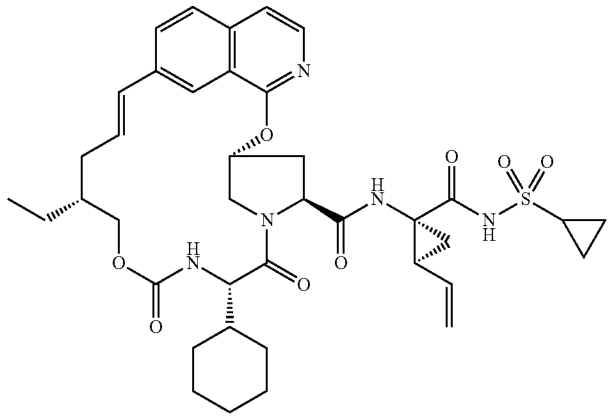 | (2R,4S,7S,12R,14E)-7-cyclohexyl-N-((1R,2S)-1-{[(cyclopropyl-sulfonyl)amino]carbonyl}-2-vinyl-cyclopropyl)-12-ethyl-6,9-dioxo-3,4,6,7,8,9,12,13-octahydro-2H,11H-16,18-etheno-2,5-methanopyrido[2,3-k][1,10,3,6]dioxadiazacyclonona-decine-4-carboxamide | 748.4 | See Example 14, separated diastereomers | A1, B43 |
| 95, III-116 | 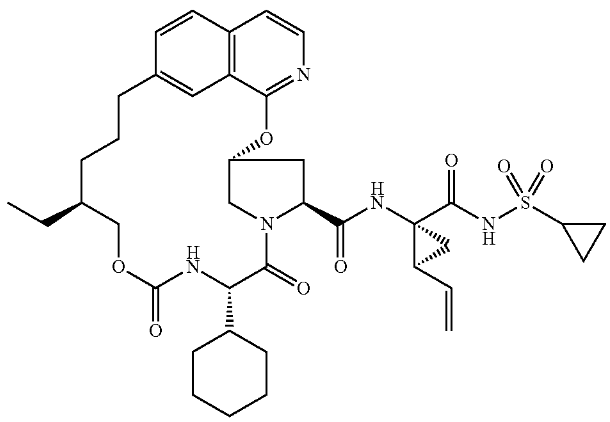 | (2R,4S,7S,12S)-7-cyclohexyl-N-((1R,2S)-1-{[(cyclopropyl-sulfonyl)amino]carbonyl}-2-vinyl-cyclopropyl)-12-ethyl-6,9-dioxo-3,4,6,7,8,9,12,13,14,15-decahydro-2H,11H-16,18-etheno-2,5-methanopyrido[2,3-k][1,10,3,6]dioxadiazacyclonona-decine-4-carboxamide | 750.4 | See Example 15, separated diastereomers | A1, B43 |
| 96, III-117 | 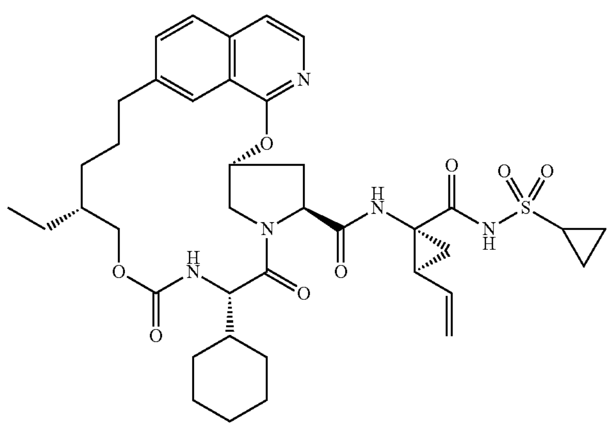 | (2R,4S,7S,12R)-7-cyclohexyl-N-((1R,2S)-1-{[(cyclopropyl-sulfonyl)amino]carbonyl}-2-vinyl-cyclopropyl)-12-ethyl-6,9-dioxo-3,4,6,7,8,9,12,13,14,15-decahydro-2H,11H-16,18-etheno-2,5-methanopyrido[2,3-k][1,10,3,6]dioxadiazacyclonona-decine-4-carboxamide | 750.5 | See Example 15, separated diastereomers | A1, B43 |

| Ex. | Structure | Name | LRMS (M + H)+ | Prepared using the appropriate Intermediates according to the procedure below. | Int. |
|---|---|---|---|---|---|
| 97, III-118 | 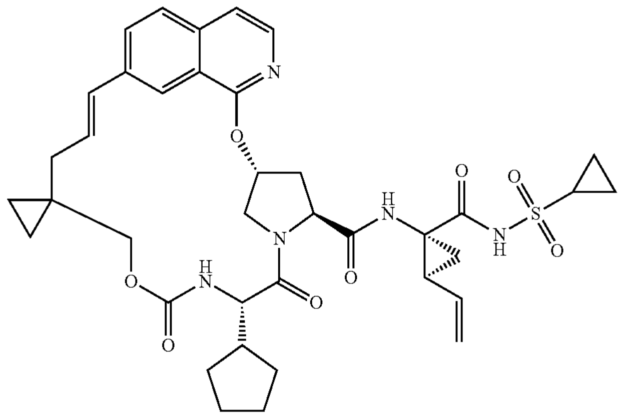 | (2'R,4'S,7'S,14'E)-7'-cyclopentyl-N-((1R,2S)-1-{[(cyclopropyl-sulfonyl)amino]carbonyl}-2-vinyl-cyclopropyl)-6',9'-dioxo-3',4',6',7',8',9'-hexahydro-2'H,13'H-spiro[cyclopropane-1,12'-[1,10]dioxa[5,8,21]triaza[16,18](ethanediylidene)[2,5]methanopyrido[2,3-k][1,10,3,6]dioxadiazacyclonona-decine]-4'-carboxamide | 732.3 | See Example 14 | A1, B44 |
| 98, III-119 | 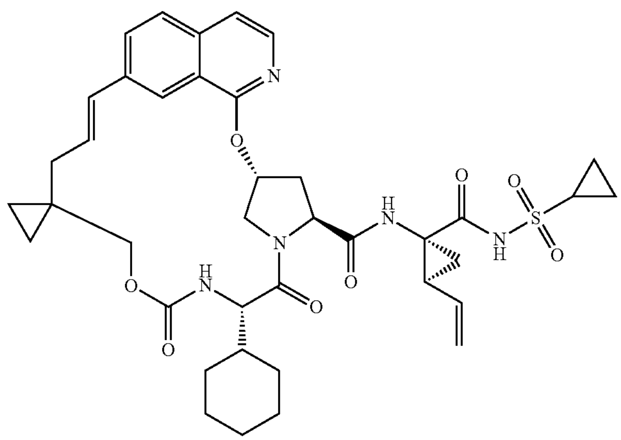 | (2'R,4'S,7'S,14'E)-7'-cyclohexyl-N-((1R,2S)-1-{[(cyclopropyl-sulfonyl)amino]carbonyl}-2-vinyl-cyclopropyl)-6',9'-dioxo-3',4',6',7',8',9'-hexahydro-2'H,13'H-spiro[cyclopropane-1,12'-[1,10]dioxa[5,8,21]triaza[16,18](ethanediylidene)[2,5]methanopyrido[2,3-k][1,10,3,6]dioxadiazacyclonona-decine]-4'-carboxamide | 746.3 | See Example 14 | A1, B45 |
| 99, III-120 | 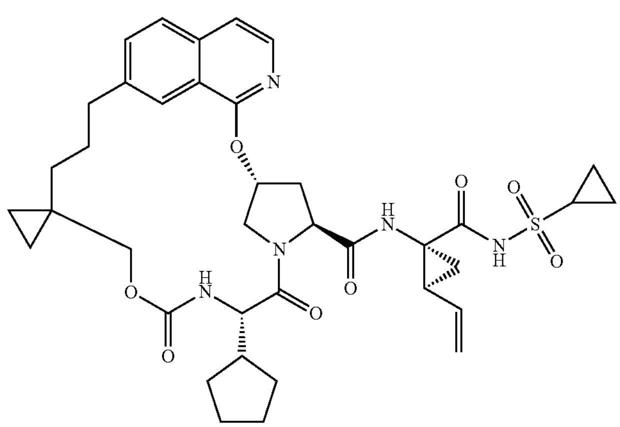 | (2'R,4'S,7'S)-7'-cyclopentyl-N-((1R,2S)-1-{[(cyclopropyl-sulfonyl)amino]carbonyl}-2-vinyl-cyclopropyl)-6',9'-dioxo-3',4',6',7',8',9',14',15'-octahydro-2'H,13'H-spiro[cyclopropane-1,12'-[1,10]dioxa[5,8,21]triaza[16,18](ethanediylidene)[2,5]methanopyrido[2,3-k][1,10,3,6]dioxadiazacyclonona-decine]-4'-carboxamide | 734.3 | See Example 15 | A1, B44 |

-continued

| Ex. | Structure | Name | LRMS (M + H)+ | Prepared using the appropriate Intermediates according to the procedure below. | Int. |
|---|---|---|---|---|---|
| 100, III-121 | 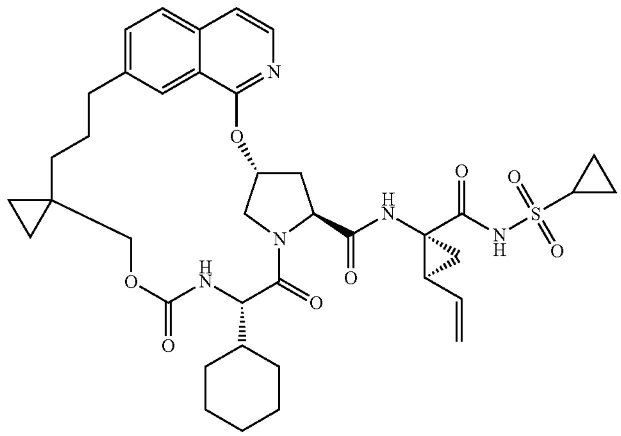 | (2'R,4'S,7'S)-7'-cyclohexyl-N-((1R,2S)-1-{[(cyclopropyl-sulfonyl)amino]carbonyl}-2-vinyl-cyclopropyl)-6',9'-dioxo-3',4',6',7',8',9',14',15'-octahydro-2'H,13'H-spiro[cyclopropane-1,12'-[1,10]dioxa[5,8,21]triaza[16,18](ethanediylidene)[2,5]methanopyrido[2,3-k][1,10,3,6]dioxadiazacyclononadecine]-4'-carboxamide | 748.3 | See Example 15 | A1, B45 |
| 101, III-122 | 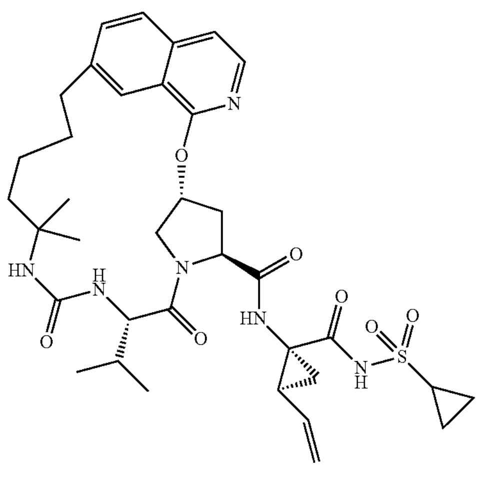 | (2R,4S,7S)-N-((1R,2S)-1-{[(cyclopropylsulfonyl)amino]carbonyl}-2-vinylcyclopropyl)-7-isopropyl-11,11-dimethyl-6,9-dioxo-3,4,6,7,8,9,10,11,12,13,14,15-dodecahydro-2H-16,18-etheno-2,5-methanopyrido[3,2-r][1,5,8,10]oxatriazacyclononadecine-4-carboxamide | 709.4 | See Example 15 | A1, B50 |
| 102, III-28 | 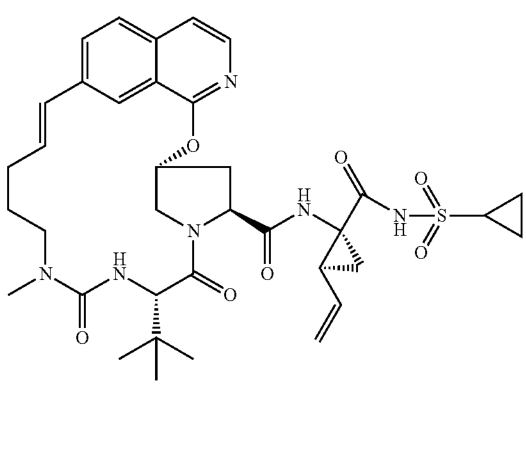 | (2R,4S,7S,14E)-7-tert-butyl-N-((1R,2S)-1-{[(cyclopropyl-sulfonyl)amino]carbonyl}-2-vinyl-cyclopropyl)-10-methyl-6,9-dioxo-3,4,6,7,8,9,10,11,12,13-decahydro-2H-16,18-(ethanediylidene)-2,5-methanopyrido[3,2-r][1,5,8,10]oxatriazacyclononadecine-4-carboxamide | 707.6 | See Example 14 | A1, B51 |

| Ex. | Structure | Name | LRMS (M + H)+ | Prepared using the appropriate Intermediates according to the procedure below. | Int. |
|---|---|---|---|---|---|
| 103, III-14 | 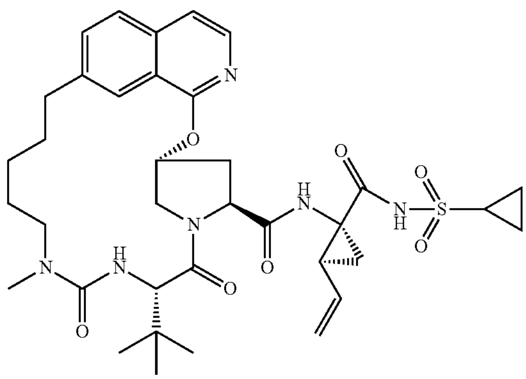 | (2R,4S,7S)-7-tert-butyl-N-((1R,2S)-1-{[(cyclopropyl-sulfonyl)amino]carbonyl}-2-vinyl-cyclopropyl)-10-methyl-6,9-dioxo-3,4,6,7,8,9,10,11,12,13,14,15-dodecahydro-2H-16,18-(ethanediylidene)-2,5-methanopyrido[3,2-r][1,5,8,10]oxatriazacyclonona-decine-4-carboxamide | 709.7 | See Example 15 | A1, B51 |
| 104, III-123 | 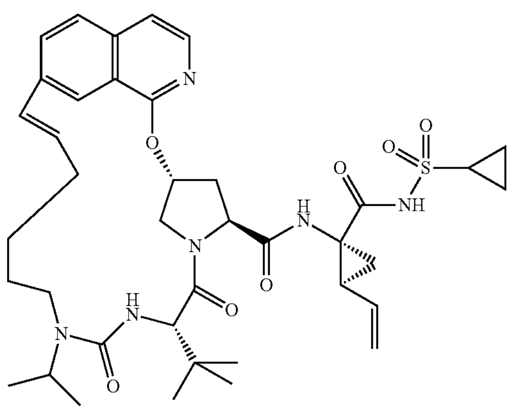 | (2R,4S,7S)-7-tert-butyl-N-((1R,2S)-1-{[(cyclopropyl-sulfonyl)amino]carbonyl}-2-vinyl-cyclopropyl)-10-isopropyl-6,9-dioxo-3,4,7,8,9,10,11,12,13,14-decahydro-2H,6H-17,19-etheno-2,5-methanopyrido[3,2-s][1,5,8,10]oxatriazacycloicosine-4-carboxamide | 749.4 | See Example 14 | A1, B52 |
| 105, III-25 | 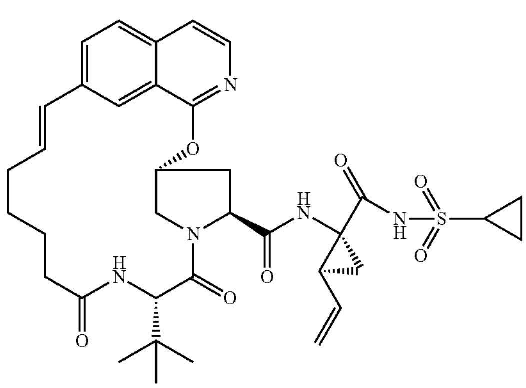 | (2R,4S,7S)-7-tert-butyl-N-((1R,2S)-1-{[(cyclopropyl-sulfonyl)amino]carbonyl}-2-vinyl-cyclopropyl)-6,9-dioxo-3,4,6,7,8,9,10,11,12,13-decahydro-2H-16,18-ethanediylidene-2,5-methanopyrido[3,2-r][1,5,8]oxadiazacyclonona-decine-4-carboxamide | 692.6 | See Example 14 | A1, B53 |

By using the appropriate procedures and the appropriate A, B and C intermediates the following compounds were prepared.

| Ex. | Structure | Name | LRMS (M + H)+ | Prepared using the appropriate Intermediates according to the procedure below. | Int. |
|---|---|---|---|---|---|
| 106, III-12 | 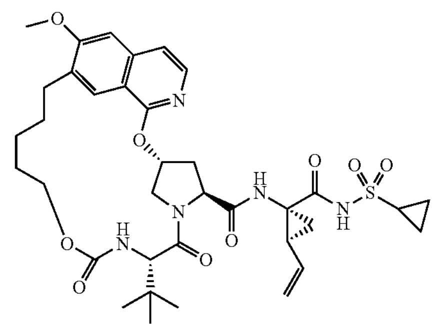 | (2R,4S,7S)-7-tert-butyl-N-((1R,2S)-1-{[(cyclopropylsulfonyl)amino]carbonyl}-2-vinylcyclopropyl)-23-methoxy-6,9-dioxo-3,4,6,7,8,9,12,13,14,15-decahydro-2H,11H-16,8-etheno-2,5-methanopyrido[2,3-k][1,10,3,6]dioxadiazacyclononadecine-4-carboxamide | 726.5 | See Example 15 | A1, B2, C1 |
| 107, III-124 | 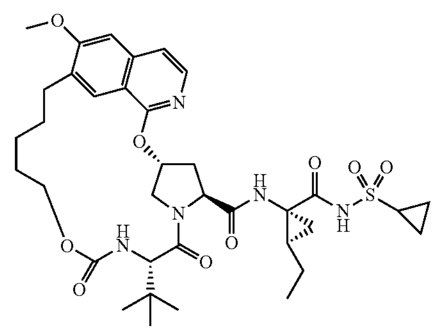 | (2R,4S,7S)-7-tert-butyl-N-((1R,2R)-1-{[(cyclopropylsulfonyl)amino]carbonyl}-2-ethylcyclopropyl)-23-methoxy-6,9-dioxo-3,4,6,7,8,9,12,13,14,15-decahydro-2H,11H-16,18-etheno-2,5-methanopyrido[2,3-k][1,10,3,6]dioxadiazacyclononadecine-4-carboxamide | 728.6 | See Example 15 | A3, B2, C1 |
| 108, III-125 | 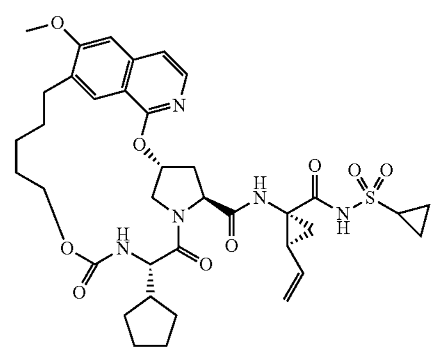 | (2R,4S,7S)-7-cyclopentyl-N-((1R,2S)-1-{[(cyclopropylsulfonyl)amino]carbonyl}-2-vinylcyclopropyl)-23-methoxy-6,9-dioxo-3,4,6,7,8,9,12,13,14,15-decahydro-2H,11H-16,18-etheno-2,5-methanopyrido[2,3-k][1,10,3,6]dioxadiazacyclononadecine-4-carboxamide | 738.5 | See Example 15 | A1, B13, C1 |
| 109, III-126 | 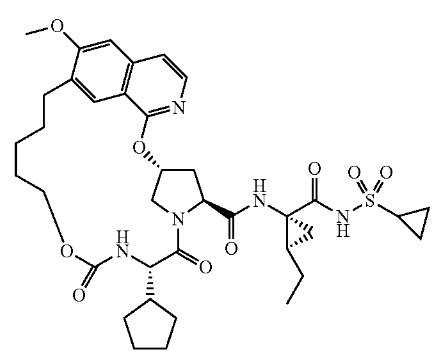 | (2R,4S,7S)-7-cyclopentyl-N-((1R,2R)-1-{[(cyclopropylsulfonyl)amino]carbonyl}-2-ethylcyclopropyl)-23-methoxy-6,9-dioxo-3,4,6,7,8,9,12,13,14,15-decahydro-2H,11H-16,18-etheno-2,5-methanopyrido[2,3-k][1,10,3,6]dioxadiazacyclononadecine-4-carboxamide | 740.6 | See Example 15 | A3, B13, C1 |

-continued

| Ex. | Structure | Name | LRMS (M + H)+ | Prepared using the appropriate Intermediates according to the procedure below. | Int. |
|---|---|---|---|---|---|
| 110, III-127 | 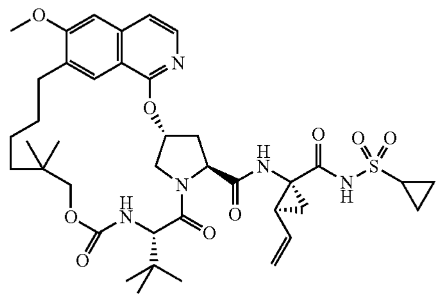 | (2R,4S,1S)-7-tert-butyl-N-((1R,2S)-1-{[(cyclopropylsulfonyl)amino]carbonyl}-2-vinylcyclopropyl)-24-methoxy-12,12-dimethyl-6,9-dioxo-3,4,6,7,8,9,11,12,13,14,15,16-dodecahydro-2H-17,19-etheno-2,5-methanopyrido[2,3-k][1,10,3,6]dioxadiazacycloicosine-4-carboxamide | 786.6 | See Example 15 | A1, B25, C1 |
| 111, III-128 | 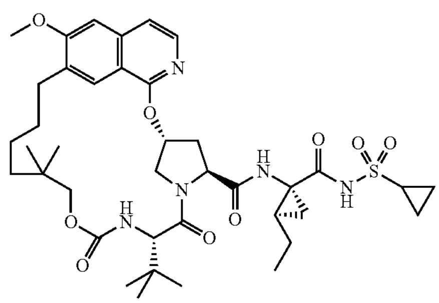 | (2R,4S,7S)-7-tert-butyl-N-((1R,2R)-1-{[(cyclopropylsulfonyl)amino]carbonyl}-2-ethylcyclopropyl)-24-methoxy-12,12-dimethyl-6,9-dioxo-3,4,6,7,8,9,11,12,13,14,15,16-dodecahydro-2H-17,19-etheno-2,5-methanopyrido[2,3-k][1,10,3,6]dioxadiazacycloicosine-4-carboxamide | 770.7 | See Example 15 | A3, B25, C1 |
| 112, III-129 | 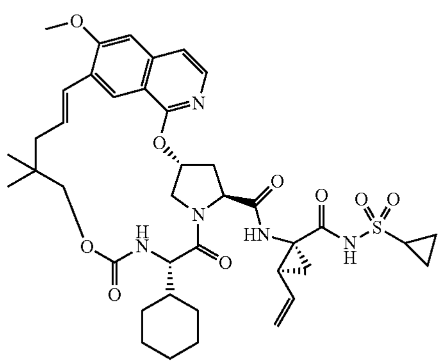 | (2R,4S,7S,14E)-7-cyclohexyl-N-((1R,2S)-1-{[(cyclopropylsulfonyl)amino]carbonyl}-2-vinylcyclopropyl)-23-methoxy-12,12-dimethyl-6,9-dioxo-3,4,6,7,8,9,12,13-octahydro-2H,11H-16,18-etheno-2,5-methanopyrido[2,3-k][1,10,3,6]dioxadiazacyclononadecine-4-carboxamide | 778.6 | See Example 14 | A1, B23, C1 |
| 113, III-130 | 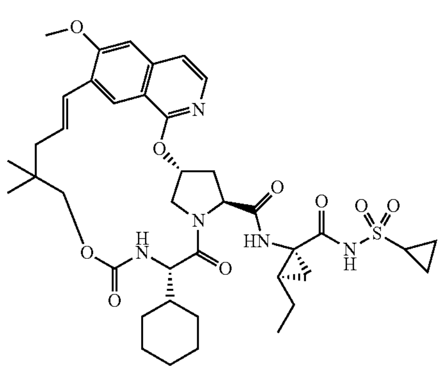 | (2R,4S,7S,14E)-7-cyclohexyl-N-((1R,2R)-1-{[(cyclopropylsulfonyl)amino]carbonyl}-2-ethylcyclopropyl)-23-methoxy-12,12-dimethyl-6,9-dioxo-3,4,6,7,8,9,12,13-octahydro-2H,11H-16,18-etheno-2,5-methanopyrido[2,3-k][1,10,3,6]dioxadiazacyclononadecine-4-carboxamide | 780.6 | See Example 14 | A3, B23, C1 |

-continued

| Ex. | Structure | Name | LRMS (M + H)+ | Prepared using the appropriate Intermediates according to the procedure below. | Int. |
|---|---|---|---|---|---|
| 114, III-131 | 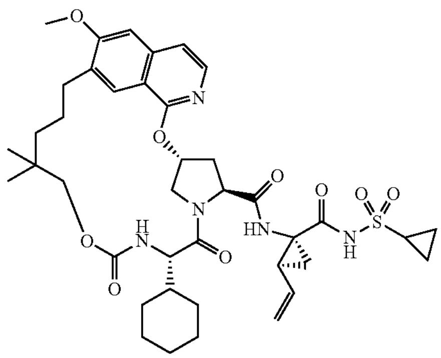 | (2R,4S,7S)-7-cyclohexyl-N-((1R,2S)-1-{[(cyclopropylsulfonyl)amino]carbonyl}-2-vinylcyclopropyl)-23-methoxy-12,12-dimethyl-6,9-dioxo-3,4,6,7,8,9,12,13,14,15-decahydro-2H,11H-16,18-etheno-2,5-methanopyrido[2,3-k][1,10,3,6]dioxadiazacyclononadecine-4-carboxamide | 780.5 | See Example 15 | A1, B23, C1 |
| 115, III-132 | 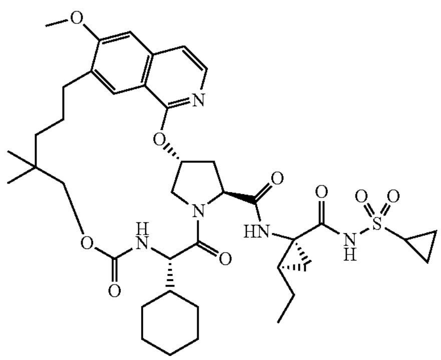 | (2R,4S,7S)-7-cyclohexyl-N-((1R,2R)-1-{[(cyclopropylsulfonyl)amino]carbonyl}-2-ethylcyclopropyl)-23-methoxy-12,12-dimethyl-6,9-dioxo-3,4,6,7,8,9,12,13,14,15-decahydro-2H,11H-16,18-etheno-2,5-methanopyrido[2,3-k][1,10,3,6]dioxadiazacyclononadecine-4-carboxamide | 782.6 | See Example 15 | A3, B23, C1 |
| 116, III-133 | 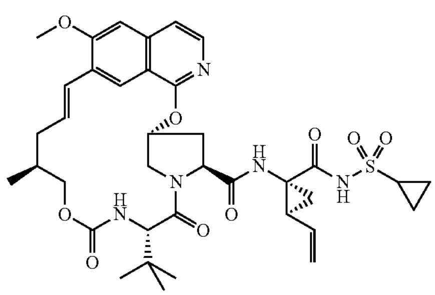 | (2R,4S,7S,12S,14E)-7-tert-butyl-N-((1R,2S)-1-{[(cyclopropylsulfonyl)amino]carbonyl}-2-vinylcyclopropyl)-23-methoxy-12-methyl-6,9-dioxo-3,4,6,7,8,9,12,13-octahydro-2H,11H-16,18-etheno-2,5-methanopyrido[2,3-k][1,10,3,6]dioxadiazacyclononadecine-4-carboxamide | 738.3 | See Example 14, separated diastereomers | A1, B46, C1 |
| 117, III-134 | 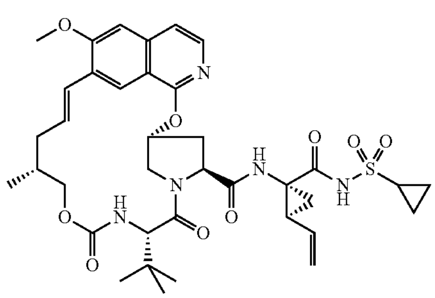 | (2R,4S,7S,12R,14E)-7-tert-butyl-N-(1R,2S)-1-{[(cyclopropylsulfonyl)amino]carbonyl}-2-vinylcyclopropyl)-23-methoxy-12-methyl-6,9-dioxo-3,4,6,7,8,9,12,13-octahydro-2H,11H-16,18-etheno-2,5-methanopyrido[2,3-k][1,10,3.6]dioxadiazacyclononadecine-4-carboxamide | 738.3 | See Example 14, separated diastereomers | A1, B46, C1 |

| Ex. | Structure | Name | LRMS (M + H)+ | Prepared using the appropriate Intermediates according to the procedure below. | Int. |
|---|---|---|---|---|---|
| 118, III-135 | 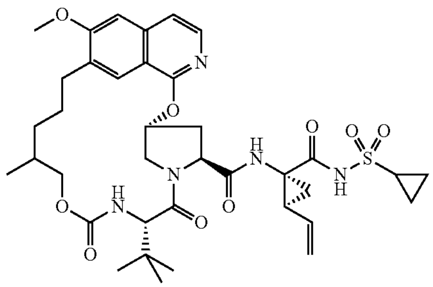 | (2R,4S,7S)-7-tert-butyl-N-((1R,2S)-1-{[(cyclopropylsulfonyl)amino]carbonyl}-2-vinylcyclopropyl)-23-methoxy-12-methyl-6,9-dioxo-3,4,6,7,8,9,12,13,14,15-decahydro-2H,11H-16,18-etheno-2,5-methanopyrido[2,3-k][1,10,3,6]dioxadiazacyclononadecine-4-carboxamide | 740.2 | See Example 15 | A1, B46, C1 |
| 119, III-136 | 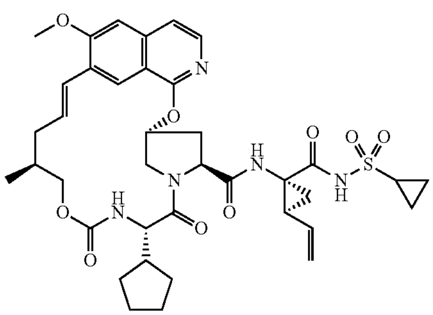 | (2R,4S,7S,12S,14E)-7-cyclopentyl-N-((1R,2S)-1-{[(cyclopropylsulfonyl)amino]carbonyl}-2-vinylcyclopropyl)-23-methoxy-12-methyl-6,9-dioxo-3,4,6,7,8,9,12,13-octahydro-2H,11H-16,18-etheno-2,5-methanopyrido[2,3-k][1,10,3,6]dioxadiazacyclononadecine-4-carboxamide | 750.4 | See Example 14, separated diastereomers | A1, B48, C1 |
| 120, III-137 | 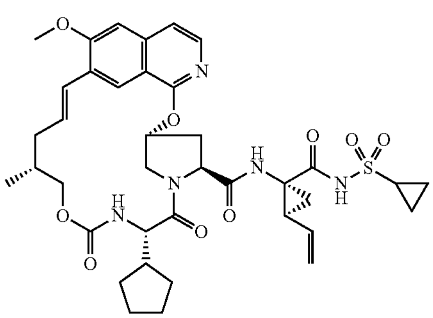 | (2R,4S,7S,12R,14E)-7-cyclopentyl-N-((1R,2S)-1-{[(cyclopropylsulfonyl)amino]carbonyl}-2-vinylcyclopropyl)-23-methoxy-12-methyl-6,9-dioxo-3,4,6,7,8,9,12,13-octahydro-2H,11H-16,18-etheno-2,5-methanopyrido[2,3-k][1,10,3,6]dioxadiazacyclononadecine-4-carboxamide | 750.4 | See Example 14, separated diastereomers | A1, B48, C1 |
| 121, III-138 | 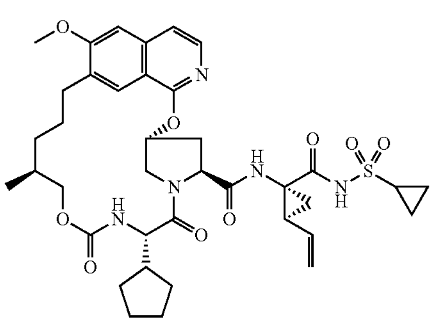 | (2R,4S,7S,12S)-7-cyclopentyl-N-((1R,2S)-1-{[(cyclopropylsulfonyl)amino]carbonyl}-2-vinylcyclopropyl)-23-methoxy-12-methyl-6,9-dioxo-3,4,6,7,8,9,12,13,14,15-decahydro-2H,11H-16,18-etheno-2,5-methanopyrido[2,3-k][1,10,3,6]dioxadiazacyclononadecine-4-carboxamide | 752.4 | See Example 15, separated diastereomers | A1, B48, C1 |

-continued

| Ex. | Structure | Name | LRMS (M + H)+ | Prepared using the appropriate Intermediates according to the procedure below. | Int. |
|---|---|---|---|---|---|
| 122, III-139 | 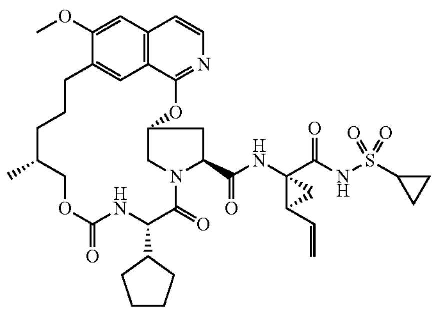 | (2R,4S,7S,12R)-7-cyclopentyl-N-((1R,2S)-1-{[(cyclopropylsulfonyl)amino]carbonyl}-2-vinylcyclopropyl)-23-methoxy-12-metiiyl-6,9-dioxo-3,4,6,7,8,9,12,13,14,15-decahydro-2H,11H-16,18-etheno-2,5-methanopyrido[2,3-k][1,10,3,6]dioxadiazacyclononadecine-4-carboxamide | 752.5 | See Example 15, separated diastereomers | A1, B48, C1 |
| 123, III-140 | 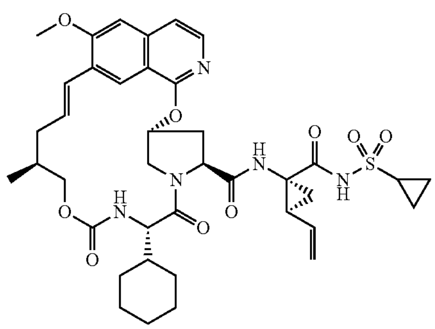 | (2R,4S,7S, 12S,14E)-7-cyclohexyl-N-((1R,2S)-1-{[(cyclopropylsulfonyl)amino]carbonyl}-2-vinylcyclopropyl)-23-methoxy-12-methyl-6,9-dioxo-3,4,6,7,8,9,12,13-octahydro-2H,11H-16,18-etheno-2,5-methanopyrido[2,3-k][1,10,3,6]dioxadiazacyclononadecine-4-carboxamide | 764.3 | See Example 14, separated diastereomers | A1, B39, C1 |
| 124, III-141 | 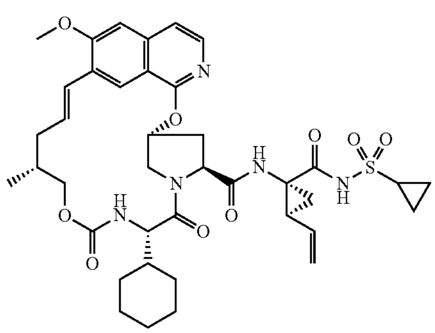 | {2R,4S,1S,12R,14E)-7-cyclohexyl-N-((1R,2S)-1-{[(cyclopropylsulfonyl)amino]carbonyl}-2-vinylcyclopropyl)-23-methoxy-12-methyl-6,9-dioxo-3,4,6,7,8,9,12,13-octahydro-2H,11H-16,18-etheno-2,5-methanopyrido[2,3-k][1,10,3,6]dioxadiazacyclononadecine-4-carboxamide | 764.3 | See Example 14, separated diastereomers | A1, B39, C1 |
| 125, III-142 | 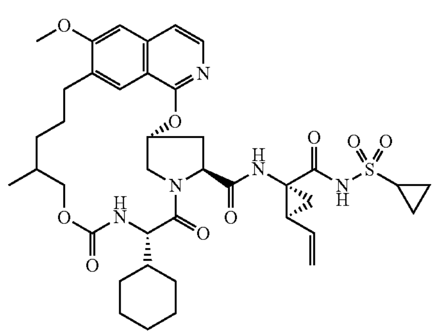 | (2R,4S,7S)-7-cyclohexyl-N-((1R,2S)-1-{[(cyclopropylsulfonyl)amino]carbonyl}-2-vinylcyclopropyl)-23-methoxy-12-methyl-6,9-dioxo-3,4,6,7,8,9,12,13,14,15-decahydro-2H,11H-16,18-etheno-2,5-methanopyrido[2,3-k][1,10,3,6]dioxadiazacyclononadecine-4-carboxamide | 766.4 | See Example 15 | A1, B39, C1 |

-continued

| Ex. | Structure | Name | LRMS (M + H)+ | Prepared using the appropriate Intermediates according to the procedure below. | Int. |
|---|---|---|---|---|---|
| 126, III-20 | 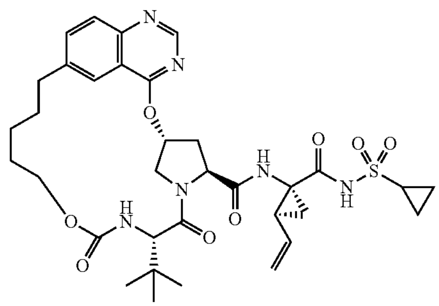 | (15S,18S,20R)-15-tert-butyl-N-((1R,2S)-1-{[(cyclopropylsulfonyl)amino]carbonyl}-2-vinylcyclopropyl)-13,16-dioxo-8,9,10,11,13,14,15,16,19,20-decahydro-7H,18H-4,6-etheno-17,20-methanopyrimido[4,5-k][1,10,3,6]dioxadiazacyclononadecine-18-carboxamide | 697.5 | See Example 15 | A1, B2, C2 |
| 127, III-143 | 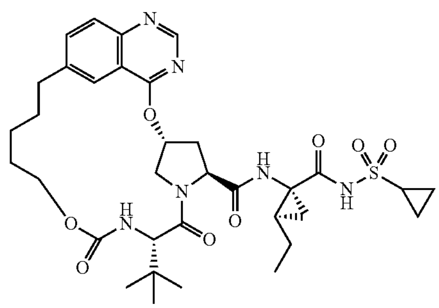 | (15S,18S,20R)-15-tert-butyl-N-((1R,2R)-1-{[(cyclopropylsulfonyl)amino]carbonyl}-2-ethylcyclopropyl)-13,16-dioxo-8,9,10,11,13,14,15,16,19,20-decahydro-7H,18H-4,6-etheno-17,20-methanopyrimido[4,5-k][1,10,3,6]dioxadiazacyclononadecine-18-carboxamide | 699.5 | See Example 15 | A3, B2, C2 |
| 128, III-34 | 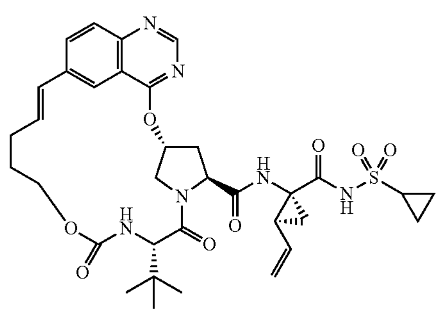 | (7E,15S,18S,20R)-15-tetr-butyl-N-((1R,2S)-1-{[(cyclopropylsulfonyl)amino]carbonyl}-2-vinylcyclopropyl)-13,16-dioxo-10,11,13,14,15,16,19,20-octahydro-9H,18H-4,6-etheno-17,20-methanopyrimido[4,5-k][1,10,3,6]dioxadiazacyclononadecine-18-carboxamide | 695.4 | See Example 14 | A1, B2, C2 |
| 129, III-31 | 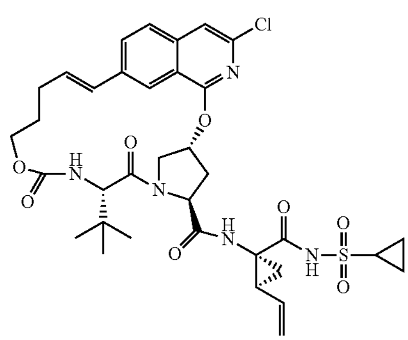 | (2R,4S,7S,14E)-7-tert-butyl-20-chloro-N-((1R,2S)-1-{[(cyclopropylsulfonyl)amino]carbonyl}-2-vinylcyclopropyl)-6,9-dioxo-3,4,6,7,8,9,12,13-octahydro-2H,11H-16,18-(ethanediylidene)-2,5-methanopyrido[2,3-k][1,10,3,6]dioxadiazacyclononadecine-4-carboxamide | 728.5 | See Example 14 | A1, B2, C3 |

| Ex. | Structure | Name | LRMS (M + H)+ | Prepared using the appropriate Intermediates according to the procedure below. | Int. |
|---|---|---|---|---|---|
| 130, III-32 | 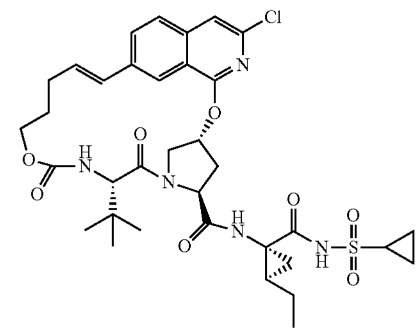 | (2R,4S,7S,14E)-7-tert-butyl-20-chloro-N-((1R,2R)-1-{[(cyclopropylsulfonyl)amino]carbonyl}-2-ethylcyclopropyl)-6,9-dioxo-3,4,6,7,8,9,12,13-octahydro-2H,11H-16,18-(ethanediylidene)-2,5-methanopyrido[2,3-k][1,10,3,6]dioxadiazacyclononadecine-4-carboxamide | 730.5 | See Example 14 | A3, B2, C3 |
| 131, III-144 | 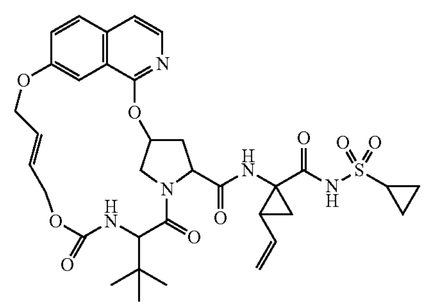 | (2R,4S,7S,12E)-7-tert-butyl-N-((1R,2S)-1-{[(cyclopropylsulfonyl)amino]carbonyl}-2-vinylcyclopropyl)-6,9-dioxo-3,4,6,7,8,9,11,14-octahydro-2H-16,18-etheno-2,5-methanopyrido[2,3-k][1,10,15,3,6]trioxadiazacyclononadecine-4-carboxamide | 696.5 | See Example 14, separated olefin isomers | A1, B49, C4 |
| 132, III-145 | 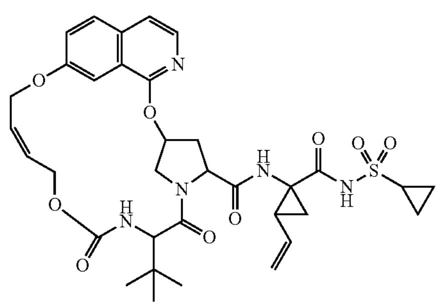 | (2R,4S,7S,12Z)-7-tert-butyl-N-((1R,2S)-1-{[(cyclopropylsulfonyl)amino]carbonyl}-2-vinylcyclopropyl)-6,9-dioxo-3,4,6,7,8,9,11,14-octahydro-2H-16,18-etheno-2,5-methanopyrido[2,3-k][1,10,15,3,6]trioxadiazacyclononadecine-4-carboxamide | 696.5 | See Example 14, separated olefin isomers | A1, B49, C4 |
| 133, III-146 | 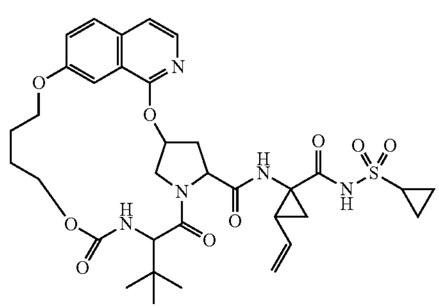 | (2R,4S,7S)-7-tert-butyl-N-((1R,2S)-1-{[(cyclopropylsulfonyl)amino]carbonyl}-2-vinylcyclopropyl)-6,9-dioxo-3,4,6,7,8,9,11,12,13,14-decahydro-2H-16,18-etheno-2,5-methanopyrido[2,3-k][1,10,15,3,6]trioxadiazacyclononadecine-4-carboxamide | 698.4 | See Example 15 | A1, B49, C4 |

| Ex. | Structure | Name | LRMS (M + H)+ | Prepared using the appropriate Intermediates according to the procedure below. | Int. |
|---|---|---|---|---|---|
| 134, III-147 | 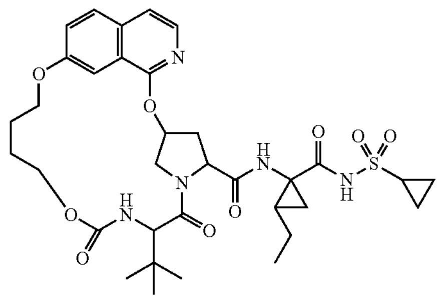 | (2R,4S,7S)-7-tert-butyl-N-((1R,2R)-1-{[(cyclopropylsulfonyl)amino]carbonyl}-2-ethylcyclopropyl)-6,9-dioxo-3,4,6,7,8,9,11,12,13,14-decahydro-2H-16,18-etheno-2,5-methanopyrido[2,3-k][1,10,15,3,6]trioxadiazacyclononadecine-4-carboxamide | 700.5 | See Example 15 | A3, B49, C4 |

By using the appropriate procedures and the appropriate A, B and D intermediates, the following compounds were prepared.

| Ex. | Structure | Name | LRMS (M + H)+ | Prepared using the appropriate Intermediates according to the procedure below. | Int. |
|---|---|---|---|---|---|
| 135, III-148 | 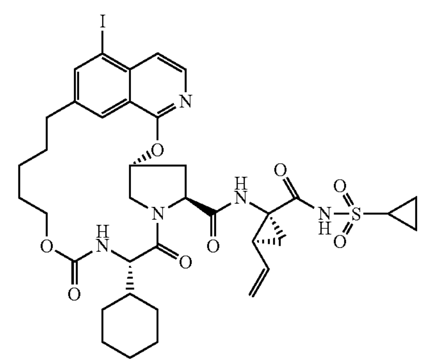 | {2R,4S,7S)-7-cyclohexyl-N-((1R,2S)-1-{[(cyclopropylsulfonyl)amino]carbonyl}-2-vinylcyclopropyl)-22-iodo-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 848.4 | See Example 13 | A1, B8 |
| 136, III-149 | 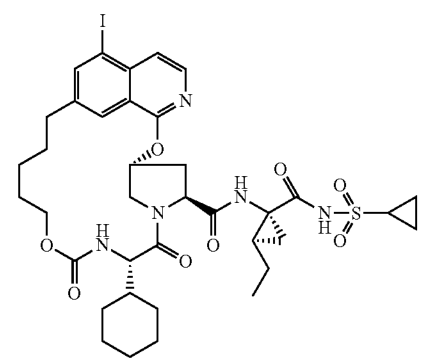 | (2R,4S,7S)-7-cyclohexyl-N-((1R,2R)-1-{[(cyclopropylsulfonyl)ammo]carbonyl}-2-ethylcyclopropyl)-22-iodo-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 850.5 | See Example 13 | A3, B8 |

-continued

| Ex. | Structure | Name | LRMS (M + H)+ | Prepared using the appropriate Intermediates according to the procedure below. | Int. |
|---|---|---|---|---|---|
| 137 III-150 | 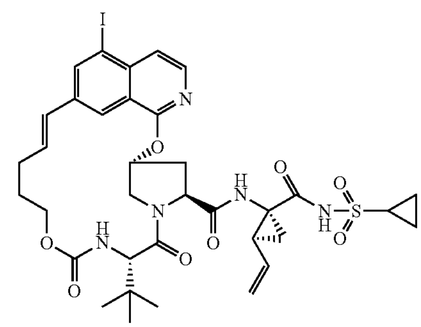 | (2R,4S,7S,14E)-7-tert-butyl-N-((1R,2S)-1-{[(cyclopropylsulfonyl)amino]carbonyl}-2-vinylcyclopropyl)-22-iodo-6,9-dioxo-3,4,6,7,8,9,12,13-octahydro-2H,11H-16,18-(ethanediylidene)2,5-methanopyrido[2,3-k][1,10,3,6]dioxadiazacyclononadecine-4-carboxamide | 820.2 | See Example 14, Step 5 | A1, D1 |
| 138, III-151 | 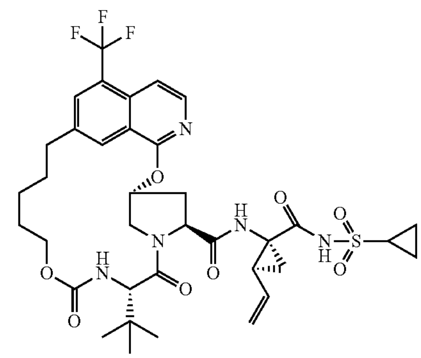 | (2R,4S,7S)-7-tert-butyl-N-((1R,2S)-1-{[(cyclopropylsulfonyl)amino]carbonyl}-2-vinylcyclopropyl)-6,9-dioxo-22-(trifluoromethyl)-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 764.3 | See Example 14, Steps 4 and 5 | A1, D5 |
| 139, III-152 | 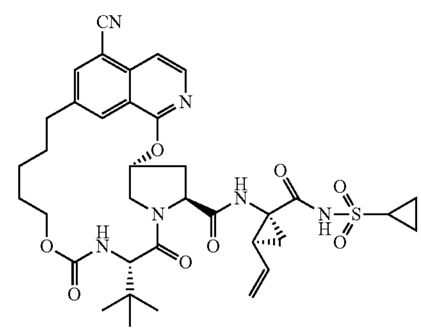 | (2R,4S,7S)-7-tert-butyl-22-cyano-N-((1R,2S)-1-{[(cyclopropylsulfonyl)amino]carbonyl}-2-vinylcyclopropyl)-6,9-dioxo-3,4,6,7,8,9,12,13,14,15-decahydxo-2H,11H-16,18-(ethanediylidene)-2,5-methanopyrido[2,3-k][1,10,3,6]dioxadiazacyclononadecine-4-carboxamide | 721.6 | See Example 14, Steps 4 and 5 | A1, D6 |
| 140, III-153 | 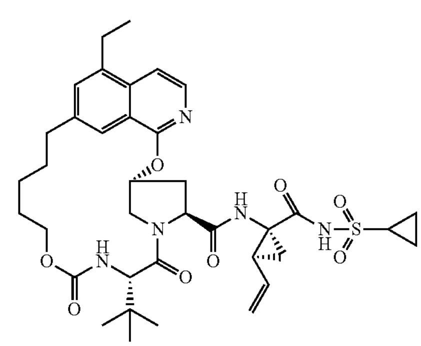 | (2R,4S,7S)-7-tert-butyl-N-((1R,2S)-1-{[(cyclopropylsulfonyl)amino]carbonyl}-2-vinylcyclopropyl)-22-ethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 724.7 | See Example 14, Steps 4 and 5 | A1, D7 |

| Ex. | Structure | Name | LRMS (M + H)+ | Prepared using the appropriate Intermediates according to the procedure below. | Int. |
|---|---|---|---|---|---|
| 141, III-154 | 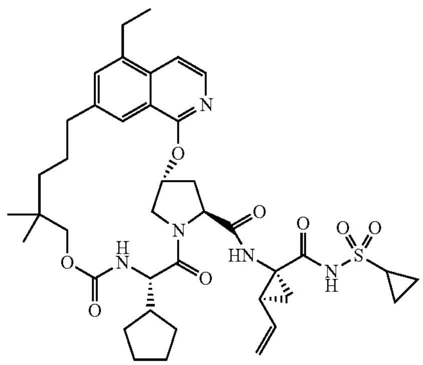 | (2R,4S,7S)-7-cyclopentyl-N-((1R,2S)-1-{[(cyclopropylsulfonyl)amino]carbonyl}-2-vinylcyclopropyl)-22-ethyl-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 764.4 | See Example 14, Steps 4 and 5 | A1, D8 |
| 142, III-155 | 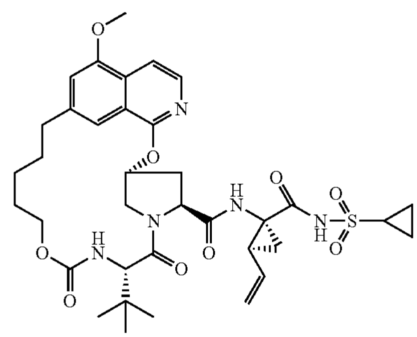 | (2R,4S,7S)-7-tert-butyl-N-((1R,2S)-1-{[(cyclopropylsulfonyl)amino]carbonyl}-2-vinylcyclopropyl)-22-methoxy-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 726.7 | See Example 14, Step 5 | A1, D9 |
| 143, III-156 | 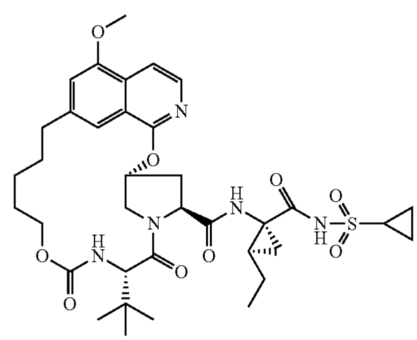 | (2R,4S,7S)-7-tert-butyl-N-((1R,2R)-1-{[(cyclopropylsulfonyl)amino]carbonyl}-2-ethylcyclopropyl)-22-methoxy-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 728.5 | See Example 14, Step 5 | A3, D9 |
| 144, III-157 | 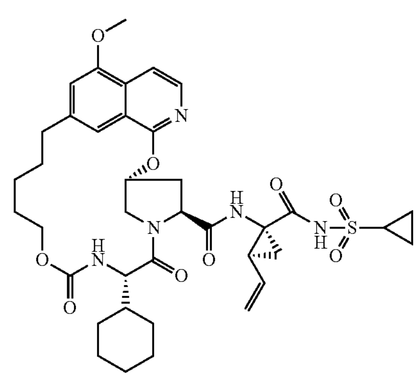 | (2R,4S,7S)-7-cyclohexyl-N-((1R,2S)-1-{[(cyclopropylsulfonyl)amino]carbonyl}-2-vinylcyclopropyl)-22-methoxy-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 752.5 | See Example 14, Step 5 | A1, D10 |

| Ex. | Structure | Name | LRMS (M + H)+ | Prepared using the appropriate Intermediates according to the procedure below. | Int. |
|---|---|---|---|---|---|
| 145, III-158 | 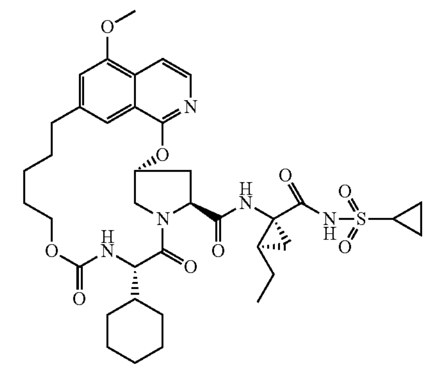 | (2R,4S,7S)-7-cyclohexyl-N-((1R,2S)-1-{[(cyclopropylsulfonyl)amino]carbonyl}-2-ethylcyclopropyl)-22-methoxy-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 754.5 | See Example 14, Step 5 | A3, D10 |
| 146 III-159 | 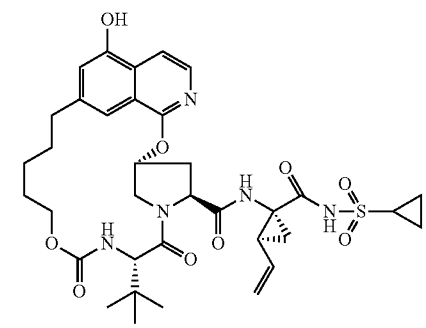 | (2R,4S,7S)-7-tert-butyl-N-((1R,2S)-1-{[(cyclopropylsulfonyl)amino]carbonyl}-2-vinylcyclopropyl)-22-hydroxy-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 712.5 | See Example 14, Step 5 | A1, D11 |
| 147, III-160 | 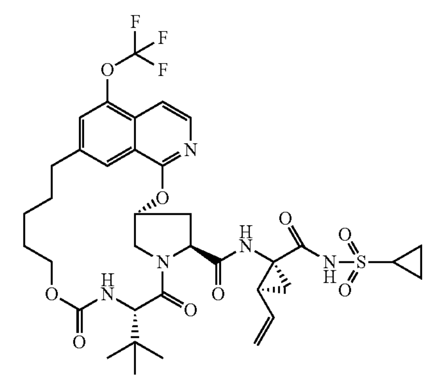 | (2R,4S,7S)-7-tert-butyl-N-((1R,2S)-1-{[(cyclopropylsulfonyl)amino]carbonyl}-2-vinylcyclopropyl)-6,9-dioxo-22-(trifluoromethoxy)-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 780.5 | See Example 15 | A1, D15 |
| 148, III-161 | 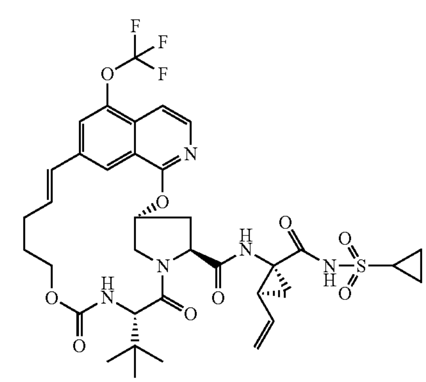 | (2R,4S,7S,14E)-7-tert-butyl-N-((1R,2S)-1-{[(cyclopropylsulfonyl)amino]carbonyl}-2-vinylcyclopropyl)-6,9-dioxo-22-(trifluoromethoxy)-3,4,6,7,8,9,12,13-octahydro-2H,11H-16,18-(ethanediylidene)-2,5-methanopyrido[2,3-k][1,10,3,6]dioxadiazacyclononadecine-4-carboxamide | 778.4 | See Example 14, Steps 4 and 5 | A1, D15 |

| Ex. | Structure | Name | LRMS (M + H)+ | Prepared using the appropriate Intermediates according to the procedure below. | Int. |
|---|---|---|---|---|---|
| 149, III-162 | 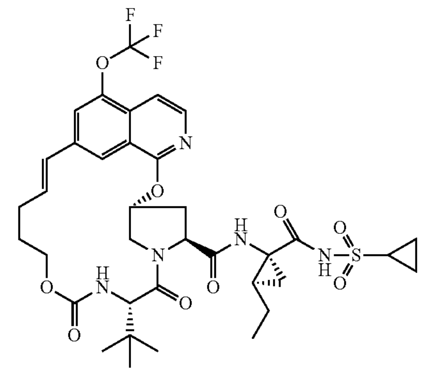 | (2R,4S,7S,14E)-7-tert-butyl-N((1R,2R)-1-{[(cyclopropylsulfonyl)amino]carbonyl}-2-ethylcyclopropyl)-6,9-dioxo-22-(trifluoromethoxy)-3,4,6,7,8,9,12,13-octahydro-2H,11H-16,18-(ethanediylidene)-2,5-methanopyrido[2,3-k][1,10,3,6]dioxadiazacyclononadecine-4-carboxamide | 780.5 | See Example 14, Steps 4 and 5 | A3, D15 |
| 150, III-163 | 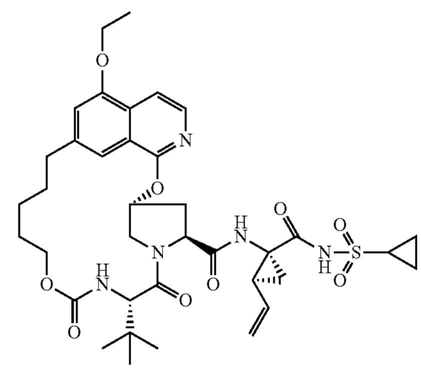 | (2R,4S,7S)-7-tert-butyl-N-((1R,2S)-1-{[(cyclopropylsulfonyl)amino]carbonyl}-2-vinylcyclopropyl)-22-ethoxy-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 740.5 | See Example 14, Steps 4 and 5 | A1, D12 |
| 151, III-164 | 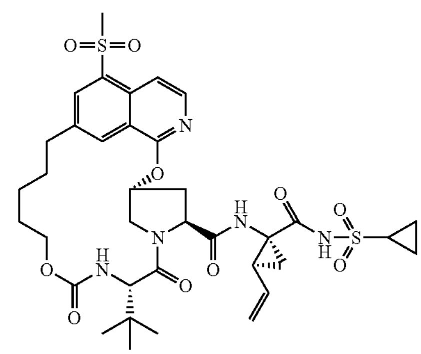 | (2R,4S,7S)7-tert-butyl-N((1R,2S)-1-{[(cyclopropylsulfonyl)amino]carbonyl}-2-vinylcyclopropyl)-22-(methylsulfonyl)-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 774.5 | See Example 14, Steps 4 and 5 | A1, D13 |
| 152, III-165 | 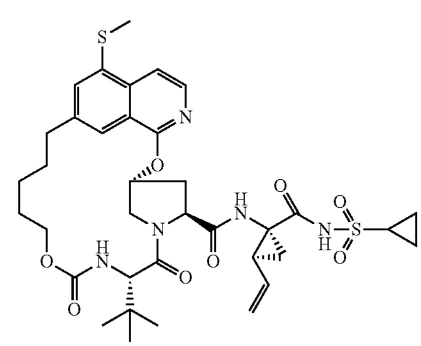 | (2R,4S,7S)-7-tert-butyl-N-((1R,2S)-1-{[(cyclopropylsulfonyl)amino]carbonyl}-2-vinylcyclopropyl)-22-(methylthio)-6,9-dioxo-3,4,6,7,8,9,12,13,14,15-decahydro-2H,11H-16,18-(ethandiylidene)-2,5-methanopyrido[2,3-k][1,10,3,6]dioxadiazacyclononadecine-4-carboxamide | 742.5 | See Example 14, Steps 4 and 5 | A1, D14 |

-continued

| Ex. | Structure | Name | LRMS (M + H)+ | Prepared using the appropriate Intermediates according to the procedure below. | Int. |
|---|---|---|---|---|---|
| 153, III-166 | 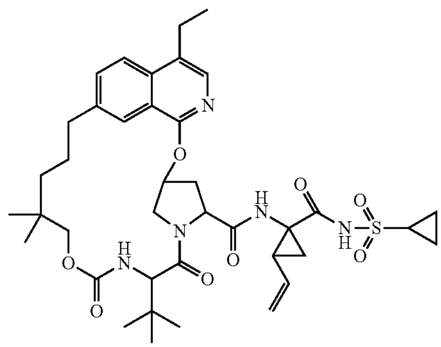 | (2R,4S,7S)-7-tert-butyl-N-((1R,2S)-1-{[(cyclopropylsulfonyl)amino]carbonyl}-2-vinylcyclopropyl)-19-ethyl-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 752.6 | See Example 14, Steps 4 and 5 | A1, D16 |
| 154, III-167 | 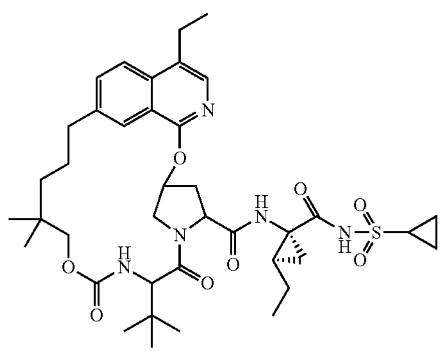 | (2R,4S,7S)-7-tert-butyl-N((1R,2R)-1-{[(cyclopropylsulfonyl)amino]carbonyl}-2-ethylcyclopropyl)-19-ethyl-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 754.5 | See Example 14, Steps 4 and 5 | A3, D16 |
| 155, III-168 | 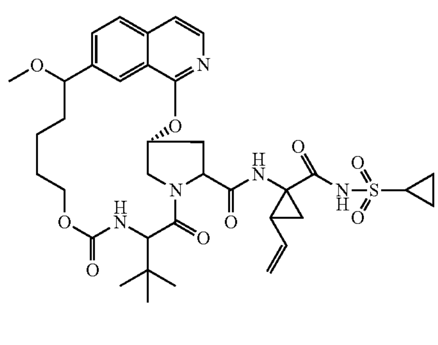 | (2R,4S,7S)-7-tert-butyl-N-((1R,2S)-1-{[(cyclopropylsulfonyl)amino]carbonyl}-2-vinylcyclopropyl)-15-methoxy-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 726.3 | See Example 14, Step 5 | A1, D2 |
| 156, III-169 | 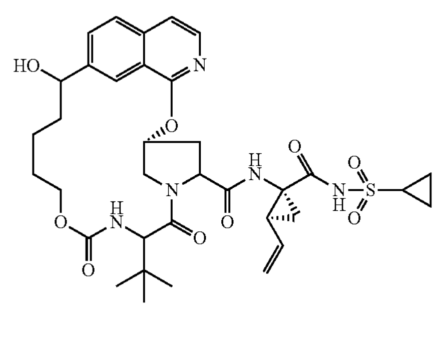 | (2R,4S,7S,15R)-7-tert-butyl-N((1R,2S)-1-{[(cyclopropylsulfonyl)amino]carbonyl}-2-vinylcyclopropyl)-15-hydroxy-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 712.6 | See Example 14, Steps 4 and 5, separated diastereomers | A1, D3 |

-continued

| Ex. | Structure | Name | LRMS (M + H)+ | Prepared using the appropriate Intermediates according to the procedure below. | Int. |
|---|---|---|---|---|---|
| 157, III-170 | 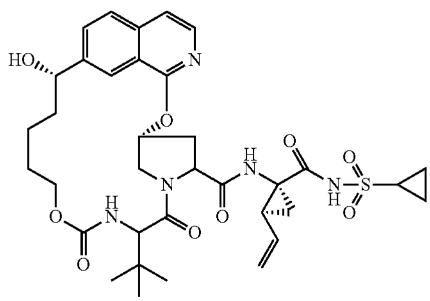 | (2R,4S,7S,15S)-7-tert-butyl-N-((1R,2S)-1-{[(cyclopropylsulfonyl)amino]carbonyl}-2-vinylcyclopropyl)-15-hydroxy-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 712.6 | See Example 14, Steps 4 and 5, separated diastereomers | A1, D3 |
| 158, III-171 | 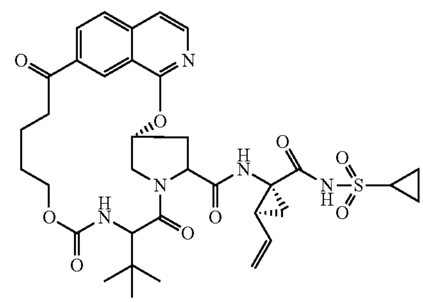 | (2R,4S,7S)-7-tert-butyl-N-((1R,2S)-1-{[(cyclopropylsulfonyl)amino]carbonyl}-2-vinylcyclopropyl)-6,9,15-trioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide | 710.5 | See Example 14, Steps 4 and 5 | A1, D4 |

EXAMPLE 159

(2R,4S,3S,14E)-7-tert-butyl-N-((1R,2S)-1-{[(cyclopropylsulfonyl)amino]carbonyl}-2-vinylcyclopropyl)-6,9-dioxo-20-phenyl-3,4,6,7,8,9,12,13-octahydro-2H,11H-16,18-(ethanediylidene)-2,5-methanopyrido[2,3-k][1,10,3,6]dioxadiazacyclononadecine-4-carboxamide (III-172)

III-172

To a solution of (2R,4S,7S,14E)-7-tert-butyl-20-chloro-N-((1R,2S)-1-{[(cyclopropylsulfonyl)amino]carbonyl}-2-vinylcyclopropyl)-6,9-dioxo-3,4,6,7,8,9,12,13-octahydro-2H, 11H-16,18-(ethanediylidene)-2,5-methanopyrido[2,3-k][1,10,3,6]dioxadiazacyclononadecine-4-carboxamide (EXAMPLE 129, III-31) (25 mg, 0.034 mmol) in THF (2 mL) was added phenylboronic acid (5.6 mg, 0.0447 mmol), cesium carbonate (56 mg, 0.16 mmol) and tricyclohexylphosphine (1.0 mg, 0.34 mmol). To this mixture was added $Pd_2(dba)_3$ (1.6 mg, 0.00172 mmol) and the mixture heated to 80° C. for 2 hours. The reaction was concentrated and purified by reverse phase HPLC to give the title compound (20 mg) as a foam. LRMS (ESI) m/z 770.6 [(M+H)+; calcd for $C_{41}H_{48}N_5O_8S$: 770.3].

EXAMPLE 160

(2R,4S,7E,14E)-7-tert-Butyl-20-chloro-N-{(1R,2S)-1-[(methylamino)carbonyl]-2-vinylcyclopropyl}-6,9-dioxo-3,4,6,7,8,9,12,13-octahydro-2H,11H-16,18-(ethanediylidene)-2,5-methanopyrido[2,3-k][1,10,3,6]dioxadiazacyclononadecine-4-carboxamide (III-173)

III-173

To a solution of (2R,4S,7S,14E)-7-tert-butyl-20-chloro-N-((1R,2S)-1-{[(cyclopropylsulfonyl)amino]carbonyl}-2-vinylcyclopropyl)-6,9-dioxo-3,4,6,7,8,9,12,13-octahydro-2H,11H-16,18-(ethanediylidene)-2,5-methanopyrido[2,3-k][1,10,3,6]dioxadiazacyclononadecine-4-carboxamide (EXAMPLE 129, III-31) (20 mg, 0.0275 mmol) in THF (1 mL) was added 40% aqueous methylamine and the mixture was heated in a microwave reactor at 180° C. for 30 min. The reaction mixture was concentrated and purified by reverse phase HPLC to give 2 mg product as foam. LRMS (ESI) m/z 638.5 [(M+H)$^+$; calcd for $C_{33}H_{41}ClN_5O_6$: 638.3].

EXAMPLE 161

(2R,4S,7S)-7-tert-butyl-N-((1R,2S)-1-{[(cyclopropylsulfonyl)amino]carbonyl}-2-vinylcyclopropyl)-6,9-dioxo-22-phenyl-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide (III-174)

III-174

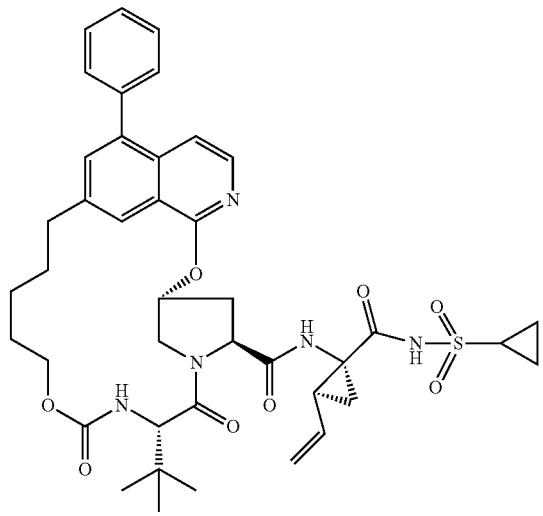

To a sealed tube containing (2R,4S,7S)-7-tert-butyl-N-((1R,2S)-1-{[(cyclopropylsulfonyl)amino]carbonyl}-2-vinylcyclopropyl)-22-iodo-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxamide (III-38) (EXAMPLE 13) (17 mg, 0.021 mmol) in toluene (1 mL) was added phenylboronic acid (3 mg, 1.1 mmol), 2M sodium carbonate (0.021 mL, 0.041 mmol), and tetrakis(triphenylphosphine)palladium (1 mg, 0.001 mmol). The reaction mixture was heated at 80 C for 10 h. The reaction mixture was diluted with EtOAc, washed with 1N HCl, brine, dried the organics, and concentrated to a yellow oil. The resulting oil was purified by reverse phase HPLC to yield the title compound as a yellow solid. (5 mg). LRMS (ESI) m/z 772.7 [(M+H)$^+$; calcd for $C_{41}H_{50}N_5O_8S$: 772.3].

EXAMPLE 162

(1R,2S)-1-({[(15S,18S,20R)-2-(Dimethylamino)-15-isopropyl-13,16-dioxo-8,9,10,11,13,14,15,16,19,20-decahydro-7H,18H-4,6-(ethanediylidene)-17,20-methanopyrimido[4,5-k][1,10,3,6]dioxadiazacyclononadecin-18-yl]carbonyl}amino)-2-vinylcyclopropanecarboxylic acid (III-175)

III-175

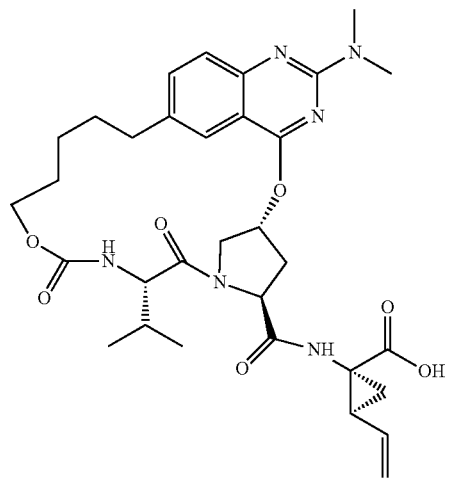

Step 1: 1-tert-Butyl 2-[2-(trimethylsilyl)ethyl](2S,4S)-4-hydroxypyrrolidine-1,2-dicarboxylate

165

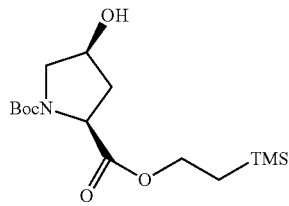

To a solution of 1-tert-butyl 2-methyl (2S,4S)-4-hydroxypyrrolidine-1,2-dicarboxylate (1.0 g, 4.08 mmol) in THF (30 mL) and water (6 mL) cooled to 0° C. was added a 1 M solution of NaOH (6.12 mL, 6.12 mmol). The mixture was stirred at this temperature for 2 h. At this time, TLC (100% Et$_2$O) indicated complete consumption of the starting material and formation of a more polar compound (KMnO$_4$ stain). The THF was then removed in vacuo, and the pH of the water layer was adjusted to 2-3 with 1 N HCl. The mixture was then extracted with EtOAc, dried over MgSO$_4$, and the solvent was removed in vacuo. LC-MS indicated that the major product had the desired mass. The crude compound was then taken up in PhMe (30 mL), O-2-trimethylsilyl-N,N'-diisopropylisourea (T. Eicher, M. Ott, A. Speicher *Synthesis*, 1996, 755-762)(1.99 g, 8.15 mmol) was added, and the mixture was refluxed for 2 h. At this time, 30% EtOAc/hexanes (10 mL) was added and the mixture was filtered. The solvent was then removed in vacuo, and the crude product was purified on silica (40% EtOAc/hex) to yield the title compound (1.23 g). LRMS (M+H)$^+$=332.2.

Step 2: 1-tert-Butyl 2-[2-(trimethylsilyl)ethyl](2S,4S)-4-[(2-chloro-6-iodoquinazolin-4-yl)oxy]pyrrolidine-1,2-dicarboxylate

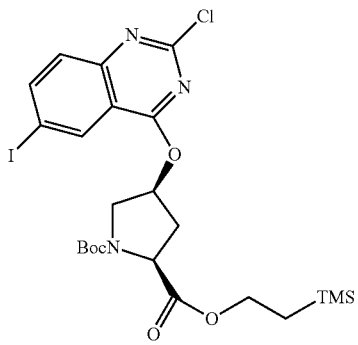

To a solution of the product from step 1 (1.02 g, 3.08 mmol) and 2,4-dichloro-6-iodoquinazoline (1.0 g, 3.08 mmol) (M. C. Venuti et al., *J. Med. Chem.* 1988, 31, 2136-2145) in toluene (25 mL) was added 60% sodium hydride (600 mg, excess) and the reaction mixture stirred at room temperature for 45 min. The reaction mixture was carefully partitioned between ice cold pH5.2 citrate buffer and EtOAc. The organic layer was washed with water and brine, dried over Na₂SO₄ and solvent evaporated. The crude product was purified by chromatography on silica (0-30% EtOAc hexane) to afford the title compound (1.61 g).

Step 3: 1-tert-Butyl 2-[2-(trimethylsilyl)ethyl](2S,4S)-4-[(2-chloro-6-vinylquinazolin-4-yl)oxy]pyrrolidine-1,2-dicarboxylate

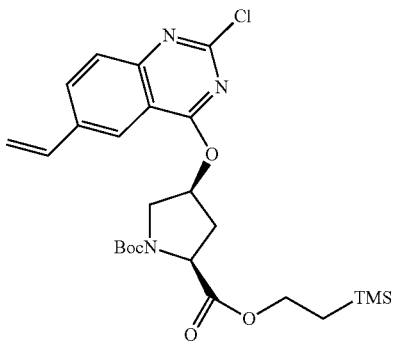

The title compound was prepared from 1-tert-butyl 2-[2-(trimethylsilyl)ethyl](2S,4S)-4-[(2-chloro-6-iodoquinazolin-4-yl)oxy]pyrrolidine-1,2-dicarboxylate as described in Example 1 Step 3.

Step 4: 2-(trimethylsilyl)ethyl N-[(pent-4-en-1-yloxy)carbonyl]-L-valyl-(4R)-4-{[2-(1H-1,2,3-benzotriazol-1-yloxy)-6-vinylquinazolin-4-yl]oxy}-L-prolinate

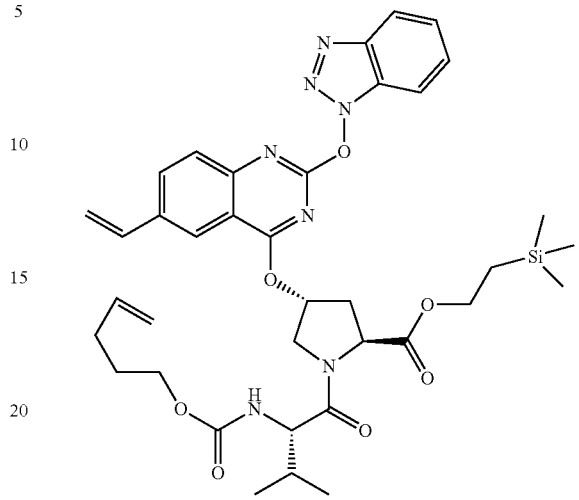

A solution of 1-tert-butyl 2-[2-(trimethylsilyl)ethyl](2S,4S)-4-[(2-chloro-6-vinylquinazolin-4-yl)oxy]pyrrolidine-1,2-dicarboxylate (495 mg, 0.95 mmol) in EtOAC (10 mL) was cooled to 0 C and hydrogen chloride bubbled through for 30 min. Nitrogen was then bubbled through for 5 min, the solvent evaporated and the residue azeotroped with EtOAc (×3). The residue was dissolved in DMF (5 mL) and DIPEA (479 μL, 2.67 mmol), Intermediate B3 (307 mg, 1.34 mmol) and TBTU (472 mg, 1.47 mmol) added. The reaction mixture was stirred at room temperature overnight and partitioned between pH 5.2 citrate buffer and EtOAc. The organic phase was washed with water, saturated NaHCO₃, brine, dried over Na₂SO₄ and the solvent evaporated. The crude product was purified by chromatography on silica (5-50% EtOAc hexane) to afford the title compound (479 mg). LRMS (M+H)⁺ =702.3.

Step 5: 2-(Trimethylsilyl)ethyl(7E,15S,18S,20R)-2-1H-1,2,3-benzotriazol-1-yloxy-15-isopropyl-13,16-dioxo-10,11,13,14,15,16,19,20-octahydro-9H,18H-4,6-(ethanediylidene)-17,20-methanopyrimido[4,5-k][1,10,3,6]dioxadiazacyclononadecine-18-carboxylate

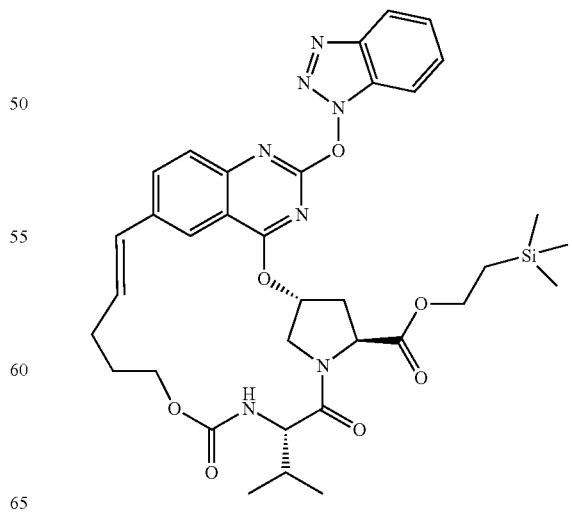

as the title compound was prepared from the product from Step 4 using the procedure described in Example 1 Step 4.

Step 6: 2-(Trimethylsilyl)ethyl (7E,15S,18S,20R)-2-(dimethylamino)-15-isopropyl-13,16-dioxo-10,11,13,14,15,16,19,20-octahydro-9H,18H-4,6-(ethanediylidene)-17,20-methanopyrimido[4,5-k][1,10,3,6]dioxadiazacyclononadecine-18-carboxylate

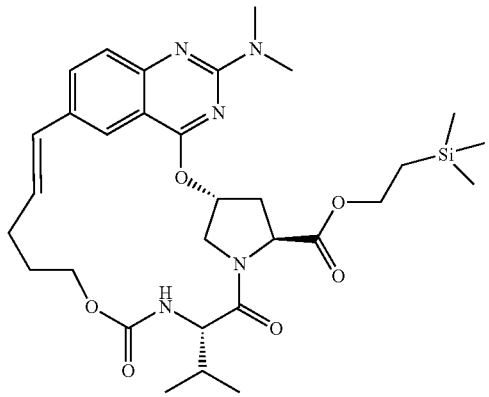

To a solution of the product from step 4 (130 mg, 0.185 mmol) in DCM (2 mL) was added a solution of 2.0M dimethylamine in THF (0.5 mL, 1.0 mmol) and the mixture was stirred at room temperature for 3 h. Additional 2.0M dimethylamine in THF (0.5 mL, 1.0 mmol) was added and the reaction was stirred for an additional 18 h. The reaction mixture was concentrated to an oil and chromatographed on silica using a gradient elution from dichloromethane to 5% acetone/dichloromethane to give the title compound as an oil (92 mg). LRMS (M+H)$^+$=612.4.

Step 7: 2-(Trimethylsilyl)ethyl (15S,18S,20R)-2-(dimethylamino)-15-isopropyl-13,16-dioxo-8,9,10,11,13,14,15,16,19,20-decahydro-7H,18H-4,6-(ethanediylidene)-17,20-methanopyrimido[4,5-k][1,10,3,6]dioxadiazacyclononadecine-18-carboxylate

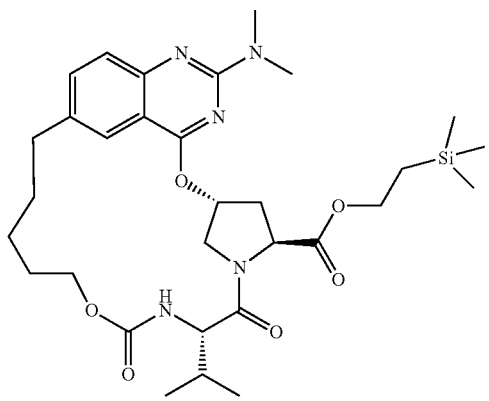

To a solution of the oil from step 5 (92 mg, 0.151 mmol) in ethyl acetate (20 mL) and under nitrogen was added 10% palladium on carbon (20 mg) and the mixture stirred under hydrogen (1 atm) for 18 h. The reaction mixture was filtered and concentrated in vacuo to give the product as an oil (92 mg). LRMS (M+H)$^+$=614.3.

Step 8: (15S,18S,20R)-2-(Dimethylamino)-15-isopropyl-13,16-dioxo-8,9,10,11,13,14,15,16,19,20-decahydro-7H,18H-4,6-(ethanediylidene)-17,20-methanopyrimido[4,5-k][1,10,3,6]dioxadiazacyclononadecine-18-carboxylic acid

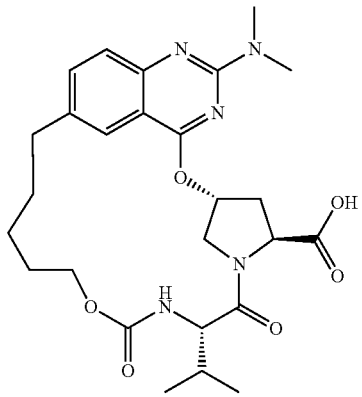

To a solution of the oil from step 6 (92 mg, 0.151 mmol) in THF (5 mL), under nitrogen, was added a solution of 1.0M tetrabutylammonium fluoride in THF (0.9 mL, 0.90 mmol). The reaction mixture was stirred for 0.5 hr and then concentrated in vacuo to give an oil. LRMS (M+H)$^+$=514.

Step 9: Ethyl(1R,2S)-1-({[(15S,18S,20R)-2-(dimethylamino)-15-isopropyl-13,16-dioxo-8,9,10,11,13,14,15,16,19,20-decahydro-7H,18H-4,6-(ethanediylidene)-17,20-methanopyrimido[4,5-k][1,10,3,6]dioxadiazacyclononadecin-18-yl]carbonyl}amino)-2-vinylcyclopropanecarboxylate

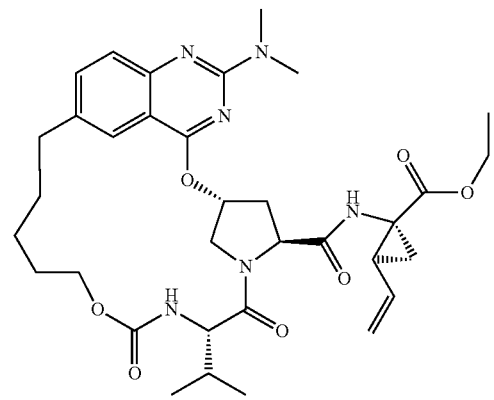

The oil from step 7 was dissolved in DMF (2 mL) and diisopropylamine (80 µL, 0.45 mmol), and (2R,3S)-3-vinyl-2-aminocyclopropyl carboxylic acid ethyl ester hydrochloride (Intermediate A2) (44 mg, 0.23 mmol) added, followed by TBTU (36 mg, 0.23 mmol) and the reaction mixture stirred at RT for 1 h. The mixture was diluted with EtOAc (20 mL), washed with pH 5.2 citric acid (10 mL), 10% aqueous sodium bicarbonate (10 mL), dried over Na$_2$SO$_4$, filtered and concentrated in vacuo to give an oil, chromatographed on silica (30 to 100% ethyl acetate/hexanes) to give the title compound as an oil, (45 mg). LRMS (M+H)$^+$=651.4.

Step 10: (1R,2S)-1-({[(15S,18S,20R)-2-(Dimethylamino)-15-isopropyl-13,16-dioxo-8,9,10,11,13,14,15,16,19,20-decahydro-7H,18H-4,6-(ethanediylidene)-17,20-methanopyrimido[4,5-k][1,10,3,6]dioxadiazacyclononadecin-18]carbonyl}amino)-2-vinylcyclopropanecarboxylic acid (III-175)

To a solution of the oil from step 8 (45 mg, 0.068 mmol) in THF (2 mL) was added a solution of lithium hydroxide (16 mg, 0.68 mmol) in water (0.4 mL) and the mixture stirred at 40° C. for 8 h. The reaction mixture was diluted with 1N hydrochloric acid (0.7 mL) and purified by reverse phase HPLC to give the title compound as a foam (45 mg) after concentration. $^1$H NMR (500 Mhz, CD$_3$OD) δ 8.69 (s, 1H), 7.82 (d, 1H, J=1.7 Hz), 7.79 (dd, 1H, J=8.5 and 1.9 Hz), 7.68 (d, 1H, J=8.5 Hz), 6.25 (m, 1H), 5.84 (m, 1H), 5.27 (dd, 1H, J=16.8 and 1.5 Hz), 5.09 (dd, 1H, J=10.3 and 1.7 Hz), 4.71 (d, 1H, J=1.7 Hz), 4.66 (t, 1H, J=10.0 Hz), 4.17 (m, 1H), 4.02 (m, 2H), 3.73 (m, 2H), 3.44 (brs, 6H), 2.86 (m, 1H), 2.69 (m, 1H), 2.19 (dd, 1H, J=17.6 and 8.8 Hz), 2.02 (m, 1H), 1.80 (m, 1H), 1.68 (m, 2H), 1.40-1.55 (m, 3H), 1.10-1.30 (m, 2H), 1.02 (d, 6H) ppm; LRMS (ESI) m/z 623.3 [(M+H)$^+$; calcd for C$_{32}$H$_{43}$N$_6$O$_7$: 623.3].

By using the appropriate procedures and the appropriate A and B intermediates, the following compounds were prepared.

| Ex. | Structure | Name | LRMS (M + H)$^+$ | Prepared using the appropriate Intermediates according to the procedure below. | Int. |
|---|---|---|---|---|---|
| 163, III-176 | 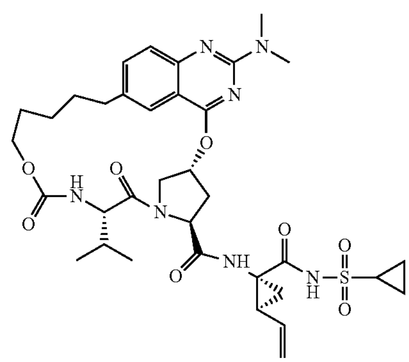 | (15S,18S,20R)-N-((1R,2S)-1-{[(cyclopropylsulfonyl)amino]carbonyl}-2-vinylcyclopropyl)-2-(dimethylamino)-15-isopropyl-13,16-dioxo-8,9,10,11,13,14,15,16,19,20-decahydro-7H,18H-4,6-(ethanediylidene)-17,20-methanopyrimido[4,5-k][1,10,3,6]dioxadiazacyclononadecine-18-carboxamide | 726.6 | Example 162 | A1 |
| 164, III-177 | 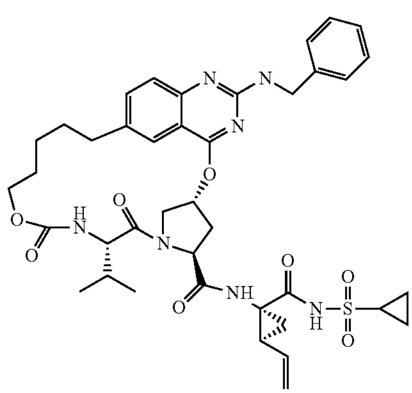 | (15S,18S,20R)-2-(benzylamino)-N-((1R,2S)-1-{[(cyclopropylsulfonyl)amino]carbonyl}-2-vinylcyclopropyl)-15-isopropyl-13,16-dioxo-8,9,10,11,13,14,15,16,19,20-decahydro-7H,18H-4,6-(ethanediylidene)-17,20-methanopyrimido[4,5-k][1,10,3,6]dioxadiazacyclononadecine-18-carboxanaide | 788.6 | Example 162 | A1, benzylamine |

EXAMPLE 165

(2R,4S,7S,14E)-7-tert-Butyl-N-[(1R,2S)-1-({[(dimethylamino)sulfonyl]amino}carbonyl)-2-vinylcyclopropyl]-6,9-dioxo-3,4,6,7,8,9,12,13-octahydro-2H,11H-16,18-etheno-2,5-methanopyrido[2,3-k][1,10,3,6]dioxadiazacyclononadecine-4-carboxamide (III-178)

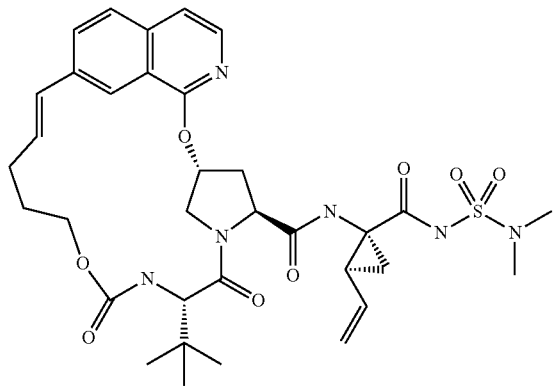

III-178

Step 1: (1R,2S)-1-({[(2R,4S,7S,14E)-7-tert-Butyl-6,9-dioxo-3,4,6,7,8,9,12,13-octahydro-2H,11H-16,18-etheno-2,5-methanopyrido[2,3-k][1,10,3,6]dioxadiazacyclononadecin-4-yl]carbonyl}amino)-2-vinylcyclopropanecarboxylic acid

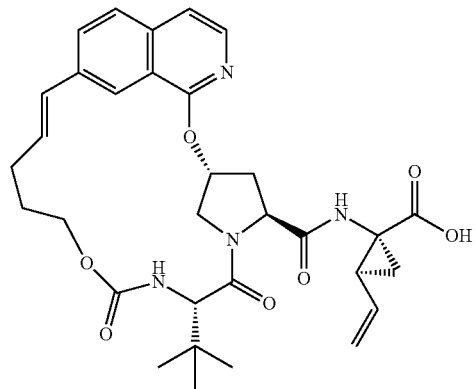

Ethyl (2R,4S,7S)-7-tert-butyl-6,9-dioxo-3,4,6,7,8,9,12,13-octahydro-2H,11H-16,18-ethanediylidene-2,5-methanopyrido[2,3-k][1,10,3,6]dioxodiazacyclononadecine-4-carboxylate (EXAMPLE 10, Step 4) (0.73 g, 0.143 mmol) was dissolved in THF (20 mL) and EtOH (10 mL) and a solution of LiOH in water (257 mg in 10 mL) added. The reaction mixture was stirred at room temperature for 1.5 h after which HPLC analysis indicated complete reaction, 3M HCl (5.0 mL) was added and the mixture was evaporated to a solid. The solid was partitioned between EtOAc (20 mL) and water (20 mL), the organic phase, dried over $Na_2SO_4$, filtered and concentrated to a foam which was used without further purification.

LRMS $(M+H)^+=591.5$.

Step 2: (2R,4S,7S,14E)-7-tert-Butyl-N-[(1R,2S)-1-({[(dimethylamino)sulfonyl]amino}carbonyl)-2-vinylcyclopropyl]-6,9-dioxo-3,4,6,7,8,9,12,13-octahydro-2H,11H-16,18-etheno-2,5-methanopyrido[2,3-k][1,10,3,6]dioxadiazacyclononadecine-4-carboxamide (III-178)

To the product from step 1 (100 mg, 0.169 mmol), N,N-dimethylsulfamide (84 mg, 0.677 mmol), DIPEA (0.148 mL, 0.847 mmol), and DMAP (83 mg, 0.677 mmol) in DMF (3 mL) was added DBU (0.115 mL, 0.762 mmol) and the mixture was stirred for 5 min. HATU (70.8 mg, 0.186 mmole) was added and mixture was stirred for 18 h. Additional HATU (15 mg) was added and the mixture stirred for an additional 3 h. The mixture was then purified by prep HPLC to give 65 mg of the title compound as a foam. $^1$H NMR (500 MHz, $CDCl_3$) δ 9.62 (s, 1H), 8.26 (s, 1H), 7.89 (d, 1H, J=6.1 Hz), 7.64 (d, 1H, J=8.3 Hz), 7.50 (dd, 1H, J=1.7 and 8.3 Hz), 7.20 (d, 1H, J=5.8 Hz), 7.17 (s, 1H), 6.50 (d, 1H, J=15.8 Hz), 6.36 (m, 1H), 5.82 (m, 1H), 5.66 (m, 2H), 5.17 (dd, 1H, J=0.8 and 17.1 Hz), 5.09 (dd, 1H, J=0.8 and 10.3 Hz), 4.61 (d, 1H, J=10.3 Hz), 4.48 (m, 3H), 3.94 (m, 2H), 2.83 (s, 6H), 2.73 (m, 1H), 2.46 (m, 1H), 2.38 (m, 2H), 2.00 (m, 2H), 1.85 (m, 2H), 1.34 (m, 1H), 1.08 (s, 9H). LRMS (ESI) m/z 697.5 $[(M+H)^+$; calcd for $C_{34}H_{45}N_6O_8S$: 697.3].

EXAMPLE 166

(2R,4S,7S,14E)-7-tert-butyl-6,9-dioxo-N-((1R,2S)-1-{[(piperidin-1-ylsulfonyl)amino]carbonyl}-2-vinylcyclopropyl)-3,4,6,7,8,9,12,13-octahydro-2H,11H-16,18-etheno-2,5-methanopyrido[2,3-k][1,10,3,6]dioxadiazacyclononadecine-4-carboxamide (III-179)

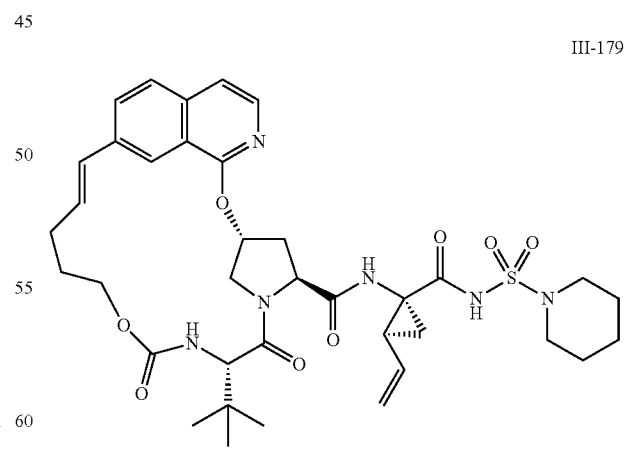

III-179

EXAMPLE 166 was prepared according to the procedure described for EXAMPLE 165 by using piperidine-1-sulfonamide in Step 2. LRMS (ESI) m/z 737.5 $[(M+H)^+$; calcd for $C_{37}H_{49}N_6O_8S$: 737.3].

EXAMPLE 167

(2R,4S,7S,14E)-N-{(1R,2S)-1-[({[benzyl(methyl)amino]sulfonyl}amino)carbonyl]-2-vinylcyclopropyl}-7-tert-butyl-6,9-dioxo-3,4,6,7,8,9,12,13-octahydro-2H,11H-16,18-etheno-2,5-methanopyrido[2,3-k][1,10,3,6]dioxadiazacyclononadecine-4-carboxamide (III-180)

III-180

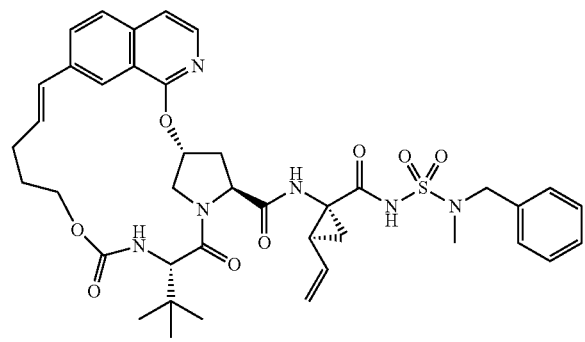

EXAMPLE 167 was prepared according to the procedure described for EXAMPLE 165 by using N-benzyl-N-methylsulfamide in Step 2. LRMS (ESI) m/z 773.6 [(M+H)$^+$; calcd for $C_{40}H_{49}N_6O_8S$: 773.3].

EXAMPLE 168

(2R,4S,7S)-7-cyclohexyl-N-[(1R,2S)-1-({[(dimethylamino)sulfonyl]amino}carbonyl)-2-vinylcyclopropyl]-23-methoxy-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide (III-181)

III-181

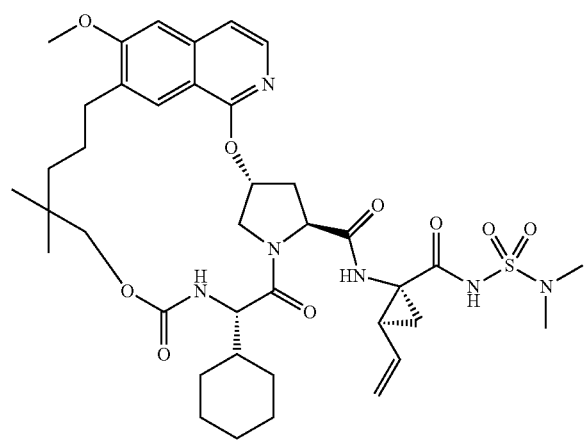

Step 1: Ethyl(1R,2S)-1-({[(2R,4S,7S)-7-cyclohexyl-23-methoxy-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecin-4-yl]carbonyl}amino)-2-vinylcyclopropanecarboxylate

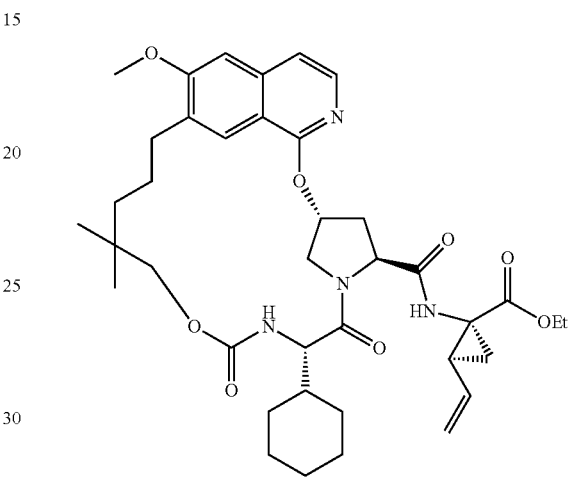

Ethyl(1R,2S)-1-({[(2R,4S,7S)-7-cyclohexyl-23-methoxy-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecin-4-yl]carbonyl}amino)-2-vinylcyclopropanecarboxylate was prepared using the procedure described for EXAMPLE 15 using Intermediates A2, B23 and C1. LRMS (M+H)$^+$=705.6.

Step 2: (2R,4S,7S)-7-cyclohexyl-N-[(1R,2S)-1-({[(dimethylamino)sulfonyl]amino}carbonyl)-2-vinylcyclopropyl]-23-methoxy-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide EXAMPLE 168 was prepared according to the procedure described for EXAMPLE 165 by using ethyl (1R,2S)-1-({[(2R,4S,7S)-7-cyclohexyl-23-methoxy-12,12-dimethyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecin-4-yl]carbonyl}amino)-2-vinylcyclopropanecarboxylate in Step 1. LRMS (ESI) m/z 783.6 [(M+H)$^+$; calcd for $C_{39}H_{55}N_6O_9S$: 783.4].

EXAMPLE 169

(2R,4S,7S)-22-bromo-7-tert-butyl-N-((1R,2S)-1-{[(cyclopropylsulfonyl)amino]carbonyl}-2-vinylcyclopropyl)-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxamide (III-182)

III-182

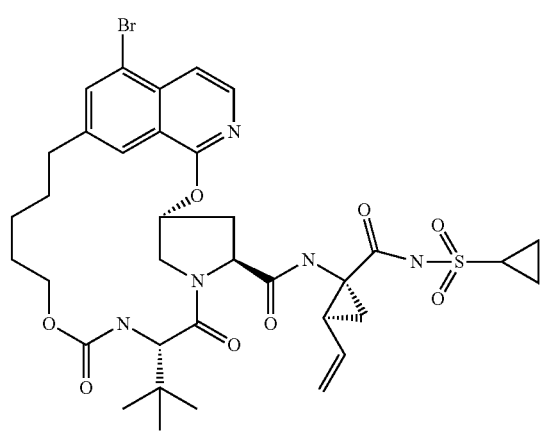

Step 1: Ethyl (2R,4S,7S)-22-bromo-7-tert-butyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate (III-186) and Ethyl(2R,4S,7S)-17,22-dibromo-7-tert-butyl-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxylate (III-187)

III-186

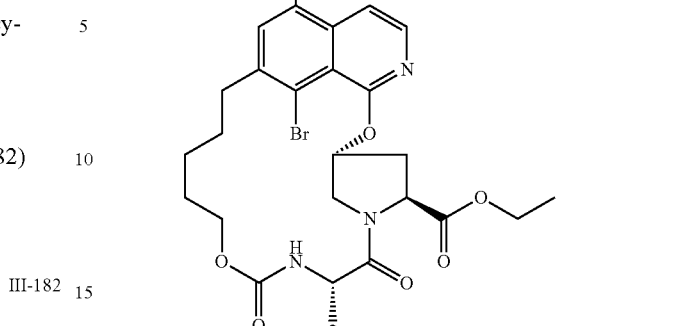

III-187

Compounds III-186 and III-187 were prepared according to the procedure given for EXAMPLE 13, Step 1 using N-bromosuccinimide. The mono- and di-brominated compounds were separated by reverse-phase HPLC. III-186: LRMS (M+H)$^+$=590.4. III-187: LRMS (M+H)$^+$=668.3.

Step 2: (2R,4S,7S)-22-bromo-7-tert-butyl-N-((1R, 2S)-1-{[(cyclopropylsulfonyl)amino]carbonyl}-2-vinylcyclopropyl)-6,9-dioxo-3,4,6,7,8,9,12,13,14,15-decahydro-2H,11H-16,18-ethanediylidene-2,5-methanopyrido[2,3-k][1,10,3,6]dioxadiazacyclononadecine-4-carboxamide (III-182)

EXAMPLE 169 was prepared from III-186 using the procedure described for EXAMPLE 14, Steps 4 and 5. LRMS (ESI) m/z 774.5 [(M+H)$^+$; calcd for $C_{35}H_{45}BrN_5O_8S$: 774.2].

EXAMPLE 170

(2R,4S,7S)-17,22-dibromo-7-tert-butyl-N-((1R,2S)-1-{[(cyclopropylsulfonyl)amino]carbonyl}-2-vinylcyclopropyl)-6,9-dioxo-3,4,6,7,8,9,12,13,14,15-decahydro-2H,11H-16,18-(ethanediylidene)-2,5-methanopyrido[2,3-k][1,10,3,6]dioxadiazacyclononadecine-4-carboxamide (III-183)

III-183

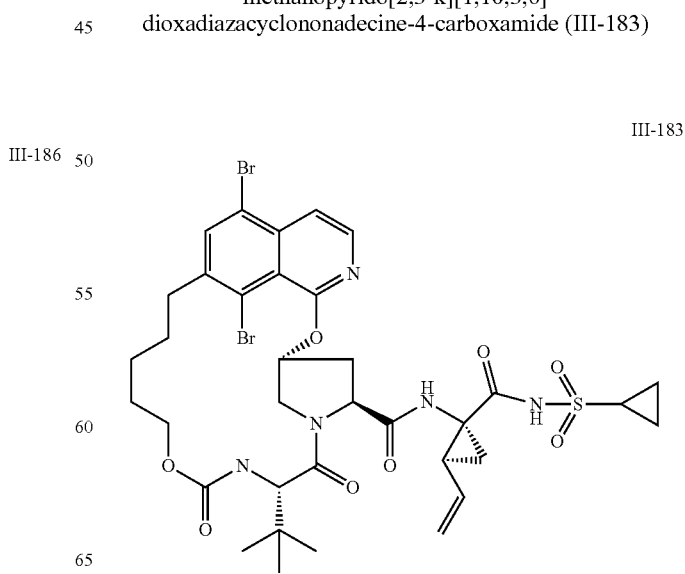

The title compound was prepared from III-187 using the procedure described for EXAMPLE 14, Steps 4 and 5. LRMS (ESI) m/z 852.5 [(M+H)+; calcd for $C_{35}H_{44}Br_2N_5O_8S$: 852.1].

EXAMPLE 171

(2R,4S,7S)-7-cyclohexyl-N-((1R,2S)-1-{[(cyclopropylsulfonyl)amino]carbonyl}-2-vinylcyclopropyl)-22-methoxy-12,12,14-trimethyl-6,9-dioxo-3,4,6,7,8,9,11,12,13,14-decahydro-2H-15,17-etheno-2,5-methanopyrido[2,3-k][1,10,3,6]dioxadiazacyclooctadecine-4-carboxamide (III-184)

III-184

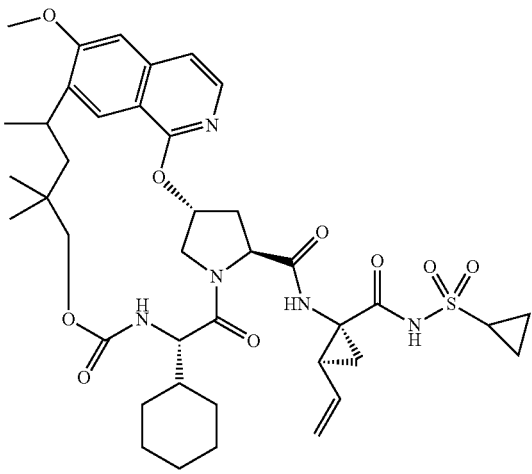

Step 1: Ethyl(4R)-4-[(7-bromo-6-methoxyisoquinolin-1-yl)oxy]-1-[(2S)-2-cyclohexyl-2-({[(2,2-dimethylpent-4-en-1-yl)oxy]carbonyl}amino)acetyl]-L-prolinate

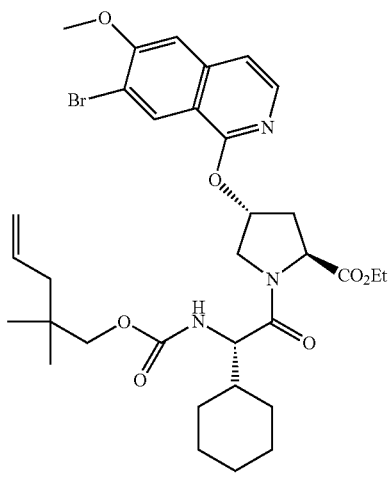

Ethyl(4R)-4-[(7-bromo-6-methoxyisoquinolin-1-yl)oxy]-1-[(2S)-2-cyclohexyl-2-({[(2,2-dimethylpent-4-en-1-yl)oxy]carbonyl}amino)acetyl]-L-prolinate was prepared according to the procedure given for EXAMPLE 14, Step 1 using intermediates B23 and C1. LRMS (M+H)+=674.3

Step 2: Ethyl(2R,4S,7S)-7-cyclohexyl-22-methoxy-12,12-dimethyl-14-methylene-6,9-dioxo-3,4,6,7,8,9,11,12,13,14-decahydro-2H-15,17-etheno-2,5-methanopyrido[2,3-k][1,10,3,6]dioxadiazacyclooctadecine-4-carboxylate

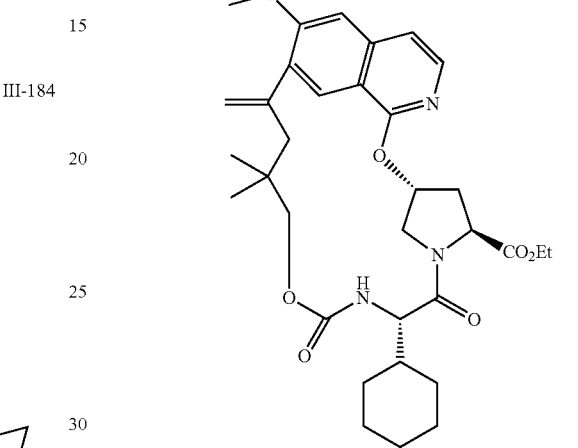

To a solution of the product from step 1 (448 mg, 0.664 mmol) dissolved in ethanol (10 mL) was added triethylamine (0.139 mL, 0.996 mmol) and [1,1'-bis(diphenylphosphino)ferrocene]dichloropalladium (II) (24.3 mg, 0.033 mmol) and the reaction mixture heated to 90° C. After 1 hour, additional catalyst (5 mg) was added and reaction mixture was stirred an additional 18 h at 90° C. The reaction mixture was concentrated in vacuo and chromatographed on silica (20 to 50% EtOAc/hexane) to give impure product. Prep HPLC purification gave the title compound (140 mg) as a foam. LRMS (M+H)+=594.5.

Step 3: (2R,4S,7S)-7-Cyclohexyl-N-((1R,2S)-1-{[(cyclopropylsulfonyl)amino]carbonyl}-2-vinylcyclopropyl)-22-methoxy-12,12,14-trimethyl-6,9-dioxo-3,4,6,7,8,9,11,12,13,14-decahydro-2H-15,17-etheno-2,5-methanopyrido[2,3-k][1,10,3,6]dioxadiazacyclooctadecine-4-carboxamide (III-184)

(2R,4S,7S)-7-Cyclohexyl-N-((1R,2S)-1-{[(cyclopropylsulfonyl)amino]carbonyl}-2-vinylcyclopropyl)-22-methoxy-12,12,14-trimethyl-6,9-dioxo-3,4,6,7,8,9,11,12,13,14-decahydro-2H-15,17-etheno-2,5-methanopyrido[2,3-k][1,10,3,6]dioxadiazacyclooctadecine-4-carboxamide (III-184) was prepared from the product from step 2 according to the procedure given for EXAMPLE 14, Steps 4 and 5 using intermediate A1 in Step 5. LRMS (ESI) m/z 780.6 [(M+H)+; calcd for $C_{40}H_{53}N_5O_9S$: 780.4].

EXAMPLE 172

(2R,4S,7S)-7-tert-Butyl-N-((1R,2S)-1-{[(cyclopropylsulfonyl)amino]carbonyl}-2-vinylcyclopropyl)-6,9-dioxo-14,15-didehydro-3,4,6,7,8,9,12,13-octahydro-2H,11H-16,18-(ethanediylidene)-2,5-methanopyrido[2,3-k][1,10,3,6]dioxadiazacyclononadecine-4-carboxamide (III-185)

III-185

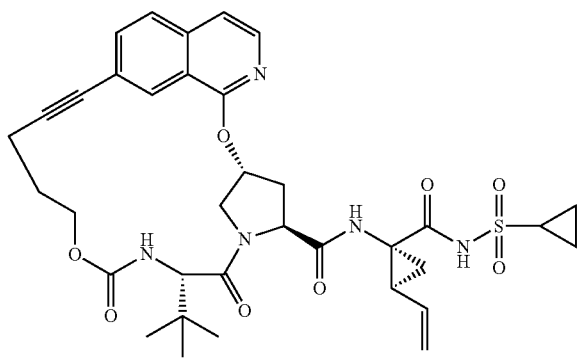

Step 1: 1,2-Pyrrolidinedicarboxylic acid, 4-[(7-bromo-1-isoquinolinyl)oxy]-, 1-(1,1-dimethylethyl) 2-ethyl ester, (2S,4R)—

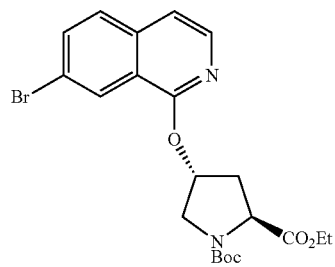

To a solution of di-tert-butyldicarbonate (1.14 g, 5.23 mmol) in CH$_3$CN (15 mL) was added Et$_3$N (2.08 mL, 14.9 mmol) and (4R)-4-[(7-bromoisoquinolin-1-yl)oxy]-L-prolinate hydrochloride (EXAMPLE 10, Step 1) (1.5 g, 3.73 mmol) at RT. After 15 min, DCM (150 mL) was added and the solution was extracted with 1 N HCl. The organic layer was dried over K$_2$CO$_3$ and the solvent was removed in vacuo. The crude material was purified on silica gel (gradient elution 0-30% EtOAc in hexanes) to yield the title compound as a foam (1.73 g). LRMS (M+H)$^+$Calcd.=465.1; found 465.2.

Step 2: N-({[5-(1-{[(3R,5S)-1-(tert-Butoxycarbonyl)-5-(ethoxycarbonyl)pyrrolidin-3-yl]oxy}isoquinolin-7-yl)pent-4-yn-1-yl]oxy}carbonyl)-3-methyl-L-valine

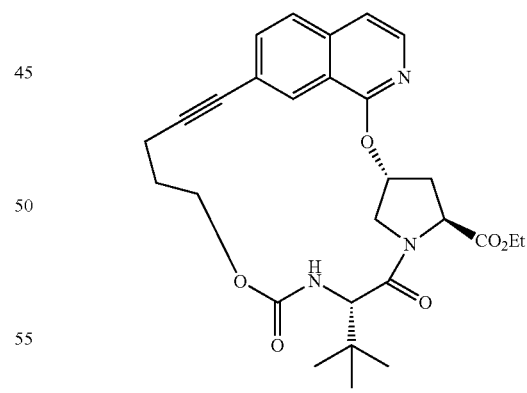

To a portion of the product from Step 1 (0.94 g, 2.02 mmol), in degassed THF (10 mL) and pyrrolidine (10 ml) was added intermediate B11, 3-methyl-N-[(pent-4-yn-1-yloxy)carbonyl]-L-valine (0.8 g, 3.33 mmol), Pd(PPh$_3$)$_4$ (58 mg, 0.05 mmol), and CuI (19 mg, 0.1 mmol). The mixture was then heated to 70° C. for 2 h. The mixture was then poured into a mixture of water and EtOAc and the pH adjusted to ~1 with 1 N HCl. The organic layer was then separated, dried over MgSO$_4$, and the solvent evaporated. The crude product was purified on silica gel (20-100% EtOAc in hexanes) to yield the title compound as a foam (1.2 g). LRMS (M+H)$^+$ Calcd.=626.3; found 626.4.

Step 3: 7-Ethyl(2R,4S,7S)-7-tert-butyl-6,9-dioxo-14,15-didehydro-3,4,6,7,8,9,12,13-octahydro-2H,11H-16,18-(ethanediylidene)-2,5-methanopyrido[2,3k][1,10,3,6]dioxadiazacyclononadecine-4-carboxylate To a portion of the product from Step 2 (0.93 g, 1.49 mmol), was added HCl/dioxane (37 mL, 4M, 148 mmol). The mixture was stirred for 30 min and then the solvent was removed in vacuo. DCM (400 mL) was then added the mixture along with DIEA (1.3 mL, 7.4 mmol) and HATU (622 mg, 1.6 mmol). After 20 h, the solvent was removed in vacuo and the crude product was purified on silica gel (gradient elution 0-60% EtOAc in hexanes) to yield the title compound as a foam (0.11 g). LRMS (M+H)$^+$Calcd.=508.3; found 508.4.

Step 4: (2R,4S,7S)-7-tert-Butyl-N-((1R,2S)-1-{[(cyclopropylsulfonyl)amino]carbonyl}-2-vinylcyclopropyl)-6,9-dioxo-14,15-didehydro-3,4,6,7,8,9,12,13-octahydro-2H,11H-16,18-(ethanediylidene)-2,5-methanopyrido[2,3-k][1,10,3,6]dioxadiazacyclononadecine-4-carboxamide (III-185)

The title compound was prepared from 7-ethyl (2R,4S,7S)-7-tert-butyl-6,9-dioxo-14,15-didehydro-3,4,6,7,8,9,12,13-octahydro-2H,11H-16,18-(ethanediylidene)-2,5-methanopyrido[2,3k][1,10,3,6]dioxadiazacyclononadecine-4-carboxylate and Intermediate A1 using the procedure described in EXAMPLE 14, Steps 4 and 5. LRMS (ESI) m/z 692.3 [(M+H)$^+$; calcd for $C_{35}H_{42}N_5O_8S$: 692.3].

What is claimed is:

1. A compound of formula (I):

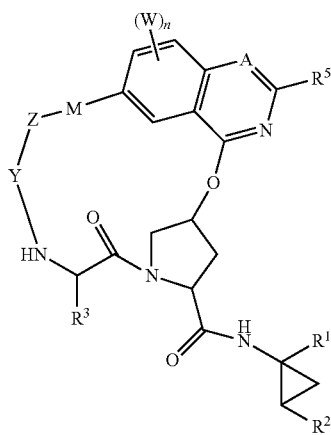

or a pharmaceutically acceptable salt thereof, wherein:
n is 1 or 2;
$R^1$ is $CO_2R^{10}$, $CONR^{10}SO_2R^6$, $CONR^{10}SO_2NR^8R^9$, or tetrazolyl;
$R^2$ is $C_1$-$C_6$ alkyl, $C_2$-$C_6$ alkenyl or $C_3$-$C_8$ cycloalkyl, wherein said alkyl, alkenyl or cycloalkyl is optionally substituted with 1 to 3 halo;
$R^3$ is $C_1$-$C_8$ alkyl, $C_3$-$C_8$ cycloalkyl, $C_3$-$C_8$ cycloalkyl($C_1$-$C_8$)alkyl, aryl($C_1$-$C_8$)alkyl, or Het, wherein aryl is phenyl or naphthyl and said alkyl, cycloalkyl, or aryl is optionally substituted with 1 to 3 substituents selected from the group consisting of halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;
Het is a 5- or 6-membered saturated cyclic ring having 1, 2 or 3 heteroatoms selected from N, O and S, wherein said ring is optionally substituted with 1 to 3 substituents selected from the group consisting of halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;
$R^4$ is H, $C_1$-$C_8$ alkyl, $C_3$-$C_8$ cycloalkyl($C_1$-$C_8$)alkyl, or aryl($C_1$-$C_8$)alkyl; wherein aryl is phenyl or naphthyl and said alkyl, cycloalkyl, or aryl is optionally substituted with 1 to 3 substituents selected from the group consisting of halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;
$R^5$ is H, halo, OH, $C_1$-$C_6$ alkoxy, $C_1$-$C_6$ alkyl, CN, $CF_3$, $SR^{10}$, $SO_2(C_1$-$C_6$ alkyl), $C_3$-$C_8$ cycloalkyl, $C_3$-$C_8$ cycloalkoxy, $C_1$-$C_6$ haloalkyl, $N(R^7)_2$, aryl, heteroaryl or heterocyclyl;
wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, $OR^{10}$, $SR^{10}$, $N(R^7)_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, $NO_2$, CN, $CF_3$, $SO_2(C_1$-$C_6$ alkyl), $NR^{10}SO_2R^6$, $SO_2N(R^6)_2$, $S(O)(C_1$-$C_6$ alkyl), $NHCOOR^6$, $NHCOR^6$, $NHCONHR^6$, $CO_2R^{10}$, $C(O)R^{10}$, and $CON(R^{10})_2$; wherein the 2 adjacent substituents of said cycloalkyl, cycloalkoxy, aryl, heteroaryl or heterocyclyl are optionally taken together to form a 3- to 6-membered cyclic ring containing 0-3 heteroatoms selected from N, O and S;
$R^6$ is $C_1$-$C_8$ alkyl, $C_3$-$C_8$ cycloalkyl, $C_3$-$C_8$ cycloalkyl($C_{1-5}$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W' substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;
Y is C(=O), $SO_2$, or C(=N—CN);
Z is C($R^{10})_2$, O, or N($R^4$);
M is $C_1$-$C_{12}$ alkylene or $C_2$-$C_{12}$ alkenylene or $C_2$-$C_{12}$ alkynylene, wherein said alkylene or alkenylene is optionally substituted with 1, 2 or 3 substituents selected from the group consisting of $C_1$-$C_8$ alkyl, $C_3$-$C_8$ cycloalkyl ($C_1$-$C_8$ alkyl), and aryl($C_1$-$C_8$ alkyl); wherein 2 substituents on adjacent carbon atoms of M are optionally taken together to form a 3- to 6-membered cyclic ring containing 0-3 heteroatoms selected from N, O and S, or 2 substituents on the same carbon atom of M are optionally taken together to form a 3- to 6-membered cyclic ring containing 0-3 heteroatoms selected from N, O and S;
A is C($R^{11}$) or N;
when $R^5$ is other than H, $R^{11}$ is H, $C_1$-$C_6$ alkyl, halo, $OR^{10}$, $SR^{10}$, or $N(R^{10})_2$;
when $R^5$ is H, $R^{11}$ is H, $C_1$-$C_6$ alkyl, halo, OH, $C_1$-$C_6$ alkoxy, CN, $CF_3$, $SR^{10}$, $SO_2(C_1$-$C_6$ alkyl), $C_3$-$C_8$ cycloalkyl, $C_3$-$C_8$ cycloalkoxy, $C_1$-$C_6$ haloalkyl, $N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, $OR^{10}$, $SR^{10}$, $N(R^7)_2$, $N(C_1\text{-}C_6$ alkyl)$O(C_1\text{-}C_6$ alkyl), $C_1\text{-}C_6$ alkyl, $C_1\text{-}C_6$ haloalkyl, halo ($C_1\text{-}C_6$ alkoxy), $C_3\text{-}C_6$ cycloalkyl, $C_3\text{-}C_6$ cycloalkoxy, $NO_2$, CN, $CF_3$, $SO_2(C_1\text{-}C_6$ alkyl), $NR^{10}SO_2R^6$, $SO_2N(R^6)_2$, $S(O)(C_1\text{-}C_6$ alkyl), $NHCOOR^6$, $NHCOR^6$, $NHCONHR^6$, $CO_2R^{10}$, $C(O)R^{10}$, and $CON(R^{10})_2$; wherein the 2 adjacent substituents of said cycloalkyl, cycloalkoxy, aryl, heteroaryl or heterocyclyl are optionally taken together to form a 3- to 6-membered cyclic ring containing 0-3 heteroatoms selected from N, O and S;

or $R^5$ and $R^{11}$ are optionally taken together to form a 5- to 6-membered saturated, unsaturated non-aromatic, or aromatic cyclic ring having 0-2 heteroatoms selected from N, O and S;

each $R^7$ is independently H, $C_1\text{-}C_6$ alkyl, $C_3\text{-}C_6$ cycloalkyl, $C_3\text{-}C_6$ cycloalkyl($C_{1\text{-}5}$)alkyl, aryl, aryl($C_1\text{-}C_4$)alkyl, heteroaryl, heteroaryl($C_1\text{-}C_4$ alkyl), heterocyclyl, or heterocyclyl($C_1\text{-}C_8$ alkyl), wherein said alkyl, cycloalkyl, aryl, heteroaryl, or heterocyclyl is optionally substituted with 1 to 2 W' substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently H, halo, $OR^7$, $C_1\text{-}C_6$ alkyl, CN, $CF_3$, $NO_2$, $SR^7$, $CO_2R^7$, $CON(R^7)_2$, $C(O)R^7$, $N(R^{10})C(O)R^7$, $SO_2(C_1\text{-}C_6$ alkyl), $S(O)(C_1\text{-}C_6$ alkyl), $C_3\text{-}C_8$ cycloalkyl, $C_3\text{-}C_8$ cycloalkoxy, $C_1\text{-}C_6$ haloalkyl, $N(R^7)_2$, $N(C_1\text{-}C_6$ alkyl)$O(C_1\text{-}C_6$ alkyl), halo($C_1\text{-}C_6$ alkoxy), $NR^{10}SO_2R^7$, $SO_2N(R^7)_2$, $NHCOOR^7$, $NHCONHR^7$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein 2 adjacent W moieties are optionally taken together with the atoms to which they are attached to form a 5- to 6-membered saturated, unsaturated non-aromatic, or aromatic cyclic ring having 0-2 heteroatoms selected from N, O and S;

each W' is independently halo, $OR^{10}$, $C_1\text{-}C_6$ alkyl, CN, $CF_3$, $NO_2$, $SR^{10}$, $CO_2R^{10}$, $CON(R^{10})_2$, $C(O)R^{10}$, $N(R^{10})C(O)R^{10}$, $SO_2(C_1\text{-}C_6$ alkyl), $S(O)(C_1\text{-}C_6$ alkyl), $C_3\text{-}C_8$ cycloalkyl, $C_3\text{-}C_8$ cycloalkoxy, $C_1\text{-}C_6$ haloalkyl, $N(R^{10})_2$, $N(C_1\text{-}C_6$ alkyl)$O(C_1\text{-}C_6$ alkyl), halo($C_1\text{-}C_6$ alkoxy), $NR^{10}SO_2R^{10}$, $SO_2N(R^{10})_2$, $NHCOOR^{10}$, $NHCONHR^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein 2 adjacent W' moieties are optionally taken together with the atoms to which they are attached to form a 5- to 6-membered saturated, unsaturated non-aromatic, or aromatic cyclic ring having 0-2 heteroatoms selected from N, O and S;

$R^8$ is $C_1\text{-}C_8$ alkyl, $C_3\text{-}C_8$ cycloalkyl, $C_3\text{-}C_8$ cycloalkyl($C_1\text{-}C_8$ alkyl), aryl, aryl($C_1\text{-}C_4$ alkyl), heteroaryl, heterocyclyl, heteroaryl($C_1\text{-}C_4$ alkyl), or heterocyclyl($C_1\text{-}C_8$ alkyl), wherein said alkyl, cycloalkyl, aryl, heteroaryl or heterocyclyl is optionally substituted with 1 to 4 substituents selected from the group consisting of aryl, $C_3\text{-}C_8$ cycloalkyl, heteroaryl, heterocyclyl, $C_1\text{-}C_6$ alkyl, halo($C_1\text{-}C_6$ alkoxy), halo, $OR^{10}$, $SR^{10}N(R^{10})_2$, $N(C_1\text{-}C_6$ alkyl)$O(C_1\text{-}C_6$ alkyl), $C_1\text{-}C_6$ alkyl, $C(O)R^{10}$, $C_1\text{-}C_6$ haloalkyl, $NO_2$, CN, $CF_3$, $SO_2(C_1\text{-}C_6$ alkyl), $S(O)(C_1\text{-}C_6$ alkyl), $NR^{10}SO_2R^6$, $SO_2N(R^6)_2$, $NHCOOR^6$, $NHCOR^6$, $NHCONHR^6$, $CO_2R^{10}$, and)$C(O)N(R^{10}_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0-3 heteroatoms selected from N, O and S;

$R^9$ is $C_1\text{-}C_8$ alkyl, $C_3\text{-}C_8$ cycloalkyl, $C_3\text{-}C_8$ cycloalkyl($C_1\text{-}C_8$ alkyl), $C_1\text{-}C_8$ alkoxy, $C_3\text{-}C_8$ cycloalkoxy, aryl, aryl($C_1\text{-}C_4$ alkyl), heteroaryl, heterocyclyl, heteroaryl($C_1\text{-}C_4$ alkyl), or heterocyclyl($C_1\text{-}C_8$ alkyl), wherein said alkyl, cycloalkyl, alkoxy, cycloalkoxy, aryl, heteroaryl or heterocyclyl is optionally substituted with 1 to 4 substituents selected from the group consisting of aryl, $C_3\text{-}C_8$ cycloalkyl, heteroaryl, heterocyclyl, $C_1\text{-}C_6$ alkyl, halo($C_1\text{-}C_6$ alkoxy), halo, $OR^{10}$, $SR^{10}$, $N(R^{10})_2$, $N(C_1\text{-}C_6$ alkyl)$O(C_1\text{-}C_6$ alkyl), $C_1\text{-}C_6$ alkyl, $C(O)R^{10}$, $C_1\text{-}C_6$ haloalkyl, $NO_2$, CN, $CF_3$, $SO_2(C_1\text{-}C_6$ alkyl), $S(O)(C_1\text{-}C_6$ alkyl), $NR^{10}SO_2R^6$, $SO_2N(R^6)_2$, $NHCOOR^6$, $NHCOR^6$, $NHCONHR^6$, $CO_2R^{10}$, and)$C(O)N(R^{10})_2$;

wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0-3 heteroatoms selected from N, O and S;

or $R^8$ and $R^9$ are optionally taken together, with the nitrogen atom to which they are attached, to form a 4- to 8-membered monocyclic ring containing 0-2 additional heteroatoms selected from N, O and S; and each $R^{10}$ is independently H or $C_1\text{-}C_6$ alkyl.

2. The compound of claim 1, or a pharmaceutically acceptable salt thereof, wherein the compound is of formula III:

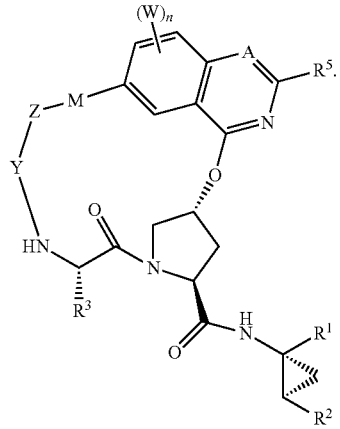

III

3. The compound of claim 2, wherein $R^1$ is $CO_2R^{10}$ or $CONR^{10}SO_2R^6$.

4. The compound of claim 3, wherein $R^1$ is $CO_2H$.

5. The compound of claim 3, wherein $R^1$ is $CONHSO_2R^6$.

6. The compound of claim 5, wherein $R^6$ is $C_3$-$C_8$ cycloalkyl, $C_1$-$C_8$ alkyl, aryl, or aryl($C_1$-$C_4$)alkyl.

7. The compound of claim 3, wherein $R^2$ is $C_1$-$C_4$ alkyl or $C_2$-$C_4$ alkenyl.

8. The compound of claim 7, wherein $R^3$ is $C_5$-$C_6$ cycloalkyl or $C_1$-$C_8$ alkyl optionally substituted with 1 to 3 halo substituents.

9. The compound of claim 8, wherein $R^5$ is H, halo, aryl, heteroaryl or $N(R^7)_2$.

10. The compound of claim 9, wherein $R^5$ is H or halo.

11. The compound of claim 9, wherein $R^5$ is aryl or heteroaryl.

12. The compound of claim 9, wherein Y is C=O.

13. The compound of claim 12, wherein Z is O, NH, N($C_1$-$C_8$ alkyl) or $C(R^{10})_2$.

14. The compound of claim 13, wherein M is unsubstituted $C_4$-$C_7$ alkylene or unsubstituted $C_4$-$C_7$ alkenylene.

15. The compound of claim 14, wherein n is 1 and W is H, $C_1$-$C_6$ alkoxyl, $C_1$-$C_6$ alkyl, OH, halo, $N(R^7)_2$ wherein $R^7$ is H or $C_1$-$C_6$ alkyl.

16. The compound of claim 15, wherein A is N.

17. The compound of claim 15, wherein A is $C(R^{11})$ wherein $R^{11}$ is H, $C_1$-$C_6$ alkyl, $C_1$-$C_6$ alkoxy, hydroxy or halo.

18. The compound of claim 10, wherein $R^2$ is $C_2$-$C_4$ alkenyl, $R^5$ is H, $R^6$ is $C_3$-$C_8$ cycloalkyl, W is $R^7$ or H, Y is C(=O), Z is O, and n is 1.

19. The compound of claim 18, wherein M is selected from the group consisting of:

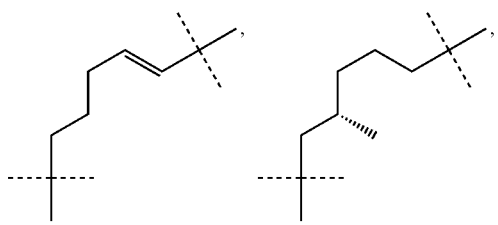

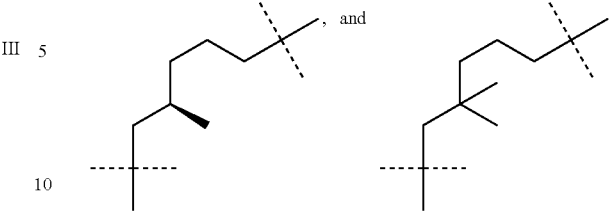

20. The compound of claim 19, wherein $R^3$ is $C_5$-$C_6$ cycloalkyl or $C_3$-$C_5$ alkyl.

21. The compound of claim 20, wherein $R^6$ is $C_3$-$C_5$ cycloalkyl.

22. The compound of claim 1, wherein the compound is selected from the group consisting of compounds III-1 to III-38:

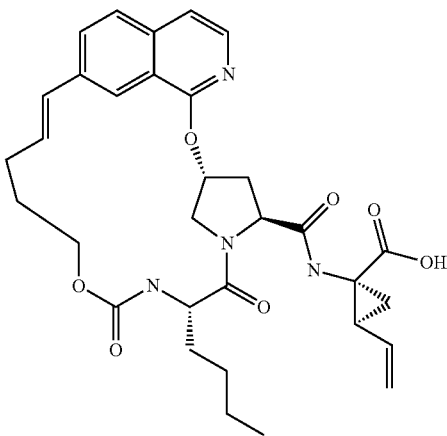

III-1

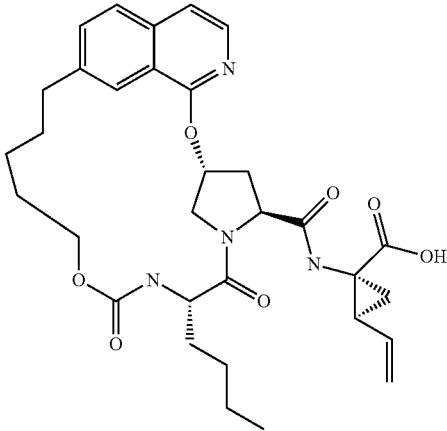

III-2

III-3
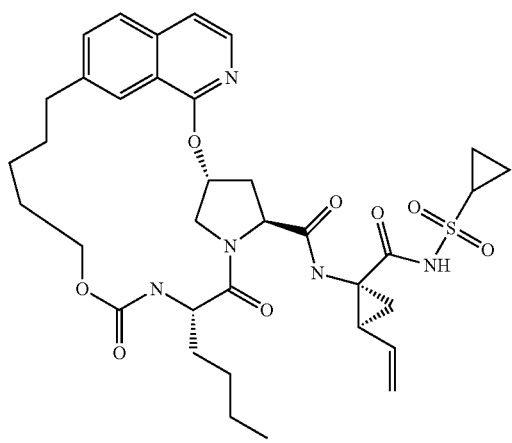
III-4
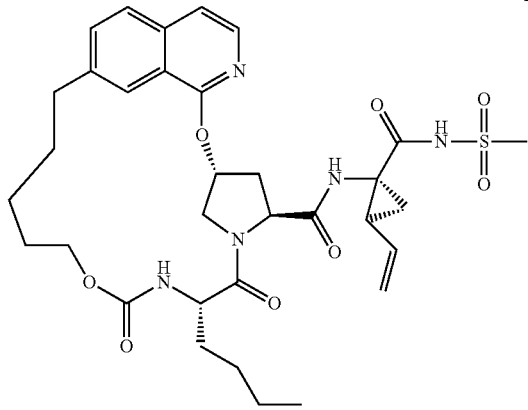
III-6
III-5
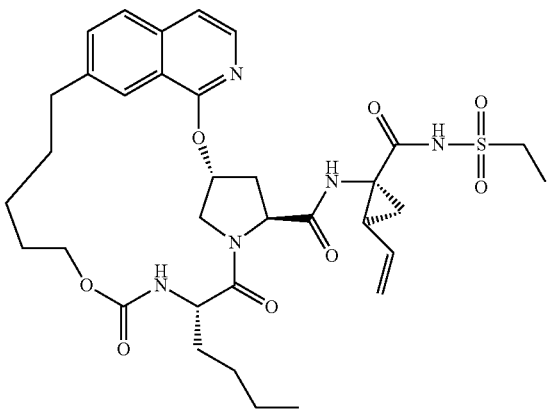
III-7
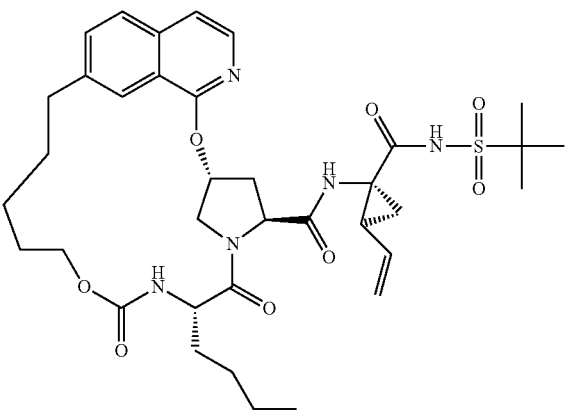
III-8

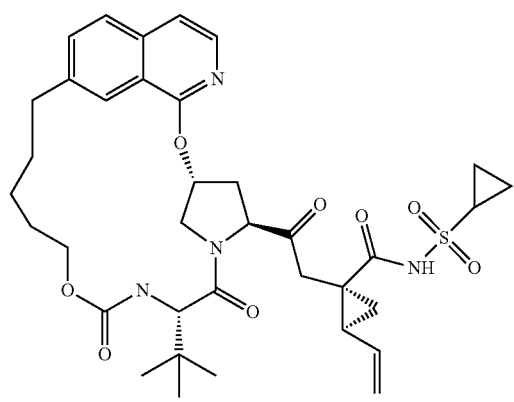
III-9
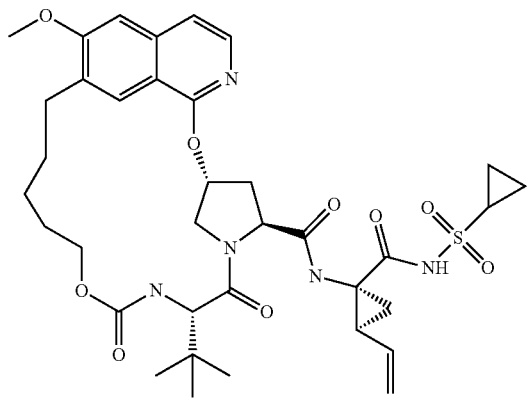
III-12
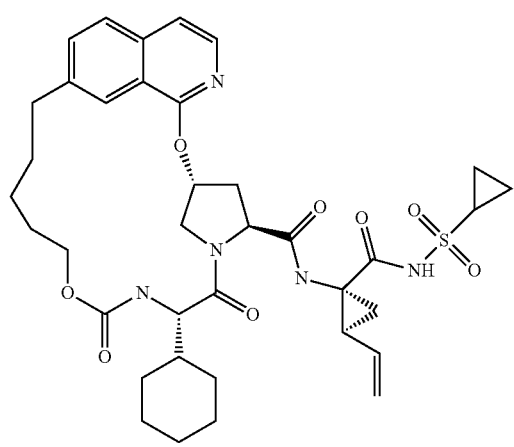
III-10
III-13
III-11
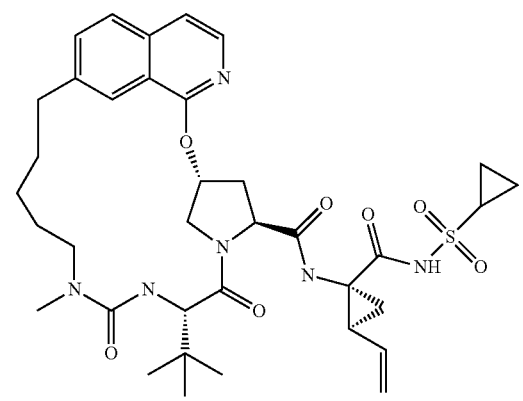
III-14

III-15
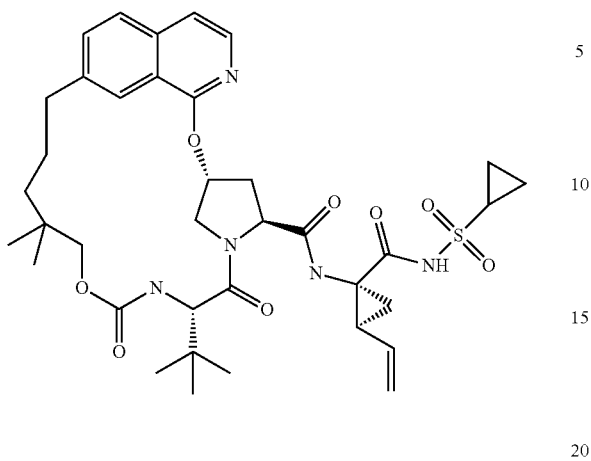
III-18
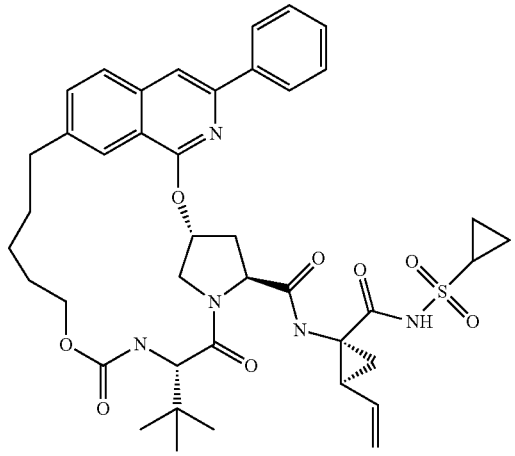
III-16
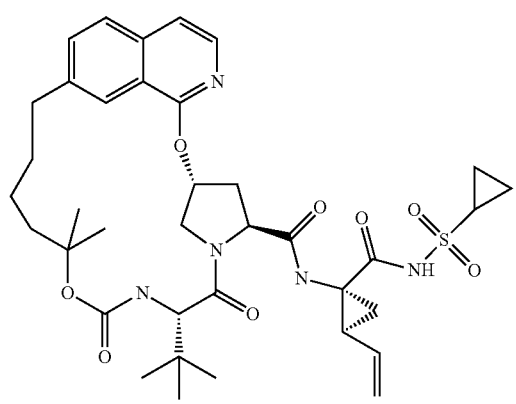
III-19
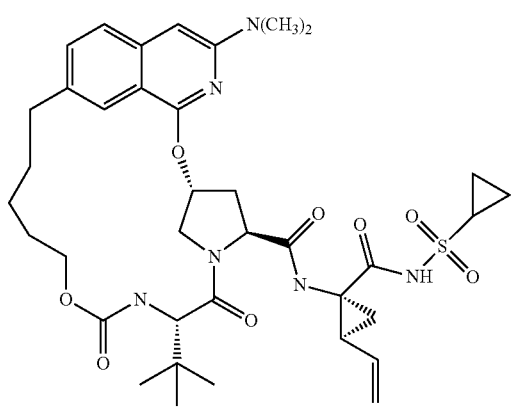
III-179
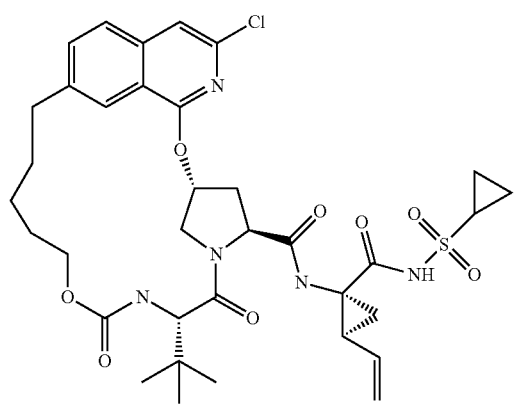
III-20
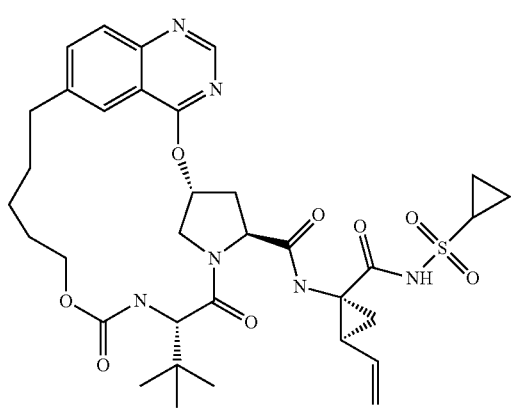

III-21
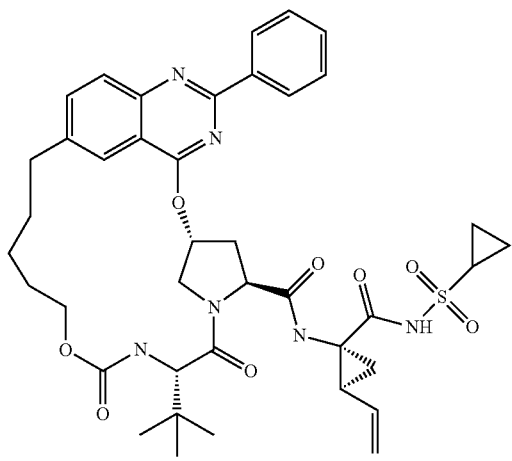
III-24
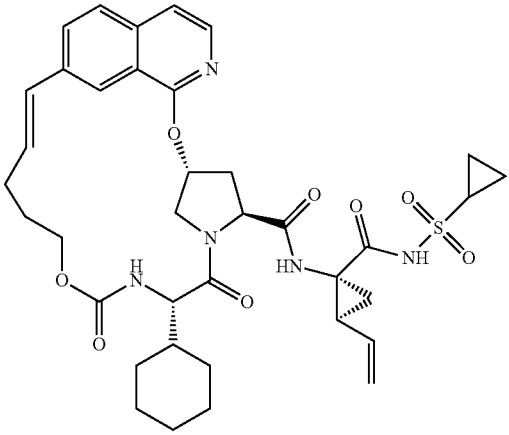
III-22
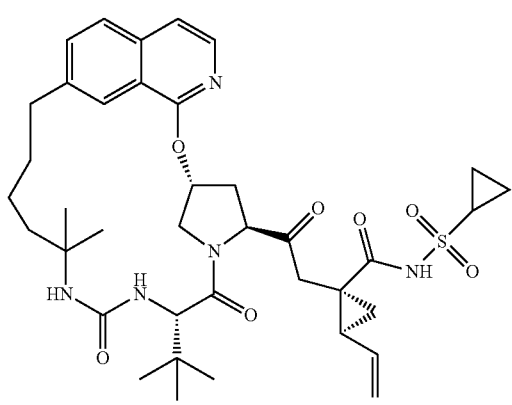
III-25
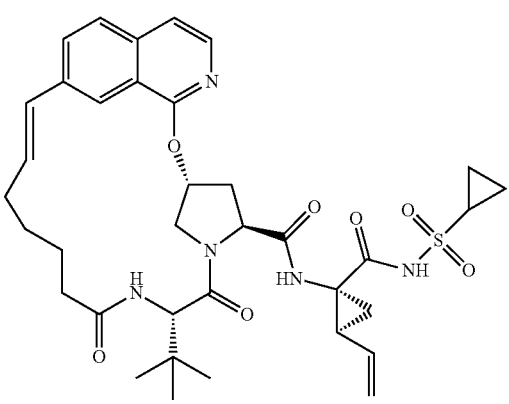
III-23
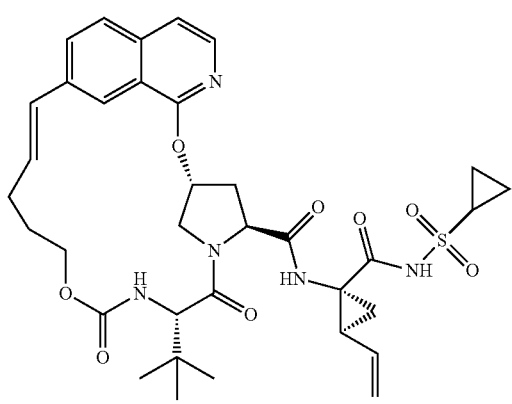
III-26
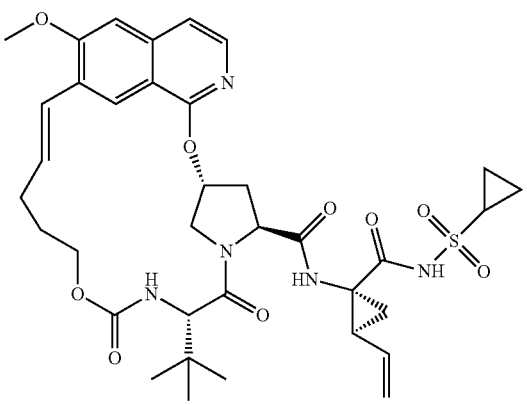

III-27
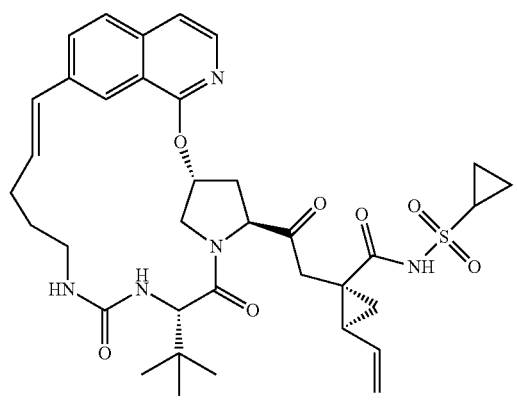
III-31
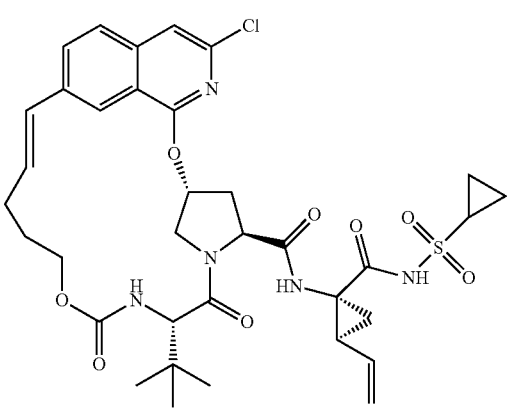
III-28
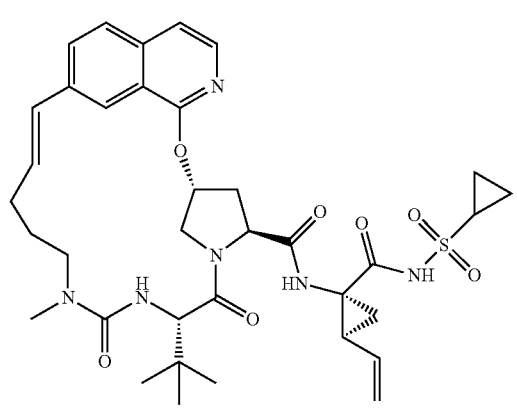
III-29
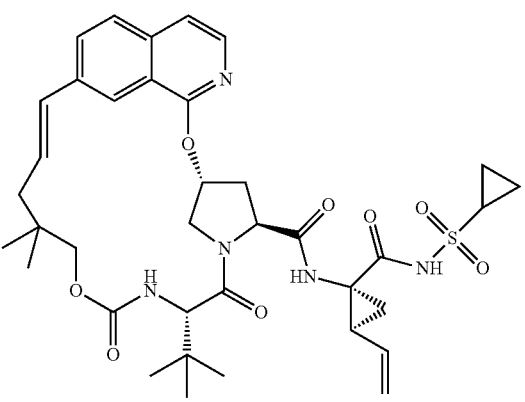
III-32
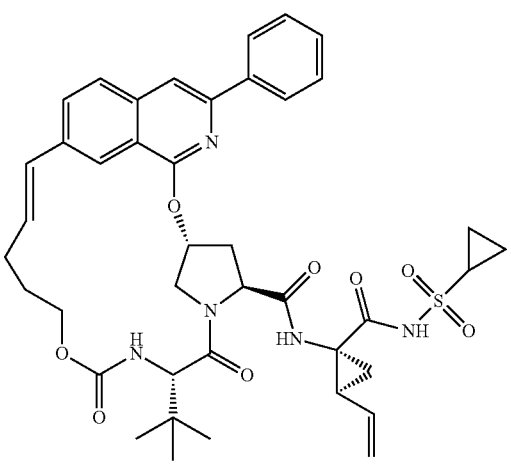
III-30
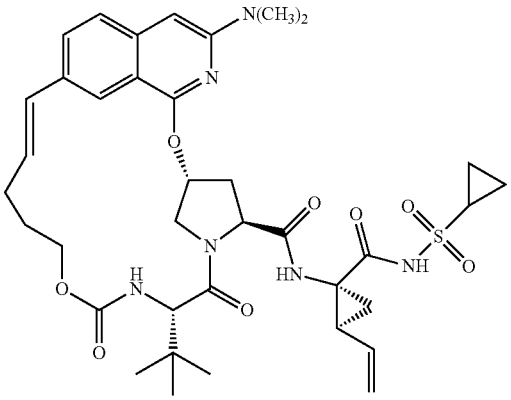
III-33

III-34
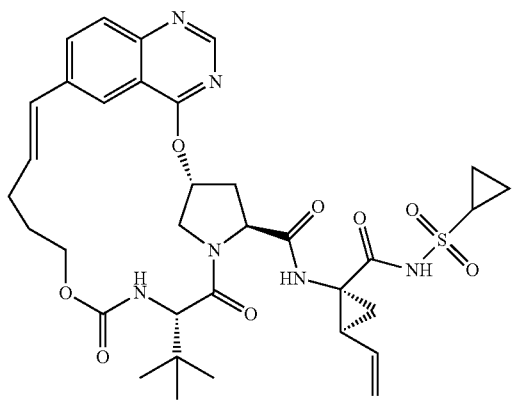
III-37
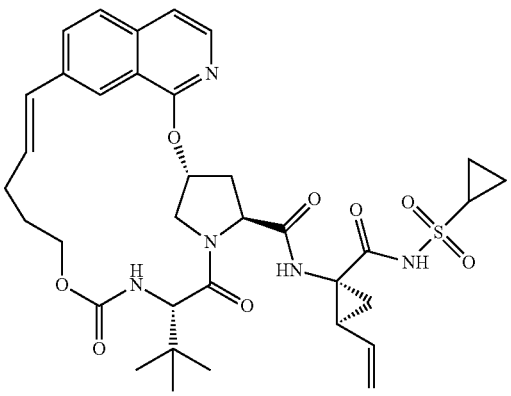
III-35
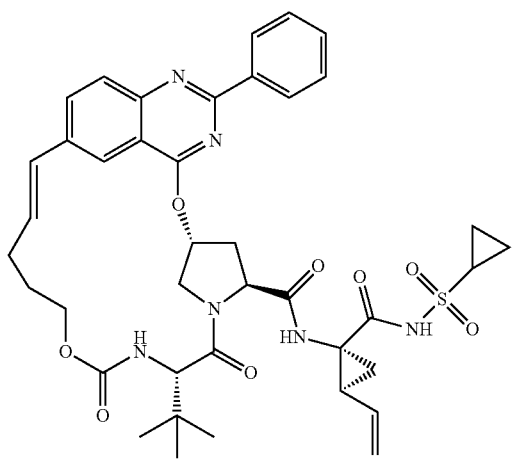
III-38
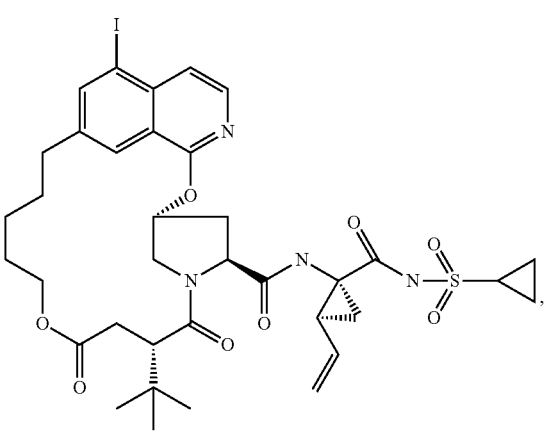
or a pharmaceutically acceptable salt thereof.
23. The compound of claim 1, wherein the compound is selected from the group consisting of compounds III-39 to III-187:
III-36
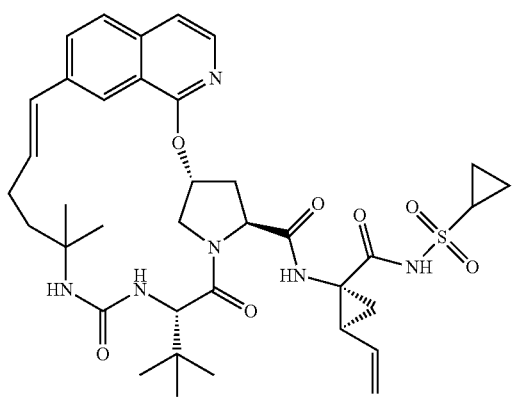
III-39
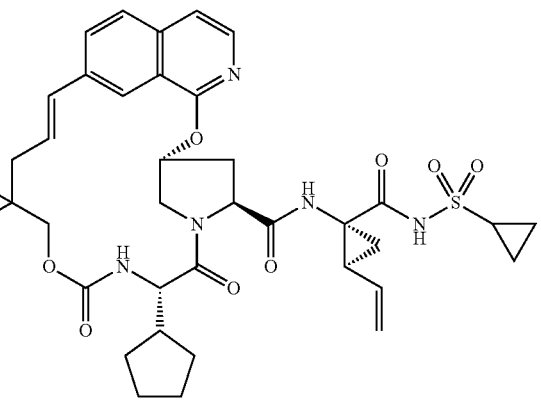

III-40
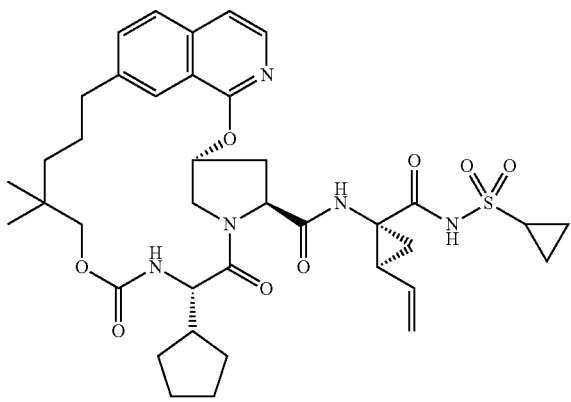
III-44
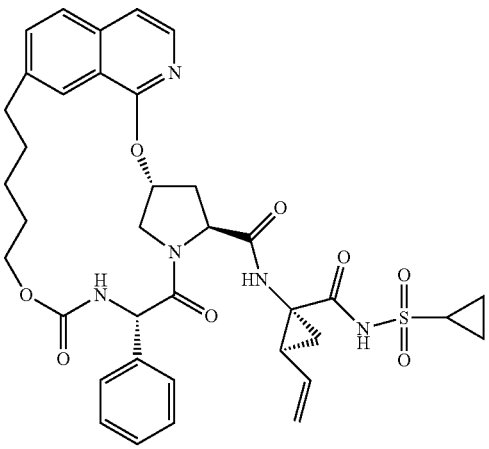
III-41
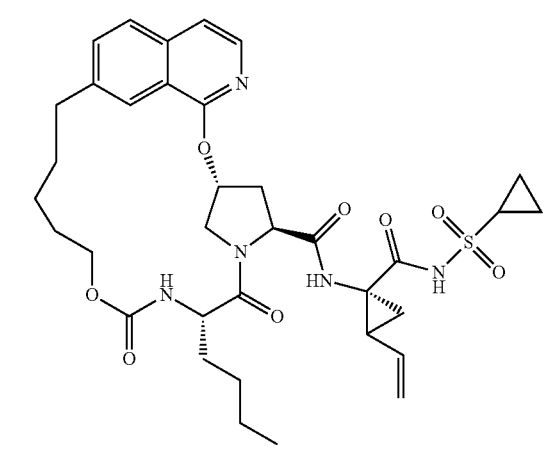
III-45
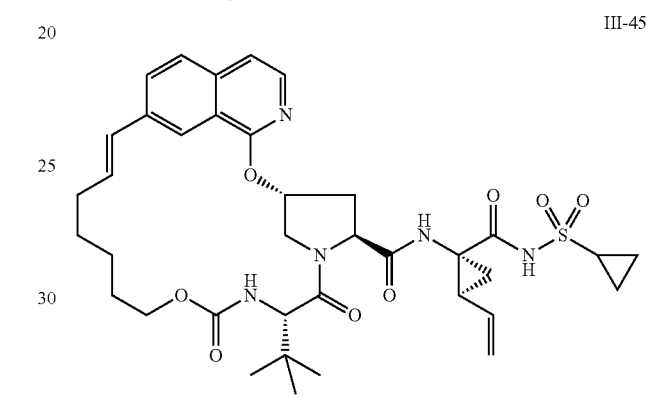
III-42
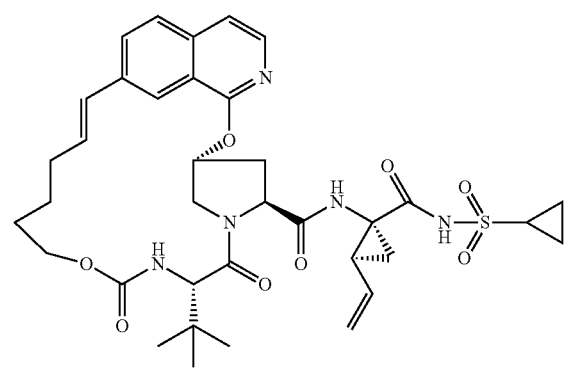
III-46
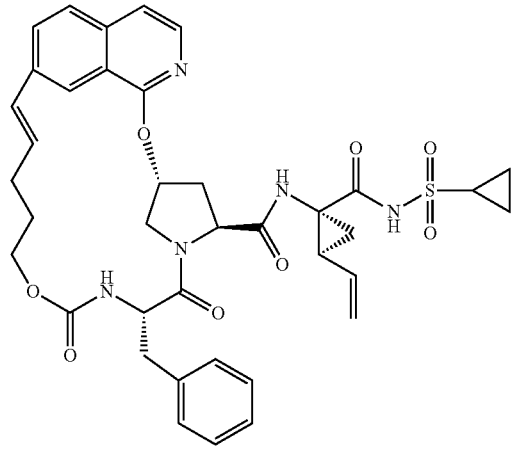
III-43
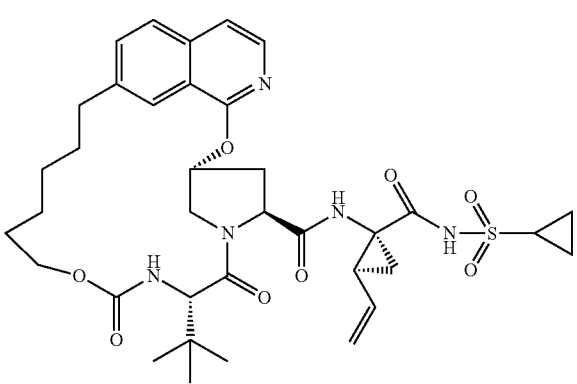
III-47
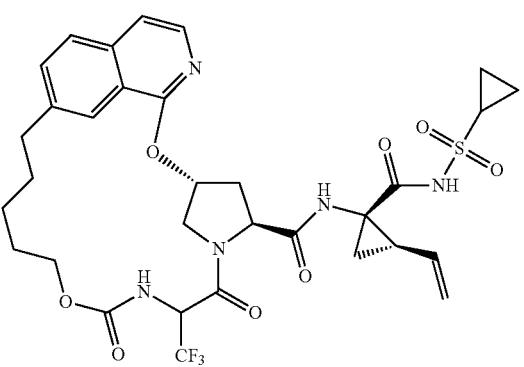

-continued
III-48
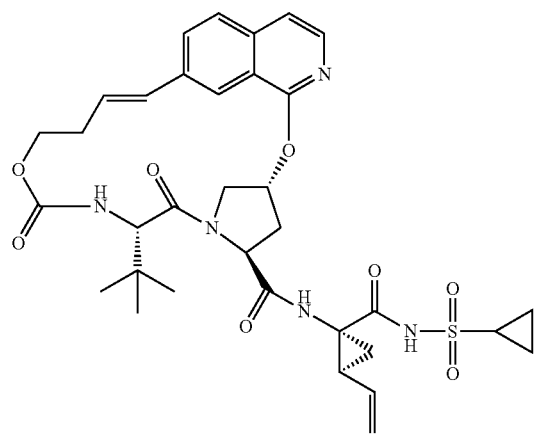
III-49
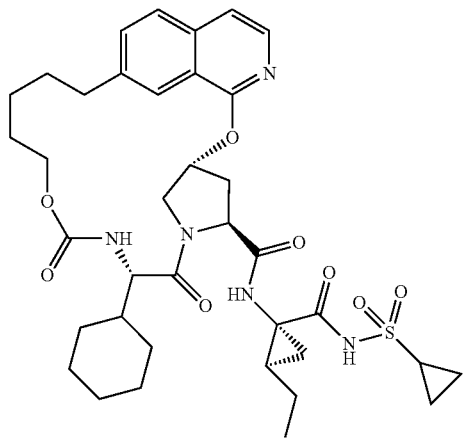
III-50
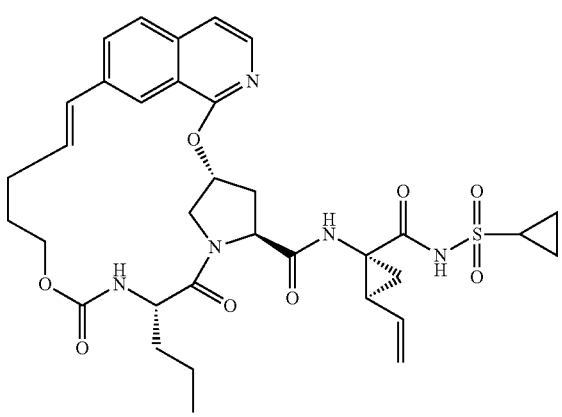
-continued
III-51
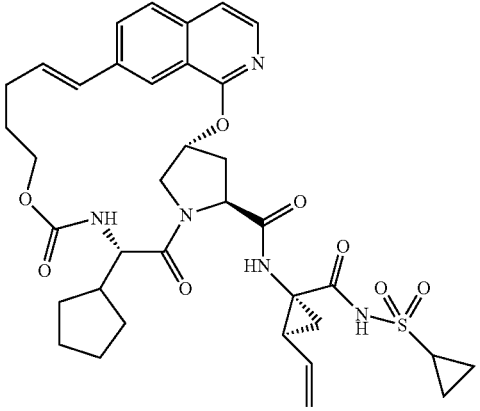
III-52
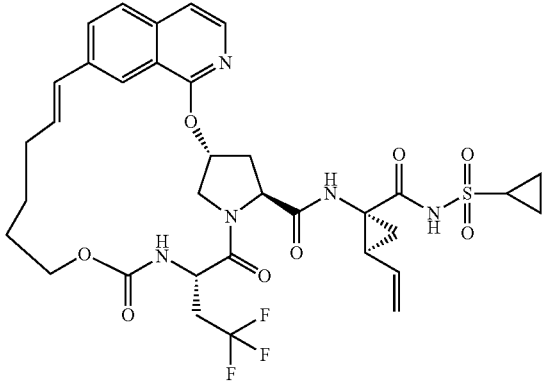
III-53
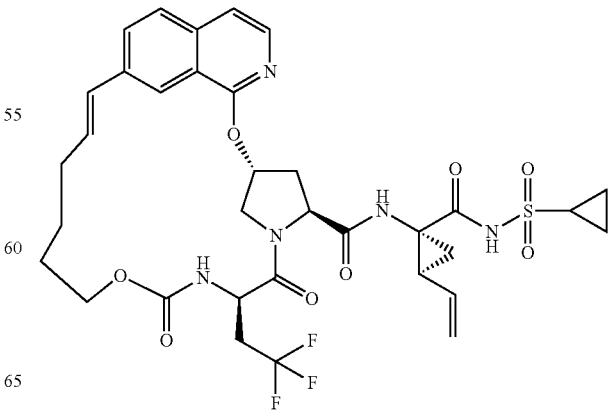

III-54
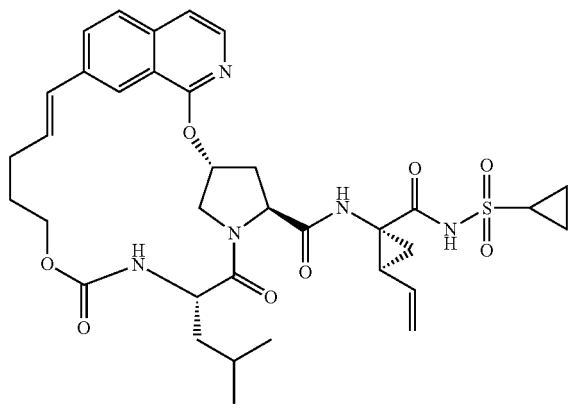
III-57
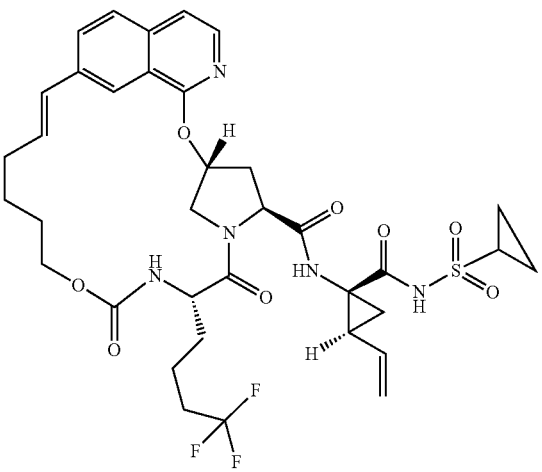
III-55
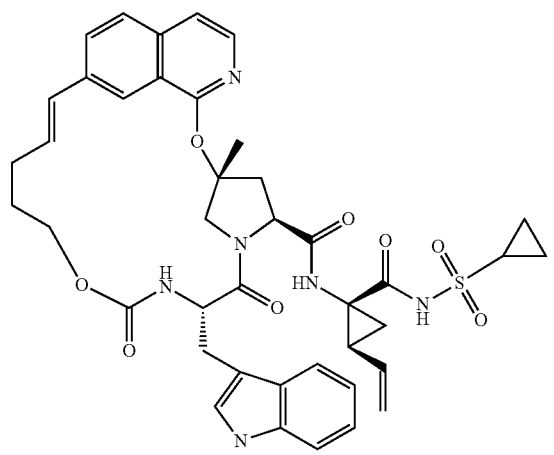
III-58
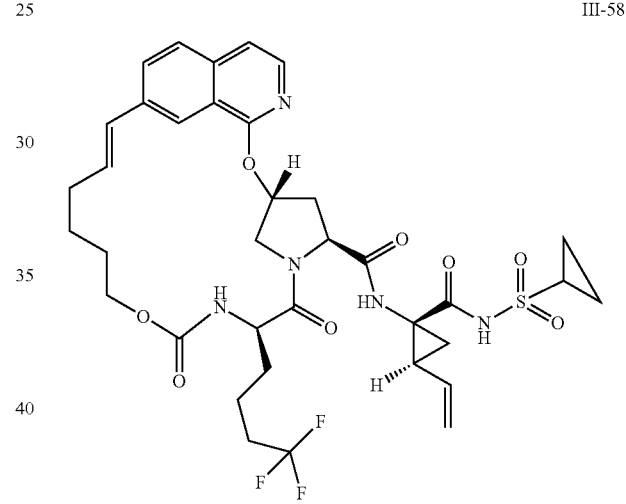
III-56
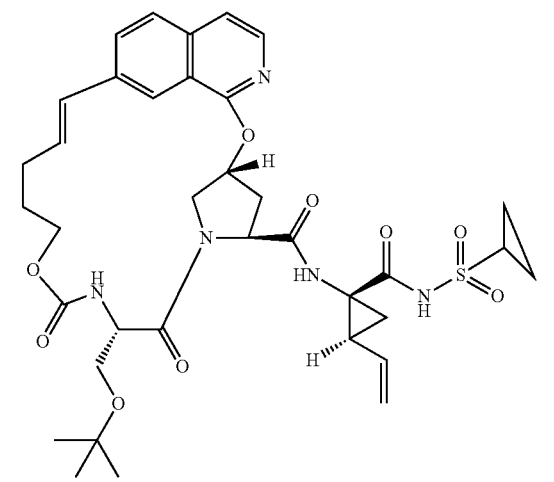
III-59
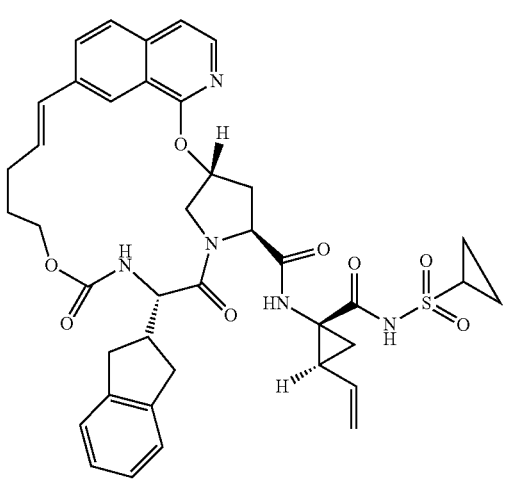

III-60
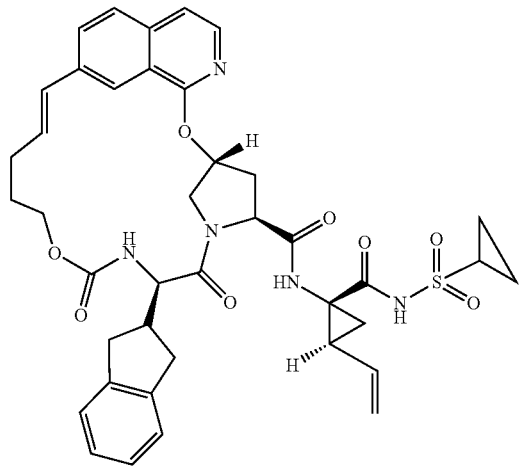
III-63
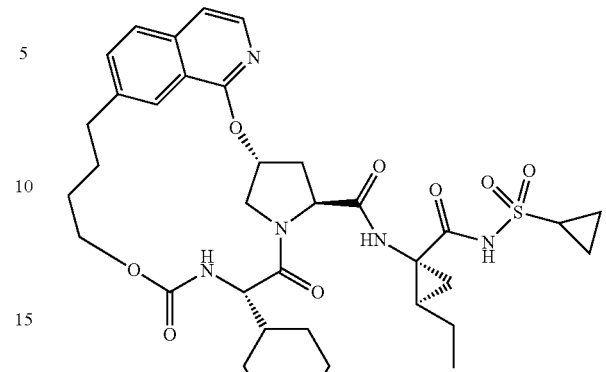
III-61
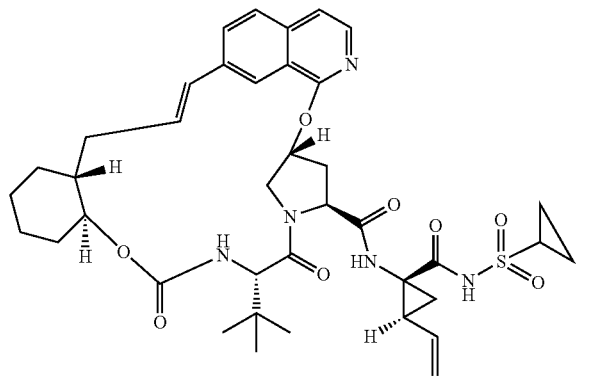
III-64
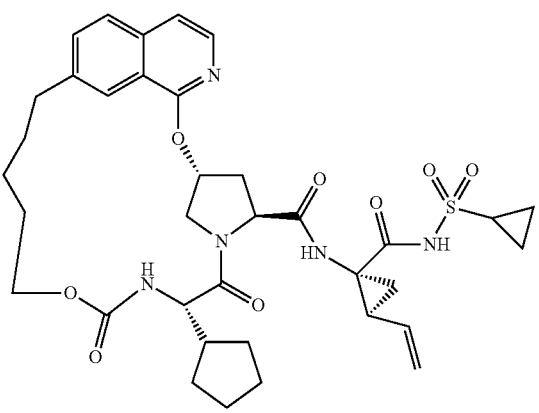
III-62
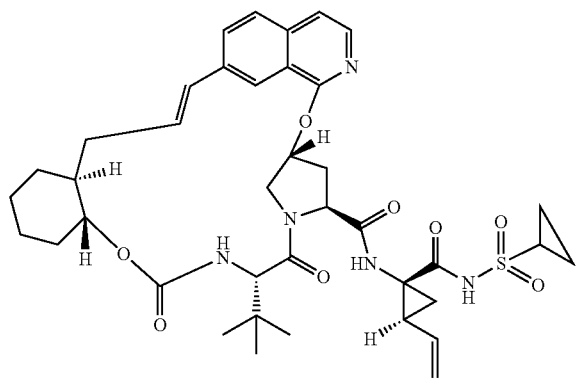
III-65
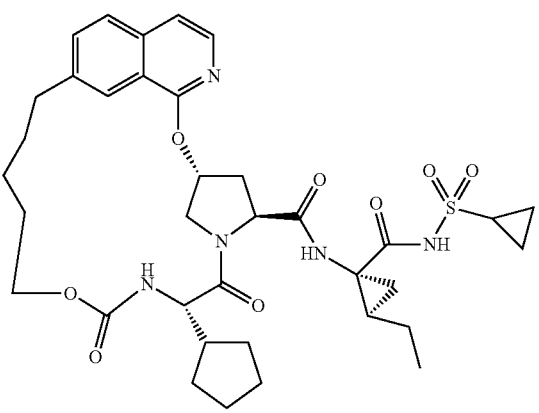

III-66
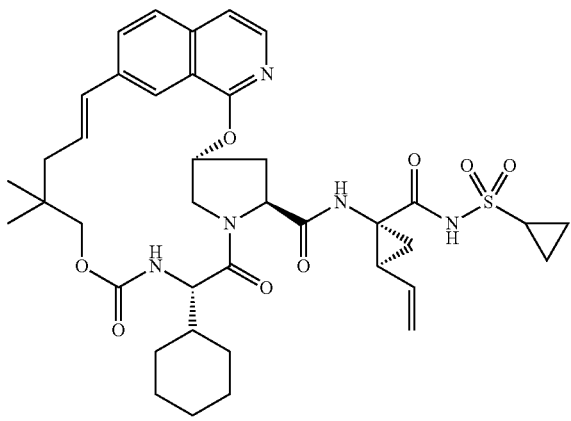
III-67
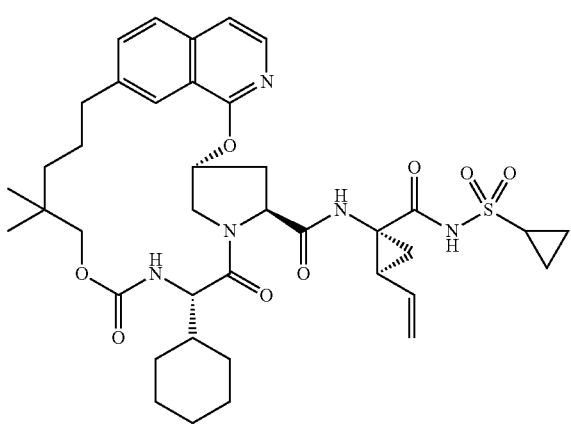
III-68
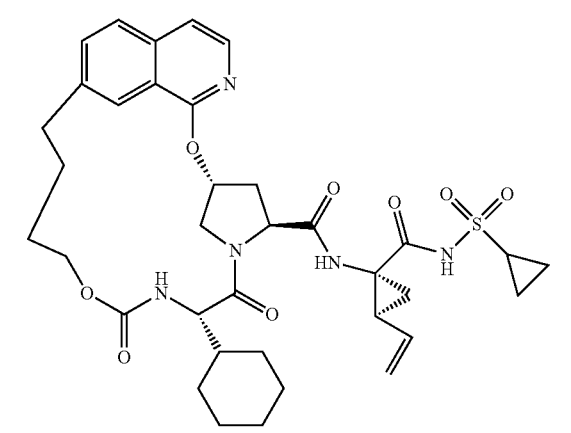
III-69
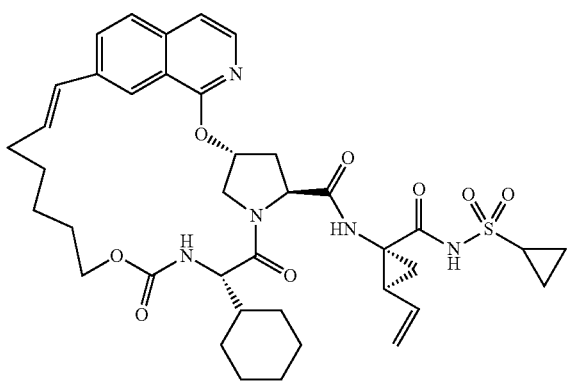
III-70
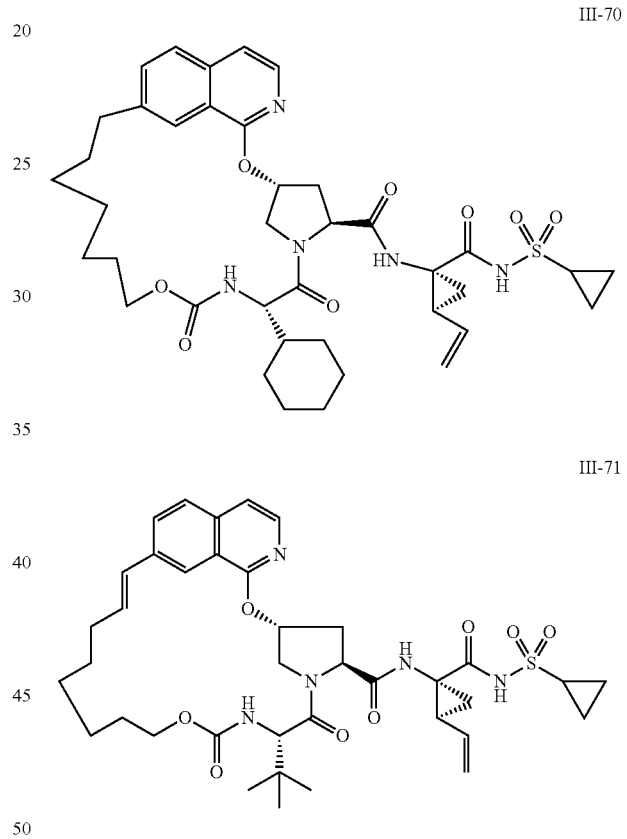
III-71
III-72
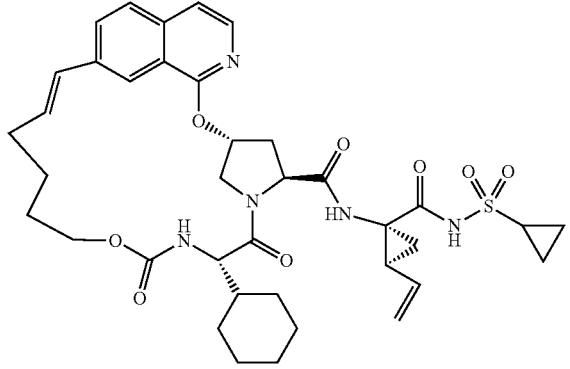

III-73
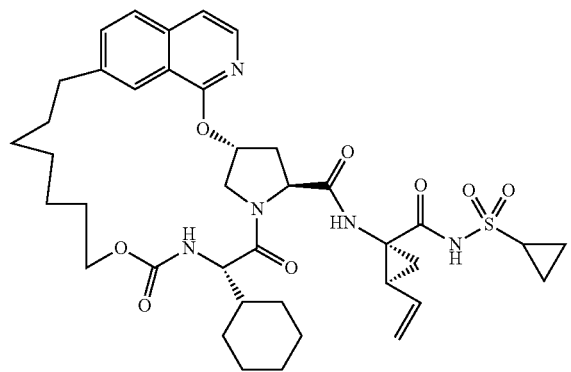
III-74
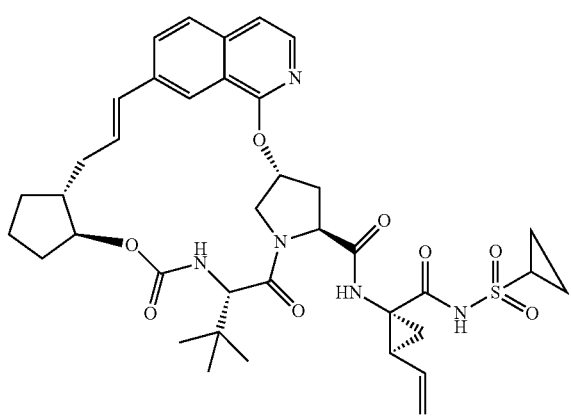
III-75
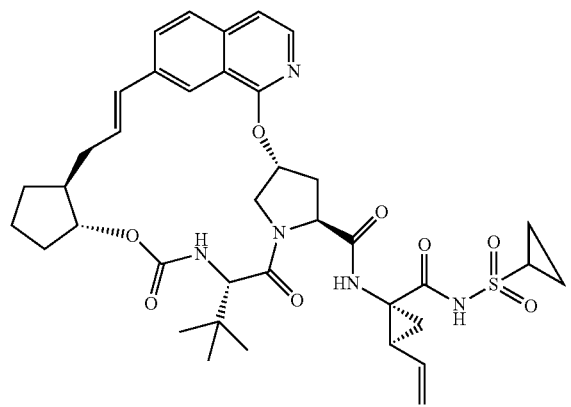
III-76
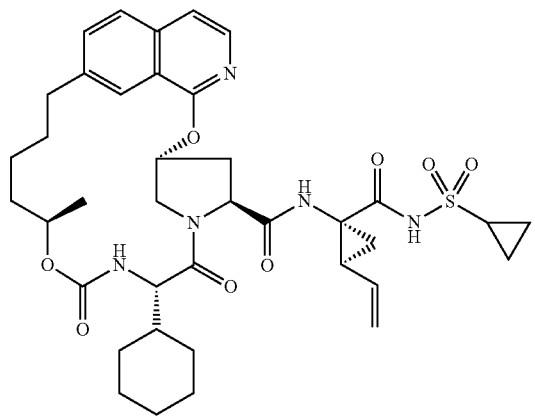
III-77
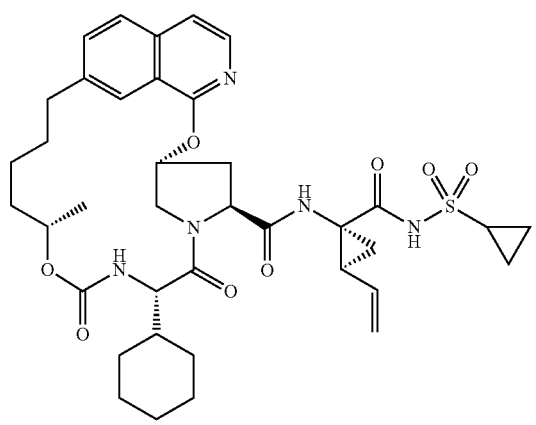
III-78
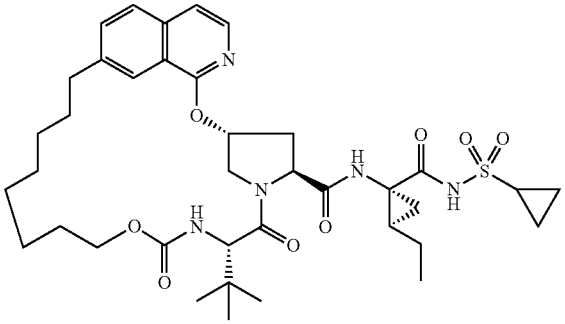
III-79
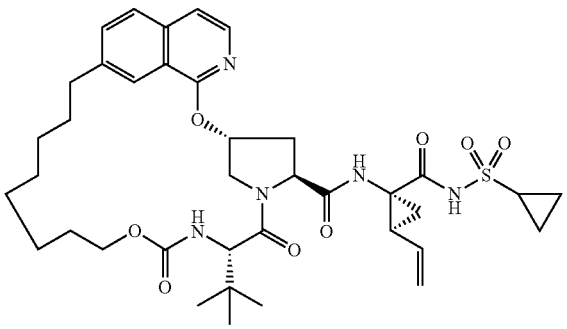

III-80
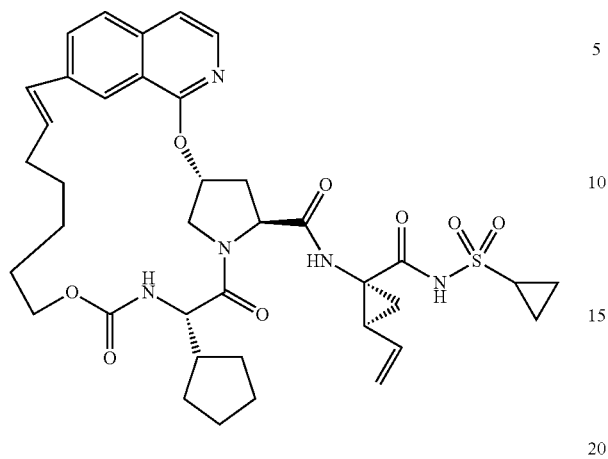
III-83
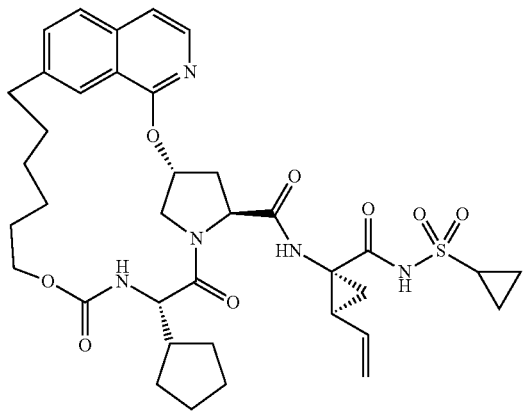
III-81
III-84
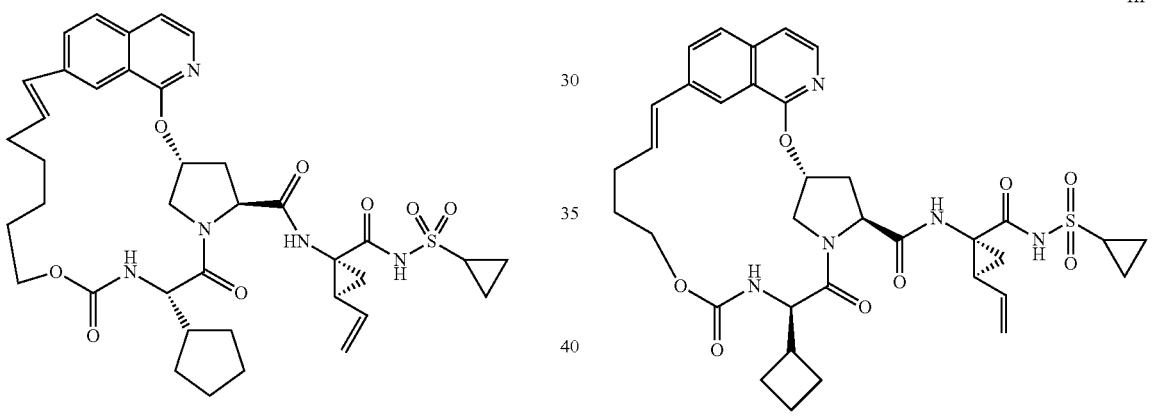
III-82
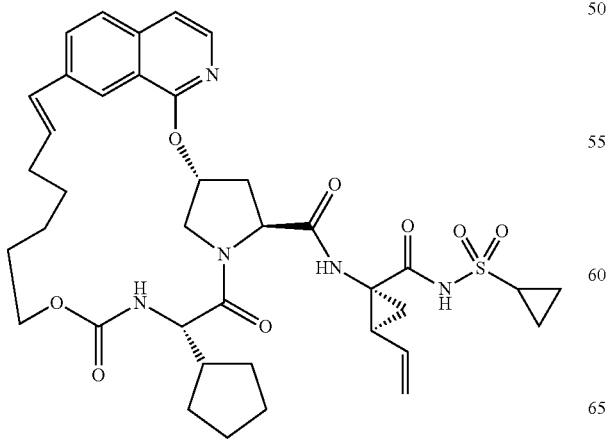
III-85
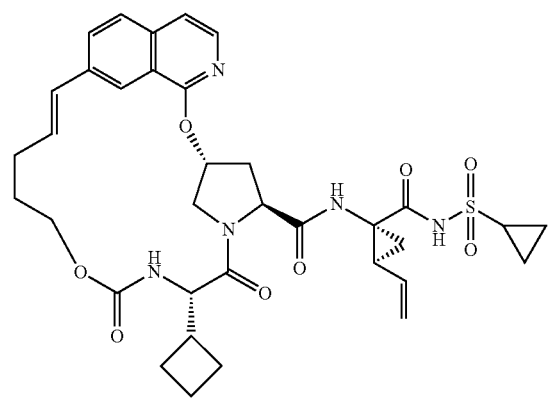

III-86
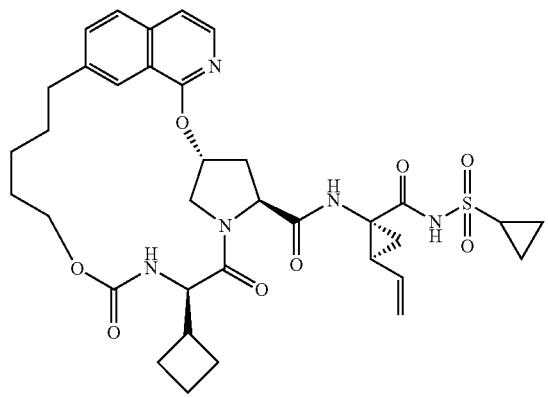
III-90
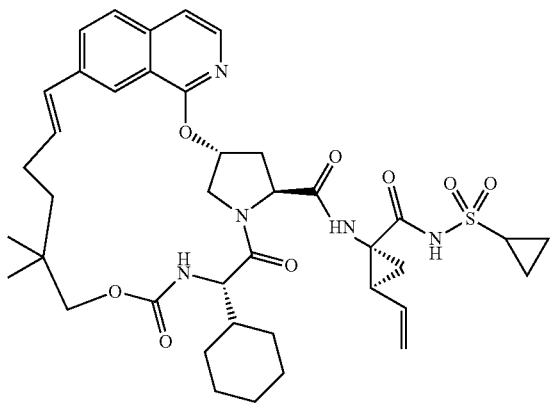
III-87
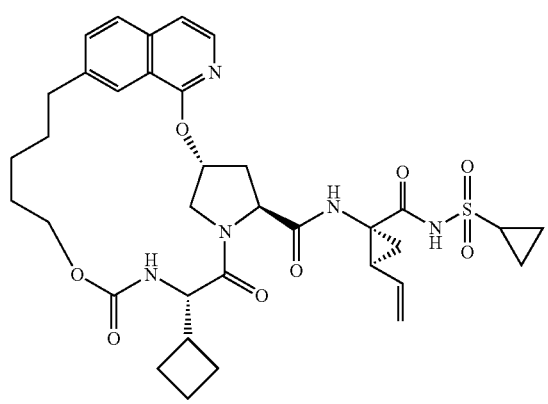
III-91
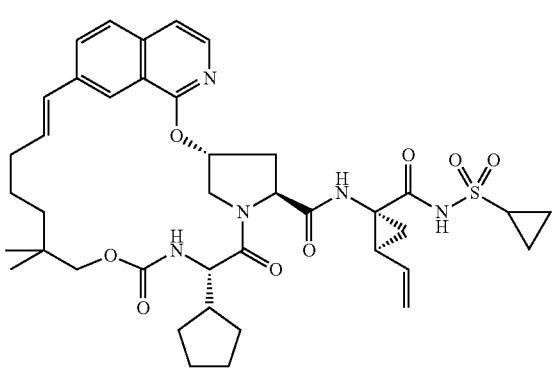
III-88
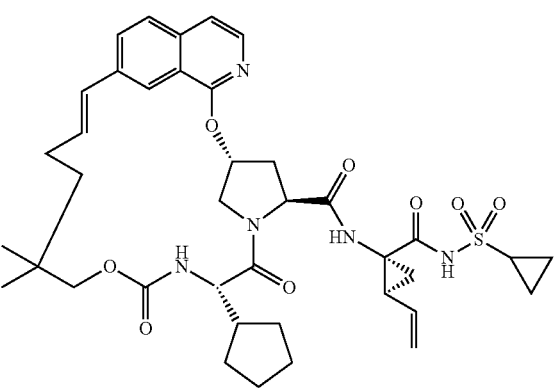
III-92
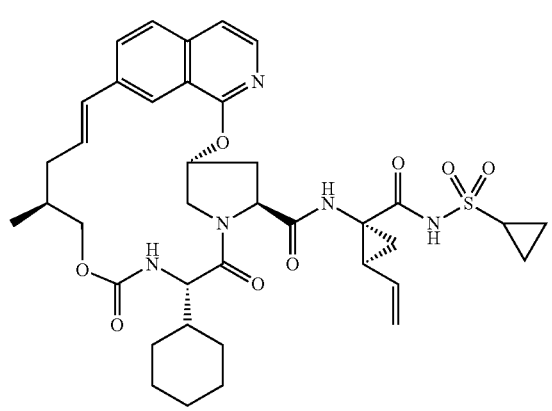
III-89
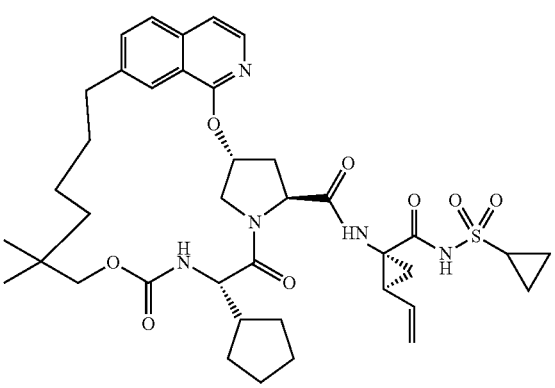
III-93
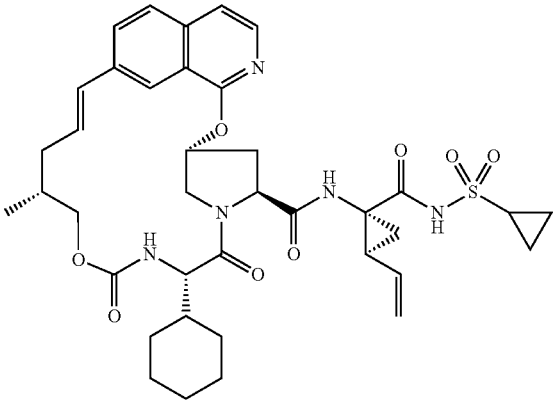

III-94
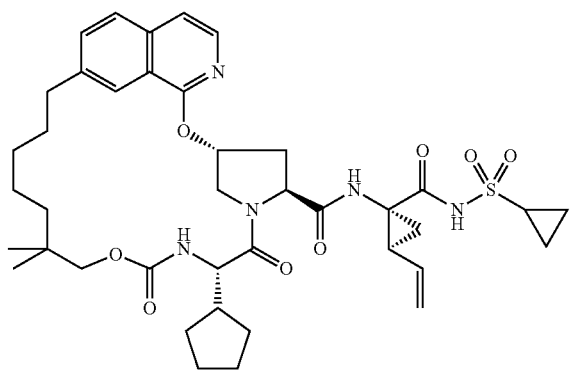
III-95
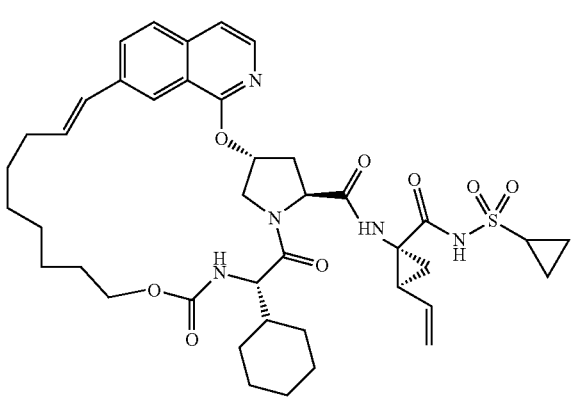
III-96
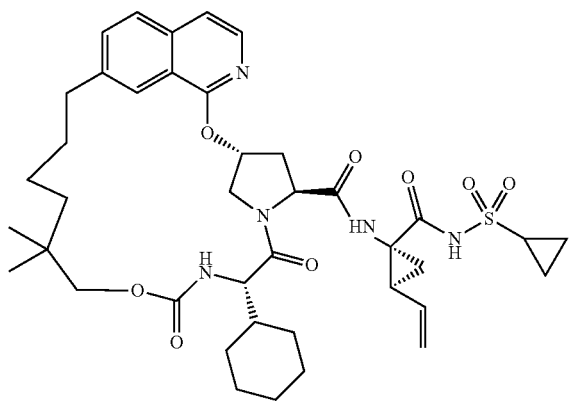
III-97
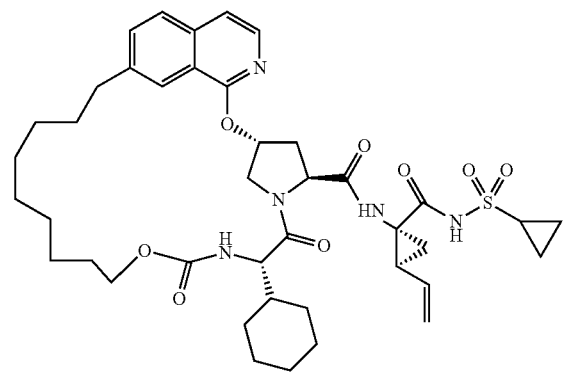
III-98
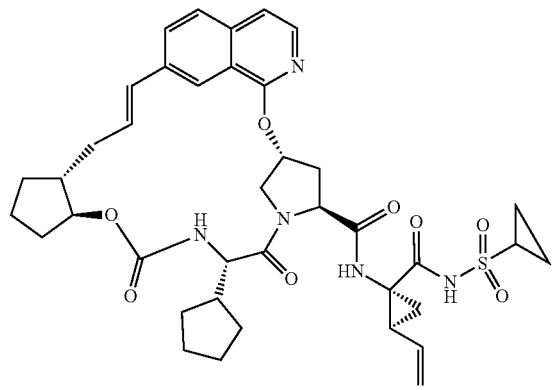
III-99
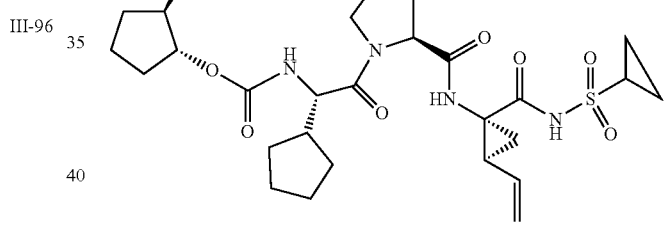
III-100
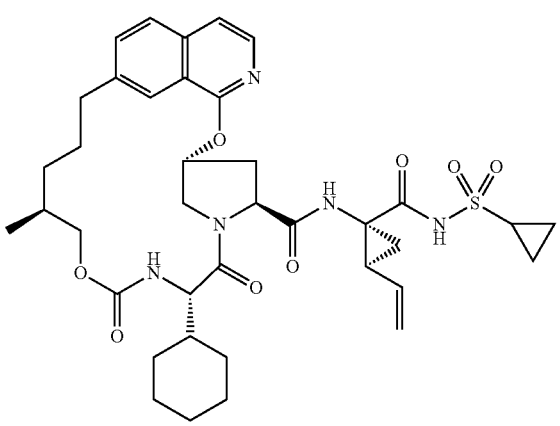

III-101
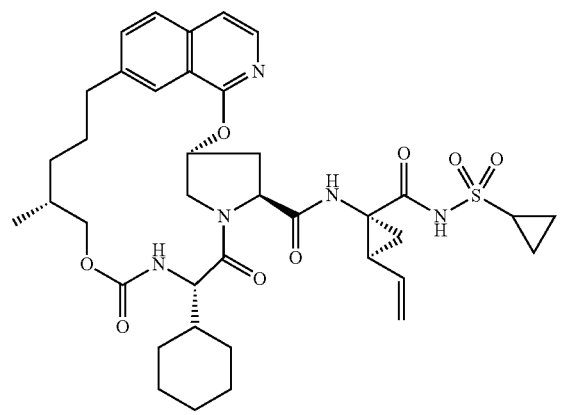
III-104
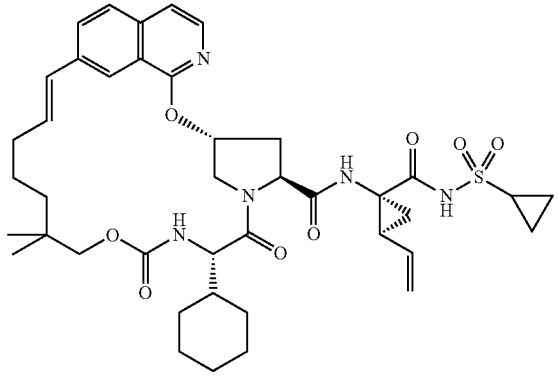
III-105
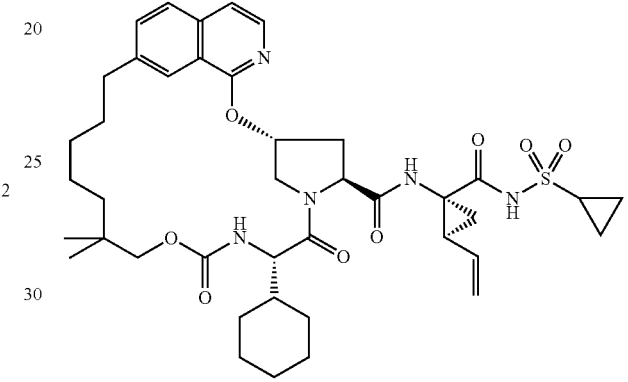
III-102
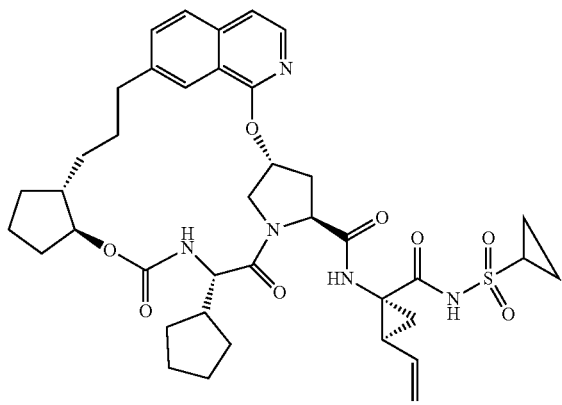
III-106
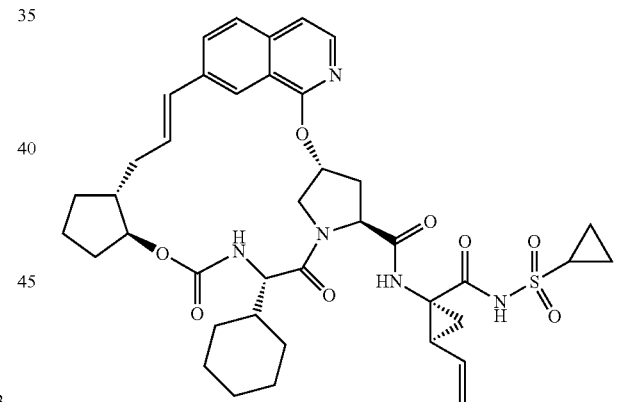
III-103
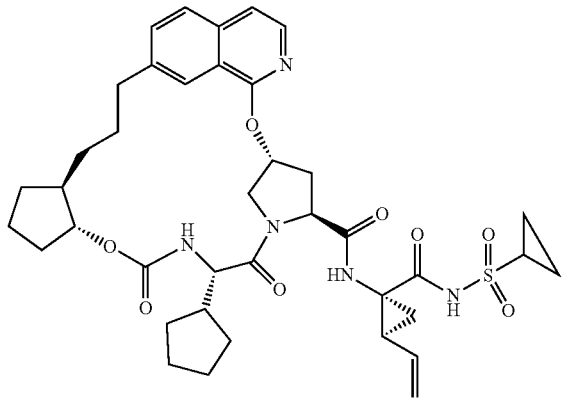
III-107
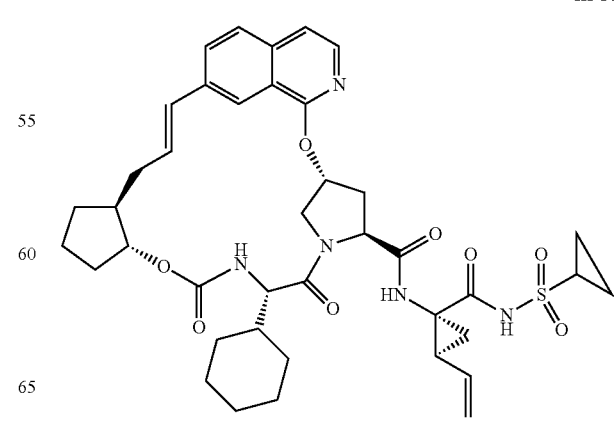

III-108
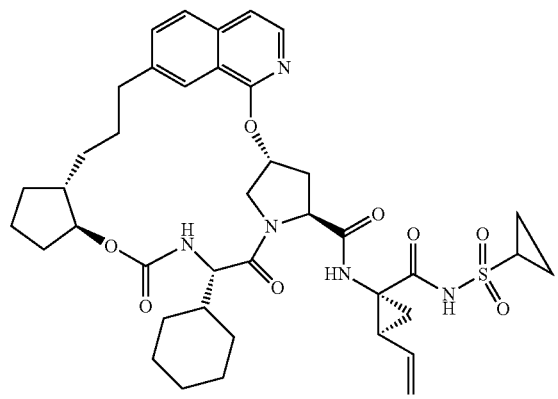
III-109
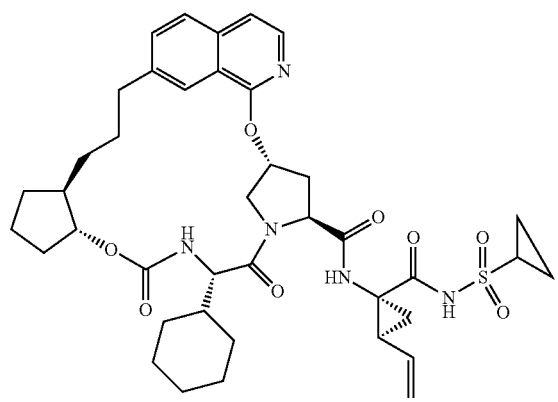
III-110
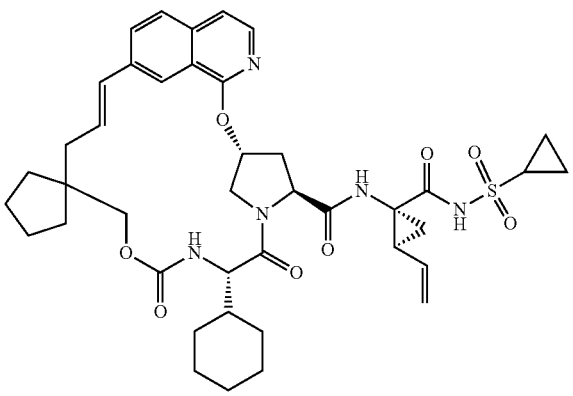
III-111
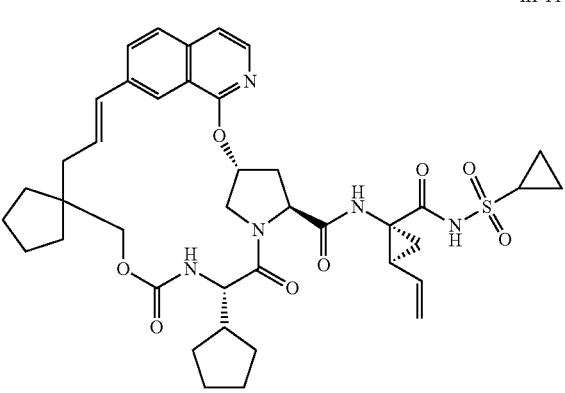
III-112
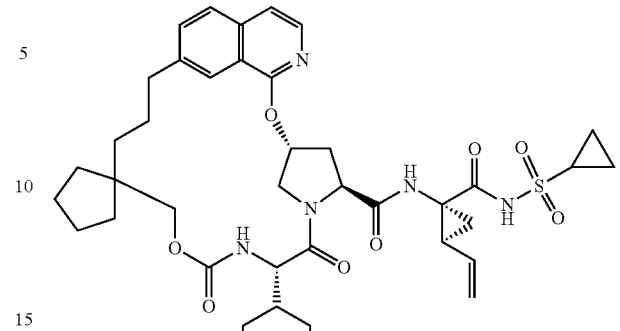
III-113
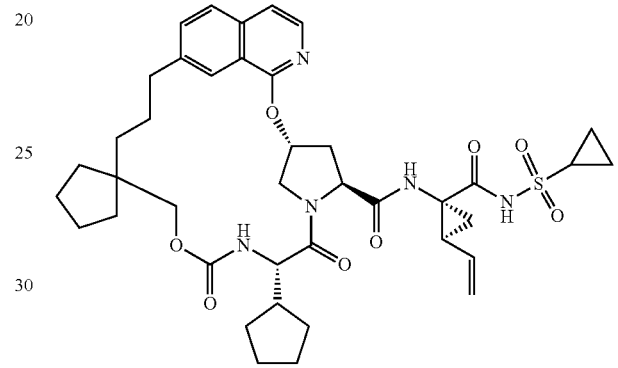
III-114
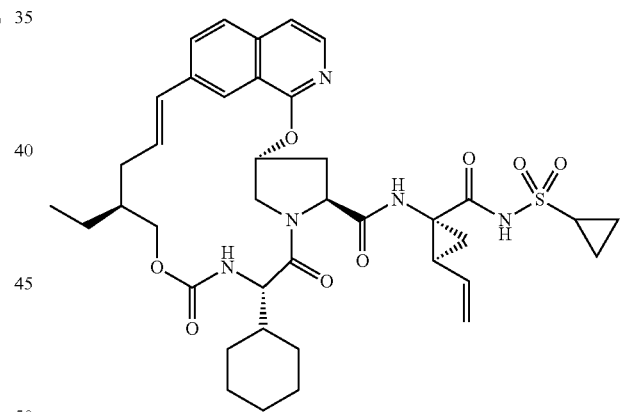
III-115
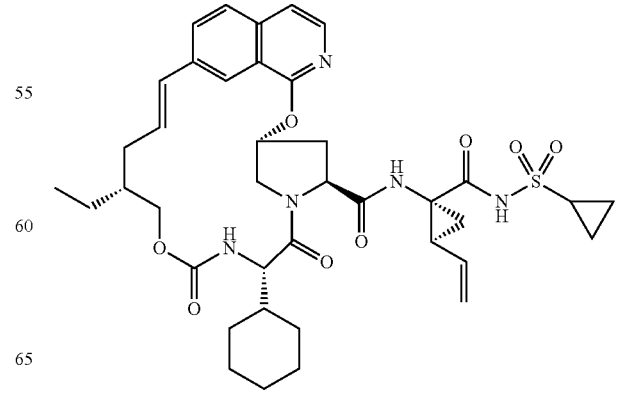

III-116
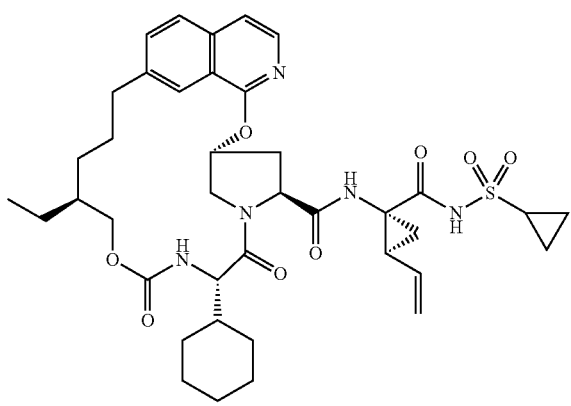
III-119
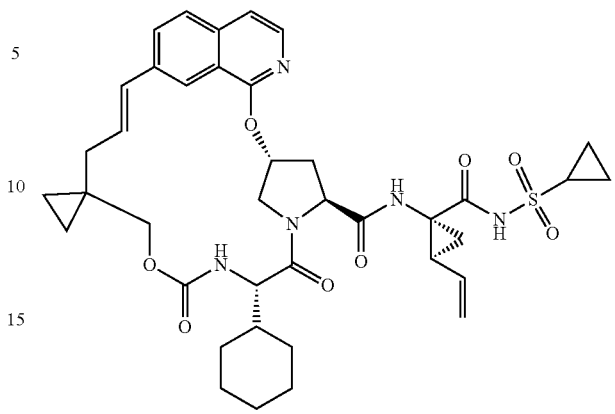
III-117
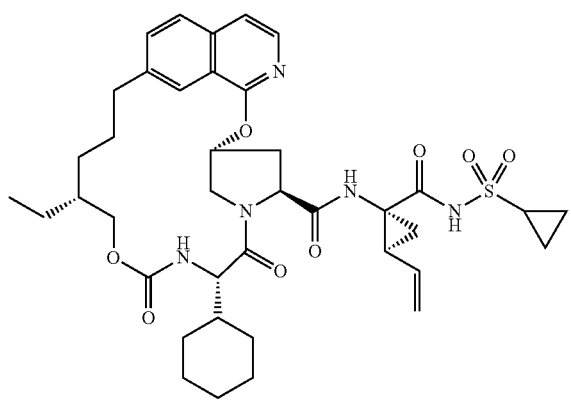
III-120
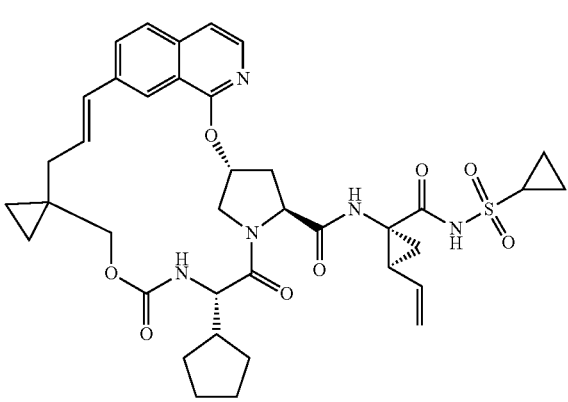
III-118
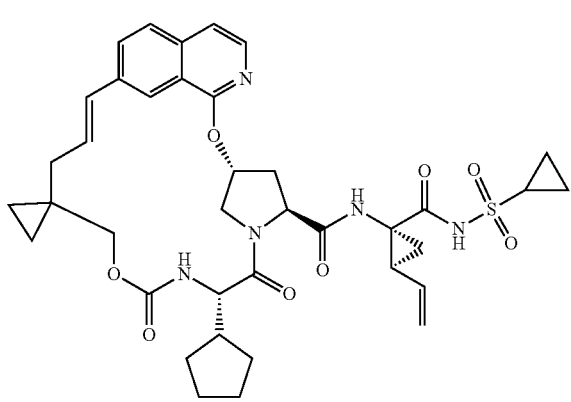
III-121
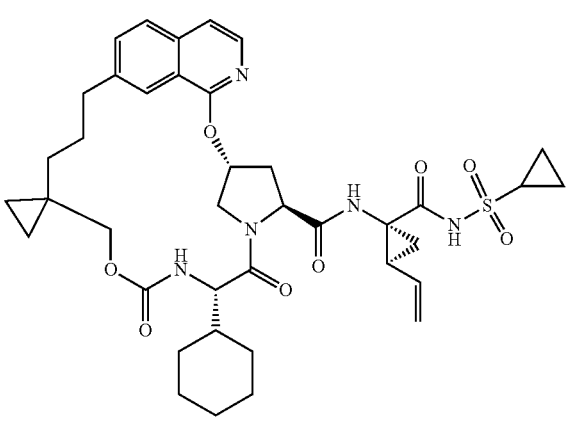

III-122
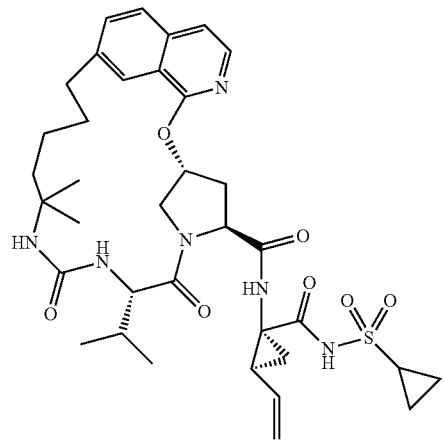
III-123
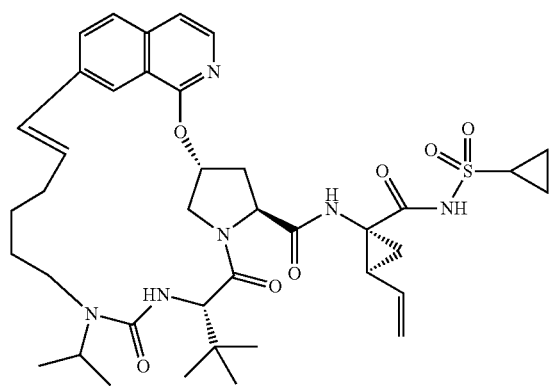
III-124
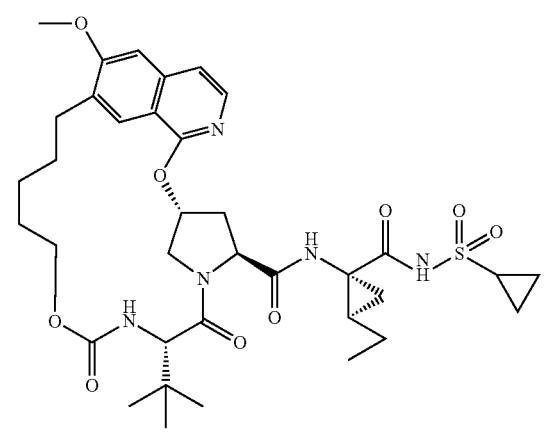
III-125
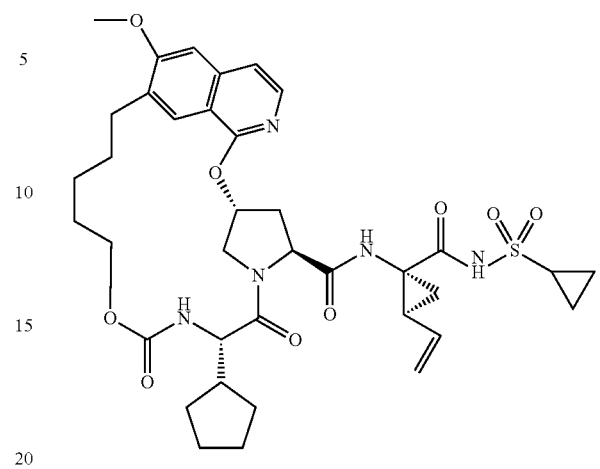
III-126
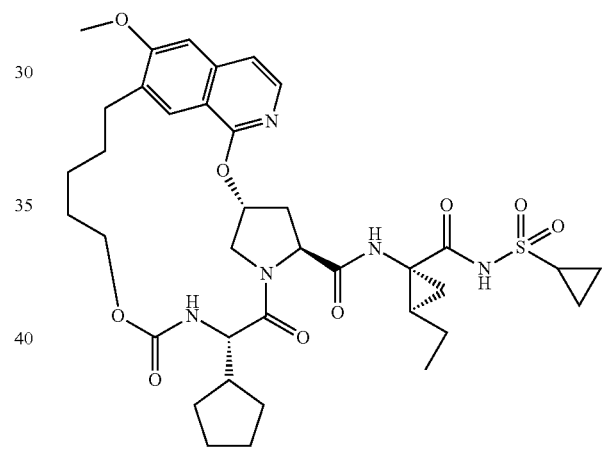
III-127
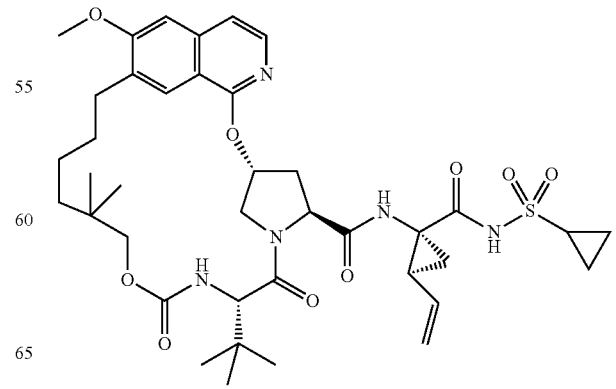

313
-continued
III-128
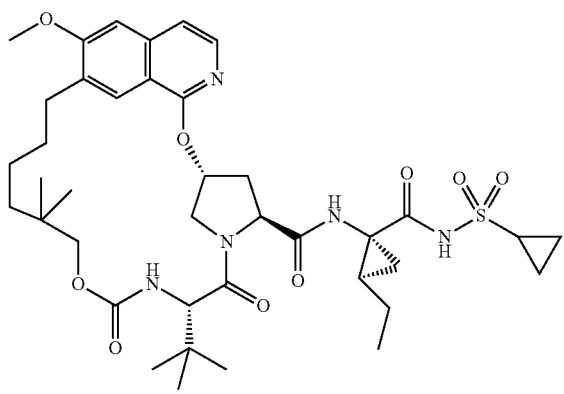
III-129
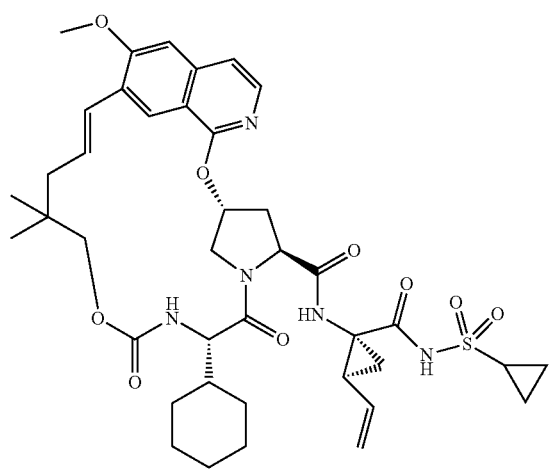
III-130
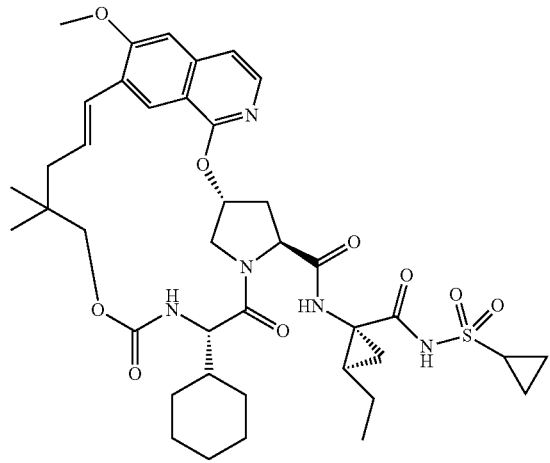
314
-continued
III-131
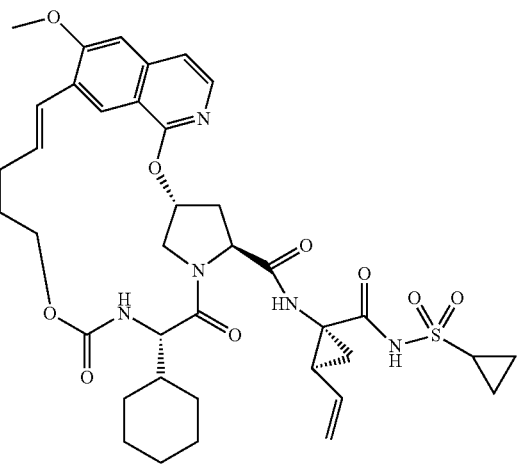
III-132
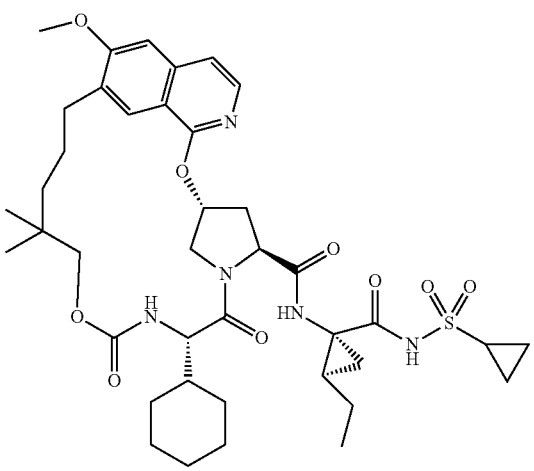
III-133
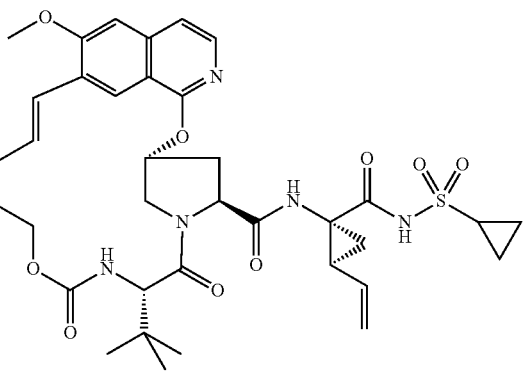

III-134
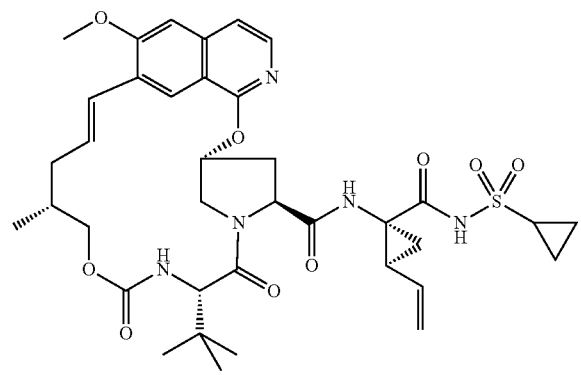
III-135
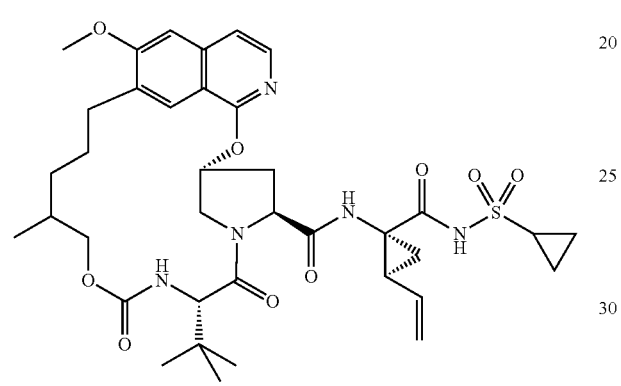
III-136
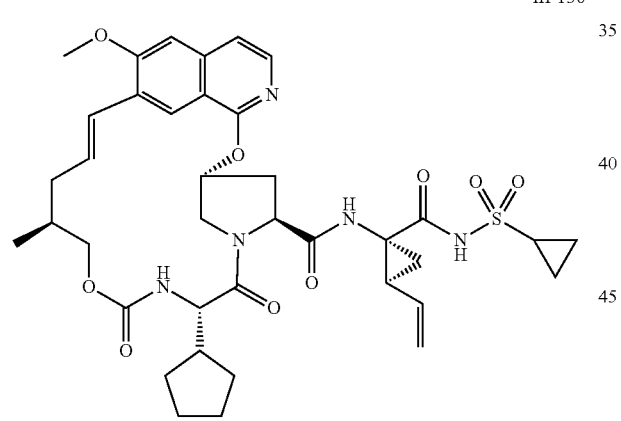
III-137
III-138
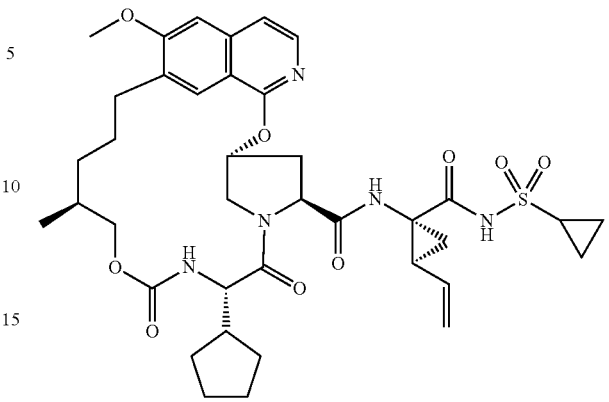
III-139
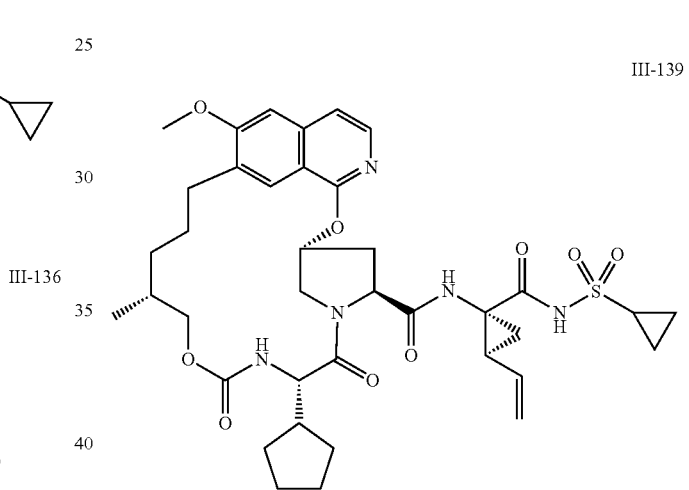
III-140
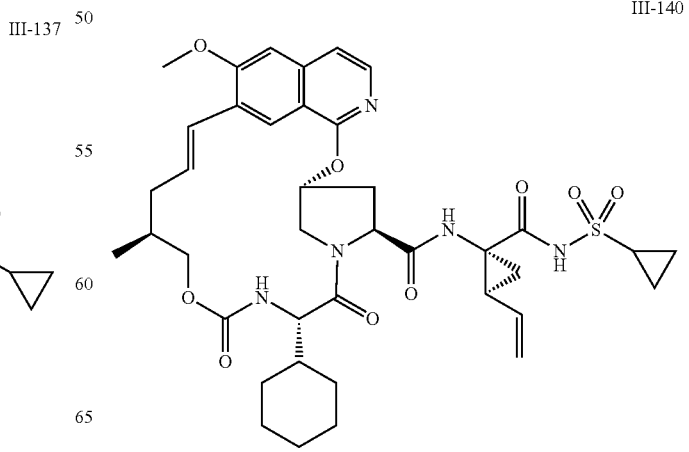

III-141
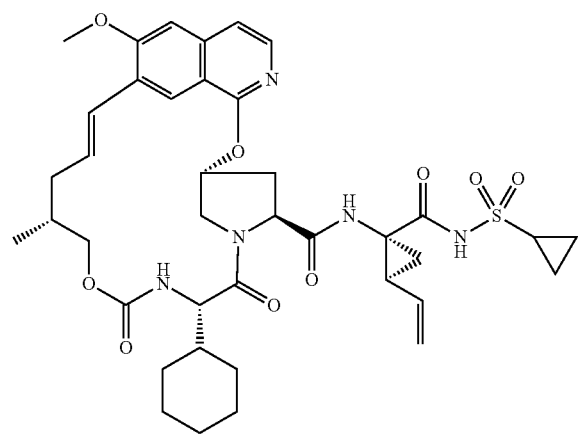
III-144
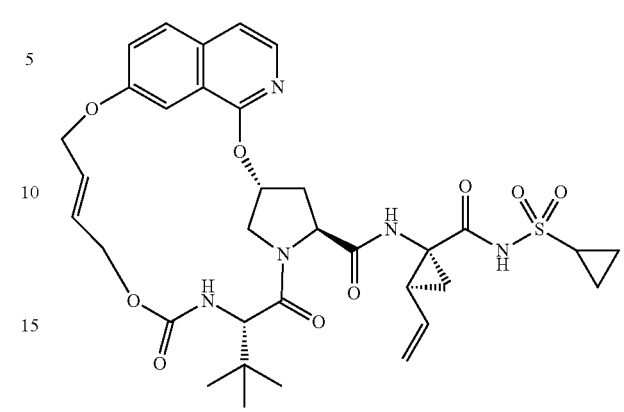
III-142
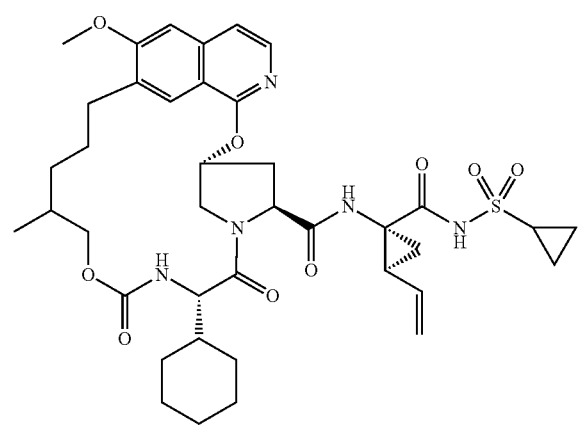
III-145
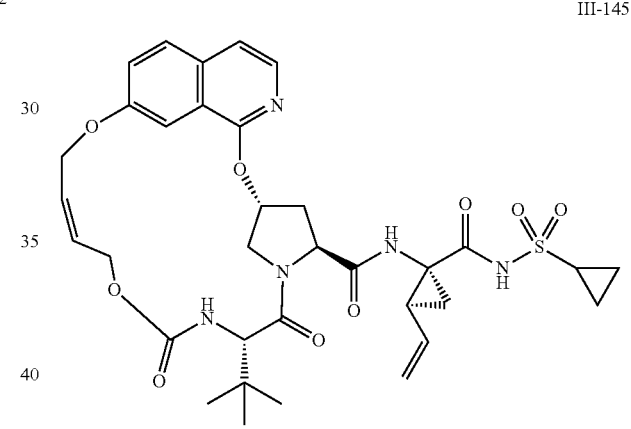
III-143
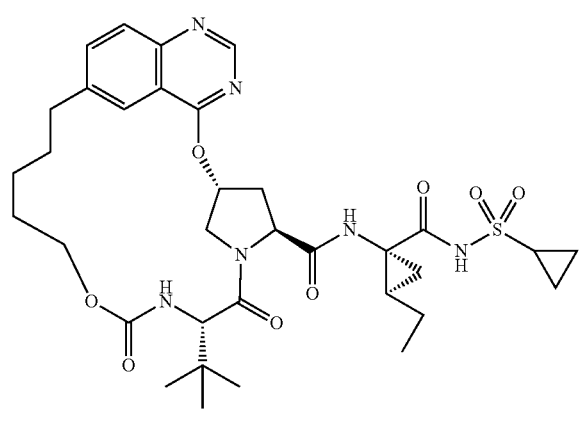
III-146
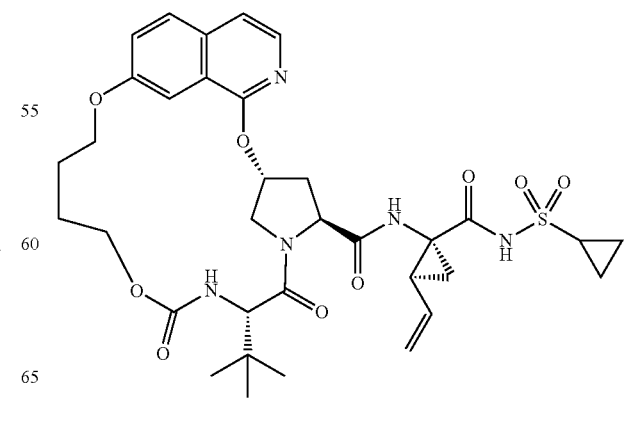

-continued
III-147
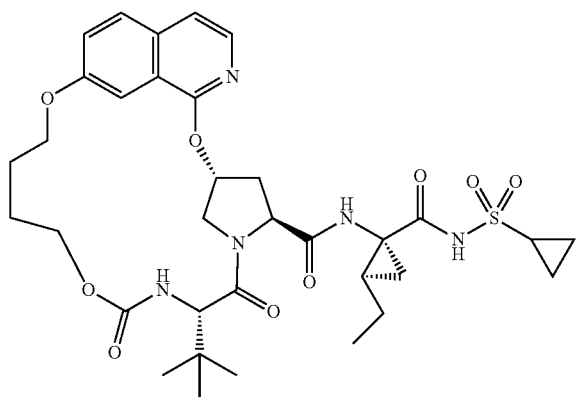
III-148
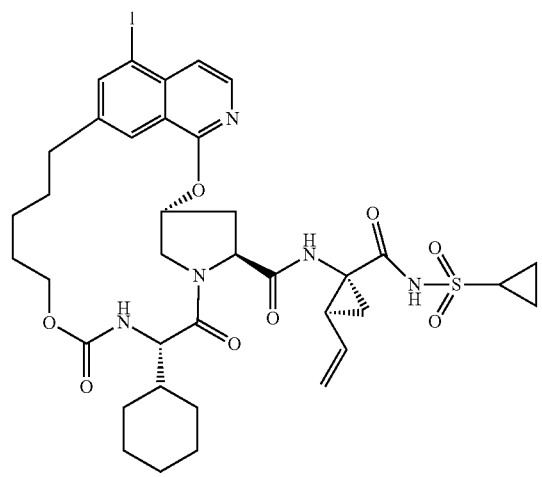
III-149
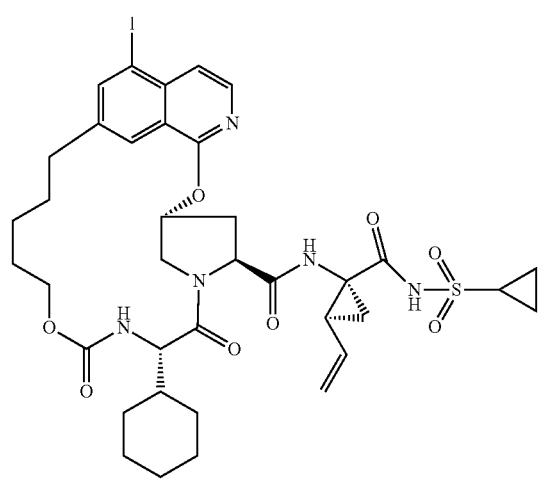
-continued
III-150
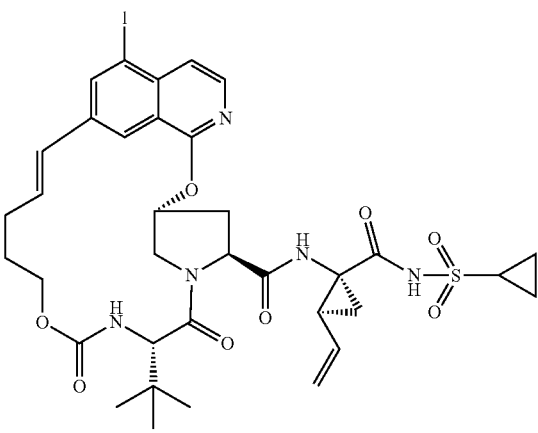
III-151
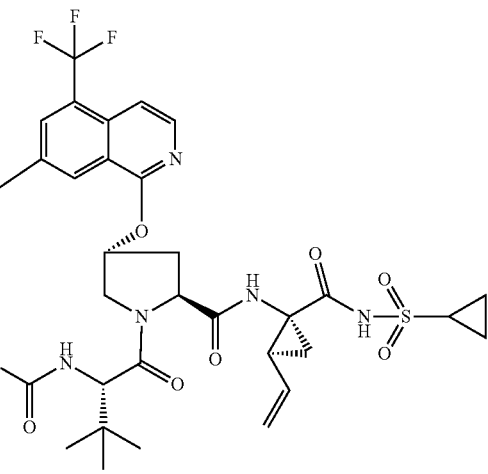
III-152
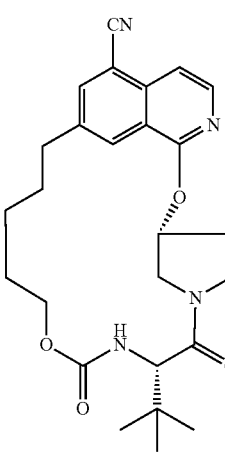

-continued
III-153
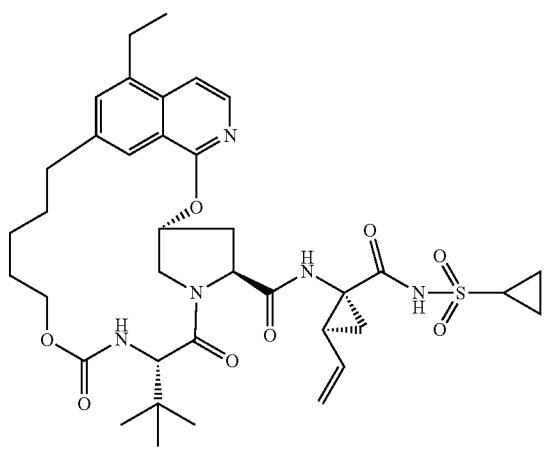
III-154
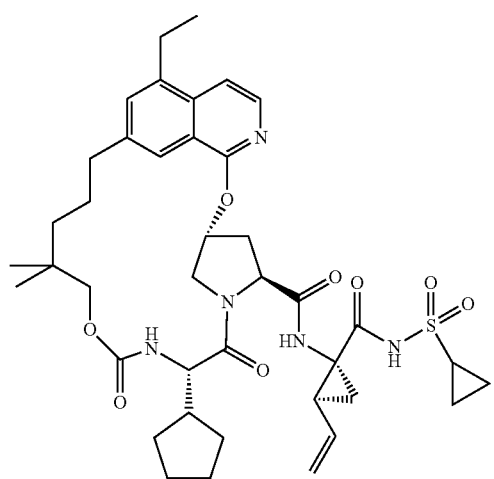
III-155
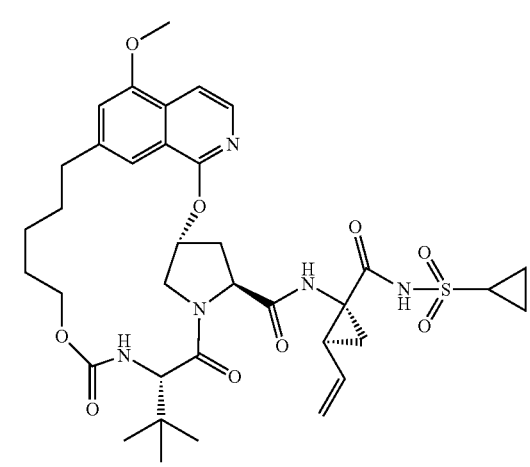
-continued
III-156
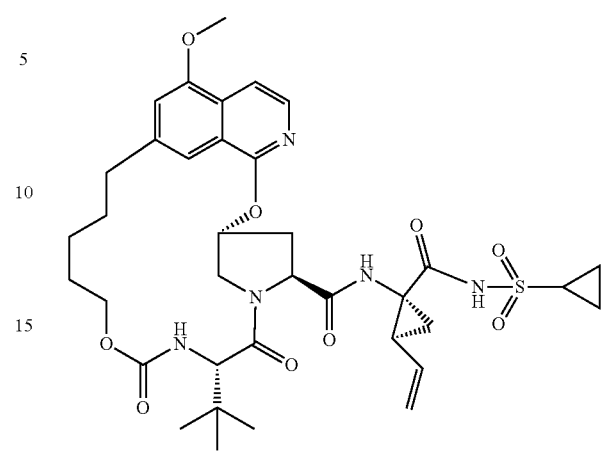
III-157
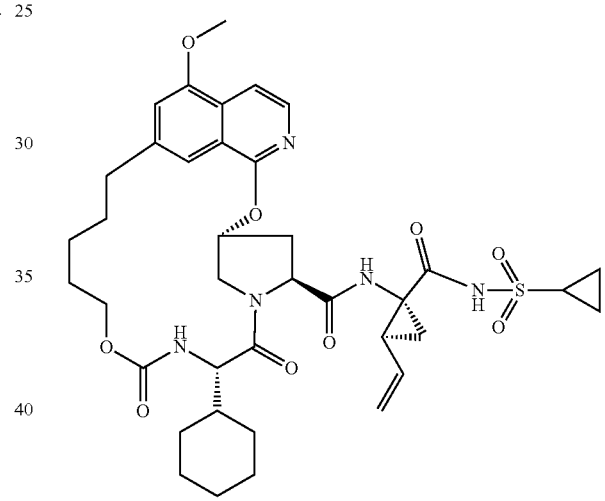
III-158
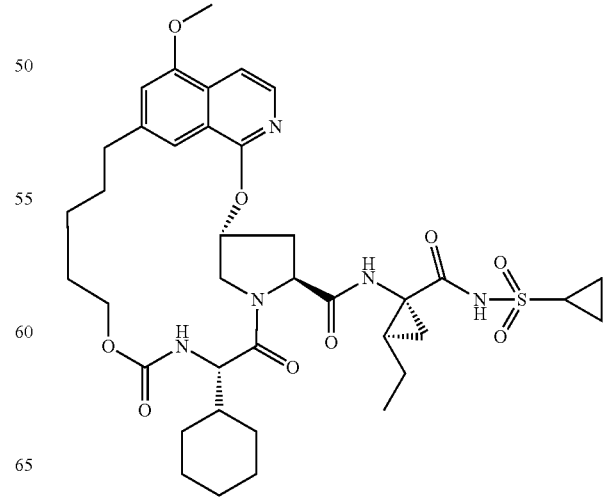

323
-continued
III-159
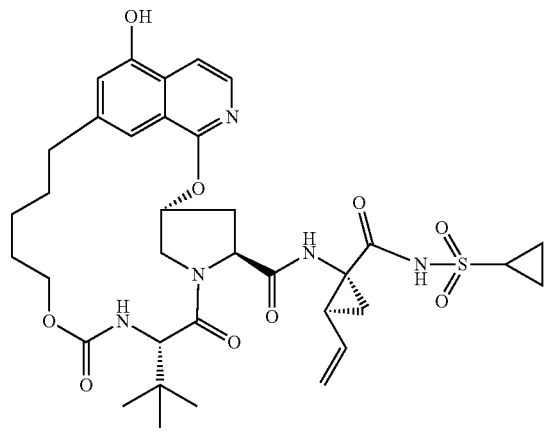
III-160
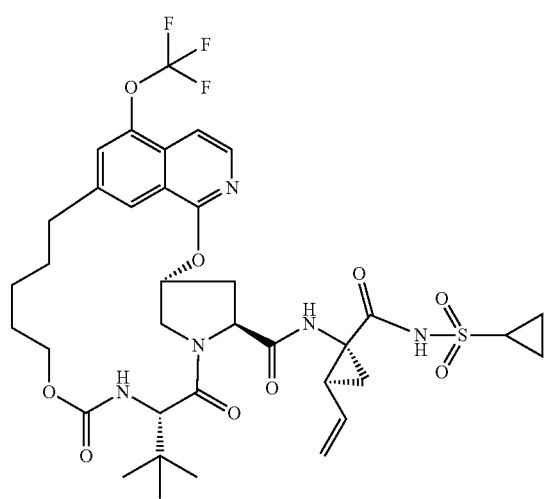
III-161
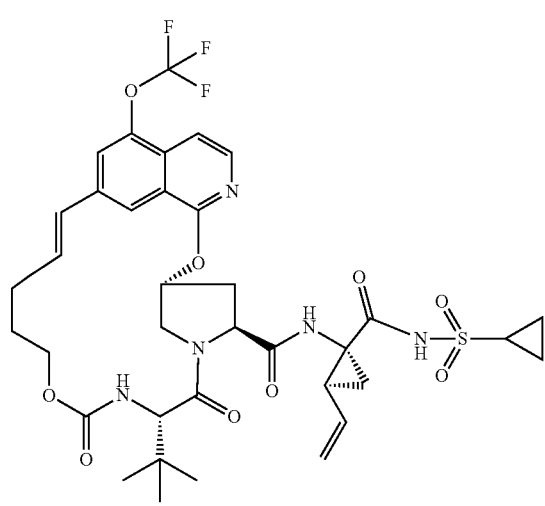
324
-continued
III-162
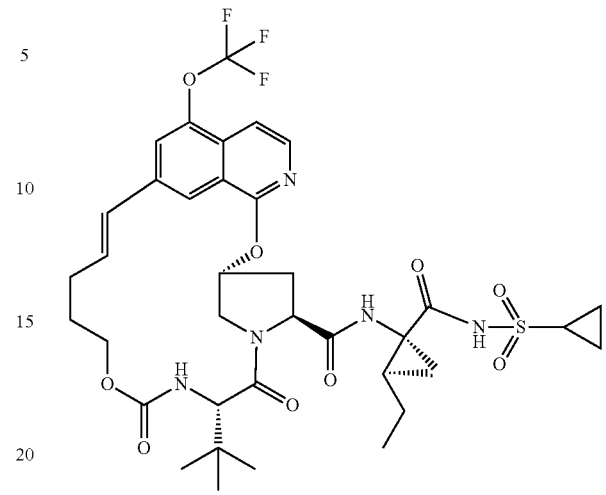
III-163
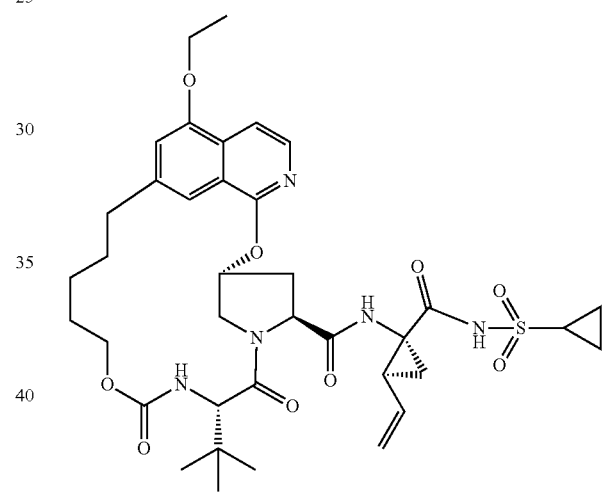
III-164
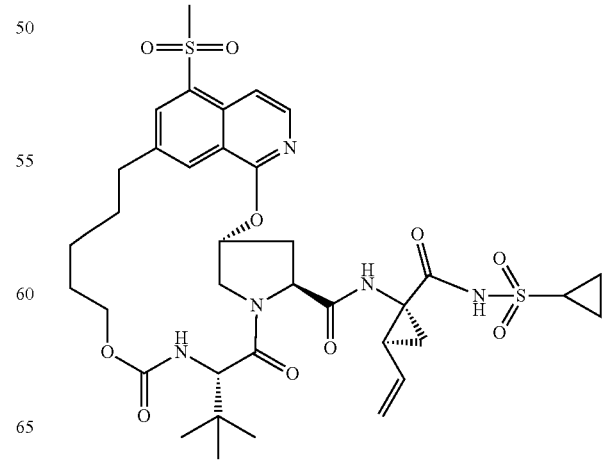

III-165
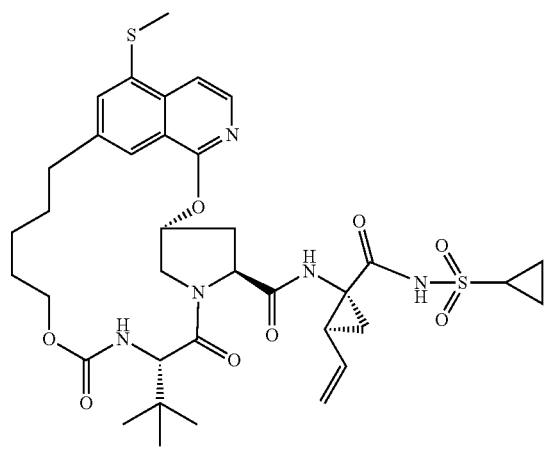
III-168
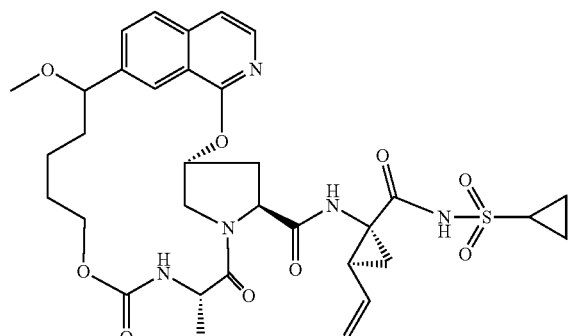
III-166
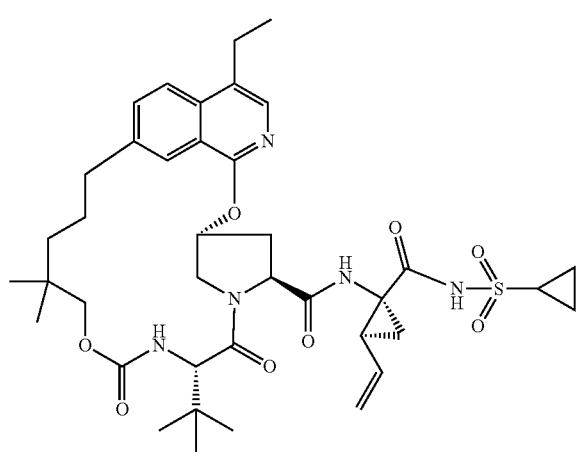
III-169
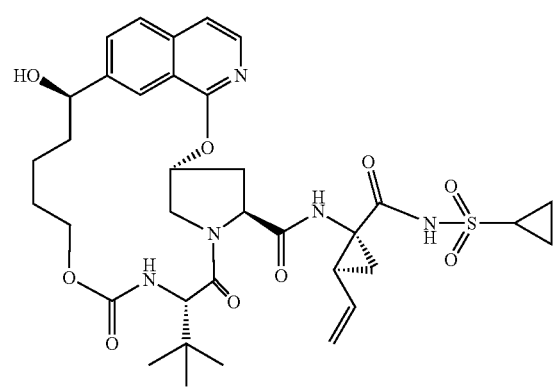
III-167
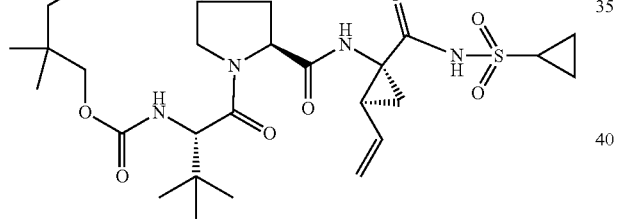
III-170
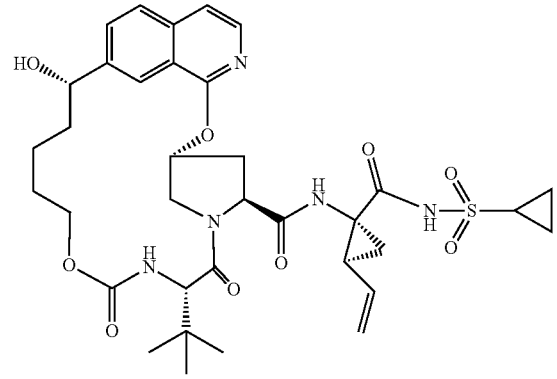
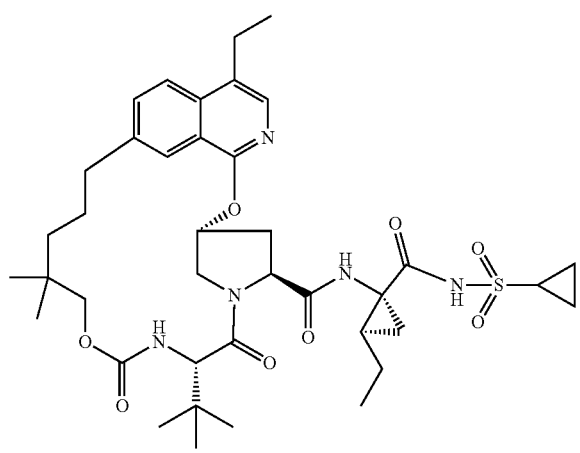
III-171
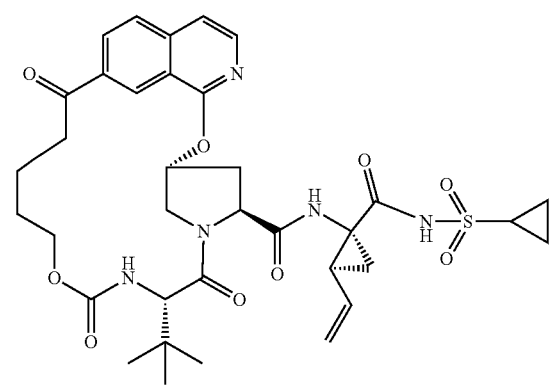

III-172
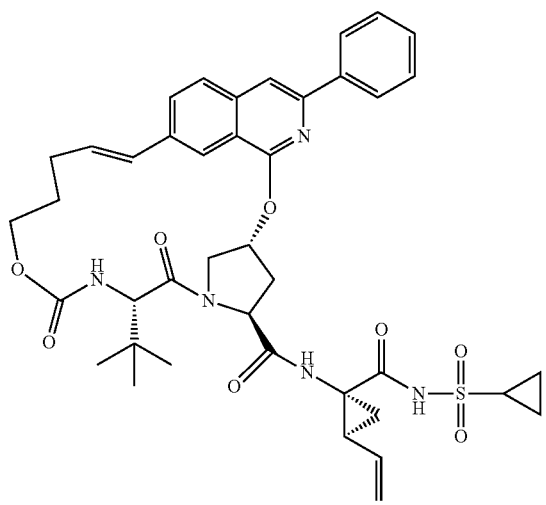
III-176
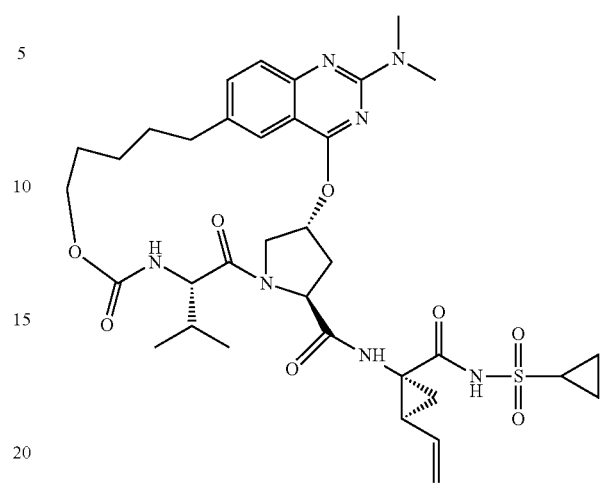
III-174
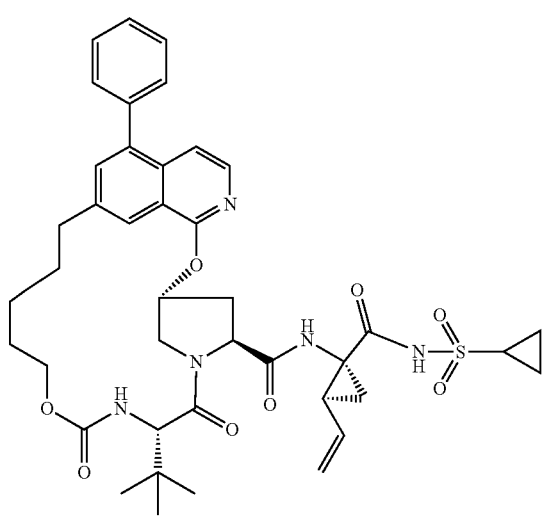
III-177
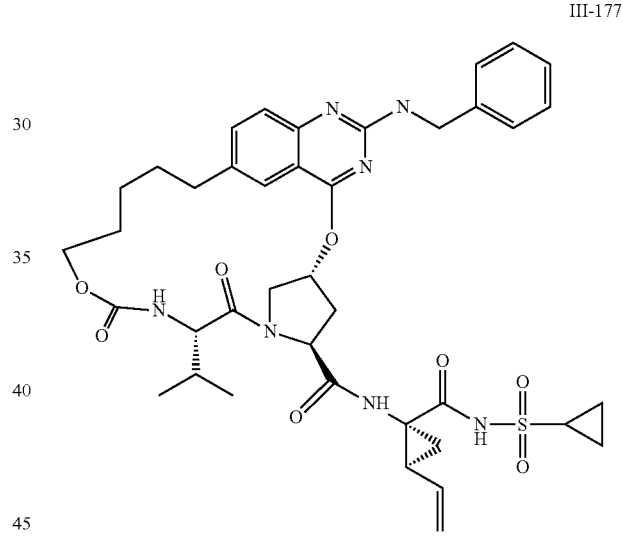
III-175
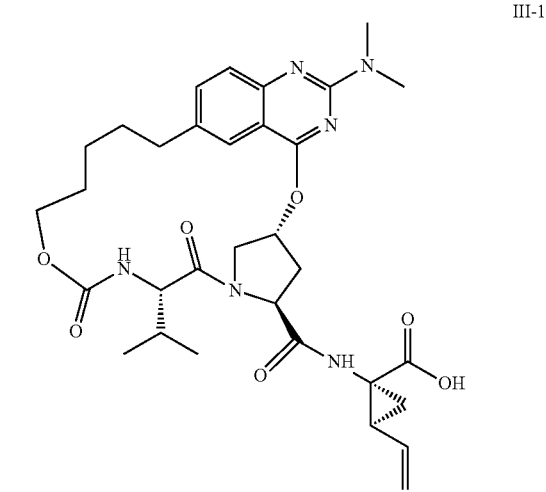
III-178
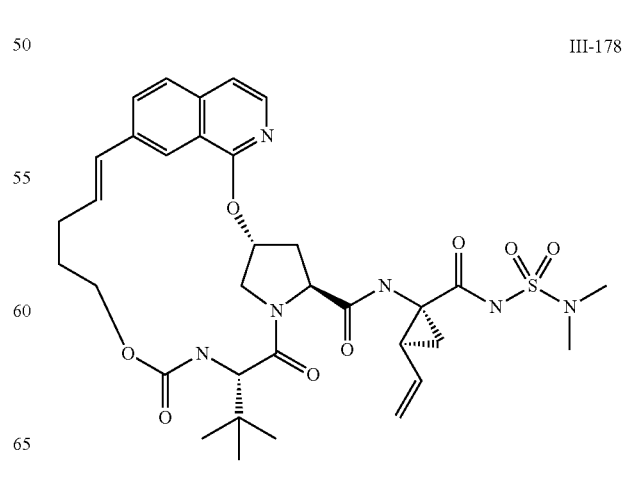

329
-continued
III-179
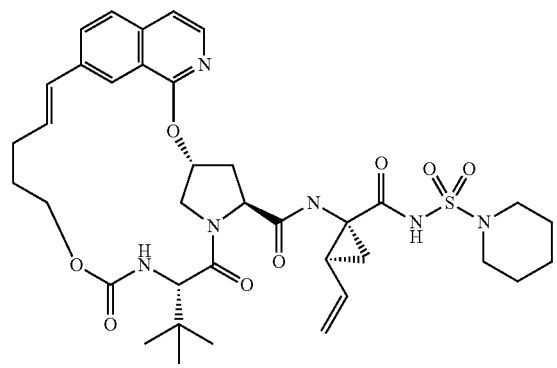
III-180
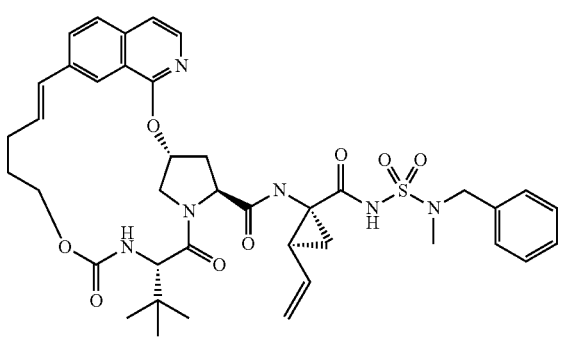
III-181
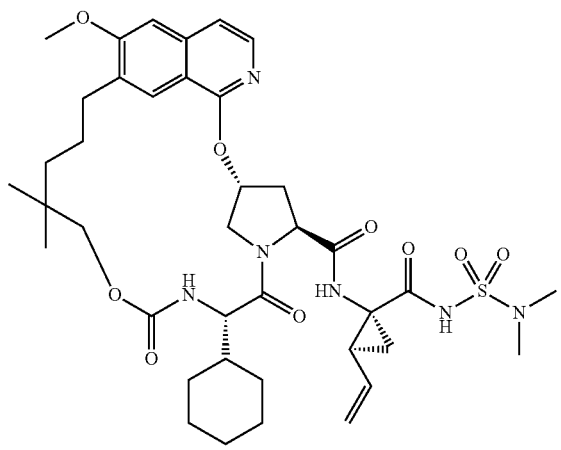
III-182
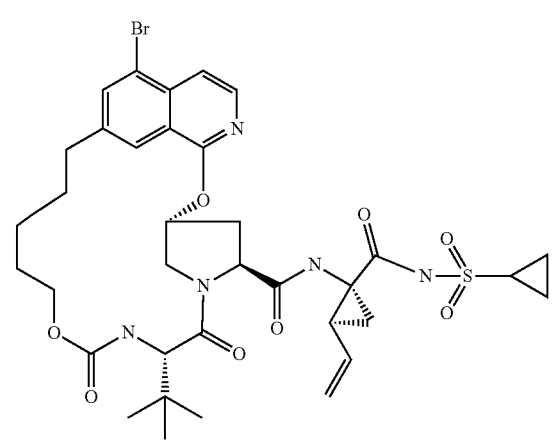
330
-continued
III-183
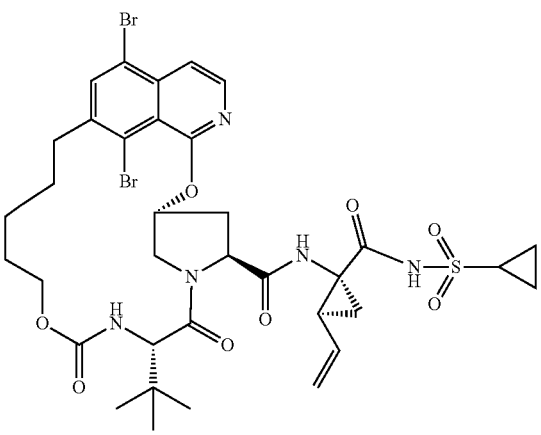
III-184
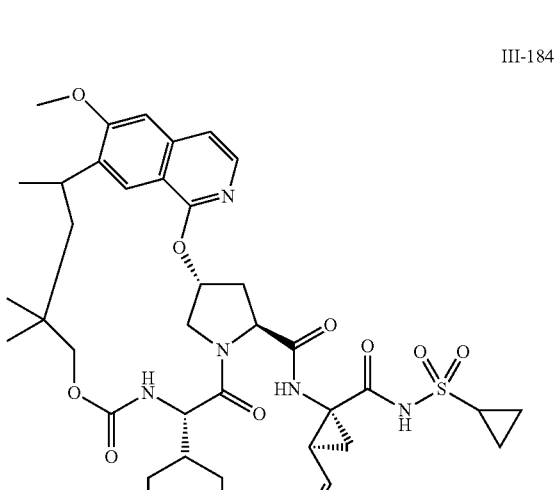
III-185
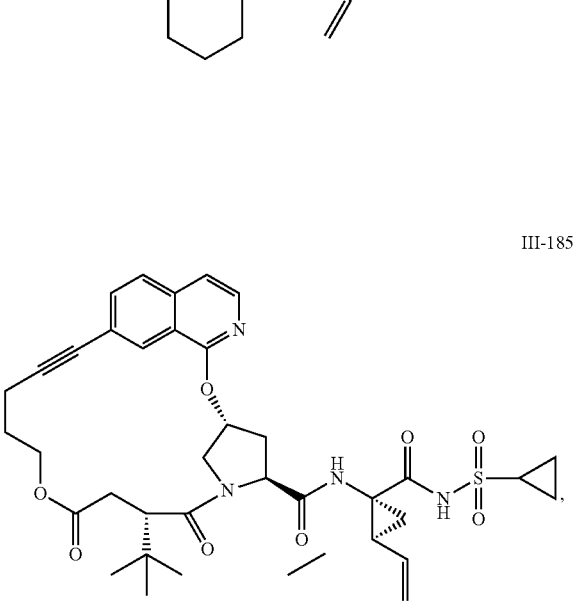
or a pharmaceutically acceptable salt thereof.

24. The compound of claim 1, wherein the compound is (1R,2S)-1-({[(2R,4S,7S)-7-tert-Butyl-6,9-dioxo-3,4,6,7,8,9,12,13-octahydro-2H,11H-16,18-ethanediylidene-2,5-methanopyrido [2,3-k][1,10,3,6]dioxadiazacyclononadecin-4-yl]carbonyl}amino)-2-vinylcyclopropanecarboxylic acid, or a pharmaceutically acceptable salt thereof.

25. A pharmaceutical composition comprising an effective amount of a compound of claim 1, and a pharmaceutically acceptable carrier.

26. The pharmaceutical composition of claim 25, further comprising a second therapeutic agent selected from the group consisting of a HCV antiviral agent, an immunomodulator, and an anti-infective agent.

27. The pharmaceutical composition of claim 26, wherein the HCV antiviral agent is an antiviral selected from the group consisting of a HCV protease inhibitor and a HCV NS5B polymerase inhibitor.

28. A method of inhibiting HCV NS3 protease activity in a subject in need thereof, said method comprising administering to said subject an effective amount of a compound of claim 1.

29. A method of treating infection by HCV in a subject in need thereof, said method comprising administering to said subject an effective amount of a compound of claim 1.

30. The method of claim 29, further comprising administering at least one second therapeutic agent selected from the group consisting of a HCV antiviral agent, an immunomodulator, and an anti-infective agent.

31. The method of claim 30, wherein the HCV antiviral agent is an antiviral selected from the group consisting of a HCV protease inhibitor and a HCV NS5B polymerase inhibitor.

32. A compound of claim 1, wherein the compound is selected from the group consisting of:

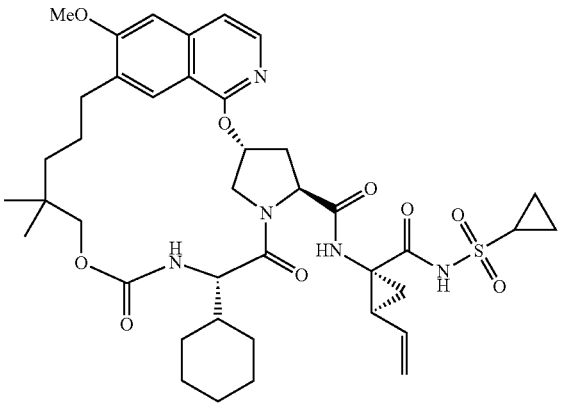

III-131

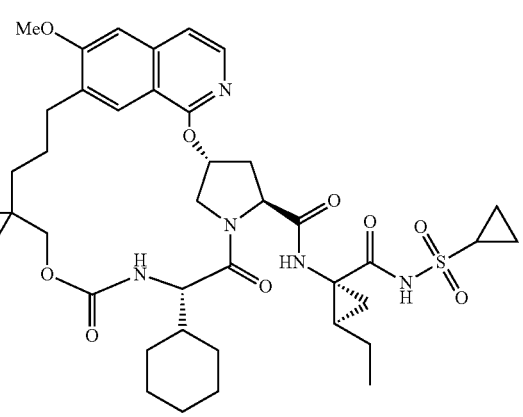

III-132 and

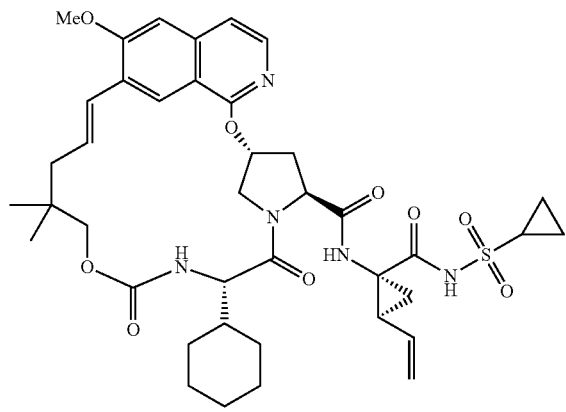

III-129

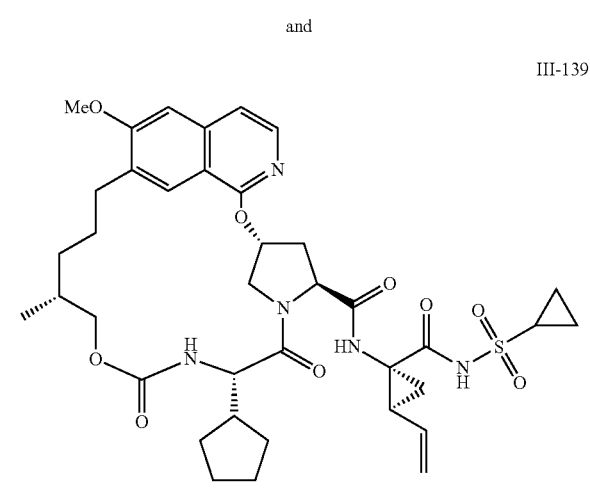

III-139 or a pharmaceutically acceptable salt thereof.

33. A pharmaceutical composition comprising an effective amount of the compound of claim 32 and a pharmaceutically acceptable carrier.

34. The pharmaceutical composition of claim 33, further comprising a second therapeutic agent selected from a HCV protease inhibitor and a HCV NS5B polymerase inhibitor.

35. A method of inhibiting HCV NS3 protease activity and/or treating infection by HCV in a subject in need thereof, said method comprising administering to said subject an effective amount of the compound of claim 32.

36. The method of claim 35, wherein said method further comprises administering at least one second therapeutic agent selected from the group consisting of a HCV antiviral agent, an immunomodulator, and an anti-infective agent.

37. The method of claim 36, wherein the HCV antiviral agent is an antiviral selected from the group consisting of a HCV protease inhibitor and a HCV NS5B polymerase inhibitor.

38. A compound of formula III-131:

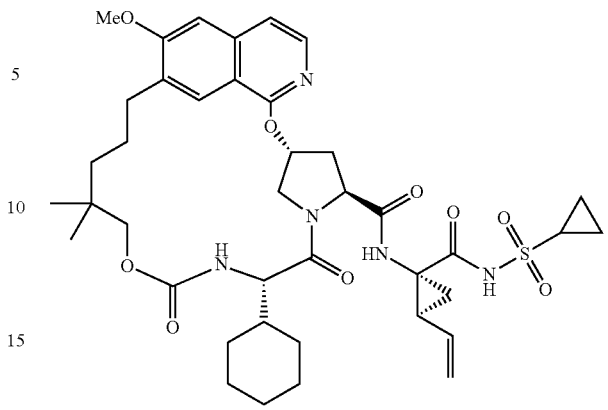

or a pharmaceutically acceptable salt thereof.

39. A pharmaceutical composition comprising an effective amount of the compound of claim 38 and a pharmaceutically acceptable carrier.

40. A method of inhibiting HCV NS3 protease activity and/or treating infection by HCV in a subject in need thereof, said method comprising administering to said subject an effective amount of the compound of claim 38.

* * * * *